US008609836B2

(12) United States Patent
Buijnsters et al.

(10) Patent No.: US 8,609,836 B2
(45) Date of Patent: Dec. 17, 2013

(54) 4-ARYL-2-ANILINO-PYRIMIDINES

(71) Applicant: Janssen Pharmaceutica NV, Beerse (BE)

(72) Inventors: Peter Jacobus Johannes Buijnsters, Etten-Leur (NL); Marc Gustaaf Celine Verdonck, Gierle (BE); Pascal Ghislain André Bonnet, Berchem (BE); Kristof Van Emelen, Sint-Niklaas (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/652,721

(22) Filed: Oct. 16, 2012

(65) Prior Publication Data

US 2013/0053379 A1    Feb. 28, 2013

Related U.S. Application Data

(62) Division of application No. 12/921,499, filed as application No. PCT/EP2009/052692 on Mar. 9, 2009, now Pat. No. 8,318,929.

(30) Foreign Application Priority Data

Mar. 10, 2008  (EP) .................................. 08152534

(51) Int. Cl.
*C07D 345/00* (2006.01)
(52) U.S. Cl.
USPC .............................................................. 540/1
(58) Field of Classification Search
USPC .............................................................. 540/1
See application file for complete search history.

(56) References Cited

FOREIGN PATENT DOCUMENTS

| WO | WO 99/33792 A2 | 7/1999 |
|----|----------------|--------|
| WO | WO 99/33793 A2 | 7/1999 |
| WO | WO 99/33795 A1 | 7/1999 |
| WO | WO 99/33815 A1 | 7/1999 |
| WO | WO 2004/078682 A2 | 9/2004 |
| WO | WO 2006/061415 A1 | 6/2006 |
| WO | WO 2007/058267 A1 | 5/2007 |
| WO | WO 2007/058627 A1 | 5/2007 |
| WO | WO 2007/058628 A1 | 5/2007 |
| WO | WO 2009/112439 A1 | 9/2009 |

OTHER PUBLICATIONS

Kollareddy et al 'Aurora kinase inhibitors: Progress towards the clinic' Invest New Drugs, vol. 30, p. 2411-2432, 2012.*
Senderowicz et al 'Preclinical and Clinical Development of Cyclin-Dependent Kinase Modulators' Journal of the National Cancer Institute, col. 92, p. 376-387, 2000.*
Savage et al 'Advances in the Development of Kinase Inhibitor Therapeutics for Alzheimer's Disease' Drug Development Research, vol. 70, p. 125-144, 2009.*
Castedo, M., et al, Oncogene, (2004), vol. 23, pp. 2825-2837.
Carvajal, R., et al. "Aurora Kinases: New Targets for Cancer Therapy", Clinical Cancer Research, vol. 2, No. 23 (2006) pp. 6869-6875.
Barr, F., et al. "Polo-Like Kinases and The Orchestration of Cell Division", Molecular Cell Biology, Nature Reviews, (2004), vol. 5, pp. 429-440.

(Continued)

*Primary Examiner* — Brandon Fetterolf
*Assistant Examiner* — Christopher R Stone

(57) ABSTRACT

The present invention relates to compounds of Formula (Ia) or (Ib), the N-oxide forms, pharmaceutically acceptable addition salts, quaternary amines, stereoisomers, tautomers, racemics, metabolites, prodrugs, hydrates, or solvates thereof,

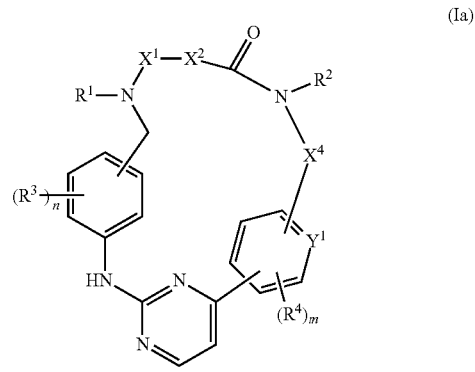

(Ia)

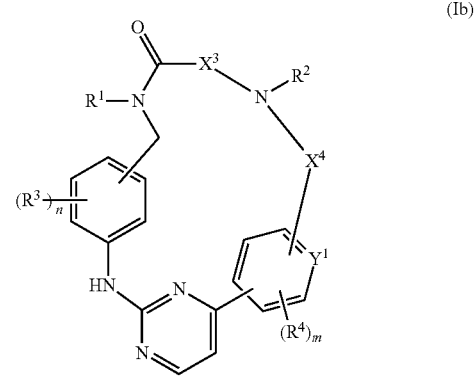

(Ib)

wherein $Y^1$, m, n, $R^1$; $X^1$; $X^2$; $R^2$; $X^3$; $X^4$; $R^3$; and $R^4$ have the meaning defined in the claims.
The present invention also relates to processes for preparing said compounds, pharmaceutical compositions containing them and their use in therapy. The invention particularly relates to compounds that are kinase inhibitors useful for the treatment of disease states mediated by kinase, especially PLK4, in particular such compounds that are useful in the treatment of pathological processes which involve an aberrant cellular proliferation, such as tumor growth, rheumatoid arthritis, restenosis and atherosclerosis.

20 Claims, No Drawings

(56) References Cited

OTHER PUBLICATIONS

Karn, T., et al. "Human SAK Related to the PLK/polo Family of Cell Cycle Kinases Shows High mRNA Expression in testis", Oncology Reports, (1997), vol. 5, pp. 505-510.

Fode, C., et al. "Sak, a Murine Protein-Serine/Threonine Kinase that is Related to the *Drosophila* Polo Kinase and Involved in Cell Proliferation", Proc. Natl. Acad., Sci, (1994), vol. 9, pp. 6388-6392.

Yuan, J., et al. "Efficient Internalization of the Polo-Box of Polo-Like Kinase 1 Fused to an Antennapedia Peptide Results in Inhibition of Cancer Cell Proliferation", Cancer Research, (2002), vol. 62, pp. 4186-4190.

Spankuch-Schmitt, Birgit et al, Oncogene, May 9 2002, vol. 21, No. 20, pp. 3162-3171.

Burns, T., et al. "Silencing of the Novel p53 Target Gene *Sank/Plk2* Leads to Mitotic Catastrophe in Paclitaxel (Taxol)-Exposed Cells", Molecular and Cellular Biology, (2003), vol. 23, No. 6, pp. 5556-5571.

Wang, Q., et al., "Cell Cycle Arrest and Apoptosis Induced by Human Polo-Like Kinase 3 Is Mediated through Perturbation of Microtubule Integrity", Molecular and Cellular Biology, (2002), pp. 3450-3459.

Li, J., et al. SAK, A New Polo-Like Kinase, is Transcriptionally Repressed by p53 and Induces Apoptosis upon RNAi Silencing, Neoplasia, (2005), vol. 7, No. 4, pp. 312-323.

Bettencourt-Dias, M., et al. "SAK/PLK4 is Required for Centriole Duplication and Flagella Development", Current Biology, (2005), vol. 15, pp. 2199-2207.

Greene "Protective Groups in Organic Synthesis", 3nd Ed., Wiley-Interscience (1999).

Delia, T.J., "The Chemistry of Heterocyclic Compounds", Wiley-Interscience, (Nov. 1991), Part 4, vol. 24, Chapter VI Pyrimidotriazines, pp. 261-304 ISBN: 978-0-471-80462-8.

Nagamatsu, T., Syntheses of 3-Substituted 1-Methyl-6-Phenylpyrimido[5,5-*e*]- 1,2-4-triazine-5,7(1H,6H)-diones (6-Phenyl Analogs of Toxoflavin) and Their 4-Oxides and Evaluation of Antimicrobial Activity of Toxoflavins and Their Analogs, Chem. Pharmaceutical Bulletin (1993), vol. 41, No. 2, pp. 362-368.

Nagamatsu, T., "General Syntheses of 1-Alkytoxoflavin and 8-Alkyfervenulin Derivatives of Biological Significance by the Regioselective Alkylation of Reumycin Derivatives and the Rates of Transalkylation From 1-Alkytoxoflavins into Nucleophiles", J. Chemical Society, Perkin Trans., (2001), vol. 1, pp. 130-137.

Benet, L. et al., "Biotransformation of Drugs.", *Goodman and Gilman's The Pharmacological Basis of Therapeutics*, Eighth Edition, (1992), pp. 13-18, McGraw-Hill Inc.

Gennaro Remington's Pharmaceutical Sciences, 19th ed., Mack Publishing Company, Part 8: Pharmaceutical Preparations and Their Manufacture (1990).

Cook, Neil D. et al, Advances in Experimental Medicine and Biology, (1991), vol. 36, pp. 525-528.

Li, Jie Jack, et al., "Palladium in Heterocyclic Chemistry, 26: A Guide for the Synthetic Chemist", Elsevier, (2006), $2^{nd}$ edition, (ISBN 13: 978-0-08-045117-6).

International Search Report PCT/EP2009/052692, mailed Jun. 9, 2009.

\* cited by examiner

4-ARYL-2-ANILINO-PYRIMIDINES

CROSS REFERENCE TO RELATED APPLICATIONS

This application is a divisional of U.S. application Ser. No. 12/921,499, filed Sep. 8, 2010, which is a national stage of PCT Application No. PCT/EP2009/052692, filed Mar. 9, 2009, which claims priority for EPO Patent Application No. 08152534.7, filed Mar. 10, 2008, all of which are hereby incorporated by reference in their entirety.

The present invention relates to 4-aryl-2-anilino-pyrimidine compounds and pharmaceutically-acceptable salts thereof having kinase inhibitory activity. The compounds are useful for the treatment of kinases mediated diseases such as aberrant cellular proliferations.

BACKGROUND OF THE INVENTION

The main goal of a mitotic cell is to equally segregate its chromosomes and centrosomes between two daughter cells. The careful orchestration of cytoskeletal and chromosomal events requires coordinated action by members of the CDK (cyclin-dependent kinase), PLKs (polo-like kinase) and Aurora kinase families. The study of these kinases, their regulatory subunits and substrates has attracted considerable attention in recent years, in part because they are all candidate targets for cancer therapy.

During mitosis, a spectacular reorganization of the cytoskeleton occurs that builds a bipolar microtubule spindle that assures proper segregation of chromosomes and requires a number of precisely coordinated cell-cycle events to occur. Considering the complexity of mitosis, not surprisingly there are many mitotic defects that can lead to the formation of aneuploid daughter cells, i.e. cells that possess an altered content of DNA. To prevent the appearance of such aneuploid cells, the cell will enter into mitotic catastrophe, i.e. a type of cell death. Cells that fail to execute mitotic catastrophe in response to mitotic failure are likely to divide asymmetrically, with the consequent generation of aneuploid cells.

Most tumors develop in an (oligo)clonal and stochastic manner, through a multi-step process. It is accordingly a hypothesis that one of the mechanisms that contribute to oncogenesis consists of 'cytogenetic catastrophe', i.e. the failure to activate mitotic catastrophe in response to mitotic failure (Castedo, M., et al., Oncogene (2004) 23, 2825-2837). In these circumstances aneuploidization could result from the asymmetric division of polyploid cells, generated from an illicit cell fusion. Polyploidy is frequently observed in neoplasia and constitutes a negative prognostic factor, while aneuploidy is a near to general characteristic of cancer.

As already mentioned above, the networks of kinases that regulate the mitotic events are all candidate targets for cancer therapy. For example, Aurora A is an oncogenic serine/threonine kinase that plays a role in centrosome separation and in the formation of the mitotic bipolar spindle. Aurora B is required for chromosome alignment, kinetochore-microtubule bi-orientation, activation of the spindle assembly checkpoint and cytokinesis. Both Aurora A and B are upregulated in various cancers, Aurora A is commonly amplified in melanoma and cancers of the breast, colon, pancreas, ovaries, bladder, liver and stomach. Aurora B is frequently increased in tumors such as colorectal cancer and high-grade gliomas, and Aurora B overexpression in CHO cells results in an increased invasiveness, suggesting a role for Aurora B in tumorigenesis (Carvajal, R. D. et al., Clin. Cancer Res. (2006) 12(23), 6869-6875).

Another member of the kinases involved in cellular mitosis, are the cyclin-dependent kinases CDKs that are at the core of the machinery that drives cell division. It is for example, well established that CDK1 interacts with cyclin B1 to form an active heterodimer, the 'mitosis-promoting factor'. The mitosis-promoting factor induces mitosis by phosphorylating and activating enzymes regulating chromatin condensation, nuclear membrane breakdown, mitosis-specific microtubule reorganization and actin cytoskeleton allowing for mitotic rounding up of the cell. Aberrant mitotic entry can result in cytogenic catastrophe as observed in many tumor cells. This requires the activation of CDK1, and it is currently assumed that premature entry of active CDK1/cyclin B1 complex into the nucleus suffices to cause premature chromatin condensation that may result in aneuploidization (Castedo M. et al., supra). It is also established that CDK4 is important for cell cycle G1 phase progression. The activity of this kinase is restricted to the G1-S phase, which is controlled by the regulatory subunits D-type cyclins and CDK inhibitor p16 (INK4a). This kinase was shown to be responsible for the phosphorylation of retinoblastoma gene product (Rb). Defects in the p16/CDK4:cyclinD/Rb pathway was found to lead to tumor formation. Genetic alteration or over expression of CDK4 has also been observed in various tumor cell types. This increasing body of evidence provides a link between tumor development and CDK related malfunctions and led to an intense search for inhibitors of the CDK family as an approach to cancer therapy.

Other members of the kinases involved in cellular mitosis are Polo-like kinases (PLKs). PLKs are key enzymes that control mitotic entry of proliferating cells and regulate many aspects of mitosis (Barr, F. A. et al., Nat. Rev. Mol. Cell. Biol. 2004, 5, 429-441). Four distinct PLKs have been identified to date in mammals. Whereas PLK1, PLK2 and PLK3 are expressed in all tissues and structurally homologous in that they comprise the N-terminal catalytic kinase domain and two polo-boxes, PLK 4 differs not only in structure, compared to the other PLKs it has only one polo-box, but also in the distribution of PLK4 mRNA in adults that is restricted to certain tissues such as testes and thymus (Karn, T. et al., Oncol. Rep. 1997, 4, 505-510; Fode, C. et al., Proc. Natl. Acad. Sci. USA 1994, 91, 6388-6392). Given the established role of PLKs as mitotic regulators, they have been regarded as validated mitotic cancer targets for a number of years. For example, PLK1 when fused to an antennapedia peptide and efficiently internalized into cells caused an inhibition of cancer cell proliferation (Yuan, J., et al., Cancer Res. 62, 2002, 4186-4190), whereas downregulation of PLK1 by antisense induced the growth inhibition of cancer cells (Spankuch-Schmitt, B., et al., Oncogene 21, 2002, 3162-3171). PLK2 was recently found to be a novel p53 target gene and RNAi silencing of PLK2 leads to mitotic catastrophe in taxol-exposed cells (Burns, T F., et al., Mol Cell Biol. 23, 2003, 5556-5571). For PLK3 it was found that it induces cell cycle arrest and apoptosis through perturbation of microtubule structure (Wang, Q., et al., Mol Cell Biol. 22, 2002, 3450-3459) and PLK4 was shown to be transcriptionally repressed by p53 and induces apoptosis upon RNAi silencing (Li, J., et al., Neoplasia 7, 2005, 312-323). PLK4 was also found to be required for centriole duplication and flagella development. The absence of centrioles, and hence basal bodies, compromises the meiotic divisions and the formation of sperm axonemes (Bettencourt-Dias M., et al., Current Biology 15, 2005, 2199-2207). Thus confirming that targeting PLKs with conventional agents may be a valid and effective anticancer strategy. The involvement of PLK4 in flagella development also implies a possible use of PLK4 antagonists as male contraceptives.

Glycogen synthase kinase (GSK)-3 has also emerged as an attractive therapeutic target for the treatment of cancer. GSK-3β is a critical regulator of nuclear factor (NF)κB nuclear activity, suggesting that inhibition of GSK-3β could be effective in the treatment of a wide variety of tumors with constitutively active NFκB.

Certain macrocyclic compounds having kinase inhibitory activity have been described. WO 2004/078682 discloses cyclic compounds, pharmaceutical compositions comprising such cyclic compounds and methods of using such compounds to treat or prevent diseases and disorders associated with the activity of CDK2 and CDK5.

WO 2007/058627 discloses oxygen linked and substituted pyrimidine compounds and the uses of these compounds in the treatment of proliferative disorders as well as other disorders or conditions related to or associated with kinases.

WO 2007/058628 discloses heteroalkyl linked pyrimidine derivatives and the uses of these compounds in the treatment of proliferative disorders as well as other-conditions or disorders associated with kinases.

However, there is still a need to develop new compounds having improved pharmacological and therapeutic activities for the treatment of kinase related diseases. It is accordingly one of the objects of the present invention to provide new compounds that are kinase inhibitors and that are useful in the treatment of kinase associated diseases such as cell proliferative disorders.

SUMMARY OF THE INVENTION

The present inventors have found that the macrocyclic 4-aryl-2-anilino-pyrimidine derivatives of the present invention act as kinase inhibitors. The compounds according to the invention and the pharmaceutically acceptable compositions thereof are therefore useful for treating or lessening the severity of a variety of disorders associated with kinases.

The present invention concerns compounds of Formula (Ia) or (Ib), the N-oxides, pharmaceutically acceptable addition salts, quaternary amines, stereoisomers, tautomers, racemics, metabolites, prodrugs, hydrates, or solvates thereof,

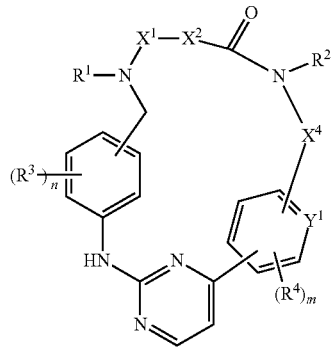

(Ia)

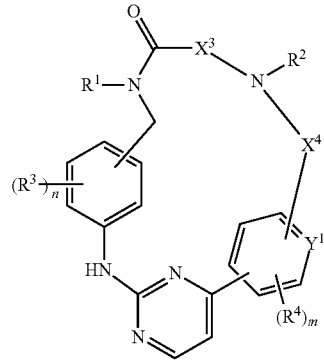

(Ib)

wherein
n is an integer selected from 1, 2, 3 or 4;
m is an integer selected from 1, 2, or 3;
$Y^1$ represents CH or N,
$R^1$ is hydrogen or $C_{1-6}$alkyl;
$X^1$ represents —$CR^5R^6$—; wherein $R^5$ and $R^6$ are each independently selected from the group comprising hydrogen, $C_{1-6}$alkyl, hydroxy$C_{1-6}$alkyl, $C_{6-10}$aryl$C_{1-6}$alkyl, and $C_{1-6}$alkoxy;
or $X^1$ and $R^1$ together with the nitrogen atom to which they are bound form a $Het^1$,
$X^2$ represents a single bond or —$CR^7R^8$—; wherein $R^7$ and $R^8$ are each independently selected from the group comprising hydrogen, $C_{1-6}$alkyl, hydroxy$C_{1-6}$alkyl, $C_{1-6}$alkoxy, and $C_{6-10}$aryl$C_{1-6}$alkyl;
$R^2$ is hydrogen or $C_{1-6}$alkyl;
$X^3$ represents a single bond or —$CR^9R^{10}$—; wherein $R^9$ and $R^{10}$ are each independently selected from the group comprising hydrogen, $C_{1-6}$alkyl, hydroxy$C_{1-6}$alkyl, $C_{6-10}$aryl$C_{1-6}$alkyl, and $C_{1-6}$alkoxy;
or $R^2$ and $X^3$ together with the nitrogen atom to which they are bound form a $Het^2$,
$X^4$ represents a single bond; —$C_{1-6}$alkylene-; —$C_{1-6}$alkylene-$NR^{14}$—; —$C_{1-6}$alkylene-$NR^{14}$—$C_{1-6}$alkylene-; or —$C_{1-6}$alkylene-O—; wherein each —$C_{1-6}$alkylene- in any of —$C_{1-6}$alkylene-; —$C_{1-6}$alkylene-$NR^{14}$—; —$C_{1-6}$alkylene-$NR^{14}$—$C_{1-6}$alkylene-; or —$C_{1-6}$alkylene-O—, is optionally substituted with one, two or three substituents each independently selected from the group comprising hydroxy, $C_{1-6}$alkyl, and $C_{6-10}$aryl; wherein $R^{14}$ is hydrogen or $C_{1-6}$alkyl; and wherein the left side of the —$C_{1-6}$alkylene-; —$C_{1-6}$alkylene-$NR^{14}$—; —$C_{1-6}$alkylene-$NR^{14}$—$C_{1-6}$alkylene-; or —$C_{1-6}$alkylene-O— is attached to the $NR^2$, and the right side thereof is attached to the

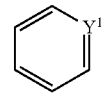

ring;
$R^3$ is hydrogen, halogen, cyano or is selected from the group comprising $C_{1-6}$alkyl, amino, aminocarbonyl, amino$C_{1-6}$alkyl, $Het^3$, $Het^3$-$C_{1-6}$alkyl, $C_{1-6}$alkoxy, $C_{1-6}$alkylaminocarbonyl, $C_{1-6}$alkyl-$Het^3$carbonyl, $Het^3$carbonyl, $C_{1-6}$alkyl-$Het^3$-$C_{1-6}$alkyl, $Het^3$-amino$C_{1-6}$alkyl, $C_{1-6}$alkylamino$C_{1-6}$alkyl, $C_{1-6}$alkylamino-$C_{1-6}$alkylamino$C_{1-6}$alkyl, $C_{1-6}$alkoxy$C_{1-6}$alkylamino$C_{1-6}$alkyl, $C_{3-6}$cycloalkylamino-$C_{1-6}$alkyl, $Het^3$aminocarbonyl, $C_{3-6}$cycloalkylaminocarbonyl, $C_{1-6}$alkylHet$^3$aminocarbonyl, $C_{1-6}$alkylamino, $C_{1-6}$alkylamino$C_{1-6}$alkylaminocarbonyl, $C_{1-6}$alkoxy$C_{1-6}$alkylaminocarbonyl, and $C_{6-10}$aryl$C_{1-6}$alkylamino; each group being optionally substituted with one or two substituents each independently selected from the group comprising $C_{1-6}$alkyl, $C_{6-10}$aryl$C_{1-6}$alkyl, Het$^3$, $C_{3-6}$cycloalkyl, $C_{1-6}$alkylamino$C_{1-6}$alkyl, $C_{1-6}$alkoxy$C_{1-6}$alkyl, $C_{6-10}$aryl, $C_{1-6}$alkylamino, and $C_{1-6}$alkoxy;

or two R$^3$ form together with the carbon atom to which they are bound a dioxolino ring;

R$^4$ is hydrogen; halo; cyano; or is selected from the group comprising $C_{1-6}$alkyl optionally substituted with one, two or three substituents each independently selected from halo or hydroxy; $C_{3-6}$cycloalkyl; $C_{1-6}$alkyloxy; $C_{3-6}$cycloalkyloxy; and Het$^4$;

Het$^1$ and Het$^2$ are each independently selected from the group comprising piperidinyl, piperazinyl, pyrrolidinyl and azetidinyl, wherein said Het$^1$ is optionally substituted with one, two or three substituents each independently selected from hydroxyl, $C_{1-4}$alkoxy, halo, cyano, amino, $C_{1-4}$alkyl, halo-$C_{1-4}$alkyl, polyhalo-$C_{1-4}$alkyl, $C_{3-6}$cycloalkyl, hydroxy-$C_{1-4}$alkyl, $C_{1-4}$alkyloxy$C_{1-4}$alkyl or polyhydroxy-$C_{1-4}$alkyl; and Het$^3$ and Het$^4$ are each independently selected from the group comprising morpholinyl, piperazinyl, piperidinyl, and tetrahydro-pyranyl.

The present invention also concerns methods for the preparation of compounds of Formula (Ia) or (Ib) and pharmaceutical compositions comprising them.

The compounds according to the present invention are kinase inhibitors. Compounds of the present invention were found to have PLK4 inhibitory activity. In addition to their activity against PLK4, some compounds according to the invention have been found to have activity against Aurora B kinase. Some compounds of the present invention, were also found to have CDK1 and/or CDK4 inhibitory activity.

Therefore the present invention also concerns the compounds of the present invention for use in the treatment of diseases mediated through PLK4, Aurora B kinase CDK1 and/or CDK4 such as cell proliferative disorders selected from the group comprising cancer, rheumatoid arthritis, restenosis and atherosclerosis. In the treatment of cancers, said cancers comprises lung cancer (especially non small-cell lung cancer), breast cancer, liver cancer, ovarian cancer, prostate cancer, pancreatic cancer, colorectal cancer, gastrointestinal cancer such as colon, rectal or stomach cancer and papillary carcinomas (such as papillary thyroid cancer) as well as squamous cell cancers of the head and neck and oesophageal cancers including oropharyngeal cancer, and fast-dividing leukaemias such as acute myelogenous leukaemia (AML).

Compounds of the present invention were also found to have Glycogen synthase kinase-3 (GSK-3) inhibitory.

Therefore the present invention also concerns the compounds of the present invention for use in the treatment of diseases mediated through GSK-3 activity selected from the group comprising cancer, bipolar disorder (in particular manic depression), diabetes, Alzheimer's disease, leukopenia, Fronto-temporal dementia associated with Parkinson's disease (FTDP-17), cortico-basal degeneration, progressive supranuclear palsy, multiple system atrophy, Pick's disease, Niemann Pick's disease type C, Dementia Pugilistica, dementia with tangles only, dementia with tangles and calcification, Downs syndrome, myotonic dystrophy, Parkinsonism-dementia complex of Guam, aids related dementia, Postencephalic Parkinsonism, prion diseases with tangles, subacute sclerosing panencephalitis, frontal lobe degeneration (FLD), argyrophilic grains disease, subacutesclerotizing panencephalitis (SSPE) (late complication of viral infections in the central nervous system), inflammatory diseases, depression, dermatological disorders such as baldness, neuroprotection, schizophrenia, pain, in particular neuropathic pain. GSK3 inhibitors can also be used to inhibit sperm motility and can therefore be used as male contraceptives. Therefore, the invention also provides the use of the compounds of the invention as male contraceptives.

In a particular embodiment, the present invention concern the use of the compounds of the present invention for the preparation of a medicament for the prevention or treatment of diseases selected from the group comprising cancer including lung cancer (especially non small-cell lung cancer), breast cancer, liver cancer, ovarian cancer, prostate cancer, pancreatic cancer, colorectal cancer, gastrointestinal cancer such as colon, bladder, rectal or stomach cancer and papillary carcinomas (such as papillary thyroid cancer) as well as squamous cell cancers of the head and neck and oesophageal cancers including oropharyngeal cancer, and fast-dividing leukaemias such as acute myelogenous leukaemia (AML); Alzheimer's disease; diabetes, in particular type 2 diabetes (non insulin dependent diabetes); bipolar disorder; pain, in particular neuropathic pain; depression; inflammatory diseases including allergies and asthma, MS, RA, arteriosclerosis, arthritis or IBD.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

The term "halo" or "halogen" as a group or part of a group is generic for fluoro, chloro, bromo, iodo.

The term "nitro" as used herein refers to the group —NO$_2$.

The term "cyano" as used herein refers to the group —CN.

The term "$C_{1-6}$alkyl" as a group or part of a group refers to a hydrocarbyl radical of Formula $C_nH_{2n+1}$ wherein n is a number ranging from 1 to 6. Generally, alkyl groups of this invention comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl includes all linear, or branched alkyl groups with between 1 and 6 carbon atoms, and thus includes methyl, ethyl, n-propyl, i-propyl, butyl and its isomers (e.g. n-butyl, i-butyl and tert-butyl); pentyl and its isomers, hexyl and its isomers.

The term "$C_{1-6}$alkylene" refers to $C_{1-6}$alkyl groups which are divalent, i.e., with two single bonds for attachment to two other groups. Non-limiting examples of alkylene groups includes methylene, ethylene, methylmethylene, propylene, ethylethylene, 1-methylethylene and 1,2-dimethylethylene.

The term "hydroxy$C_{1-6}$alkyl" as a group or part of a group refers to a —$R^a$—OH group wherein $R^a$ is $C_{1-6}$alkylene as defined herein. For example, "hydroxy$C_{1-6}$alkyl" includes but is not limited to hydroxymethyl, 1-hydroxyethyl, 2-hydroxyethyl, 1-hydroxypropyl, 2-hydroxypropyl, 2-hydroxy-2-methylethyl, 1-hydroxypropyl, 2-hydroxypropyl, 3-hydroxypropyl, 1-hydroxybutyl, 2-hydroxybutyl, 3-hydroxybutyl, 4-hydroxybutyl, 2-hydroxy-2-methylpropyl, 1-(hydroxymethyl)-2-methylpropyl, 1,1-dimethyl-2-hydroxyethyl, 5-hydroxypentyl, 2-methyl-3-hydroxypropyl, 3,4-dihydroxybutyl, and so forth.

The term "$C_{1-6}$alkoxy" or "$C_{1-6}$alkyloxy" as a group or part of a group refers to a radical having the Formula —$OR^b$ wherein $R^b$ is $C_{1-6}$alkyl. Non-limiting examples of suitable alkoxy include methoxy, ethoxy, propoxy, isopropoxy, butoxy, isobutoxy, sec-butoxy, tert-butoxy, pentyloxy and hexyloxy.

The term "$C_{1-6}$alkoxy$C_{1-6}$alkyl" as a group or part of a group refers to an alkyl group substituted with one to two $R^c$, wherein $R^c$ is $C_{1-6}$alkoxy as defined below.

The term "$C_{3-6}$cycloalkyl" as a group or part of a group defines cyclic saturated hydrocarbon radicals having from 3 to 6 carbon atoms such as cyclopropyl, cyclobutyl, cyclopentyl or cyclohexyl.

The term "$C_{3-6}$cycloalkyl$C_{1-6}$alkyl" by itself or as part of another substituent refers to a group having one of the aforementioned $C_{3-6}$cycloalkyl groups attached to one of the aforementioned $C_{1-6}$alkyl chains. Non-limiting examples of such $C_{3-6}$cycloalkyl-$C_{1-6}$alkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, 3-cyclopentylbutyl, cyclohexylbutyl and the like.

The term "halo$C_{3-6}$alkyl" alone or in combination, refers to an alkyl radical having the meaning as defined above wherein one hydrogen is replaced with a halogen as defined above. The term "polyhalo$C_{3-6}$alkyl" alone or in combination, refers to an alkyl radical having the meaning as defined above wherein more than one hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl and the like. In case more than one halogen atom is attached to an alkyl group within the definition of halo$C_{1-6}$alkyl, they may be the same or different.

The term "carbonyl" as a group or part of a group refers to a C=O moiety.

The term "$C_{6-10}$aryl" as used herein refers to a polyunsaturated, aromatic hydrocarbyl group having a single ring (i.e. phenyl) or multiple aromatic rings fused together (e.g. naphthalenyl), or linked covalently, typically containing 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein. Non-limiting examples of aryl comprise phenyl, biphenylyl, biphenylenyl, or naphthalen-1- or -2-yl.

The term "$C_{1-6}$alkylamino" as a group or part of a group refers to —$N(R^h)(R^i)$ wherein $R^h$ and $R^i$ are each independently selected from hydrogen or $C_{1-6}$alkyl, wherein al least one $R^h$ or $R^i$ is $C_{1-6}$alkyl. $C_{1-6}$Alkylamino includes mono-$C_{1-6}$ alkylamino group such as methylamino and ethylamino, and di-$C_{1-6}$alkylamino group such as dimethylamino and diethylamino Non-limiting examples of suitable $C_{1-6}$alkylamino groups also include n-propylamino, isopropylamino, n-butylamino, isobutylamino, sec-butylamino, tert-butylamino, pentylamino, n-hexylamino, di-n-propylamino, diisopropylamino, ethylmethylamino, methyl-n-propylamino, methyl-i-propylamino, n-butylmethylamino, i-butylmethylamino, tert-butylmethylamino, ethyl-n-propylamino, ethyl-i-propylamino, n-butylethylamino, i-butylethylamino, tert-butylethylamino, di-n-butylamino, di-i-butylamino, methylpentylamino, methylhexylamino, ethylpentylamino, ethylhexylamino, propylpentylamino, propylhexylamino, and the like.

The term "amino$C_{1-6}$alkyl" refers to the group —$R^j$—$NR^kR^l$ wherein $R^j$ is $C_{1-6}$alkylene or substituted $C_{1-6}$alkylene, $R^k$ is hydrogen or $C_{1-6}$alkyl or substituted $C_{1-6}$alkyl as defined herein, and $R^l$ is hydrogen or $C_{1-6}$alkyl as defined herein.

The term "aminocarbonyl" refers to the group —(C=O)—$NH_2$.

The term "$C_{1-6}$alkylaminocarbonyl" refers to a group —(C=O)—$NR^eR^f$ wherein $R^e$ is hydrogen or $C_{1-6}$alkyl or substituted $C_{1-6}$alkyl as defined herein, and $R^f$ is $C_{1-6}$alkyl or substituted $C_{1-6}$alkyl as defined herein.

Lines drawn into ring systems indicate that the bond may be attached to any suitable ring atom.

When any variable occurs more than one time in any constituent, each definition is independent.

It will be appreciated that some of the compounds of Formula (Ia), (Ib) and their N-oxides, addition salts, prodrugs, hydrates, solvates, quaternary amines and stereochemically isomeric forms may contain one or more centers of chirality and exist as stereochemically isomeric forms.

The term "stereochemically isomeric forms" as used hereinbefore or hereinafter defines all the possible stereoisomeric forms which the compounds of Formula (Ia), (Ib) and their N-oxides, addition salts, prodrugs, hydrates, solvates, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of Formula (Ia), (Ib) and their N-oxides, salts, solvates, quaternary amines substantially free, i.e. associated with less than 10%, preferably less than 5%, in particular less than 2% and most preferably less than 1% of the other isomers. Stereochemically isomeric forms of the compounds of Formula (Ia), (Ib) are obviously intended to be embraced within the scope of this invention.

For therapeutic use, salts of the compounds of Formula (Ia), (Ib) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of Formula (Ia), (Ib) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (Ia), (Ib) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term addition salt as used hereinabove also comprises the solvates which the compounds of Formula (Ia), (Ib), as well as the salts thereof, are able to form. Such solvates are for example hydrates, alcoholates and the like.

The term "quaternary amine" as used hereinbefore defines the quaternary ammonium salts which the compounds of Formula (Ia), (Ib) are able to form by reaction between a basic nitrogen of a compound of Formula (Ia), (Ib) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include for example chloro, bromo, iodo, trifluoroacetate and acetate. The counterion of choice can be made using ion exchange resin columns.

The N-oxide forms of the present compounds are meant to comprise the compounds of Formula (Ia), (Ib) wherein one or several tertiary nitrogen atoms are oxidized to the so-called N-oxide.

Some of the compounds of Formula (Ia), (Ib) may also exist in their tautomeric form. Such forms although not explicitly indicated in the above formula are intended to be included within the scope of the present invention.

As used in the specification and the appended claims, the singular forms "a", "an," and "the" also include plural referents unless the context clearly dictates otherwise. By way of example, "a compound" means one compound or more than one compound.

The terms described above and others used in the specification are well understood to those in the art.

Preferred features of the compounds of this invention are now set forth.

According to an embodiment, the present invention provides compounds of Formula (Ia) or (Ib), wherein: the $C_{6-10}$aryl as a group or part of a group is phenyl.

According to an embodiment, the present invention provides compounds of Formula (Ia) or (Ib), wherein: n is an integer selected from 1, or 2; m is an integer selected from 1, or 2; and $Y^1$; $R^1$; $X^1$; $X^2$; $R^2$; $X^3$; $X^4$; $R^3$; and $R^4$ have the same meaning as that defined herein.

According to an embodiment, the present invention provides compounds of Formula (Ia) or (Ib), wherein $Y^1$ represents CH and n, m, $R^1$; $X^1$; $X^2$; $R^2$; $X^3$; $X^4$; $R^3$; and $R^4$ have the same meaning as that defined herein.

According to another embodiment, the present invention provides compounds of Formula (Ia) or (Ib), wherein $Y^1$ represents N and n, m, $R^1$; $X^1$; $X^2$; $R^2$; $X^3$; $X^4$; $R^3$; and $R^4$ have the same meaning as that defined herein.

According to an embodiment, the present invention provides compounds of Formula (Ia) or (Ib), wherein Het$^1$ and Het$^2$ are each independently selected from the group comprising piperidinyl, piperazinyl, and pyrrolidinyl; wherein said Het$^1$ is optionally substituted with one or where possible two or more substituents selected from hydroxyl, $C_{1-4}$alkoxy, halo, $C_{1-4}$alkyl, halo-$C_{1-4}$alkyl, polyhalo-$C_{1-4}$alkyl, $C_{3-6}$cycloalkyl, or hydroxy-$C_{1-4}$alkyl; and $Y^1$, n, m, $R^1$; $X^1$; $X^2$; $R^2$; $X^3$; $X^4$; $R^3$; and $R^4$ have the same meaning as that defined herein.

According to another embodiment, the present invention provides compounds of Formula (Ia) or (Ib), having one of the structural Formula (II), (III), (IV), or (V),

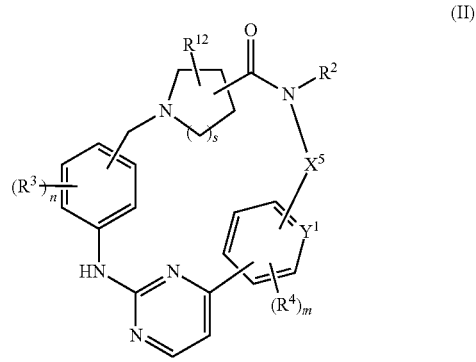

(II)

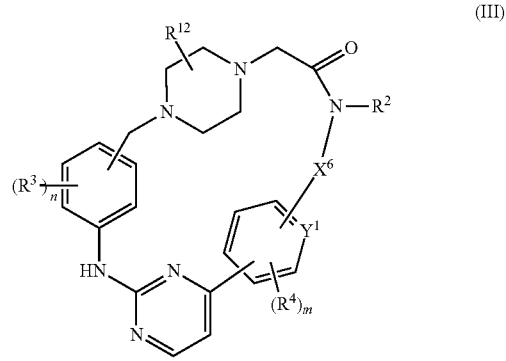

(III)

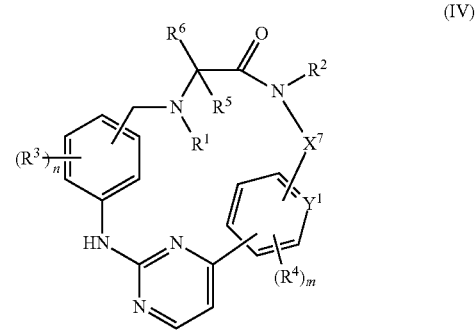

(IV)

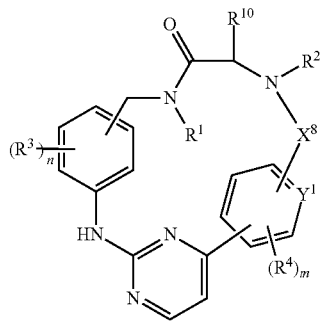

(V)

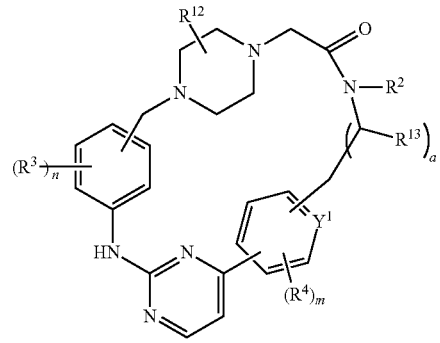

(VII)

wherein:
s is an integer selected from 1 or 2;
$R^{12}$ is selected from the group comprising hydrogen, hydroxyl, $C_{1-4}$alkoxy, halo, cyano, amino, $C_{1-4}$alkyl, halo-$C_{1-4}$alkyl, polyhalo-$C_{1-4}$alkyl, $C_{3-6}$cycloalkyl, hydroxy-$C_{1-4}$alkyl, $C_{1-4}$alkyloxy$C_{1-4}$alkyl and polyhydroxy-$C_{1-4}$alkyl;
$X^5$, $X^6$, $X^7$, and $X^8$ each independently represent a single bond or —$C_{1-6}$alkylene-; —$C_{1-6}$alkylene-$NR^{14}$—; —$C_{1-6}$alkylene-$NR^{14}$—$C_{1-6}$alkylene-; or —$C_{1-6}$alkylene-O—; wherein each —$C_{1-6}$alkylene- in any of —$C_{1-6}$alkylene-; —$C_{1-6}$alkylene-$NR^{14}$—; —$C_{1-6}$alkylene-$NR^{14}$—$C_{1-6}$alkylene-; or —$C_{1-6}$alkylene-O— is optionally substituted with one, two or three substituents each independently selected from the group comprising hydroxy, $C_{1-6}$alkyl, $C_{6-10}$aryl; wherein $R^{14}$ is hydrogen or $C_{1-6}$alkyl; and wherein the left side of the —$C_{1-6}$alkylene-; —$C_{1-6}$alkylene-$NR^{14}$—; —$C_{1-6}$alkylene-$NR^{14}$—$C_{1-6}$alkylene-; or —$C_{1-6}$alkylene-O— is attached to the $NR^2$, and the right side of thereof is attached to the

ring;
or N—$R^2$ and $CHR^{10}$ form together a $Het^2$, wherein $Het^2$ is selected from piperidinyl, or, pyrrolidinyl,
and $R^1$, $R^2$, $R^3$, $R^4$, $R^5$, $R^6$, $R^{10}$, $Y^1$, n and m have the same meaning as that defined herein.

According to an embodiment, the present invention provides compounds of Formula (Ia) or (Ib), having one of the structural Formula (VI), (VII), (VIII), (IX), (X), (XI), (XII), (XIII), (XIV), (XV), (XVI), (XVII), (VIII)

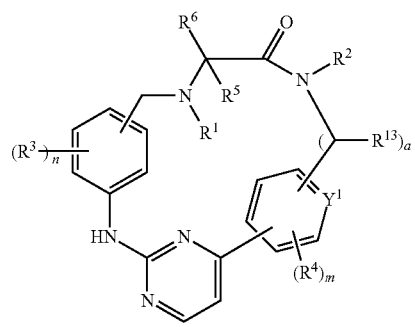

(IX)

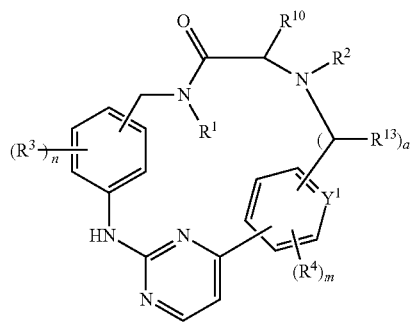

(VI)

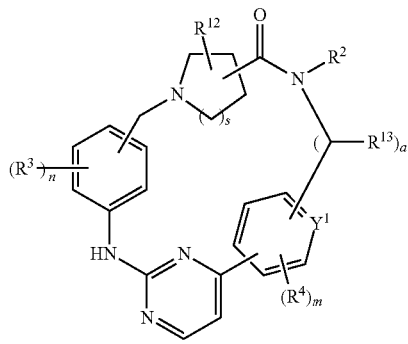

(X)

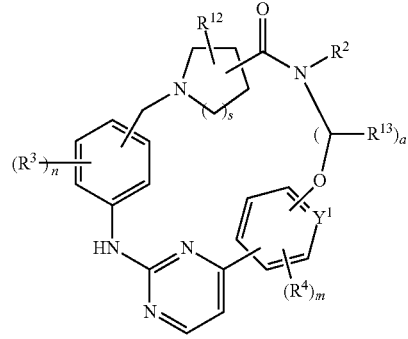

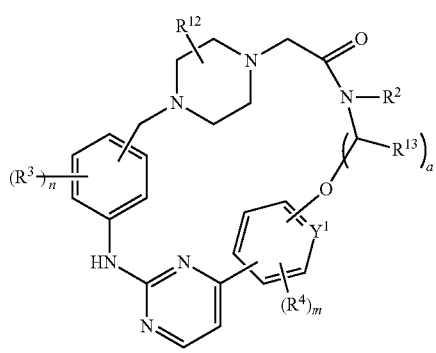
(XI)

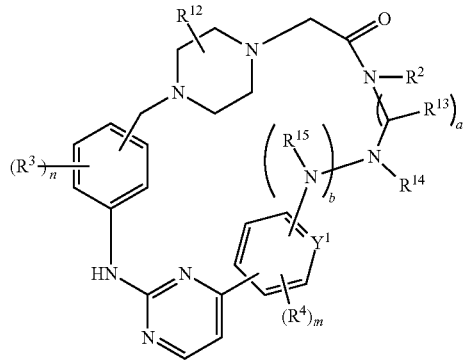
(XV)

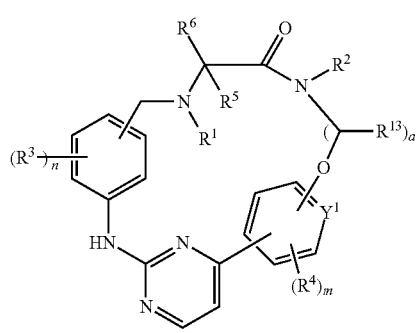
(XII)

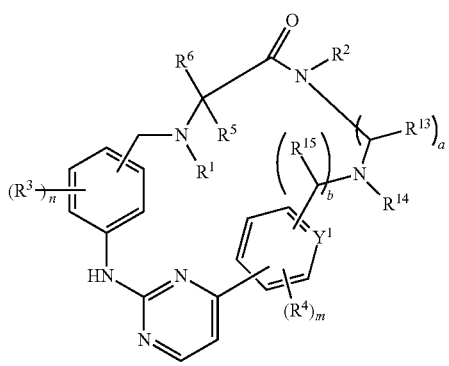
(XVI)

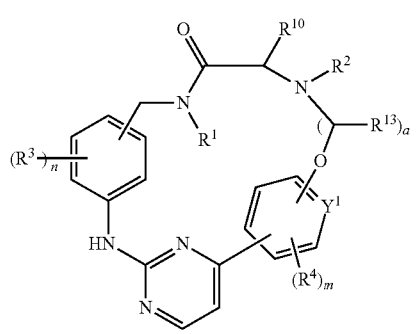
(XIII)

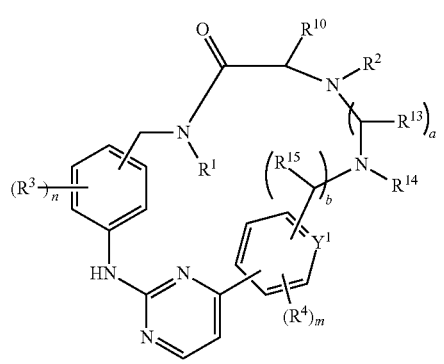
(XVII)

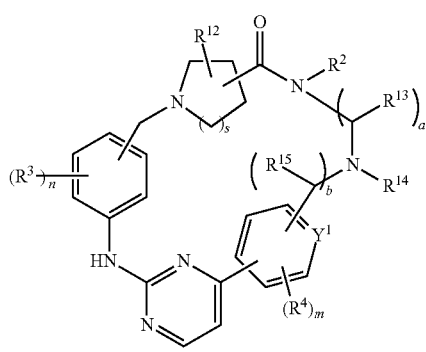
(XIV)

wherein
a is an integer selected from 1, 2 or 3;
b is an integer selected from 0 or 1;
$R^{13}$ and $R^{15}$ are each independently selected from the group comprising hydrogen, hydroxy, $C_{1-6}$alkyl, and $C_{6-10}$aryl;
$R^1$, $R^2$, $R^3$, $R^4$, $R^5$, $R^6$, $R^{10}$, $R^{12}$, $R^{14}$, $Y^1$, s, n and m have the same meaning as that defined herein.

According to an embodiment, the present invention provides compounds of Formula (Ia) or (Ib), having one of the structural Formula (XVIII), (XIX), (XX), (XXI), (XXII), (XXIII), (XXIV), (XXV), (XXVI), (XXVII), (XXVIII), (XXIX), (XXX), (XXXI),

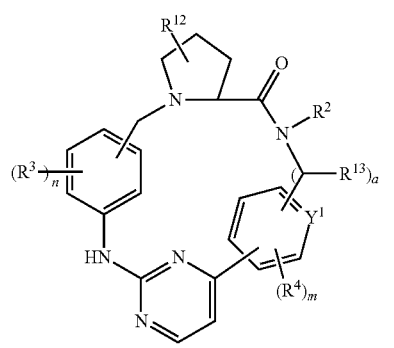
(XVIII)
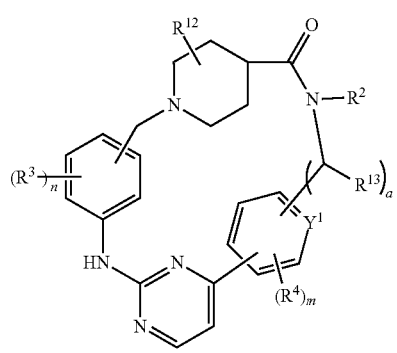
(XIX)
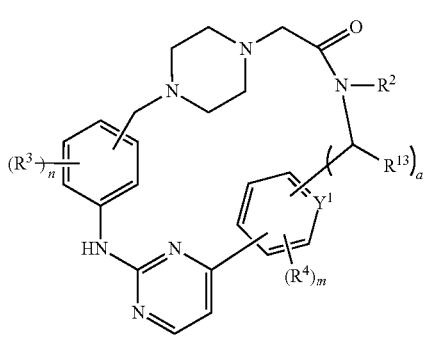
(XX)
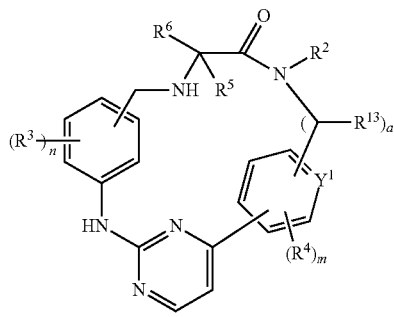
(XXI)
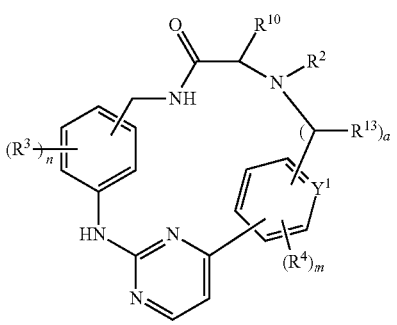
(XXII)
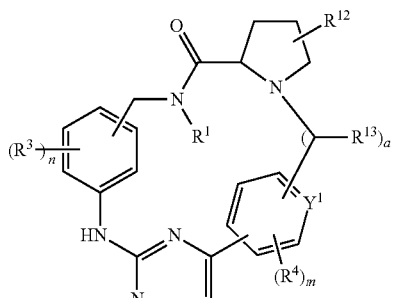
(XXIII)
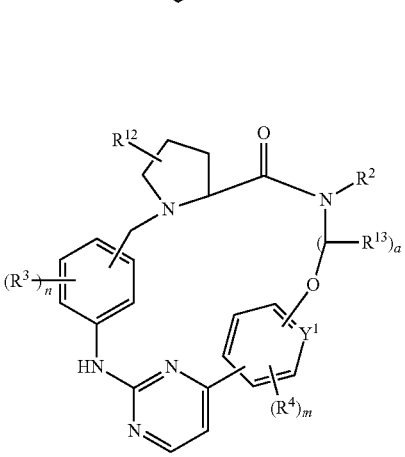
(XXIV)
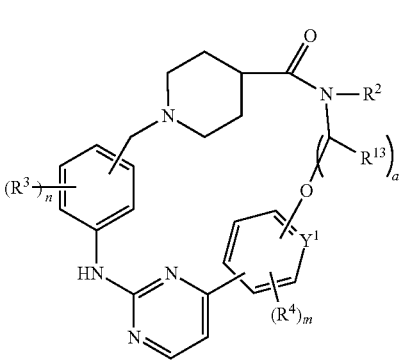
(XXV)
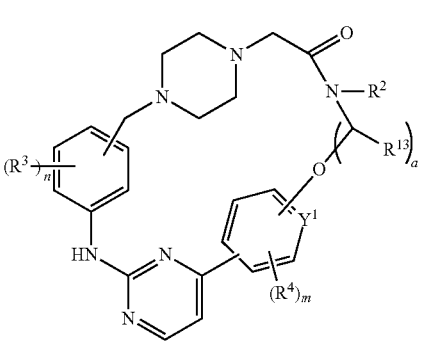
(XXVI)

-continued (XXVII)
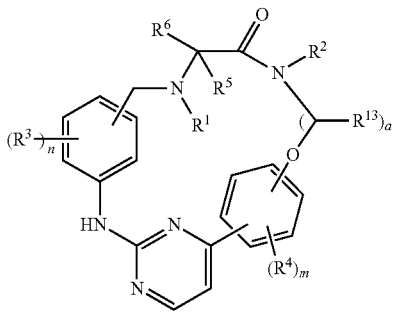

(XXVIII)
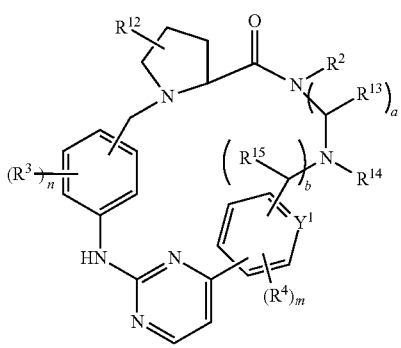

(XXIX)
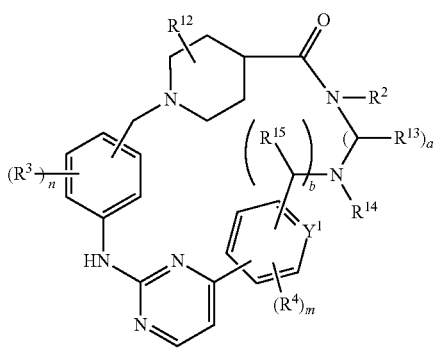

(XXX)
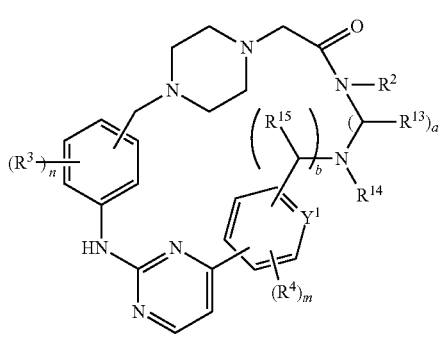

-continued (XXXI)
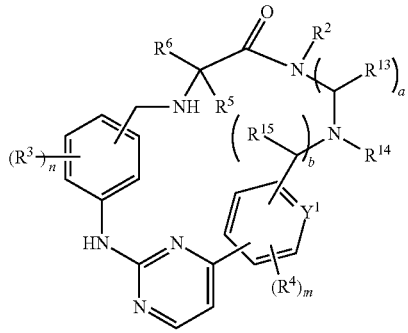

wherein $R^1$, $R^2$, $R^3$, $R^4$, $R^5$, $R^6$, $R^{10}$, $R^{12}$, $R^{13}$, $R^{14}$, $R^{15}$, $Y^1$, a, b, s, n and m have the same meaning as that defined herein.

According to an embodiment, the present invention provides compounds of Formula (Ia) or (Ib), (II) to (XLII), wherein
$R^1$ is hydrogen, or $C_{1-4}$alkyl;
$R^2$ is hydrogen or $C_{1-4}$alkyl;
$R^3$ is hydrogen, halogen, cyano or is selected from the group comprising $C_{1-6}$alkyl, amino, aminocarbonyl, amino$C_{1-6}$alkyl, $Het^3$, $Het^3$-$C_{1-6}$alkyl, $C_{1-6}$alkoxy, $C_{1-6}$alkylaminocarbonyl, $C_{1-6}$alkyl-$Het^3$carbonyl, $Het^3$carbonyl, $C_{1-6}$alkyl-$Het^3$-$C_{1-6}$alkyl, $Het^3$-amino$C_{1-6}$alkyl, $C_{1-6}$alkylamino$C_{1-6}$alkyl, $C_{1-6}$alkylamino-$C_{1-6}$alkylamino$C_{1-6}$alkyl, $C_{1-6}$alkoxy$C_{1-6}$alkylamino$C_{1-6}$alkyl, $C_{3-6}$cycloalkylamino-$C_{1-6}$alkyl, $Het^3$aminocarbonyl, $C_{3-6}$cycloalkylaminocarbonyl, $C_{1-6}$alkyl$Het^3$aminocarbonyl, $C_{1-6}$alkylamino, $C_{1-6}$alkylamino$C_{1-6}$alkylaminocarbonyl, $C_{1-6}$alkoxy$C_{1-6}$alkylaminocarbonyl, and $C_{6-10}$aryl$C_{1-6}$alkylamino; each group being optionally substituted with one or two substituents each independently selected from the group comprising $C_{1-6}$alkyl, $C_{6-10}$aryl$C_{1-6}$alkyl, $Het^3$, $C_{3-6}$cycloalkyl, $C_{1-6}$alkylamino$C_{1-6}$alkyl, $C_{1-6}$alkoxy$C_{1-6}$alkyl, $C_{6-10}$aryl, $C_{1-6}$alkylamino, and $C_{1-6}$alkoxy;
or two $R^3$ form together with the carbon atom to which they are bound a dioxolino ring;
$R^4$ is hydrogen; halo; or is selected from the group comprising $C_{1-6}$alkyl optionally substituted with one, two or three substituents each independently selected from halo or hydroxy; and $C_{1-6}$alkyloxy; hydroxyl; and
$Het^3$ is selected from the group comprising morpholinyl, piperazinyl, piperidinyl, and tetrahydro-pyranyl.

According to an embodiment, the present invention provides compounds of Formula (Ia) or (Ib), (II) to (XLII) wherein:
$R^1$ is hydrogen, or $C_{1-4}$alkyl;
$R^2$ is hydrogen or $C_{1-4}$alkyl;
$R^3$ is hydrogen, halogen, cyano or is selected from the group comprising $Het^3$, $Het^3$-$C_{1-6}$alkyl, $C_{1-6}$alkoxy, $C_{1-6}$alkylaminocarbonyl, $C_{1-6}$alkyl-$Het^3$carbonyl, $Het^3$carbonyl, $C_{1-6}$alkyl-$Het^3$-$C_{1-6}$alkyl, $Het^3$-amino$C_{1-6}$alkyl, $C_{1-6}$alkylamino$C_{1-6}$alkyl, $C_{1-6}$alkylamino$C_{1-6}$alkylamino$C_{1-6}$alkyl, $C_{1-6}$alkoxy$C_{1-6}$alkylamino$C_{1-6}$alkyl, $C_{3-6}$cycloalkylamino$C_{1-6}$alkyl, $Het^3$aminocarbonyl, $C_{3-6}$cycloalkylaminocarbonyl, $C_{1-6}$alkyl$Het^3$aminocarbonyl, $C_{1-6}$alkylamino, $C_{1-6}$alkylamino$C_{1-6}$alkylaminocarbonyl, $C_{1-6}$alkoxy$C_{1-6}$alkylaminocarbonyl, and $C_{6-10}$aryl$C_{1-6}$alkylamino; each group being optionally substituted with one or two $C_{1-6}$alkyl substituents;
or two $R^3$ form together with the carbon atom to which they are bound a dioxolino ring;

$R^4$ is hydrogen, halo, $C_{1-6}$alkyl, or $C_{1-6}$alkyloxy; and $Het^3$ is selected from the group comprising morpholinyl, piperazinyl, piperidinyl, and tetrahydro-pyranyl.

According to an embodiment, the present invention provides compounds of Formula (Ia) or (Ib), (II) to (XLII) wherein $R^1$ is hydrogen, or $C_{1-4}$alkyl; preferably hydrogen, methyl, ethyl or propyl;

$R^2$ is hydrogen or $C_{1-4}$alkyl; preferably hydrogen, methyl, ethyl or propyl;

$R^3$ is hydrogen, halogen, cyano or is selected from the group comprising $Het^3$, $Het^3$-$C_{1-6}$alkyl, $C_{1-6}$alkoxy, $C_{1-6}$alkylaminocarbonyl, $C_{1-6}$alkyl-$Het^3$carbonyl, $Het^3$carbonyl, $C_{1-6}$alkyl-$Het^3$-$C_{1-6}$alkyl, $Het^3$-amino$C_{1-6}$alkyl, $C_{1-6}$alkylamino$C_{1-6}$alkyl, $C_{1-6}$alkylamino$C_{1-6}$alkylamino$C_{1-6}$alkyl, $C_{1-6}$alkoxy$C_{1-6}$alkylamino$C_{1-6}$alkyl, $C_{3-6}$cycloalkylamino$C_{1-6}$alkyl, $Het^3$aminocarbonyl, $C_{3-6}$cycloalkylaminocarbonyl, $C_{1-6}$alkylHet$^3$aminocarbonyl, $C_{1-6}$alkylamino, $C_{1-6}$alkylamino$C_{1-6}$alkylaminocarbonyl, $C_{1-6}$alkoxy$C_{1-6}$alkylaminocarbonyl, and $C_{6-10}$aryl$C_{1-6}$alkylamino; or two $R^3$ form together with the carbon atom to which they are bound a dioxolino ring; preferably $R^3$ is selected from hydrogen, Cl, Br, Fr, cyano;

$R^4$ is hydrogen or $C_{1-6}$alkyloxy; preferably hydrogen, methoxy or ethoxy; and $Het^3$ is selected from the group comprising morpholinyl, piperazinyl, piperidinyl, and tetrahydro-pyranyl.

The present invention also encompasses processes for the preparation of compounds Formula (Ia) or (Ib) and any subgroup thereof. In the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999.

The compounds Formula (Ia) or (Ib) and the subgroups thereof can be prepared as described hereunder. They are generally prepared from starting materials which are either commercially available or prepared by standard means obvious to those skilled in the art. The compounds of the present invention can be also prepared using standard synthetic processes commonly used by those skilled in the art of organic chemistry and described for instance in the following references; "Heterocyclic Compounds" —Vol. 24 (part 4) p 261-304 Fused Pyrimidines, Wiley-Interscience; Chem. Pharm. Bull., Vol 41(2) 362-368 (1993); and J. Chem. Soc., Perkin Trans. 1, 2001, 130-137.

Compounds of Formula (Ia), and (Ib) can be prepared as illustrated in Scheme 1 by condensing the acid and amino moieties of a compound of Formula (M) or (K) respectively. The condensation reaction can be effected in an appropriate solvent (e.g. DMF), optionally in the presence of a coupling reagent (e.g. HBTU, HATU, DCC, CDI, PyBOP or EDCI with or without the presence of HOBT), and a base (e.g. triethylamine, diisopropylethylamine) at a temperature range of about 0 to about 25° C. and can require from about 2 to about 10 hours to complete.

In the general schemes described below, all substituents are defined as in the general Formula (Ia), (Ib), unless otherwise mentioned or indicated.

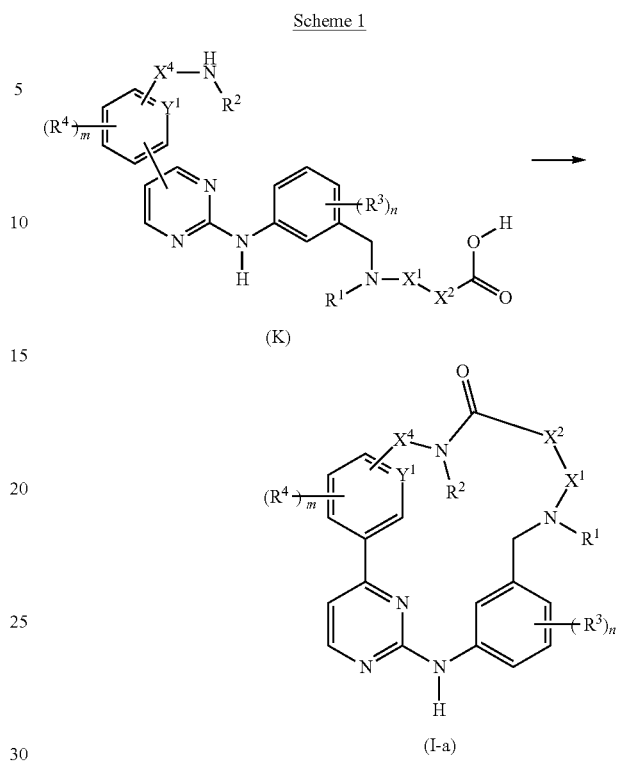

Scheme 1

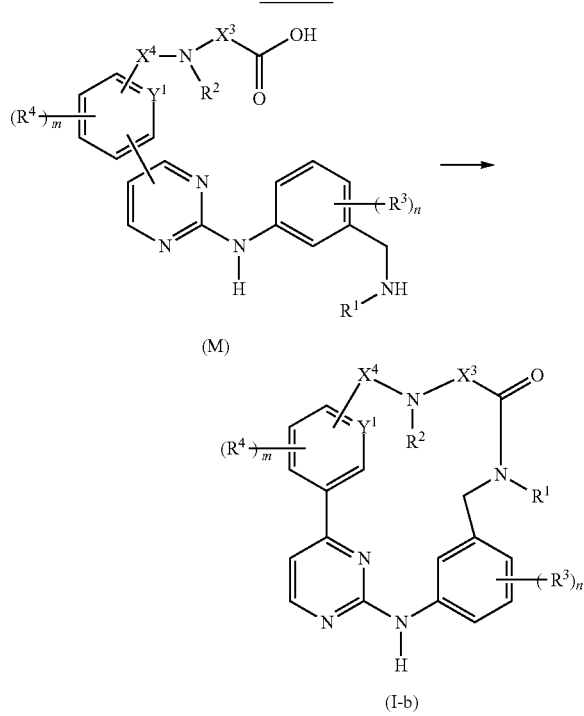

Scheme 2

The above general processes are illustrated by the following more specific processes illustrated by reaction Schemes 3-11, which describe the preparation of various subgroups of compounds of Formula (Ia), (Ib) above.

Compounds of Formula (Ia) having Formula (XXXV) can be prepared by proceeding as in the following scheme 3, wherein $P^1$ is an amino protecting group such as terbutoxy carbonyl and $P^2$ is a carboxy protecting group such as a $C_{1-6}$alkyl group, and $R^1$, $R^3$, $R^4$, $X^1$, $X^2$, m and n have the same meaning as that defined above.
Scheme 3
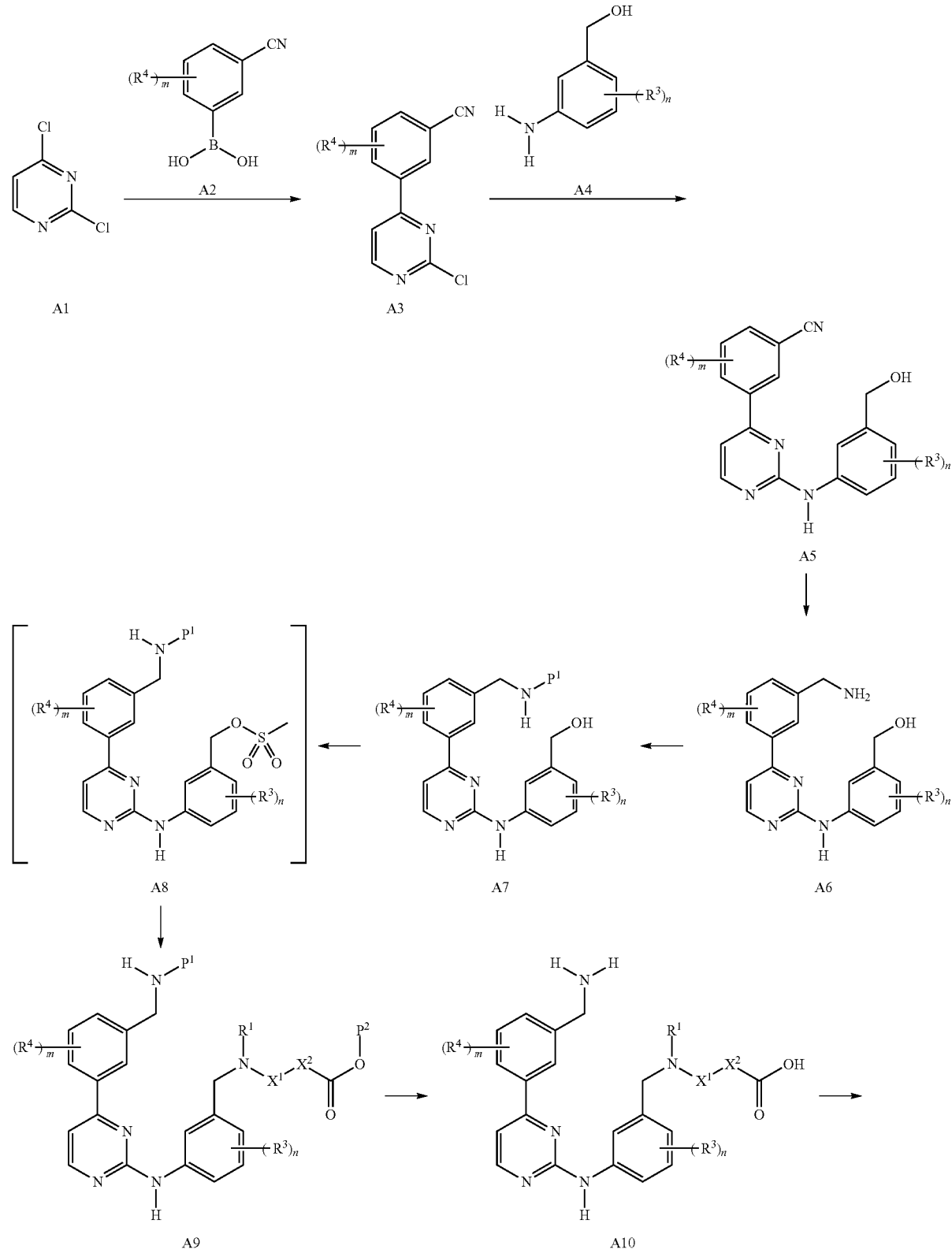

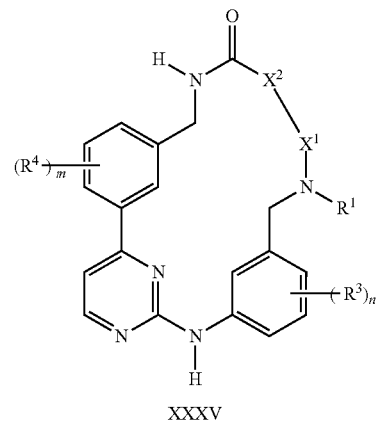

XXXV

As can be seen in scheme 3, 2,4-dichloropyrimidine (A1) is treated under Suzuki coupling conditions (catalyzed by a palladium complex e.g. conditions described in Example A1) with an appropriately substituted (3-cyanophenyl)-boronic acid of Formula (A2) to afford compounds of Formula (A3). The compound of Formula (A3) is further reacted with the aniline of Formula (A4) under standard conditions, for e.g. in a suitable solvent such as dioxane and in the presence of p-toluenesulfonic acid (PTSA), to yield compound of Formula (A5). These compounds (A5) can also be obtained via coupling of (A4) and (A3) by means of a Buchwald-Hartwig Pd-catalyzed aryl C—N formation using a suitable Pd catalyst, ligand, base and solvent (e.g. $Pd_2(dba)_3$, X-Phos, $K_2CO_3$ and tert-BuOH, respectively). Other suitable catalytic species and the like can be found in "Paladium in Heterocyclic Chemistry, A guide for the Synthetic Chemist, $2^{nd}$ Ed. Ji Jack Li and Gordon W. Gribble, Elsevier (ISBN978-0-08-045117-6) and the references cited therein.

Compound of Formula (A5) is hydrogenated under standard conditions to yield compound of Formula (A6), the amino group of which is further protected, for example using di-tert-butyl dicarbonate under suitable condition to yield compound of Formula (A7).

Compound of Formula (A7) is further reacted under suitable conditions with methanesulfonyl chloride thereby forming compound of Formula (A8) which is further reacted with a protected-carboxyl containing amino compound (such as amino acids) to yield compound of Formula (A9). Deprotection of the amino and carboxyl group of compound (A9) under suitable conditions such as by hydrolysis under acidic conditions yields compound of Formula (A10). Cyclisation of compound (A10) can be performed by treatment with a suitable agent such as HBTU in the presence of a suitable base in an organic solvent to yield compound of Formula (XXXV).

Compounds of Formula (Ib) having Formula (XXXVI) can be prepared by proceeding as in the following scheme 4, wherein $P^1$ is an amino protecting group such as terbutoxy carbonyl and $P^2$ is a carboxy protecting group such as a $C_{1-6}$alkyl group, and $R^1$, $R^2$, $R^3$, $R^4$, $X^3$, m and n have the same meaning as that defined above.

Scheme 4

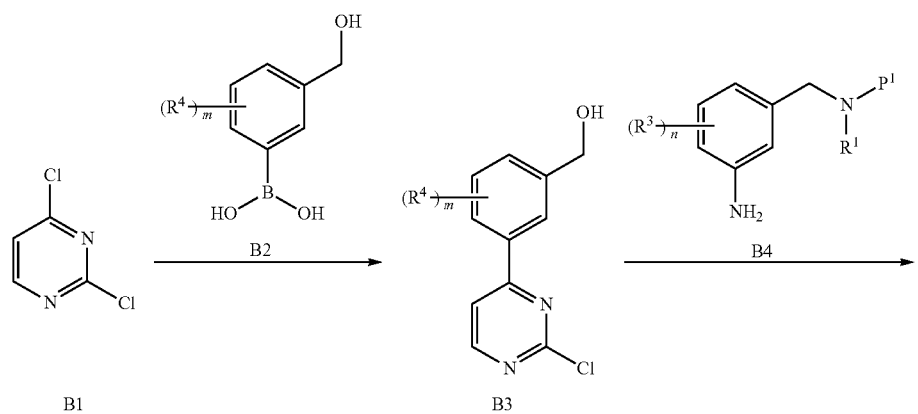

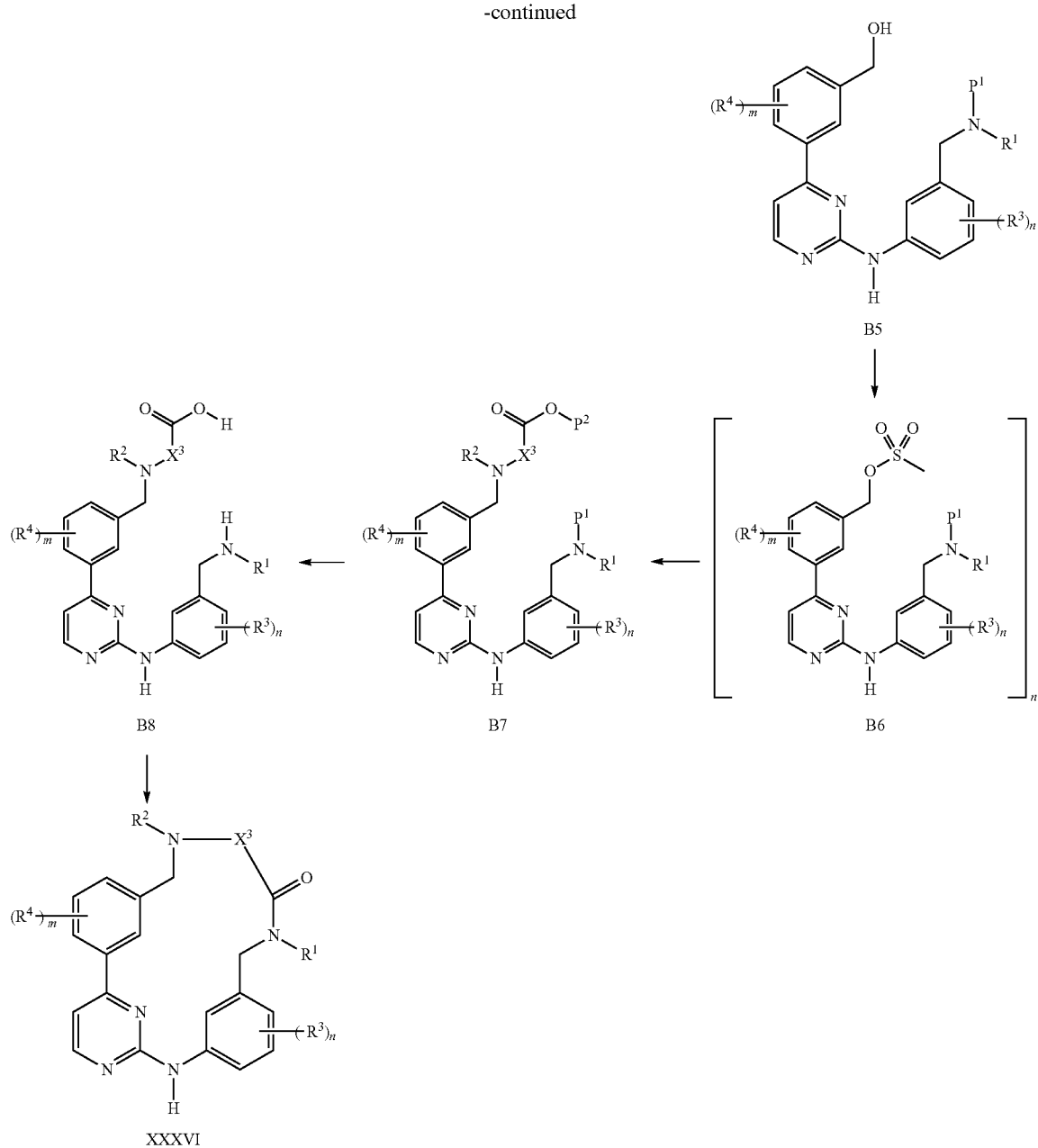

As can be seen in scheme 4, 2,4-dichloropyrimidine (B1) is treated under Suzuki coupling conditions with an appropriately substituted (3-hydroxy-methylphenyl)-boronic acid of Formula (B2) to afford compounds of Formula (B3). The compound of Formula (B3) is further reacted with the 3-($P^1$ protected aminomethyl)-aniline of Formula (B4) under standard conditions, for e.g. in a suitable solvent such as dioxane and in the presence of p-toluenesulfonic acid (PTSA), to yield compound of Formula (B5). These compounds (B5) can also be obtained via coupling of (B4) and (B3) by means of a Buchwald-Hartwig Pd-catalyzed aryl C—N formation using a suitable Pd catalyst, ligand, base and solvent (e.g. Pd$_2$(dba)$_3$, X-Phos, K$_2$CO$_3$ and tert-BuOH, respectively). Vide supra.

Compound of Formula (B5) is further reacted under suitable conditions with methanesulfonyl chloride thereby forming compound of Formula (B6) which is further reacted with a protected-carboxyl containing amino compound (such as amino acids) to yield compound of Formula (B7). Deprotection of the amino and carboxyl group of compound (B7) under suitable conditions such as by hydrolysis under acidic conditions yields compound of Formula (B8). Cyclisation of compound (B8) can be performed by treatment with a suitable agent such as HBTU in the presence of a suitable base in an organic solvent to yield compound of Formula (XXXVI).

Compounds of Formula (Ia) having Formula (XXXIX) can be prepared by proceeding as in the following scheme 5, wherein p is an integer selected from 1 or 2, $P^1$ is an amino protecting group such as terbutoxy carbonyl and $P^2$ is a carboxy protecting group such as a $C_{1-6}$alkyl group, and $R^1$, $R^2$, $R^3$, $R^4$, $X^1$, $X^2$, m and n have the same meaning as that defined above.

27 28
Scheme 5
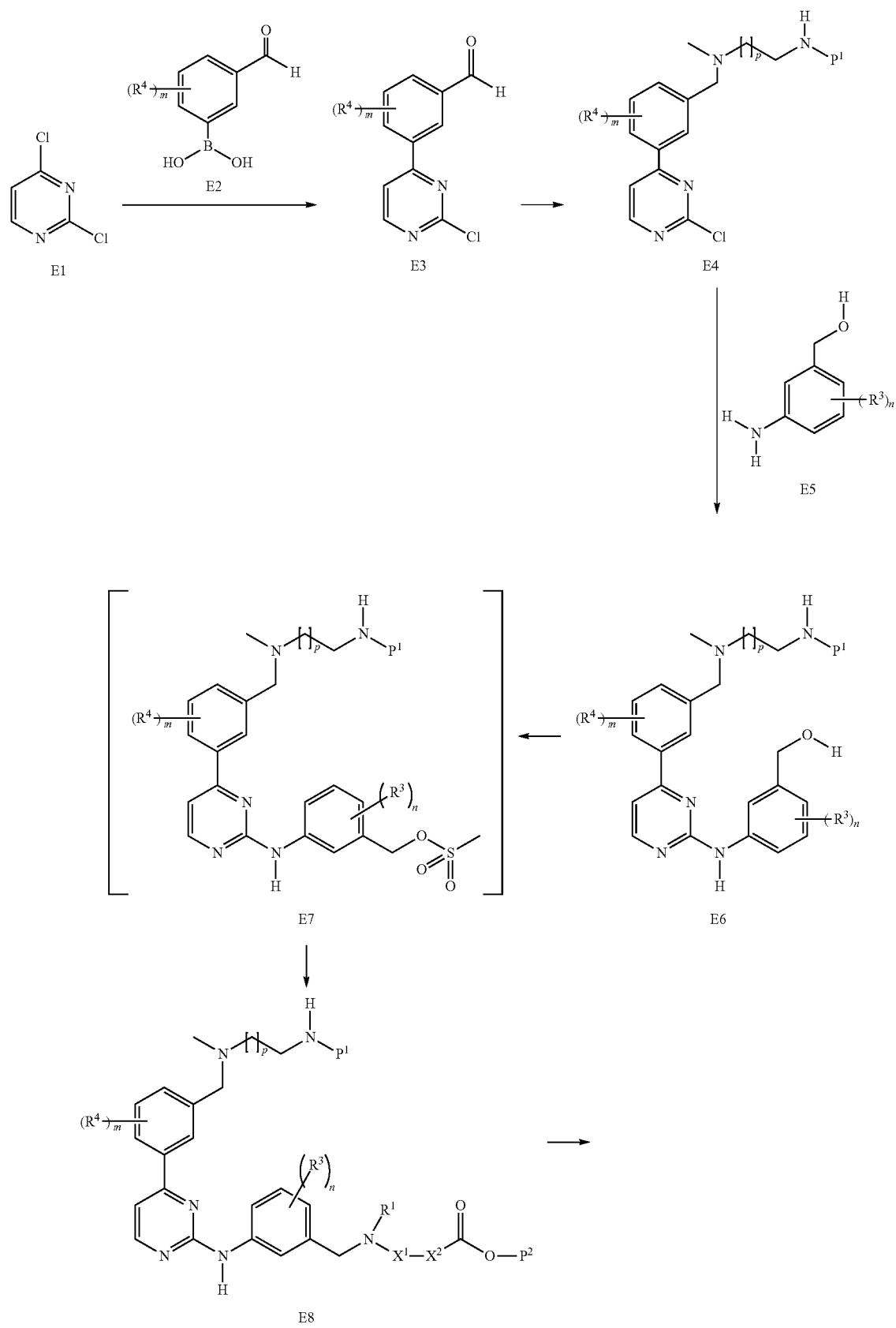

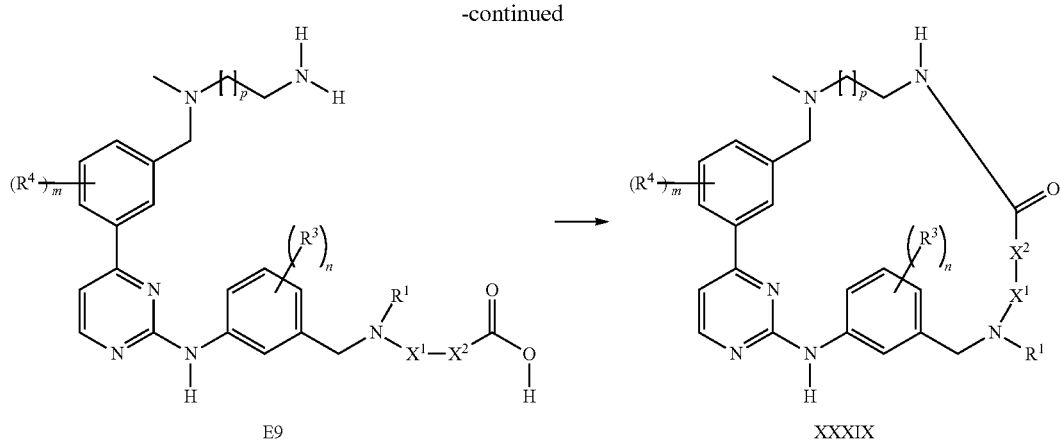

As can be seen in scheme 5, 2,4-dichloropyrimidine (E1) is treated under Suzuki coupling conditions with an appropriately substituted B-(3-formyl-4-methoxyphenyl)-boronic of Formula (E2) to afford compounds of Formula (E3). The compound of Formula (E3) is reacted with a suitable protected diamino compound in the presence of NaBH(OAc)$_3$ to yield compound of Formula (E4). Compound of Formula (E4) is then reacted further reacted with the aniline of Formula (E5) under standard conditions, for e.g. in a suitable solvent such as dioxane and in the presence of p-toluenesulfonic acid (PTSA), to yield compound of Formula (E6). These compounds (E6) can also be obtained via coupling of (E4) and (E5) by means of a Buchwald-Hartwig Pd-catalyzed aryl C—N formation using a suitable Pd catalyst, ligand, base and solvent (e.g. Pd$_2$(dba)$_3$, X-Phos, K$_2$CO$_3$ and tert-BuOH, respectively). Vide supra.

Compound of Formula (E6) is further reacted under suitable conditions with methanesulfonyl chloride thereby forming compound of Formula (E7) which is further reacted with a protected-carboxyl containing amino compound (such as amino acids) to yield compound of Formula (E8). Deprotection of the amino and carboxyl group of compound (E8) under suitable conditions such as by hydrolysis under acidic conditions yields compound of Formula (E9). Cyclisation of compound (E9) can be performed by treatment with a suitable cycling or coupling agent such as HBTU in the presence of a suitable base in an organic solvent to yield compound of Formula (XXXIX).

Compounds of Formula (Ia) having Formula (XL) can be prepared by proceeding as in the following scheme 6, wherein p is an integer selected from 1 or 2, P$^1$ is P$^2$ is an amino protecting group such as terbutoxy carbonyl and P is a carboxy protecting group such as a C$_{1-6}$alkyl group, and R$^1$, R$^2$, R$^3$, R$^4$, X$^1$, X$^2$, m and n have the same meaning as that defined above.

Scheme 6

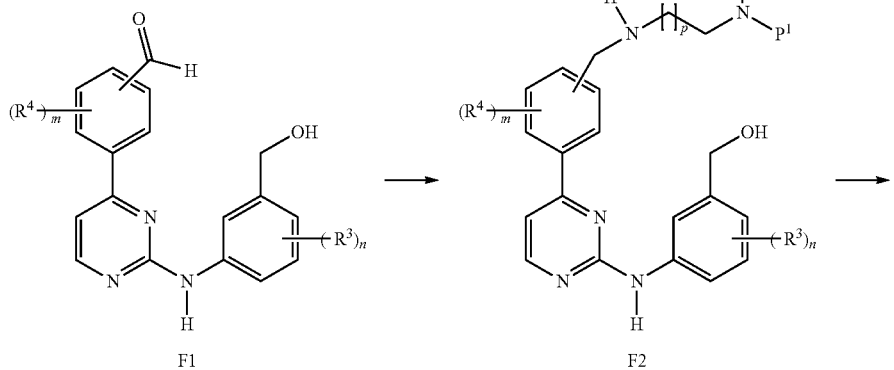

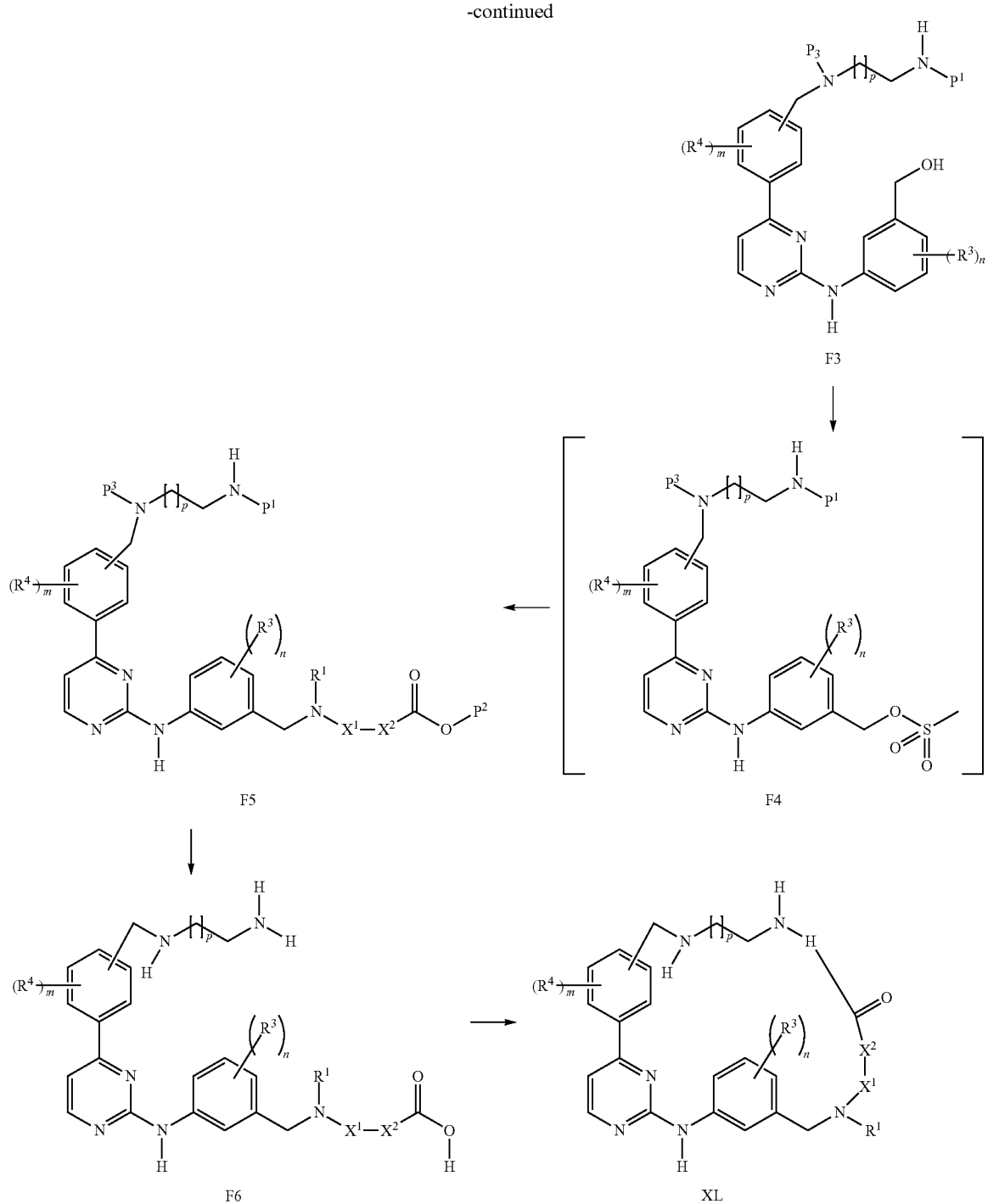

Compound of Formula (F1) can be prepared by reacting under Suzuki coupling conditions 2,4-dichloropyrimidine with an appropriately substituted B-(3-formyl-4-methoxyphenyl)-boronic acid. The product of this reaction is then further reacted with an appropriately substituted (5-Amino-2-substituted-4-yl-phenyl)-methanol to yield compound of Formula (F1).

As can be seen in Scheme 6, the compound of Formula (F1) is reacted with a suitable protected diamino compound in the presence of NaBH(OAc)$_3$ to yield compound of Formula (F2). The amino group of compound of Formula (F2) is further protected under standard conditions to yield compound of Formula (F3).

Compound of Formula (F3) is further reacted under suitable conditions with methanesulfonyl chloride thereby forming compound of Formula (F4) which is further reacted with a protected-carboxyl containing amino compound (such as amino acids) to yield compound of Formula (F5). Deprotection of the amino and carboxyl group of compound (F5) under suitable conditions such as by hydrolysis under acidic conditions yields compound of Formula (F6). Cyclisation of compound (F6) can be performed by treatment with a suitable agent such as HBTU in the presence of a suitable base in an organic solvent to yield compound of Formula (XL).

Compounds of Formula (Ia) having Formula (XLI) can be prepared by proceeding as in the following scheme 7, wherein p is an integer selected from 1 or 2, $P^1$ is an amino protecting group such as terbutoxy carbonyl and $P^2$ is a carboxy protecting group such as a $C_{1-6}$alkyl group, and $R^1$, $R^2$, $R^3$, $R^4$, $X^1$, $X^2$, m and n have the same meaning as that defined above.

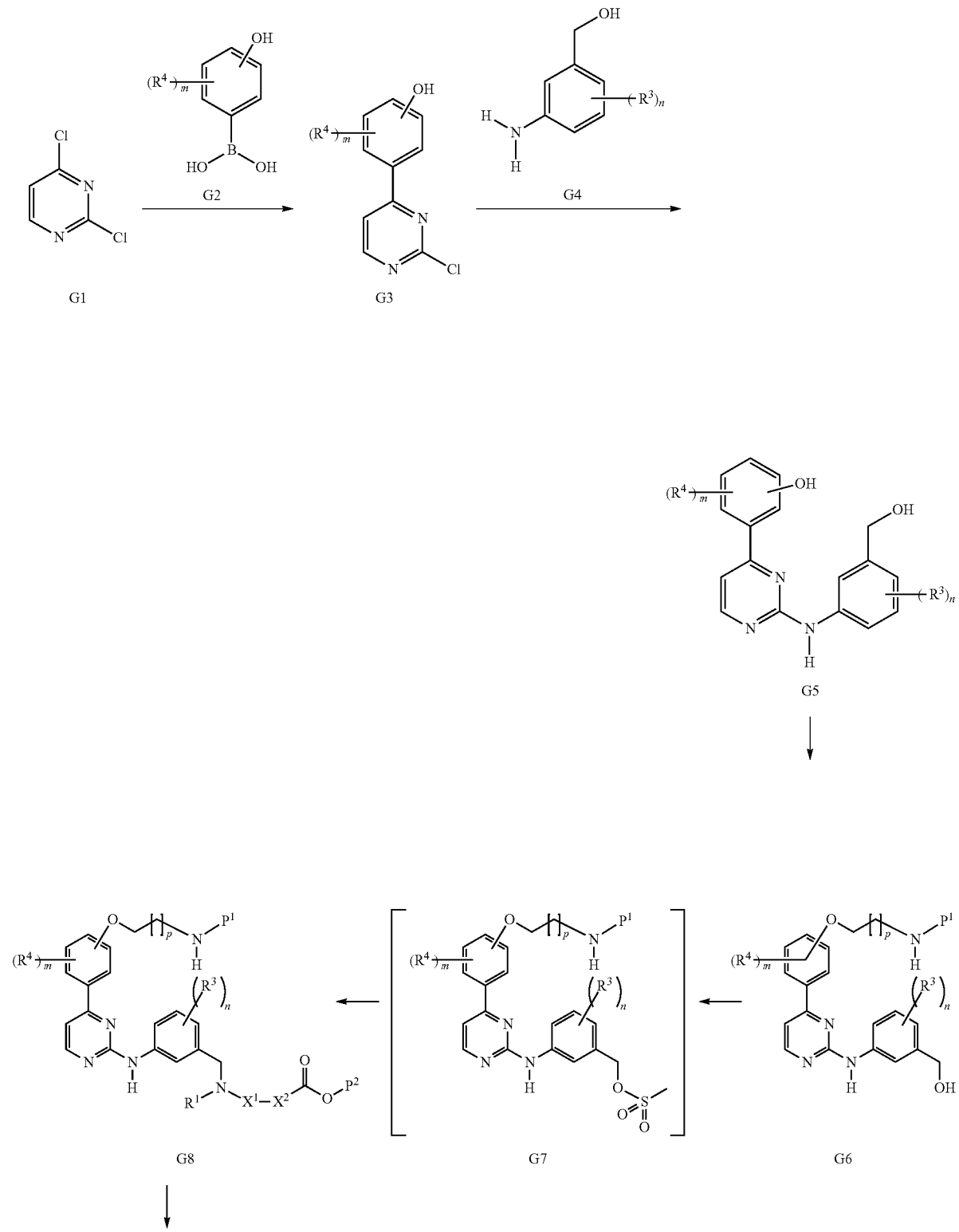

Scheme 7

-continued

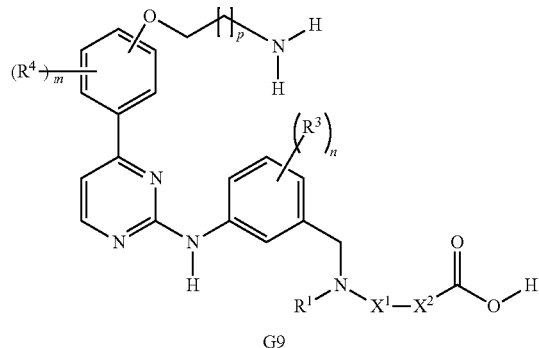
G9

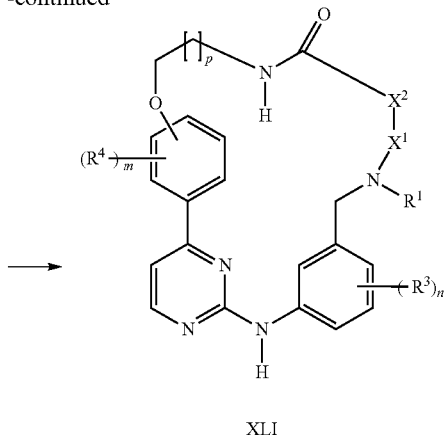
XLI

As can be seen in scheme 7, 2,4-dichloropyrimidine (G1) is treated under Suzuki coupling conditions with an appropriately substituted (phenol)-boronic acid of Formula (G2) to afford compounds of Formula (G3). The compound of Formula (G3) is further reacted with the aniline of Formula (G4) under standard conditions, for e.g. in a suitable solvent such as dioxane and in the presence of p-toluenesulfonic acid (PTSA), to yield compound of Formula (G5). These compounds (G5) can also be obtained via coupling of (G4) and (G3) by means of a Buchwald-Hartwig Pd-catalyzed aryl C—N formation using a suitable Pd catalyst, ligand, base and solvent (e.g. $Pd_2(dba)_3$, X-Phos, $K_2CO_3$ and tert-BuOH, respectively). Vide supra.

$Cs_2CO_3$ promoted O-alkylation of compound of Formula (G5) with a suitable N-protected amino compound under suitable conditions yield compound of Formula (G6). Compound of Formula (G6) is further reacted under suitable conditions with methanesulfonyl chloride thereby forming compound of Formula (G7) which is further reacted with a protected-carboxyl containing amino compound (such as amino acids) to yield compound of Formula (G8). Deprotection of the amino and carboxyl group of compound (G8) under suitable conditions such as by hydrolysis under acidic conditions yields compound of Formula (G9). Cyclisation of compound (G9) can be performed by treatment with a suitable agent such as HBTU in the presence of a suitable base in an organic solvent to yield compound of Formula (XLI).

Compounds of Formula (Ia) having Formula (XLII) can be prepared by proceeding as in the following scheme 8, wherein $P^1$ is an amino protecting group such as terbutoxy carbonyl and $P^2$ is a carboxy protecting group such as a $C_{1-6}$alkyl group, and $R^1$, $R^2$, $R^3$, $R^4$, $X^1$, $X^2$, m and n have the same meaning as that defined above.

Scheme 8

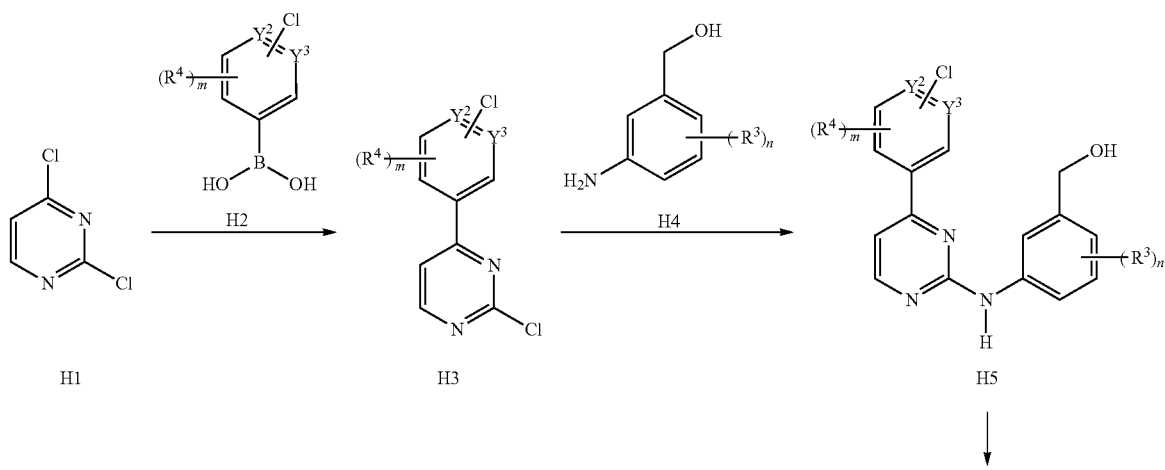

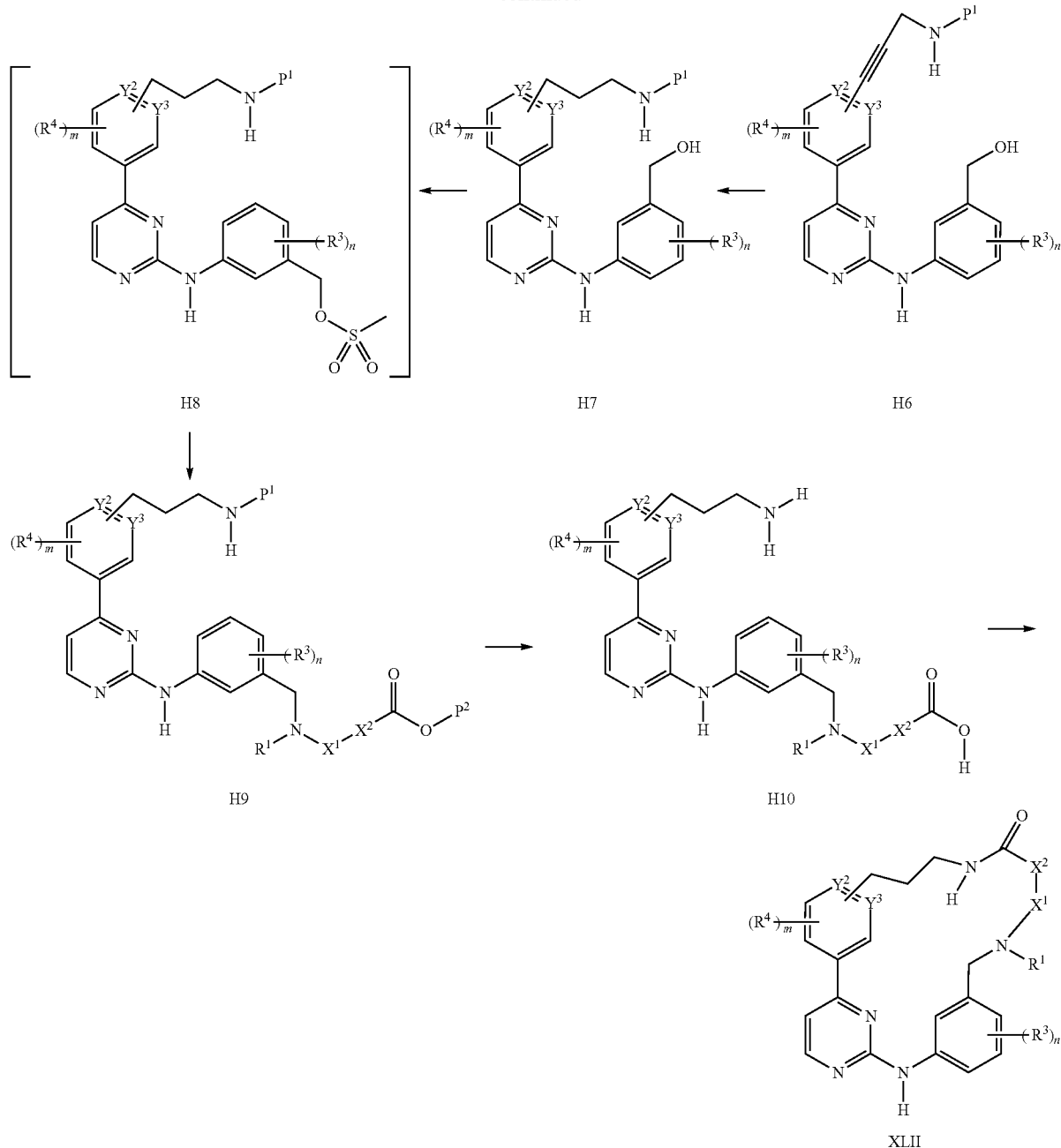

As can be seen in scheme 8, 2,4-dichloropyrimidine (H1) is treated under Suzuki coupling conditions with an appropriately substituted (chloropyridinyl)-boronic acid of Formula (H2) to afford compounds of Formula (H3). The compound of Formula (H3) is further reacted with the aniline of Formula (H4) under standard conditions, for e.g. in a suitable solvent such as dioxane and in the presence of p-toluenesulfonic acid (PTSA), to yield compound of Formula (H5). These compounds (H5) can also be obtained via coupling of (H4) and (H3) by means of a Buchwald-Hartwig Pd-catalyzed aryl C—N formation using a suitable Pd catalyst, ligand, base and solvent (e.g. $Pd_2(dba)_3$, X-Phos, $K_2CO_3$ and tert-BuOH, respectively). Vide supra.

Compound of Formula (H5) is further reacted under catalyzed condition using for example Dichlorobis(triphenylphosphine)palladium ($Pd(PPh_3)Cl_2$) with a suitable N-protected propynyl-amine to yield compound of Formula (H6), which is further hydrogenation under standard conditions to yield compound of Formula (H7).

Compound of Formula (H7) is further reacted under suitable conditions with methanesulfonyl chloride thereby forming compound of Formula (H8) which is further reacted with a protected-carboxyl containing amino compound (such as amino acids) to yield compound of Formula (H9). Deprotection of the amino and carboxyl group of compound (H9) under suitable conditions such as by hydrolysis under acidic conditions yields compound of Formula (H10). Cyclisation of compound (H10) can be performed by treatment with a suitable agent such as HBTU in the presence of a suitable base in an organic solvent to yield compound of Formula (XLII).

More specific examples for the synthesis of compounds of Formula (Ia), (Ib) and subgroup thereof are provided in the examples hereinafter.

Where necessary or desired, any one or more of the following further steps in any order may be performed:
(i) removing any remaining protecting group(s);
(ii) converting a compound of Formula (Ia) or (Ib), any subgroup thereof or a protected form thereof into a further compound of Formula (Ia) or (Ib) or a protected form thereof;
(iii) converting a compound of Formula (Ia) or (Ib), any subgroup thereof or a protected form thereof into a N-oxide, a salt, a quaternary amine or a solvate of a compound of Formula (Ia) or (Ib), any subgroup thereof or a protected form thereof;
(iv) converting a N-oxide, a salt, a quaternary amine or a solvate of a compound of Formula (Ia) or (Ib), any subgroup thereof or a protected form thereof into a compound of Formula (Ia) or (Ib), any subgroup thereof or a protected form thereof;
(v) converting a N-oxide, a salt, a quaternary amine or a solvate of a compound of Formula (Ia) or (Ib), any subgroup thereof or a protected form thereof into another N-oxide, a pharmaceutically acceptable addition salt a quaternary amine or a solvate of a compound of Formula (Ia) or (Ib), any subgroup thereof or a protected form thereof;
(vi) where the compound of Formula (Ia) or (Ib), any subgroup thereof is obtained as a mixture of (R) and (S) enantiomers resolving the mixture to obtain the desired enantiomer.

Compounds of Formula (Ia) or (Ib), any subgroup thereof, N-oxides, addition salts, hydrates, solvates, prodrugs, quaternary amines and stereochemical isomeric forms thereof can be converted into further compounds according to the invention using procedures known in the art.

It will be appreciated by those skilled in the art that in the processes described above the functional groups of intermediate compounds may need to be blocked by protecting groups.

Functional groups, which are desirable to protect, include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{1-6}$alkyl or benzyl esters.

The protection and deprotection of functional groups may take place before or after a reaction step.

Additionally, the N-atoms in compounds of Formula (Ia) or (Ib) can be methylated by art-known methods using $CH_3$—I in a suitable solvent such as, for example 2-propanone, tetrahydrofuran or dimethylformamide. Alternatively N-atoms can be alkylated by treatment with an appropriate aldehyde and a reducing agent such as $NaBH(OAc)_3$.

The compounds of Formula (Ia) or (Ib) or any subgroup thereof can also be converted into each other following art-known procedures of functional group transformation of which some examples are mentioned hereinafter.

The compounds of Formula (Ia) or (Ib) or any subgroup thereof may also be converted to the corresponding N-oxide forms following art-known procedures for converting a trivalent nitrogen into its N-oxide form. Said N-oxidation reaction may generally be carried out by reacting the starting material of Formula (Ia) or (Ib) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboper-oxoic acid or halo substituted benzenecarbo-peroxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alcohols, e.g. ethanol, methanol, propanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of Formula (Ia) or (Ib), or any subgroup thereof may be obtained by the application of art-known procedures. Diastereomers may be separated by physical methods such as fractional crystallization and chromatographic techniques, e.g. countercurrent distribution, liquid chromatography and the like.

Some of the compounds of Formula (Ia) or (Ib) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as fractional crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, fractional crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of Formula (Ia) or (Ib) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures.

The invention also generally covers all pharmaceutically acceptable predrugs and prodrugs of the compounds of Formula I for which general reference is made to the prior art cited hereinbelow.

The term "prodrug" as used herein means the pharmacologically acceptable derivatives such as esters, amides and phosphates, such that the resulting in vivo biotransformation product of the derivative is the active drug. The reference by Goodman and Gilman (The Pharmacological Basis of Therapeutics, 8th Ed, McGraw-Hill, Int. Ed. 1992, "Biotransformation of Drugs", p 13-15) describing pro-drugs generally is hereby incorporated. Pro-drugs of the compounds of the invention can be prepared by modifying functional groups present in said component in such a way that the modifications are cleaved, either in routine manipulation or in vivo, to the parent component. Typical examples of pro-drugs are described for instance in WO 99/33795, WO 99/33815, WO 99/33793 and WO 99/33792 all incorporated herein by reference. Pro-drugs are characterized by increased bio-availability and are readily metabolized into the active inhibitors in vivo. The term "predrug", as used herein, means any compound that will be modified to form a drug species, wherein the modification may take place either inside or outside of the body, and either before or after the pre-drug reaches the area of the body where administration of the drug is indicated.

The compounds of the present invention have been found to be kinase inhibitors. The compounds of the invention can then be used for the inhibition of kinases in vitro or in vivo, preferably in vitro, for modulating biological pathways and/or processes in which such kinases are involved; and/or to prevent and/or treat diseases or disorders in which such kinases, pathways and/or processes are involved.

In view of the above-described pharmacological properties, the compounds of Formula (Ia), (Ib) or any subgroup thereof, their N-oxides, pharmaceutically acceptable addition salts, prodrugs, solvates, hydrates, quaternary amines and stereochemical isomeric forms, may be used as a medicine. As used herein the compounds of the present invention includes the compounds of Formula (Ia), (Ib) as defined hereinbefore, including all subgroups and combinations thereof.

According to a particular embodiment, the compounds of the invention may be used to inhibit selectively PLK4; and as such may be used for any purposes known per se for inhibitors of PLK4. Said inhibition may be effected in vitro and/or in vivo.

In the invention, particular preference is given to compounds of Formula (Ia), (Ib) or any subgroup thereof that in the inhibition assay for PLK4 described below inhibit PLK4 with an $pIC_{50}$ value of more than 3, preferably more than 4, more preferably more than 5, preferably more than 6, even more preferably more than 7 as determined by a suitable assay, such as the assay used in the Examples below.

According to an embodiment, the invention provides a method for treating or lessening the severity of a PLK4-mediated disease or condition in a patient comprising the step of administering to said patient a compound according to the present invention.

Some compounds of the present invention, were also found to have CDK1 and/or CDK4 inhibitory activity.

In the invention, particular preference is given to compounds of Formula (Ia), (Ib) or any subgroup thereof that in the inhibition assay for CDK1 and/or CDK4 described below inhibit CDK1 and/or CDK4 with an $pIC_{50}$ value of more than 3, preferably more than 4, more preferably more than 5, preferably more than 6, even more preferably more than 7 as determined by a suitable assay, such as the assay used in the Examples below.

According to an embodiment, the invention provides a method for treating or lessening the severity of a CDK1 and/or CDK4-mediated disease or condition in a patient comprising the step of administering to said patient a compound according to the present invention.

In addition to their activity against PLK4, some compounds according to the invention have been found to have activity against Aurora B kinase.

In the invention, particular preference is given to compounds of Formula (Ia), (Ib) or any subgroup thereof that in the inhibition assay for Aurora B kinase described below inhibit Aurora B kinase with an $pIC_{50}$ value of more than 3, preferably more than 4, more preferably more than 5, preferably more than 6, even more preferably more than 7 as determined by a suitable assay, such as the assay used in the Examples below.

According to an embodiment, the invention provides a method for treating or lessening the severity of an Aurora B kinase-mediated disease or condition in a patient comprising the step of administering to said patient a compound according to the present invention.

The compounds defined hereinbefore possess anti-tumor activity. Without wishing to imply that the compounds disclosed in the present invention possess pharmacological activity only by virtue of an effect on a single biological process, it is believed that the compounds provide an anti-tumor effect by way of inhibition of one or more of protein kinases that are involved in the regulation of cellular mitosis and which lead to cytogenetic catastrophe in case of aberrant activity.

The compounds of the present invention may be therefore useful for the treatment or prevention of cell proliferative disorders, including cancer, rheumatoid arthritis, restenosis and atherosclerosis. In the treatment of cancers said cancers include lung cancer (especially non small-cell lung cancer), breast cancer, liver cancer, ovarian cancer, prostate cancer, pancreatic cancer, colorectal cancer, gastrointestinal cancer such as colon, rectal or stomach cancer and papillary carcinomas (such as papillary thyroid cancer), squamous cell cancers of the head and neck, oesophageal cancers including oropharyngeal cancer, and fast-dividing leukaemias such as acute myelogenous leukaemia (AML).

Some compounds of the present invention, were also found to have GSK-3 activity.

In the invention, particular preference is given to compounds of Formula (Ia), (Ib) or any subgroup thereof that in the inhibition assay for GSK-3 described below inhibit GSK-3 with an $pIC_{50}$ value of more than 3, preferably more than 4, more preferably more than 5, preferably more than 6, even more preferably more than 7 as determined by a suitable assay, such as the assay used in the Examples below.

According to an embodiment, the invention provides a method for treating or lessening the severity of a GSK-3-mediated disease or condition in a patient comprising the step of administering to said patient a compound according to the present invention.

Therefore the present invention also concerns the compounds of the present invention for use in the treatment of diseases mediated through GSK-3 activity such as cancer, bipolar disorder, diabetes, Alzheimer's disease, leukopenia, FTDP-17, cortico-basal degeneration, progressive supranuclear palsy, multiple system atrophy, Pick's disease, Niemann Pick's disease type C, Dementia Pugilistica, dementia with tangles only, dementia with tangles and calcification, Downs syndrome, myotonic dystrophy, Parkinsonism-dementia complex of Guam, aids related dementia, Postencephalic Parkinsonism, prion diseases with tangles, subacute sclerosing panencephalitis, FLD, argyrophilic grains disease, SSPE, inflammatory diseases, depression, cancer, dermatological disorders such as baldness, neuroprotection, schizophrenia, pain, in particular neuropathic pain. GSK3 inhibitors can also be used to inhibit sperm motility and can therefore be used as male contraceptives.

Accordingly, the compounds of the present invention can be administered to mammals, preferably humans, for the treatment of a variety of conditions and disorders, selected from the group comprising lung cancer, breast cancer, liver cancer, ovarian cancer, prostate cancer, pancreatic cancer, colorectal cancer, colon cancer, bladder cancer, rectal cancer, stomach cancer, papillary carcinomas, squamous cell cancers of the head and neck, oesophageal cancers, fast-dividing leukaemias; Alzheimer's disease; diabetes; bipolar disorder; pain; depression; inflammatory diseases. The compounds of the present invention can also be administered to mammals, preferably humans as male contraceptives.

In particular, the present compounds can be used for the manufacture of a medicament for the prevention or treatment of any one of the disease conditions mentioned hereinbefore, in particular for the manufacture of a medicament for the prevention or treatment of a disease selected from the group comprising cancer; Alzheimer's disease; diabetes; bipolar disorder; pain; depression; and inflammatory diseases.

In view of the utility of the compounds of Formula (Ia) or (Ib), there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (Ia), (Ib), a N-oxide form, a pharmaceutically acceptable addition salt, a prodrug, a solvate, a hydrate, a racemic, a quaternary amine or a stereoisomer thereof, to warm-blooded animals, including humans.

One skilled in the art will recognize that a therapeutically effective amount of the compounds of the present invention is the amount sufficient to have anti-tumor activity and that this amount varies inter alias, depending on the type of disease, the concentration of the compound in the therapeutic formulation, and the condition of the patient. Generally, the amount of a compound of the present invention to be administered as a therapeutic agent for treating cell proliferative disorders such as cancer, rheumatoid arthritis, restenosis and atherosclerosis will be determined on a case by case by an attending physician.

Generally, a suitable dose is one that results in a concentration of the compounds of the present invention at the treatment site in the range of 0.5 nM to 200 µM, and more usually 5 nM to 50 µM. To obtain these treatment concentrations, a patient in need of treatment likely will be administered between 0.01 mg/kg to 250 mg/kg body weight, in particular from 0.1 mg/kg to 50 mg/kg body weight. The amount of a compound according to the present invention, also referred to here as the active ingredient, which is required to achieve a therapeutically effect will be, of course vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

The compounds of the present invention may be administered alone or in combination with one or more additional therapeutic agents. Combination therapy includes administration of a single pharmaceutical dosage formulation which contains a compound of Formula (Ia) or (Ib) and one or more additional therapeutic agents, as well as administration of the compound of Formula (Ia) or (Ib) and each additional therapeutic agents in its own separate pharmaceutical dosage formulation. For example, a compound of Formula (Ia) or (Ib) and a therapeutic agent may be administered to the patient together in a single oral dosage composition such as a tablet or capsule, or each agent may be administered in separate oral dosage formulations.

Where separate dosage formulations are used, the compounds of the present invention and one or more additional therapeutic agents may be administered at essentially the same time (e.g., concurrently) or at separately staggered times (e.g., sequentially).

For example the compounds of the present invention could be used in combination with other anti-cancer agents. Examples of anti-cancer agents are:
    platinum coordination compounds for example cisplatin, carboplatin or oxalyplatin;
    taxane compounds for example paclitaxel or docetaxel;
    topoisomerase I inhibitors such as camptothecin compounds for example irinotecan or topotecan;
    topoisomerase II inhibitors such as anti-tumour podophyllotoxin derivatives for example etoposide or teniposide;
    anti-tumour vinca alkaloids for example vinblastine, vincristine or vinorelbine;
    anti-tumour nucleoside derivatives for example 5-fluorouracil, gemcitabine or capecitabine;
    alkylating agents such as nitrogen mustard or nitrosourea for example cyclophosphamide, chlorambucil, carmustine or lomustine;
    anti-tumour anthracycline derivatives for example daunorubicin, doxorubicin, idarubicin or mitoxantrone;
    HER2 antibodies for example trastuzumab;
    estrogen receptor antagonists or selective estrogen receptor modulators for example tamoxifen, toremifene, droloxifene, faslodex or raloxifene;
    aromatase inhibitors such as exemestane, anastrozole, letrazole and vorozole;
    differentiating agents such as retinoids, vitamin D and retinoic acid metabolism blocking agents (RAMBA) for example accutane;
    DNA methyl transferase inhibitors for example azacytidine;
    kinase inhibitors for example flavoperidol, imatinib mesylate or gefitinib;
    farnesyltransferase inhibitors for example tipifarnib;
    Histone Deacetylase (HDAC) inhibitors for example sodium butyrate, suberoylanilide hydroxamide acid (SAHA), R306465, JNJ26481585 and trichostatin A;
    Inhibitors of the ubiquitin-proteasome pathway for example PS-341, MLN.41 or bortezomib;
    Yondelis;
    Telomerase inhibitors for example telomestatin;
    Matrix metalloproteinase inhibitors for example batimastat, marimastat, prinostat and metastat.

The term "platinum coordination compound" is used herein to denote any tumour cell growth inhibiting platinum coordination compound which provides platinum in the form of an ion.

The term "taxane compounds" indicates a class of compounds having the taxane ring system and related to or derived from extracts from certain species of yew (Taxus) trees.

The term "topisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topisomerase II has a similar mechanism of action which involves the induction of DNA strand breaks or the formation of free radicals.

The term "camptothecin compounds" is used to indicate compounds that are related to or derived from the parent camptothecin compound which is a water-insoluble alkaloid derived from the Chinese tree *Camptothecin acuminata* and the Indian tree *Nothapodytes foetida*.

The term "podophyllotoxin compounds" is used to indicate compounds that are related to or derived from the parent podophyllotoxin, which is extracted from the mandrake plant.

The term "anti-tumor vinca alkaloids" is used to indicate compounds that are related to or derived from extracts of the periwinkle plant (*Vinca rosea*).

The term "alkylating agents" encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties.

The term "anti-tumor anthracycline derivatives" comprise antibiotics obtained from the fungus *Strep. peuticus* var. *caesius* and their derivatives, characterized by having a tetracycline ring structure with an unusual sugar, daunosamine, attached by a glycosidic linkage.

Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affinity and specificity to the extracellular domain of the HER2 receptor.

Many breast cancers have estrogen receptors and growth of these tumors can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, modulating its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "antiestrogen agent" is used herein to include not only estrogen receptor antagonists and selective estrogen receptor modulators but also aromatase inhibitors as discussed above.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promoters of selected genes is usually associated with inactivation of the involved genes. The term "DNA methyl transferase inhibitors" is used to indicate compounds that act through pharmacological inhibition of DNA methyl transferase and reactivation of tumor suppressor gene expression.

The term "farnesyltransferase inhibitors" is used to indicate compounds that were designed to prevent farnesylation of Ras and other intracellular proteins. They have been shown to have effect on malignant cell proliferation and survival.

The term "histone deacetylase inhibitor" or "inhibitor of histone deacetylase" is used to identify a compound, which is capable of interacting with a histone deacetylase and inhibiting its activity, more particularly its enzymatic activity Inhibiting histone deacetylase enzymatic activity means reducing the ability of a histone deacetylase to remove an acetyl group from a histone.

The term "other inhibitors of the ubiquitin-proteasome pathway" is used to identify compounds that inhibit the targeted destruction of cellular proteins in the proteasome, including cell cycle regulatory proteins.

The term "telomerase inhibitor" refers to compounds which target, decrease or inhibit the activity of telomerase, especially compounds which inhibit the telomerase receptor.

The term "matrix metalloproteinase inhibitor" includes but is not limited to, collagen peptidomimetic and non-peptidomimetic inhibitors.

The compounds of the present invention can be used as "radiosensitizer" and/or "chemosensitizer".

Radiosensitizers are known to increase the sensitivity of cancerous cells to the toxic effects of ionizing radiation. Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumor with or without additional radiation; or other therapeutically effective compounds for treating cancer or other disease. Examples of additional therapeutic agents that may be used in conjunction with radiosensitizers include, but are not limited to: 5-fluorouracil, leucovorin, 5'-amino-5'-deoxythymidine, oxygen, carbogen, red cell transfusions, perfluorocarbons (e.g., Fluosol 10 DA), 2,3-DPG, BW12C, calcium channel blockers, pentoxyfylline, antiangiogenesis compounds, hydralazine, and LBSO. Examples of chemotherapeutic agents that may be used in conjunction with radiosensitizers include, but are not limited to: adriamycin, camptothecin, carboplatin, cisplatin, daunorubicin, docetaxel, doxorubicin, interferon (alpha, beta, gamma), interleukin 2, irinotecan, paclitaxel, topotecan, and therapeutically effective analogs and derivatives of the same.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumor or other therapeutically effective compounds for treating cancer or other disease.

While it is possible for the active ingredient to be administered alone, it is preferable to present it as a pharmaceutical composition.

Accordingly, the present invention further provides a pharmaceutical composition comprising a compound according to the present invention, together with a pharmaceutically acceptable carrier or diluent.

The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound of Formula (Ia), (Ib) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The following examples illustrate the present invention.

EXPERIMENTAL PART

Hereinafter, the term 'Na$_2$CO$_3$' means sodium carbonate, 'MgSO$_4$' means magnesium sulfate, 'CH$_2$Cl$_2$' means dichloromethane, 'HCl' means hydrochloric acid, 'CH$_3$CN' means acetonitrile, 'DMAP' means N,N-dimethylpyridin-4-amine, 'THF' means tetrahydrofuran, 'DIPE' means diisopropyl ether, 'HBTU' means 1-[bis(dimethylamino)methylene]-1H-benzotriazol-1-ium 3-oxide hexafluorophosphate, 'HATU' means 1-[bis(dimethylamino)methylene]-1H-[1,2,3]triazolo[4,5-b]pyridin-1-ium 3-oxide, 'DCC' means N,N'-dicyclohexylcarbodiimide, 'PyBOP' means (1H-benzotriazol-1-yloxy)(tripyrrolidin-1-yl)phosphonium hexafluorophosphate 'Et$_3$N' means triethylamine, 'EtOAc' means ethyl acetate, 'Pd(PPh$_3$)$_4$' means tetrakis(triphenylphosphine)palladium(0), 'X-phos' means dicyclohexyl (2',4',6'-triisopropylbiphenyl-2-yl)phosphine, 'DMF' means N,N-dimethylformamide, 'DIPEA' means N-ethyl-N-isopropylpropan-2-amine, 'NaBH(OAc)$_3$' means sodium triacetoxyborohydride, 'TIS' means triisopropylsilane, 'TFA' or CF$_3$COOH' means 2,2,2-trifluoroacetic acid, 'K$_2$CO$_3$' means potassium carbonate, 'NH$_4$Cl' means ammonium chloride, 'Cs$_2$CO$_3$' means cesium carbonate, "Et$_2$O" means diethyl ether, 'Na$_2$SO$_4$' means sodium sulfate, ', 'CH$_3$OH' means methanol, EtOH means ethanol, tert-BuOH means tert-butanol, 'PPh₃' means triphenylphosphine, 'Pd₂(dba)₃' means tris[μ-[(1,2-η:4,5-η)-(1E,4E)-1,5-diphenyl-1,4-pentadien-3-one]]dipalladium, 'NH₄OH' means ammonium hydroxide, 'HOAc' means acetic acid, 'NaHCO₃' means sodium hydrogen carbonate, 'NH₄HCO₃' means ammonium hydrogen carbonate, 'NH₃' means ammonia, 'DCE' means 1,2-dichloroethane, 'BOC' means tert-butoxy carbonyl, EDCI means 1-(3-Dimethylaminopropyl)-3-ethylcarbodiimide hydrochloride, 'DEAD' means diethyl azodicarboxylate, 'XANT-PHOS' means (9,9-dimethyl-9H-xanthene-4,5-diyl)bis(diphenylphosphine), 'HOBt' means 1-hydroxy-1H-benzotriazole, 'CDI' means 1,1'-carbonyldiimidazole (also 1,1'-carbonylbis-1H-imidazole), 'DIAD' means diisopropyl diazodicarboxylate, 'q.s.' means quantum sufficit.

MP-NCO or MP-isocyanate is a macroporous polystyrene-bound scavenger (polystyrene methyl isocyanate). Resin type: Highly cross-linked macroporous poly(styrene-co-divinylbenzene).

PS-NCO or PS-isocyanate is also a nucleophile scavenger (polystyrene methyl isocyanate) but with a different resin type than MP-NCO: 1% cross-linked poly(styrene-co-divinylbenzene).

ScavengePore® is based on a macroporous high crosslinked polystyrene/divinylbenzene resin matrix.

A. Preparation of the Intermediates

Example A1 a) Preparation of Intermediate (1)

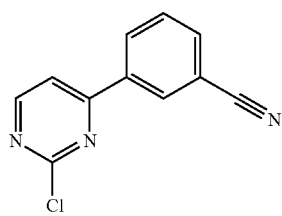 [SMILES: N#Cc1cccc(-c2ccnc(Cl)n2)c1]

2,4-Dichloro-pyrimidine (0.1360 mol) and B-(3-cyanophenyl)-boronic acid (0.1360 mol) were suspended in toluene/EtOH (9/1; 500 ml). A 0.4M Na₂CO₃ (350 ml) was added and the reaction mixture was heated on an oil bath of 50° C. Then Pd(dppf)Cl₂ (0.0014 mol) was added and the mixture was stirred for 4 hours. The reaction mixture was cooled, the solid collected and dried in a vacuum stove at 50° C. The organic layer of the filtrate was dried (MgSO₄), filtered and concentrated. This residue was triturated with hexane/CH₂Cl₂ (1/1, 100 ml) and stirred overnight. The solid was collected and dried. Both fraction were combined to give an off white solid, yielding 23.77 g (81.1%) of intermediate (1).

Example A2 a) Preparation of Intermediate (2)

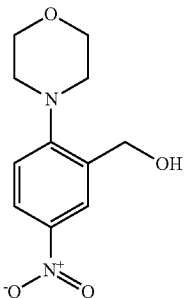

A mixture of 2-fluoro-5-nitro-benzenemethanol (0.1750 mol) and morpholine (0.5700 mol) in 2-propanol (50 ml) was boiled under reflux over the weekend. The reaction mixture was concentrated and was then diluted with water (100 ml) and toluene (500 ml). The layers were separated and the aqueous layer was extracted with toluene (200 ml) and CH₂Cl₂ (300 ml). The combined organic layers were dried (MgSO₄), filtered and concentrated to give an dark yellow oil. This was dissolved in CH₂Cl₂ (500 ml) washed with 1M HCl until pH±2. The organic was dried (MgSO₄), filtered and concentrated, yielding 43 g (100%) of intermediate (2).

b) Preparation of Intermediate (3)

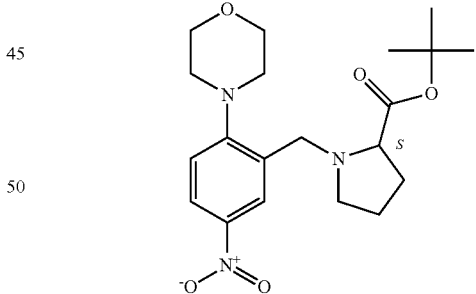

Methanesulfonyl chloride (0.0471 mol) was added dropwise to a solution of intermediate (2) in CH₃CN and DMAP (0.0502 mol). L-proline, tert. butyl ester (0.0437 mol) a catalytic amount of potassium iodide were added and the reaction mixture was boiled under reflux for 16 hours. The reaction mixture was cooled, filtered over a small plug of Dicalite and concentrated. The residue was dissolved in CH₂Cl₂ (0.3 L) and washed with water (2×0.1 L), dried (MgSO₄), filtered and concentrated to give an orange-yellow oil, yielding 17.0 g (100%) of intermediate (3) (S-enantiomer).

c) Preparation of Intermediate (4)

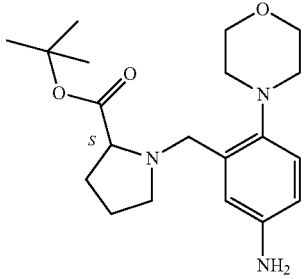

A mixture of intermediate (3) (0.0430 mol) in THF (200 ml) was hydrogenated with Pd/C (2 g) as a catalyst in the presence of a thiophene solution (1 ml; 4% in DIPE). After uptake of H$_2$ (3 equivalents), the catalyst was filtered off and the solvent was evaporated, yielding 15.0 g (96.5%) of intermediate (4) (S-enantiomer) as a viscous oil.

d) Preparation of Intermediate (5)

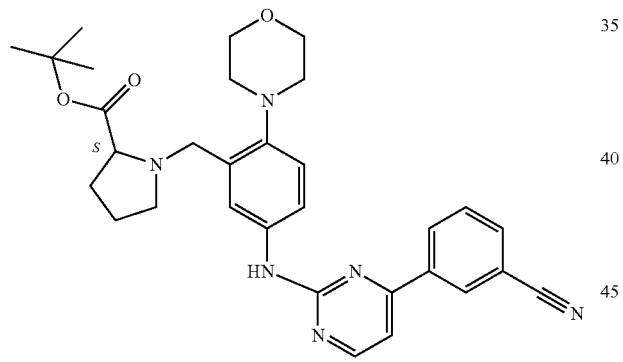

Intermediate (4) (0.0415 mol) and intermediate (1) (0.0415 mol) in tert.-BuOH (200 ml) were heated at 65° C. K$_2$CO$_3$ (6.0 g) and XANTPHOS (0.0008 mol) were added and then palladium(II) acetate (0.0004 mol) was added. The heterogeneous reaction mixture was heated overnight at this temperature. Then additional XANTPHOS (0.0008 mol), palladium (II) acetate (0.0004 mol) and tert.-BuOH (100 ml) were added. After 16 hours at this temperature the reaction mixture was poured onto ice (1000 ml) and the aqueous layer was extracted with CH$_2$Cl$_2$ (3×300 ml). The combined organic layers were dried (MgSO$_4$), filtered and concentrated. The residue was chromatographed (glass filter, SiO$_2$ (0.5 kg), eluent CH$_2$Cl$_2$/CH$_3$OH from 100/0 till 97/3). This gave a brownish solid, yielding 14.7 g (65.6%) of intermediate (5) (S-enantiomer), used as such in the next step.

e) Preparation of Intermediate (6)

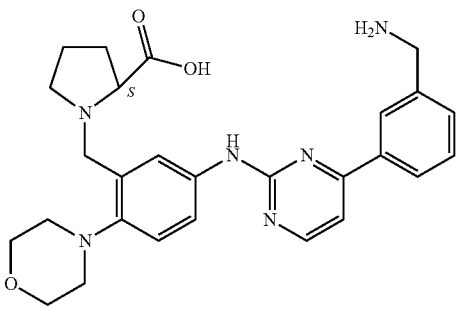

A mixture of intermediate (5) (0.0270 mol) in 7N NH$_3$ in CH$_3$OH (q.s.) was hydrogenated with Raney Nickel as a catalyst. After uptake of H$_2$ (2 equivalents), the reaction mixture was filtered over a small plug of Dicalite and concentrated to give a brown oil. This oil was dissolved in CH$_2$Cl$_2$ (50 ml) and treated with TFA (25 ml). The reaction mixture was stirred overnight at room temperature. The reaction mixture was concentrated and co-evaporated with CH$_3$CN (3×). The oily residue was used as such, yielding 32 g of crude intermediate (6) (S-enantiomer).

Example A3 a) Preparation of Intermediate (7)

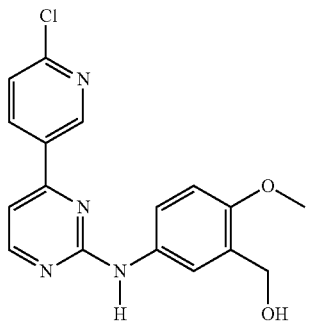 [SMILES: COc1ccc(Nc2nccc(-c3ccc(Cl)nc3)n2)cc1CO]

2-Chloro-4-(6-chloro-3-pyridinyl)-pyrimidine (0.0088 mol), 5-amino-2-methoxy-benzenemethanol (0.0088 mol) and 4-methylbenzenesulfonic acid (0.0022 mol) in dioxane (150 ml) was stirred for 20 hours at reflux. The solvent was evaporated and the residue was diluted with H$_2$O and Na$_2$CO$_3$ 10% aqueous solution. This mixture was extracted 2 times with CH$_2$Cl$_2$/CH$_3$OH. The separated organic layer was washed with H$_2$O, dried (MgSO$_4$), filtered and the solvent was evaporated. The residue was suspended in CH$_2$Cl$_2$. The precipitate was filtered off and dried (vacuo), yielding 1.17 g (38.9%) of intermediate (7).

b) Preparation of Intermediate (8)

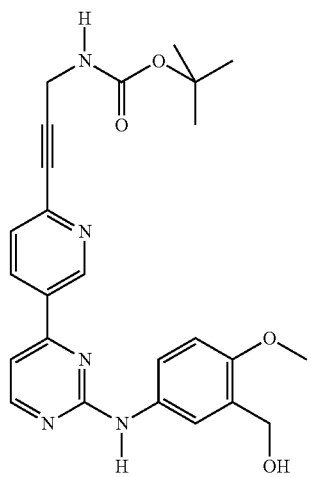 [SMILES: COc1ccc(Nc2nccc(-c3ccc(C#CCNC(=O)OC(C)(C)C)nc3)n2)cc1CO]

Intermediate (7) (0.016 mol), Copper iodide (200 mg) and PPh$_3$ (400 mg) in Et$_3$N (100 ml) and DMF (200 ml) was flushed with N$_2$. Pd(PPh$_3$)Cl$_2$ (500 mg) was added and the mixture was flushed with N$_2$. tert-butyl prop-2-yn-1-ylcarbamate (5.5 g) in DMF (30 ml) was added to the reaction mixture at 50° C. and then stirred for 20 hours at 60° C. The solvent was evaporated and the residue was diluted with H$_2$O. This mixture was extracted 3 times with CH$_2$Cl$_2$. The separated organic layer was washed with H$_2$O, dried (MgSO$_4$), filtered and the solvent was evaporated. The residue was purified by column chromatography over silica gel (eluent: CH$_2$Cl$_2$/(CH$_3$OH/NH$_3$) 96/4). The product fractions were collected and the solvent was evaporated. The residue was suspended in DIPE. The precipitate was filtered off and dried vacuo, yielding 3.5 g (47.4%) of intermediate (8).

c) Preparation of Intermediate (9)

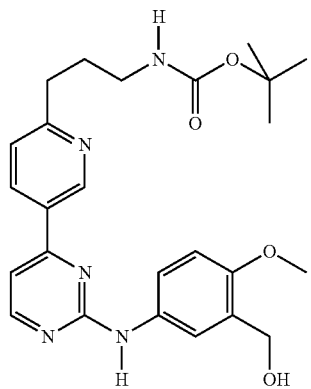 [SMILES: COc1ccc(Nc2nccc(-c3ccc(CCCNC(=O)OC(C)(C)C)nc3)n2)cc1CO]

A mixture of intermediate (8) (0.01 mol) in CH$_3$OH (150 ml) was hydrogenated at room temperature for 1 hour with Raney Nickel (cat. quant.) as a catalyst. After uptake of H$_2$ (2 equivalents), the catalyst was filtered off and the filtrate was evaporated. The residue was purified by column chromatography over silica gel (eluent: CH$_2$Cl$_2$/(CH$_3$OH/NH$_3$) 96/4). The product fractions were collected and the solvent was evaporated. The residue was suspended in DIPE. The precipitate was filtered off and dried (vacuo), yielding 3.5 g (75%) of intermediate (9).

d) Preparation of Intermediate (10)

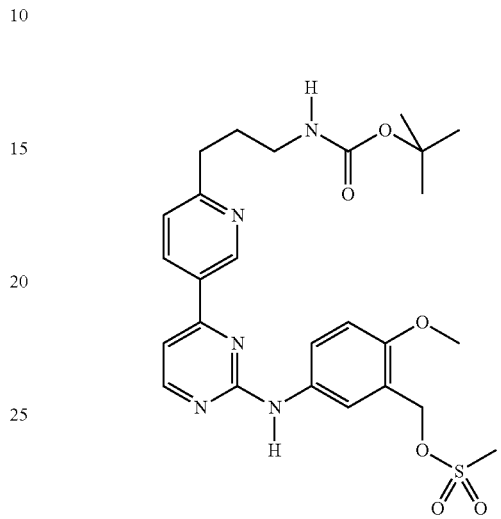

Intermediate (9) (0.0075 mol), methanesulfonyl chloride (0.027 mol) and DIPEA (11.2 ml) in CH$_3$CN (350 ml) was stirred at room temperature for 2 hours. Again DIPEA (14 ml) was added to the reaction mixture, yielding intermediate (10) which was used as such in the next step.

e) Preparation of Intermediate (11)

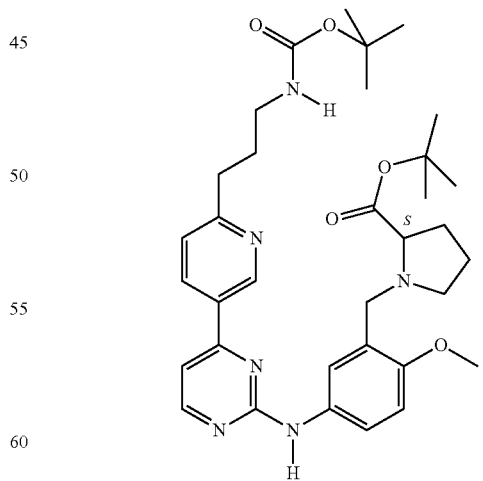

Intermediate (10) (0.001 mol) and L-proline, tert-butyl ester (0.0012 mol) were stirred for 20 hours at 70° C. Benzyl isocyanate resin (500 mg) was added to the reaction mixture and stirred another 20 hours at 70° C. The reaction mixture was filtered. The filtrate's solvent was evaporated, yielding intermediate (11) (S-enantiomer) used as such in the next step.

f) Preparation of Intermediate (12)

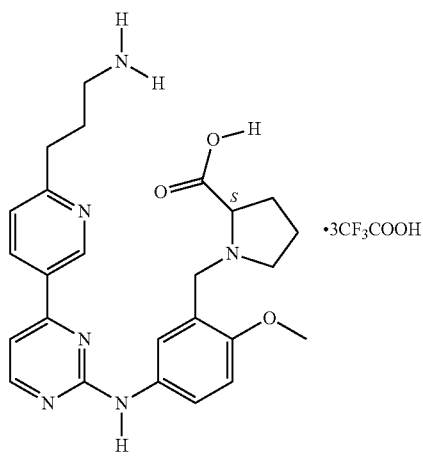

Intermediate (11) (0.001 mol) in CF$_3$COOH (30 ml) and CH$_2$Cl$_2$ (30 ml) was stirred for 20 hours at room temperature. The solvent was evaporated and co-evaporated with toluene, yielding intermediate (12) (0.3CF$_3$COOH) (S-enantiomer) used as such in the next step.

Example A4 a) Preparation of Intermediate (13)

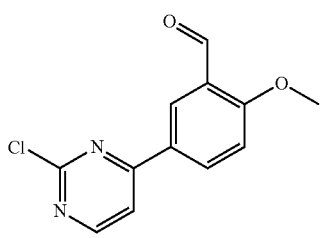 [SMILES: COc1ccc(-c2ccnc(Cl)n2)cc1C=O]

Pd(PPh$_3$)$_4$ (0.0016 mol) was added under nitrogen atmosphere to a mixture of 2,4-dichloropyrimidine (0.068 mol) in CH$_3$CN (110 ml) (mixture was purged with N$_2$). The mixture was heated on an oil bath at 60° C. A solution of B-(3-formyl-4-methoxyphenyl)-boronic acid (6.12 g, 0.034 mol) in 0.4M solution of Na$_2$CO$_3$ (110 ml) and CH$_3$CN (50 ml) was added dropwise over 30 minutes. The mixture was stirred for 3 hours at this temperature and was then cooled to room temperature. The precipitate was filtered off, washed with CH$_3$CN (2×20 ml) and dried under vacuum, yielding 5.54 g of fraction (I). The organic layer of the filtrate (CH$_3$CN) was evaporated and the aqueous concentrate was extracted with CH$_2$Cl$_2$ (2×100 ml). The separated organic layer was dried (MgSO$_4$), filtered and the solvent was evaporated. The residue was recrystal- lized from CH$_3$CN, yielding 0.94 g of a white solid fraction (II). Fractions (I) and (II) were combined, yielding 6.48 g of (76%) of intermediate (13).

b) Preparation of Intermediate (14)

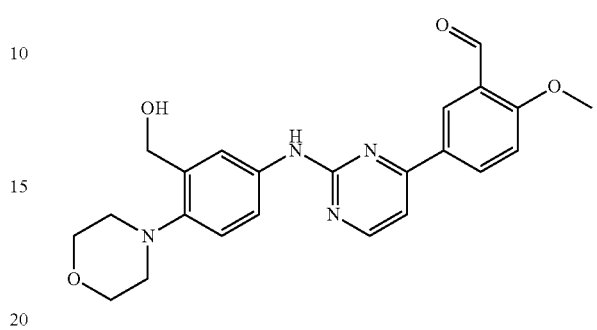

A mixture of intermediate (13) (0.0174 mol), intermediate (2) (0.0226 mol), Pd$_2$(dba)$_3$ (0.0005 mol), X-Phos (0.0015 mol) and K$_2$CO$_3$ (0.0348 mol) was flushed with N$_2$. tert-BuOH (80 ml) was added and N$_2$ was purged through the suspension for 10-15 minutes. The mixture was heated overnight at 80° C. Then the mixture was cooled to room temperature. H$_2$O (50 ml) and EtOAc (150 ml) were added. The mixture was filtered through a pad of Celite and the organic layer was separated, dried (MgSO$_4$) and the solvent was evaporated. The residue was taken up in CH$_2$Cl$_2$ (50 ml). A precipitate formed upon standing. The solid was filtered off and washed with CH$_2$Cl$_2$ (3×10 ml), yielding 2.38 g of intermediate (14) (yellow solid).

c) Preparation of Intermediate (15)

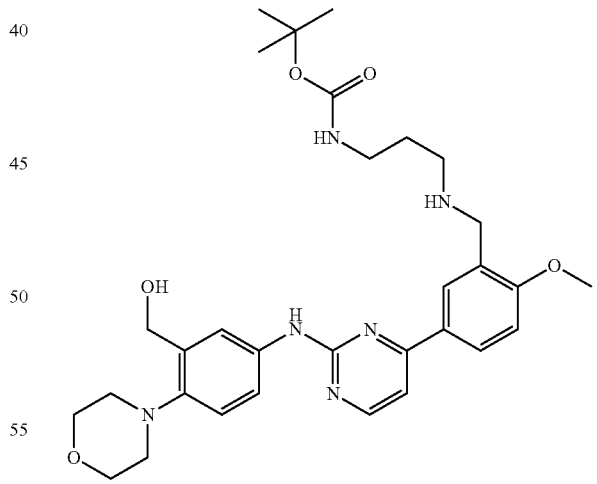

A mixture of intermediate (14) (0.00573 mol) and tert-butyl (3-aminopropyl)carbamate (0.00859 mol) was stirred in THF (50 ml). NaBH(OAc)$_3$ (0.00859 mol) was added after 10 minutes and the reaction was continued at room temperature for 3 hours. Then the reaction mixture was quenched with NaOH (75 ml; 1M) and extracted with CH$_2$Cl$_2$ (1×150 ml, 1×50 ml). The combined organic layers were washed with brine, dried (MgSO$_4$), filtered and the solvent was evaporated to yield an oily residue which was purified by column chromatography over silica gel (eluent first EtOAc but product was eluted with CH$_2$Cl$_2$/CH$_3$OH 10/1). The desired fractions were collected and the solvent was evaporated, yielding 2.15 g (65%) of intermediate (15).

d) Preparation of Intermediate (16)

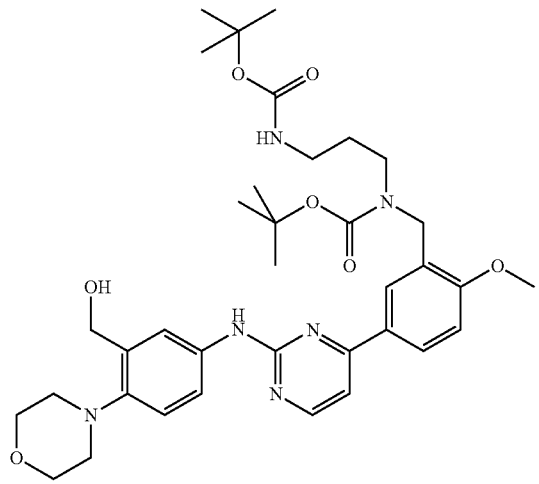 [SMILES: COc1ccc(-c2ccnc(Nc3ccc(N4CCOCC4)c(CO)c3)n2)cc1CN(CCCNC(=O)OC(C)(C)C)C(=O)OC(C)(C)C]

CH$_2$Cl$_2$ (0.000185 mol) was added to a mixture of intermediate (15) (0.003715 mol) and di-tert-butyl dicarbonate (0.004458 mol) in CH$_2$Cl$_2$ (30 ml). The reaction mixture was stirred overnight at room temperature. Silica gel (10 g) was added and the solvent was evaporated. The product was purified by column chromatography (eluent: hexane/EtOAc 1/2). The desired fractions were collected and the solvent was evaporated, yielding 2.01 g (79.7%) of intermediate of intermediate (16).

e) Preparation of Intermediate (17)

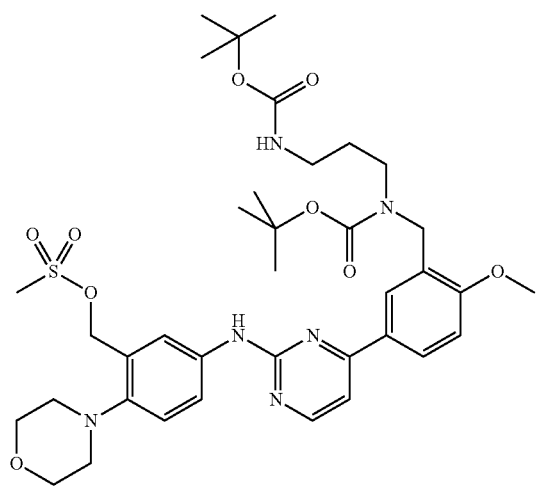 [SMILES: COc1ccc(-c2ccnc(Nc3ccc(N4CCOCC4)c(COS(C)(=O)=O)c3)n2)cc1CN(CCCNC(=O)OC(C)(C)C)C(=O)OC(C)(C)C]

Methanesulfonyl chloride (0.00355 mol) was slowly added to a solution of intermediate (16) (0.00296 mol), DIPEA (0.017 mol) and DMF (57 ml). The mixture was stirred for 1 hour, yielding intermediate (17) used as such in the next step.

f) Preparation of Intermediate (18)

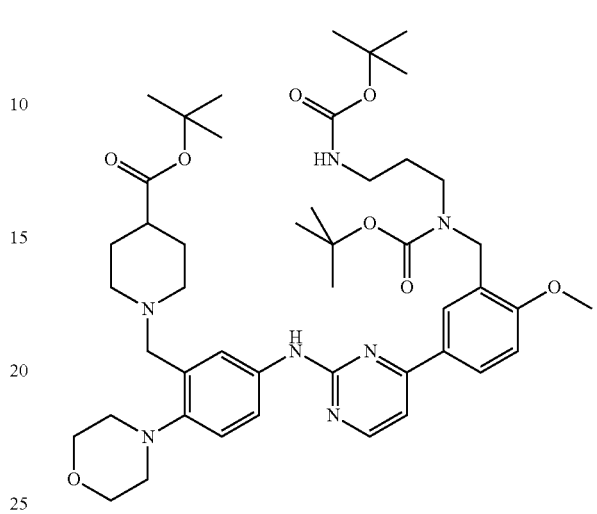

tert-butyl piperidine-4-carboxylate (0.000500 mol) was weighed in a reaction tube. A solution of intermediate (17) (0.000250 mol) in DIPEA and DMF was added and the mixture was heated overnight at 65° C. Scavenging with MP-NCO was performed at room temperature. The scavenger was filtered off and washed twice alternatively with CH$_3$OH (5 ml) and CH$_2$Cl$_2$/CH$_3$OH (10/1, v/v). The filtrate was evaporated and the resulting crude intermediate (18) was used as such in the next step.

g) Preparation of Intermediate (19)

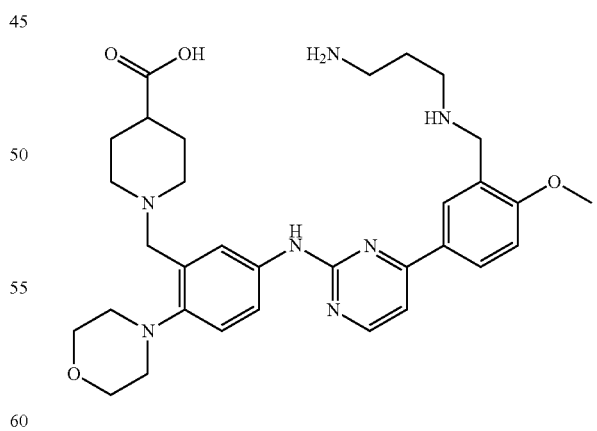

A mixture of the intermediate (18) (0.000250 mol) and TFA/CH$_2$Cl$_2$/TIS (5 ml) was reacted overnight at room temperature. Then the mixture was evaporated to dryness, yielding intermediate (19) used as such in the next reaction step.

Example A5 a) Preparation of Intermediate (20)

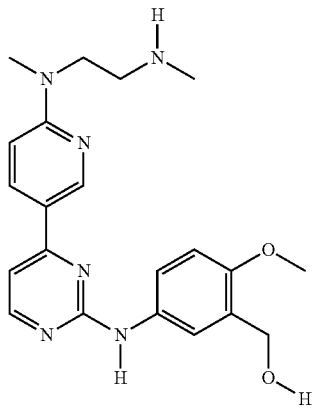 [SMILES: CNCCN(C)c1ccc(-c2ccnc(Nc3ccc(OC)c(CO)c3)n2)cn1]

Intermediate (7) (0.016 mol) in N,N'-dimethylethane-1,2-diamine (100 ml) was refluxed for 4 hours. The solvent was evaporated. The residue was diluted with H₂O. This mixture was extracted 2 times with CH₂Cl₂. The combined organic layers were dried (MgSO₄), filtered and the solvent was evaporated. The residue was re-crystallized from CH₃CN and the precipitate was filtered, yielding 1.85 g (70%) of intermediate (20).

b) Preparation of Intermediate (21)

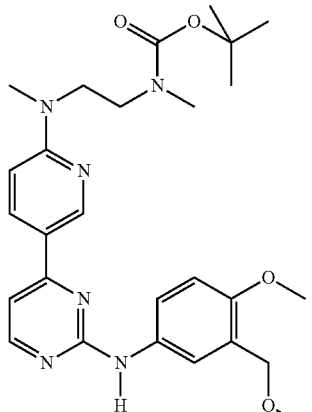

A mixture of intermediate (20) (0.0047 mol) in CH₂Cl₂ (100 ml) stirred at room temperature. Di-tert-butyl dicarbonate (0.0060 mol) in CH₂Cl₂ (20 ml) was added drop wise to the reaction mixture at room temperature. The reaction mixture was stirred another hour at room temperature. NH₄OH aqueous solution was added and then the reaction mixture was washed with H₂O. The separated organic layer was dried (MgSO₄), filtered and the solvent was evaporated, yielding 2.5 g (100%) of intermediate (21).

c) Preparation of Intermediate (22)

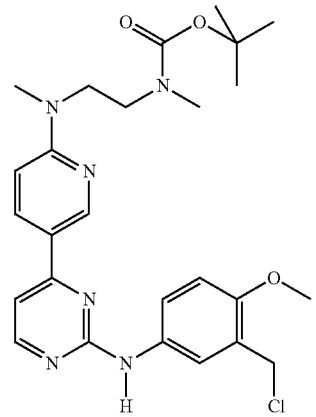 [SMILES: COc1ccc(Nc2nccc(-c3ccc(N(C)CCN(C)C(=O)OC(C)(C)C)nc3)n2)cc1CCl]

Methanesulfonyl chloride (0.017 mol) was added to a mixture of intermediate (21) (0.0045 mol) and DIPEA (7.2 ml) in CH₃CN (200 ml) and was stirred for 2 hours at room temperature. DIPEA (8 ml) was added again. The reaction mixture was used as intermediate (22) in next reaction step.

d) Preparation of Intermediate (23)

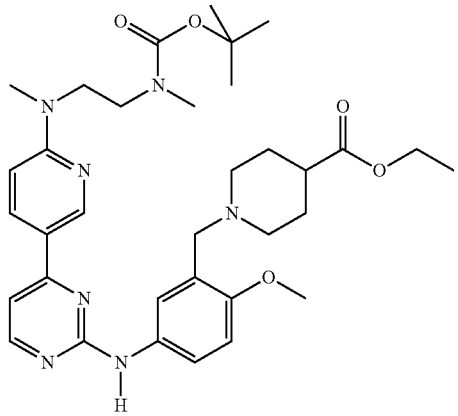 [SMILES: CCOC(=O)C1CCN(Cc2cc(Nc3nccc(-c4ccc(N(C)CCN(C)C(=O)OC(C)(C)C)nc4)n3)ccc2OC)CC1]

Intermediate (22) (0.001 mol) and ethyl piperidine-4-carboxylate (0.0012 mol) was stirred at 60° C. for 20 hours. MP-NCO (0.500 g) was added and the reaction mixture was stirred another 20 hours at 60° C. The reaction mixture was filtered and the filtrate's solvent was evaporated, yielding (100%) intermediate (23).

e) Preparation of Intermediate (24)

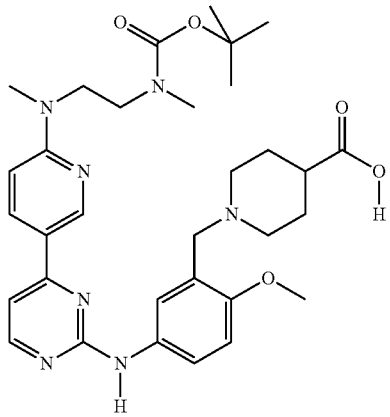 [SMILES: COc1ccc(Nc2nccc(-c3ccc(N(C)CCN(C)C(=O)OC(C)(C)C)nc3)n2)cc1CN1CCC(C(=O)O)CC1]

A mixture of intermediate (23) (0.001 mol) in an aqueous, 1N NaOH solution (15 ml), THF (p.a.) (20 ml) and CH₃OH (p.a.) (5 ml) were stirred for 20 hours at room temperature. The reaction mixture was neutralized to pH=7 with an aqueous 1N HCl solution. This mixture was extracted 3 times with CH₂Cl₂. The separated organic layer was dried (MgSO₄), filtered and the solvent was evaporated, yielding (100%) intermediate (24), used as such in the next step.

f) Preparation of Intermediate (25)

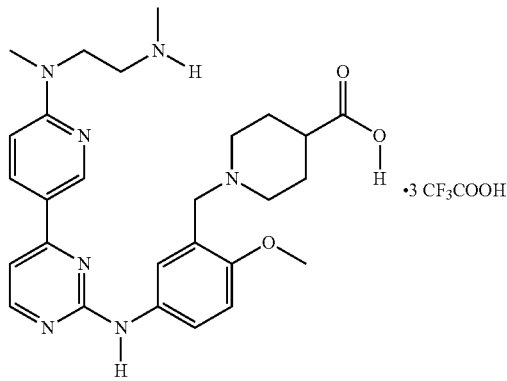 [SMILES: CNCCN(C)c1ccc(-c2ccnc(Nc3ccc(OC)c(CN4CCC(C(=O)O)CC4)c3)n2)cn1]

Intermediate (24) (0.001 mol) in CF₃COOH (20 ml; p.a.) and CH₂Cl₂ (20 ml; p.a.) was stirred for 20 hours at room temperature. The solvent was evaporated, yielding (100%) intermediate (25) (0.3CF₃COOH) used as such in the next step.

Example A6 a) Preparation of Intermediate (26)

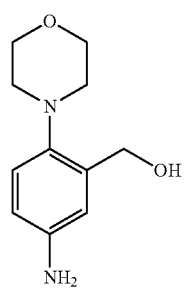 [SMILES: Nc1ccc(N2CCOCC2)c(CO)c1]

Intermediate (2) (0.1800 mol) in CH₃OH (500 ml) and a 4% thiophene solution in DIPE (2 ml) was hydrogenated with Pt/C₅% and H₂. After 16 hours the reaction mixture was filtered over a small plug of Dicalite and concentrated to give a grey solid, yielding 37 g (98.7%) of intermediate (26).

Example A7 a) Preparation of Intermediate (27)

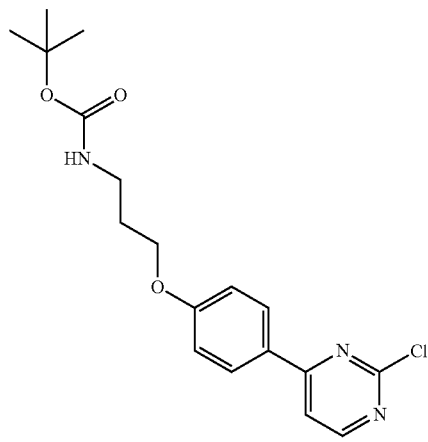 [SMILES: CC(C)(C)OC(=O)NCCCOc1ccc(-c2ccnc(Cl)n2)cc1]

(4-Ethenylphenyl)diphenyl-phosphine, polymer with diethenylbenzene and ethenylbenzene (0.0675 mol) (CA Registry Number: [39319-11-4]) and then tert-butyl (3-hydroxypropyl)carbamate (0.0495 mol) were added to a mixture of 4-(2-chloropyrimidin-4-yl)phenol (0.045 mol) in THF (220 ml). DEAD (0.0675 mol) was added to the reaction mixture and stirred for 3 hours at room temperature. The reaction mixture was filtered over dicalite and was evaporated till almost dry. CH₂Cl₂ was added to the concentrate and this mixture was washed with H₂O. The separated organic layer was dried (MgSO₄), filtered and the solvent was evaporated. The residue was purified by column chromatography over silica gel (eluent: CH₂Cl₂/(CH₃OH/NH₃) 90/10). The product fractions were collected and the solvent was evaporated.

The residue was crystallized from DIPE, the precipitate was filtered off and dried (vacuo, 60° C.), yielding 9.1 g (56%) of intermediate (27).

b) Preparation of Intermediate (28)

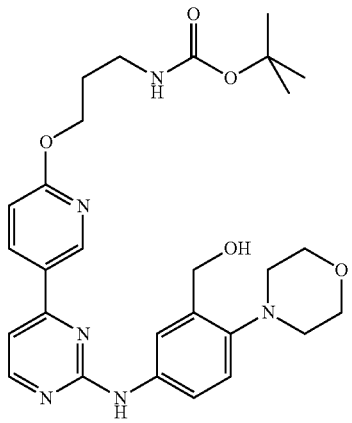 [SMILES: CC(C)(C)OC(=O)NCCCOc1ccc(-c2ccnc(Nc3ccc(N4CCOCC4)c(CO)c3)n2)cn1]

Intermediate (27) (0.0253 mol) was dissolved in tert.-BuOH (300 ml), the reaction mixture was purged with N₂ for 15 minutes, intermediate (0.0278 mol) was added, K₂CO₃ (0.0506 mol) was added, X-Phos (0.0028 mol) was added, Pd₂(dba)₃ (0.0003 mol) was added, the reaction mixture was stirred and purged with N₂ for 5 minutes. The reaction mixture was heated at 80° C. for 18 hours under N₂-atmosfeer. The reaction mixture was allowed to reach room temperature. The reaction mixture was poured into H₂O (300 ml) and the product was extracted with CH₂Cl₂. The organic layer was separated, dried (MgSO₄), filtered and concentrated in vacuo. The residue was purified with column chromatography (SiO₂, Biotage flash purification system; gradient going from 100% CH₂Cl₂ to 5% CH₃OH/CH₂Cl₂). The product fractions were collected and the solvent was evaporated. The Product was crystallized from CH₃CN, the precipitate was filtered off and dried in vacuum at 60° C., yielding 4.7 g (35%) of intermediate (28) (m.p.: 164.6° C. (DSC)).

c) Preparation of Intermediate (29)

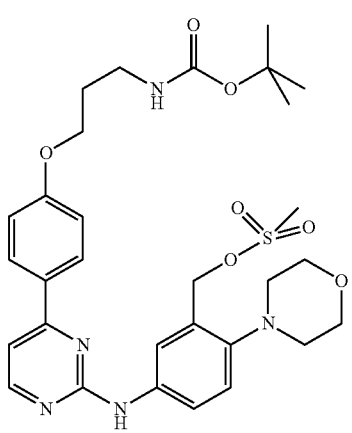 [SMILES: CC(C)(C)OC(=O)NCCCOc1ccc(-c2ccnc(Nc3ccc(N4CCOCC4)c(COS(C)(=O)=O)c3)n2)cc1]

DIPEA (0.0107 mol) was added to a stirred solution of intermediate (28) (0.0018 mol) in DMF (q.s.). Subsequently methanesulfonyl chloride (0.00304 mol) was added. The mixture was stirred at room temperature for 4 hours. The solution was used as intermediate (29) in the next reaction step.

d) Preparation of Intermediate (30)

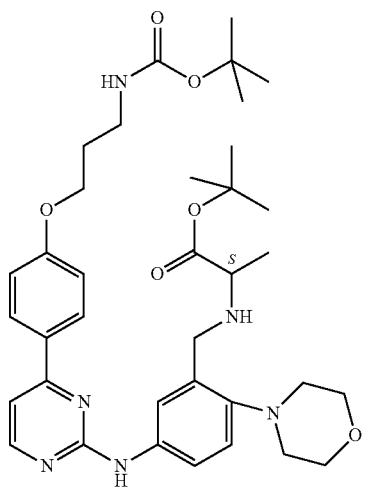

tert-butyl L-alaninate (0.0025 mol) was added to a mixture of intermediate (29) (0.0005 mol) and DIPEA in DMF (5 ml). The mixture was heated overnight at 70° C. and cooled to room temperature. Scavenging was done by adding 3 equivalents of MP-CHO (2 g). Upon shaking overnight, the resin was filtered off and washed with CH₃OH and a mixture of CH₂Cl₂/CH₃OH (10:1). The solvent was evaporated and the resulting crude was used as intermediate (30) (S-enantiomer) in the next reaction step.

e) Preparation of Intermediate (31)

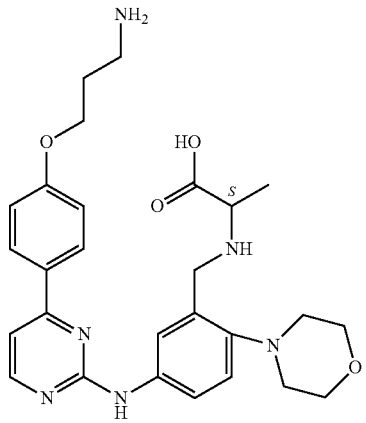

TFA/CH₂Cl₂/TIS (49/49/2; 5 ml) was added to crude intermediate (30) (0.0005 mol) and the mixture was stirred for 6 hours at room temperature. Then the solvent was evaporated and the crude compound was used as intermediate (31) (S-enantiomer) in the next reaction step.

Example A8 a) Preparation of Intermediate (32)

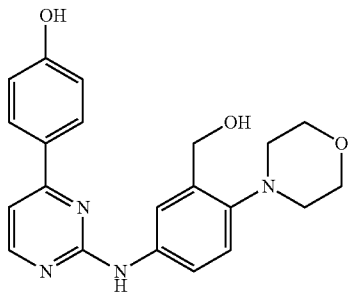 [SMILES: OCc1cc(Nc2nccc(-c3ccc(O)cc3)n2)ccc1N1CCOCC1]

A mixture of 4-(2-chloropyrimidin-4-yl)phenol (0.041 mol), X-Phos (0.0037 mol), $K_2CO_3$ (0.082 mol) and tert.-BuOH (200 ml) was heated to 80° C. while purging with $N_2$ for 15 minutes. Then $Pd_2(dba)_3$ (0.0006 mol) was added and subsequently a slurry of 5-amino-2-(4-morpholinyl)-benzenemethanol (0.049 mol) and $K_2CO_3$ (0.082 mol) in tert.-BuOH was added dropwise. The mixture was heated for 15 hours at 80° C. and was then cooled to room temperature. The precipitate was filtered off and was washed with $H_2O$. The product was dried (vacuum, room temperature), yielding 14.2 g of (91%; brown solid) of intermediate (32).

b) Preparation of Intermediate (33)

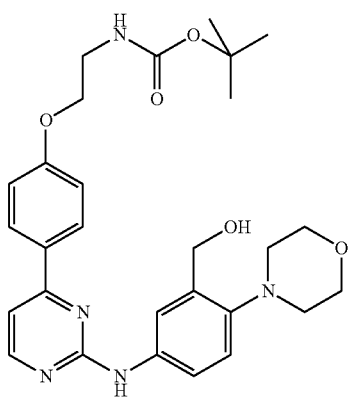 [SMILES: CC(C)(C)OC(=O)NCCOc1ccc(-c2ccnc(Nc3ccc(N4CCOCC4)c(CO)c3)n2)cc1]

$Cs_2CO_3$ (0.055 mol) was added (at room temperature) to a solution of intermediate (32) (0.0184 mol) in DMF (60 ml). This mixture was stirred at room temperature for 30 minutes and then tert-butyl (2-bromoethyl)carbamate (0.028 mol) was added. The reaction mixture was stirred for 15 hours at room temperature. $CH_2Cl_2$ (30 ml) was added and the mixture was washed with brine (3×20 ml), dried ($MgSO_4$), filtered and the solvent was evaporated. The crude product was purified by flash column chromatography (eluent: hexane/EtOAc from 2/1 to 1/1 to 1/2 to 0/1). The desired fractions were collected and the solvent was evaporated. The product was dried (vacuum, room temperature), yielding 5.27 g (55%; pale yellow solid) of intermediate (33).

c) Preparation of Intermediate (34)

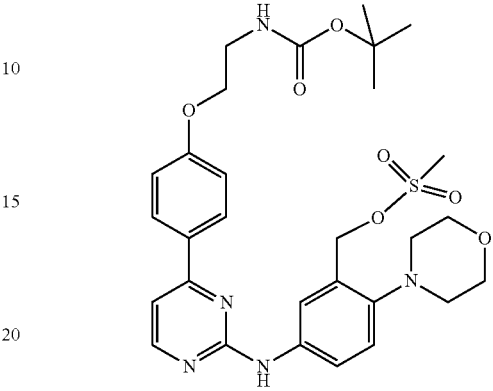

DIPEA (0.025 mol) was added to a stirred solution of intermediate (33) (0.0041 mol) in DMF (80 ml). Then methanesulfonyl chloride (0.007 mol) was added and the mixture was stirred for 1 hour at room temperature. The mixture was used as intermediate (34) in the next reaction step.

d) Preparation of Intermediate (35)

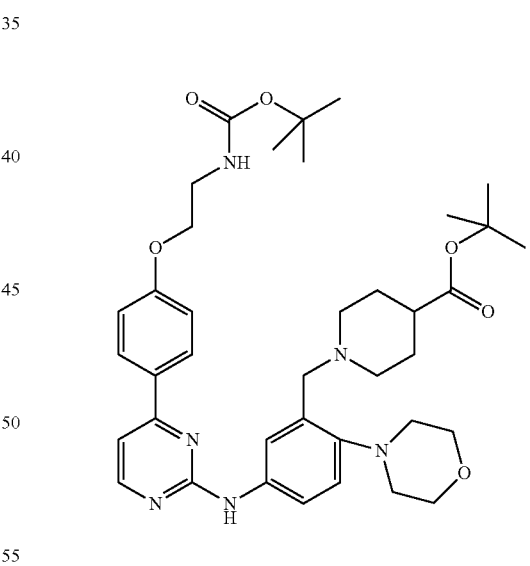

tert-butyl piperidine-4-carboxylate (0.0005 mol) was added to a mixture of intermediate (34) (0.00025 mol) and DIPEA (q.s.) in DMF (5 ml). The reaction mixture was heated overnight at 70° C. and then cooled to room temperature. Scavenging was done overnight, while the mixture was shaken, by adding 3 equivalents MP-NCO (benzyl-isocyanate resin, 0.750 g). The resin was filtered off and washed with $CH_3OH$ and a mixture of $CH_2Cl_2/CH_3OH$ (10:1). The filtrate's solvent was then evaporated and the resulting crude was used as intermediate (35) in the next reaction step.

e) Preparation of Intermediate (36)

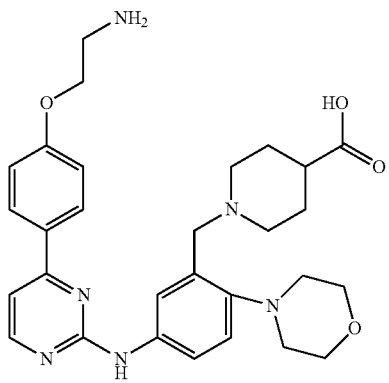 [SMILES: NCCOc1ccc(-c2ccnc(Nc3ccc(N4CCOCC4)c(CN4CCC(C(=O)O)CC4)c3)n2)cc1]

TFA/CH$_2$Cl$_2$/TIS (5 ml) was added to intermediate (35) (0.0003 mol). The mixture was stirred for 6 hours at room temperature. Then the solvent was evaporated and the crude compound was used as intermediate (36) in the next reaction step.

Example A9 a) Preparation of Intermediate (37)

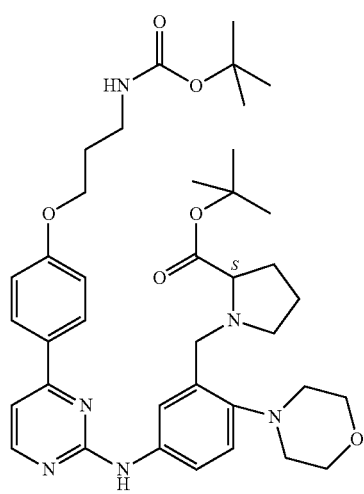

tert-butyl L-prolinate (0.0006 mol) was added to a mixture of intermediate (29) (0.0003 mol) and DIPEA (q.s.) in DMF (5 ml). The mixture was heated overnight to 70° C. Then the mixture was cooled to room temperature and 3 equivalents of MP-NCO (0.75 g) were added. The mixture was shaken overnight. The resins were filtered off and washed with a mixture of CH$_2$Cl$_2$/CH$_3$OH. The solvents were evaporated and the crude product was used as intermediate (37) (S-enantiomer) in the next reaction step.

b) Preparation of Intermediate (38)

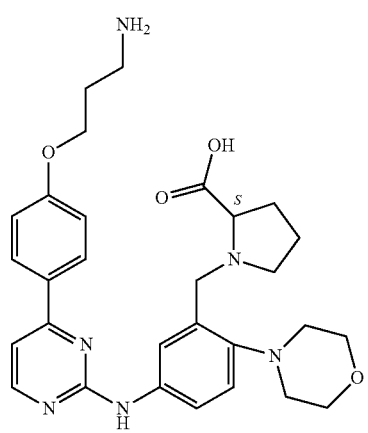

TFA/CH$_2$Cl$_2$/TIS (49/49/2; 5 ml) was added to crude intermediate (37) (0.0003 mol) and the mixture was stirred at room temperature for 6 hours. The solvent was evaporated and the crude compound was used as intermediate (38) (S-enantiomer) for the next reaction step.

Example A10 a) Preparation of Intermediate (39)

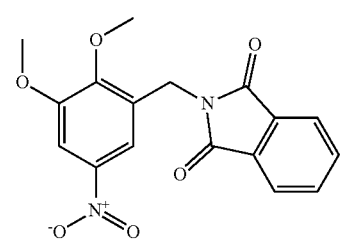

(2,3-dimethoxy-5-nitrophenyl)methanol (0.0770 mol), THF (500 ml), 1H-Isoindole-1,3(2H)-dione (0.0850 mol) and triphenyl-phosphine (0.0850 mol) were stirred at room temperature. DIAD (0.0850 mol) was added dropwise at room temperature. The reaction mixture was cooled on an ice-bath (exothermic reaction). The reaction mixture was stirred at ambient temperature for 30 minutes. The precipitate was collected on a filter, washed with THF and dried in vacuo, yielding 24.5 g (92.1%) of intermediate (39).

b) Preparation of Intermediate (40)

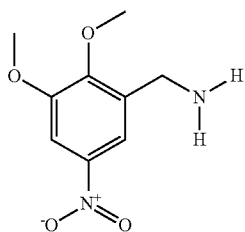

Intermediate (39) (0.0029 mol), hydrazine, monohydrate (0.0146 mol) and EtOH (40 ml) were stirred at 50° C. for 1 hour. The precipitate was collected on a filter and the filtrate was evaporated. The residue was dissolved in $CH_2Cl_2$ and washed with $H_2O$. The separated organic layer was dried ($MgSO_4$), filtered and the solvent was evaporated, yielding 0.45 g (73.8%) of intermediate (40) (m.p.: 88° C.).

c) Preparation of Intermediate (41)

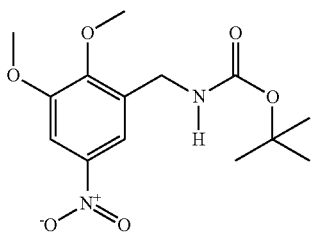

Intermediate (40) (0.0029 mol), dioxane (30 ml) and $Et_3N$ was stirred at room temperature. Di-tert-butyl dicarbonate (0.0030 mol) dissolved in dioxane (10 ml) was added dropwise at room temperature. The reaction mixture was stirred at room temperature for 30 minutes. The reaction mixture was diluted with $H_2O$ and the product extracted with $CH_2Cl_2$ (2×50 ml). The organic layers were combined, dried ($MgSO_4$), filtered and the solvent was evaporated, yielding 0.6 g (66.6%) of intermediate (41).

d) Preparation of Intermediate (42)

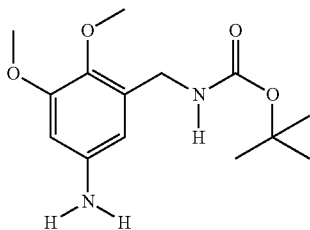 [SMILES: COc1cc(N)cc(CNC(=O)OC(C)(C)C)c1OC]

Intermediate (41) (0.0570 mol), $H_2$ (3 equivalents), thiophene solution (1 ml; 4% in DIPE), THF (p.a.; 250 ml) and Pd/C were stirred at room temperature for 20 hours. The catalyst was removed by filtration over Dicalite. The filtrate was evaporated. The residue was dissolved in $CH_2Cl_2$ (500 ml) and washed with water. The organic layer was dried ($MgSO_4$), filtrated and evaporated, yielding 16 g (100%) of intermediate (42).

e) Preparation of Intermediate (43)

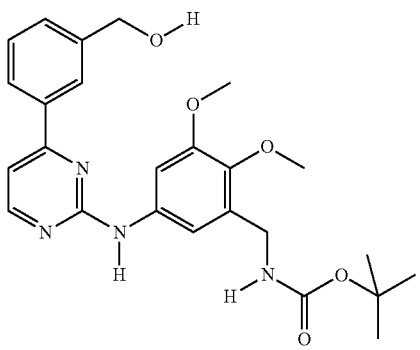 [SMILES: COc1cc(Nc2nccc(-c3cccc(CO)c3)n2)cc(CNC(=O)OC(C)(C)C)c1OC]

[3-(2-chloropyrimidin-4-yl)phenyl]methanol (0.0180 mol), intermediate (42) (0.0180 mol), 1,4-dioxane (200 ml) and 4-methyl-benzenesulfonic acid, hydrate (1:1) (0.0010 mol) were stirred at 100° C. for 20 hours. The reaction mixture was cooled. The precipitate was collected on a filter and washed with $CH_2Cl_2$. The filtrate was evaporated. The residue was diluted with $H_2O$ (100 ml) and the product extracted with $CH_2Cl_2$ (2×100 ml). The organic layers were combined, then washed with $H_2O$, dried ($MgSO_4$), filtrated and the solvent was evaporated. The residue was purified by column chromatography (silica gel:$CH_2Cl_2$/($CH_3OH/NH_3$) 97/3). The pure fractions were collected and evaporated. The residue was crystallized from $CH_3CN$/DIPE (4/1; 50 ml); with a few drops $H_2O$). The precipitate was collected on a filter and dried in vacuo, yielding 3.84 g (45.7%) intermediate (43).

f) Preparation of Intermediate (44)

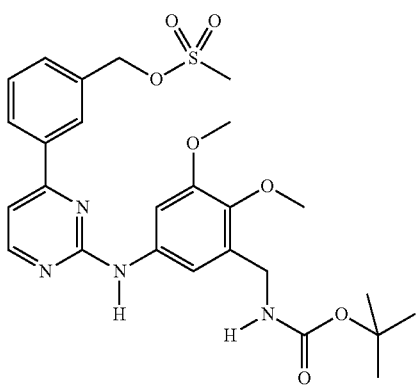 [SMILES: COc1cc(Nc2nccc(-c3cccc(COS(C)(=O)=O)c3)n2)cc(CNC(=O)OC(C)(C)C)c1OC]

Intermediate (43) (0.0640 mol), $CH_3CN$ (250 ml) and DIPEA (0.0500 mol) were stirred at room temperature. Methanesulfonyl chloride (0.0320 mol) was added dropwise at ambient temperature (slightly exotherm). The reaction mixture was stirred at room temperature for 3 hours and was used as intermediate (44) in the next reaction step.

g) Preparation of Intermediate (45)

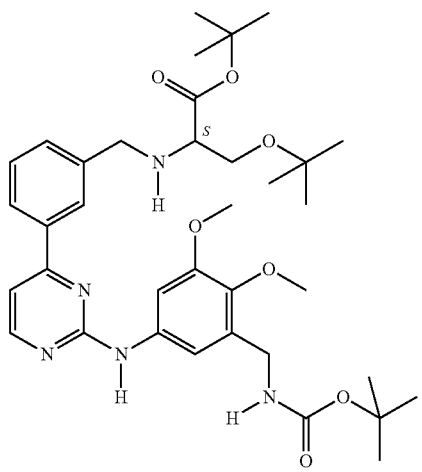

Intermediate (44) (0.0011 mol), tert-butyl-O-tert-butyl-L-serinate, hydrochloride (1:1) (0.0040 mol), DIPEA (2 ml) and CH₃CN (50 ml) was stirred at 70° C. for 3 days. MP-NCO (1 g) was added and the reaction mixture was stirred for another 20 hours at 70° C. The reaction mixture was filtered and the filtrate was evaporated. The residue was used as intermediate (45) (S-enantiomer) in the next reaction step.

h) Preparation of Intermediate (46)

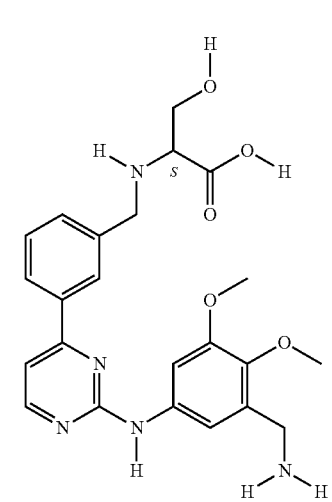

Intermediate (45) (0.0011 mol), CF₃COOH (25 ml) and CH₂Cl₂ (25 ml) were stirred at room temperature for 20 hours. The reaction mixture was evaporated. The residue was washed with DIPE. The DIPE layer was separated, yielding 1.1 g (100%) of intermediate (46) (S-enantiomer).

Example A11 a) Preparation of Intermediate (47)

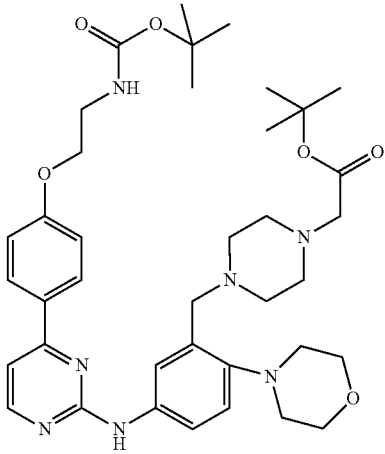 [SMILES: CC(C)(C)OC(=O)CN1CCN(Cc2cc(Nc3nccc(-c4ccc(OCCNC(=O)OC(C)(C)C)cc4)n3)ccc2N2CCOCC2)CC1]

The reaction was done analogously to Example A8 d), using intermediate (34) prepared as described in Example A8 c) and tert-butyl piperazin-1-ylacetate, yielding intermediate (47).

b) Preparation of Intermediate (48)

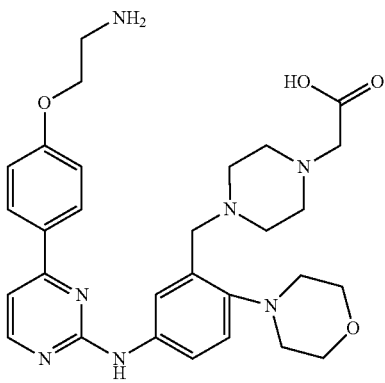 [SMILES: NCCOc1ccc(-c2ccnc(Nc3ccc(N4CCOCC4)c(CN4CCN(CC(=O)O)CC4)c3)n2)cc1]

The reaction was done analogously to Example A8 e), using intermediate (47) prepared as described in Example A11 a), yielding intermediate (48).

Example A12 a) Preparation of Intermediate (49)

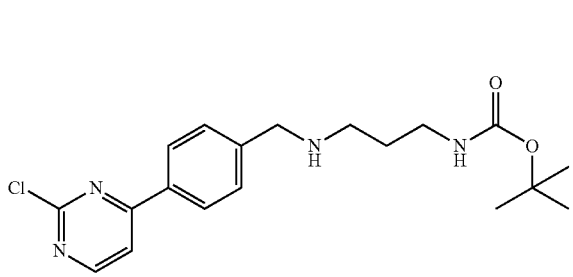 [SMILES: CC(C)(C)OC(=O)NCCCNCc1ccc(-c2ccnc(Cl)n2)cc1]

4-(2-chloropyrimidin-4-yl)benzaldehyde (0.018 mol), tert-butyl (3-aminopropyl)carbamate (0.027 mol) and HOAc (0.018 mol) were dissolved in DCE (90 ml). NaBH(OAc)$_3$ (0.027 mol) was added to the solution and the reaction mixture was stirred for 5 hours at room temperature. Then the mixture was quenched with NaOH (1M) and the layers were separated. The aqueous layer was extracted once more with CH$_2$Cl$_2$. The combined organic layers were dried (MgSO$_4$), filtered and the solvent was evaporated, yielding intermediate (49) used as such in the next reaction step.

b) Preparation of Intermediate (50)

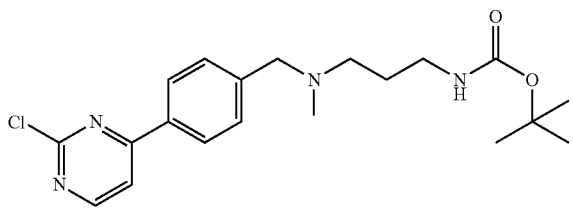 [SMILES: CN(CCCNC(=O)OC(C)(C)C)Cc1ccc(-c2ccnc(Cl)n2)cc1]

Intermediate (49) (0.018 mol) was dissolved in CH$_3$OH (100 ml) and formaldehyde (0.036 mol) was added. Then NaBH$_3$CN (0.0135 mol) was added and the mixture was stirred for 2 hours. More NaBH$_3$CN (0.0135 mol) was added and the reaction mixture was stirred for another 4 hours. CH$_2$Cl$_2$ (300 ml) was added and the mixture was washed with NaOH (100 ml; 1 M). The aqueous layer was washed once more with CH$_2$Cl$_2$. The combined organic layers were dried (MgSO$_4$), filtered and the solvent was evaporated. The residue was purified by column chromatography over silica gel (eluent: hexane/EtOAc 1/2). The desired fractions were collected and the solvent was evaporated, yielding 4.53 g (65%) of intermediate (50).

c) Preparation of Intermediate (51)

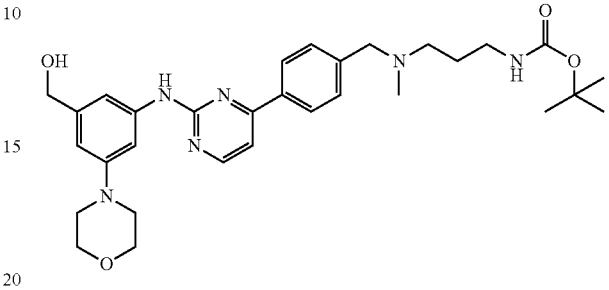

A mixture of intermediate (50) (0.00763 mol), (3-amino-5-morpholin-4-ylphenyl)methanol (0.00916 mol) and 4-methyl-benzenesulfonic acid, hydrate (1:1) (0.00763 mol) in 1,4-dioxane/2-propanol (4/1; 35 ml) was stirred and refluxed at 80° C. for 5 days. The mixture was cooled down to room temperature. Et$_3$N (2.0 equiv.) and di-tert-butyl dicarbonate (0.7 equivalents) were added and the mixture was reacted for 6 hours. Then the mixture was extracted with CH$_2$Cl$_2$ and washed with NaOH (1M). The phases were separated and the water layer was extracted once again with CH$_2$Cl$_2$. The combined organic layers were dried (MgSO$_4$), filtered and the solvent was evaporated. The residue was purified by flash column chromatography over silica gel (eluent: CH$_2$Cl$_2$/CH$_3$OH 20/1). The desired fractions were collected and the solvent was evaporated, yielding 3.20 g (74%) of intermediate (51).

d) Preparation of Intermediate (52)

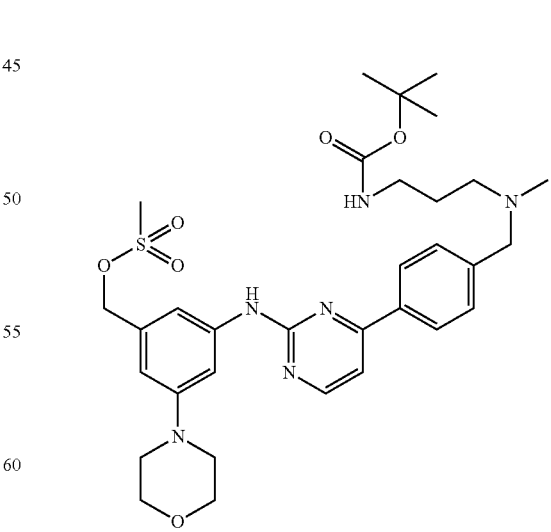

Methanesulfonyl chloride (0.00675 mol) was added to a mixture of intermediate (51) (0.0045 mol) and DIPEA (0.027 mol) in CH$_3$CN (90 ml) and then the mixture was stirred at room temperature for 1 hour. The crude was used as intermediate (52) in the next reaction step.

e) Preparation of Intermediate (53)

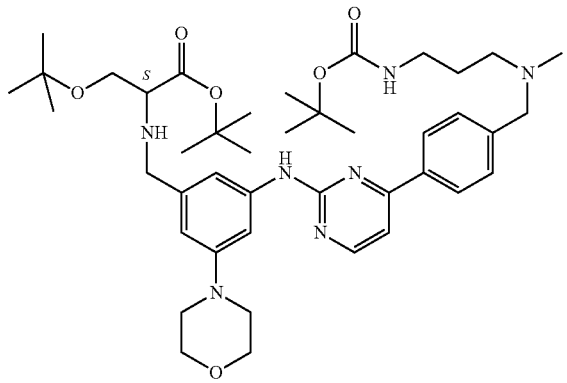

The amino ester tert-butyl-O-tert-butyl-L-serinate, hydrochloride (1:1) (0.0015 mol; HCl-salt) was weighed in a reaction tube. A solution (10 ml) of intermediate (52) (0.0005 mol), DIPEA and $CH_3CN$ was added and the mixture was stirred at room temperature for 3 hours. Then the mixture was heated overnight at 70° C. Scavenging was done overnight with Wang aldehyde resin (q.s.). The resin was filtered off and washed with $CH_3OH$ and $CH_2Cl_2/CH_3OH$ (4:1). The filtrate's solvent was evaporated. The residue was taken in $CH_2Cl_2$ and washed with saturated $NaHCO_3$ (3 ml). The separated organic layer was dried ($MgSO_4$), filtered and the solvent was removed, yielding intermediate (53) (S-enantiomer) used as such in the next reaction step.

f) Preparation of Intermediate (54)

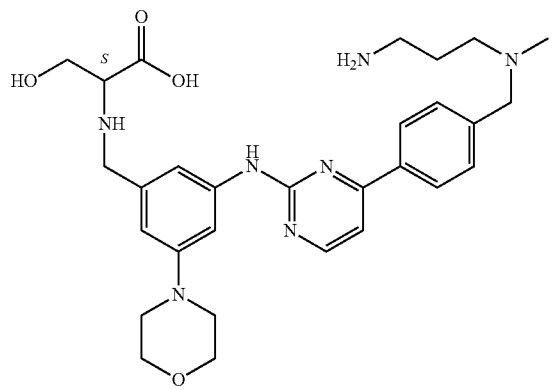

A mixture of the intermediate (53) (0.0005 mol) and TFA/$CH_2Cl_2$/TIS (49/49/2; 10 ml) was stirred overnight at room temperature. The mixture was concentrated to dryness, yielding intermediate (54) (S-enantiomer) used as such in the next reaction step.

Example A13 a) Preparation of Intermediate (55)

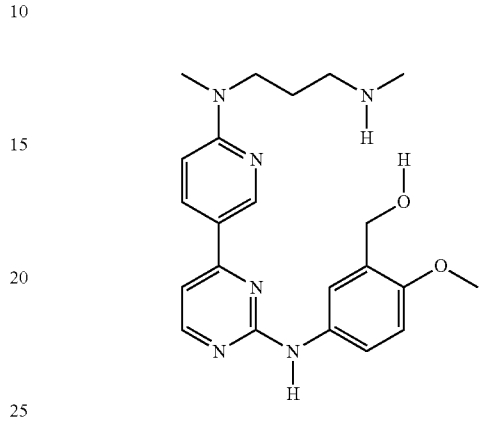

A mixture of intermediate (7) (0.0064 mol) in N,N'-dimethyl-1,3-propanediamine (60 ml) was stirred for 3 hours at 150° C. The solvent was evaporated. The residue was diluted with water, then extracted twice with $CH_2Cl_2$. The separated organic layer was washed with water, dried ($MgSO_4$), filtered and the solvent was evaporated. The residue was crystallized from $CH_3CN$. The precipitate was filtered off and dried. This fraction was recrystallized from 2-propanol. The precipitate was filtered off and dried (vacuum), yielding 0.053 g of intermediate (55).

b) Preparation of Intermediate (56)

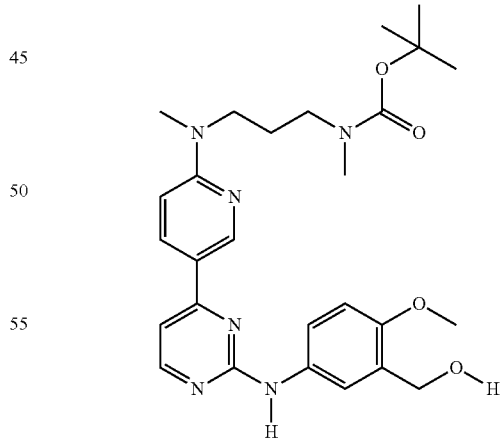

A mixture of intermediate (55) (0.0046 mol) in $CH_2Cl_2$ (100 ml) was stirred at room temperature. Di-tert-butyl dicarbonate (0.0060 mol) in $CH_2Cl_2$ (20 ml) was added dropwise at room temperature and stirred for 20 hours at room temperature. The reaction mixture was washed with $H_2O$, diluted with $NH_4OH$. The separated organic layer was dried (MgSO₄), filtered and the solvent was evaporated, yielding 2.33 g (100%) of intermediate (56).

c) Preparation of Intermediate (57)

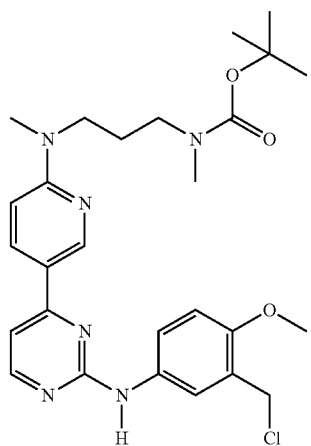 [SMILES: COc1ccc(Nc2nccc(-c3ccc(N(C)CCCN(C)C(=O)OC(C)(C)C)nc3)n2)cc1CCl]

A mixture of intermediate (56) (0.0047 mol), methanesulfonyl chloride (0.020 mol) and DIPEA (8 ml) in CH₃CN (200 ml) was stirred for 4 hours at room temperature. DIPEA (8 ml) was added again, yielding intermediate (57).

d) Preparation of Intermediate (58)

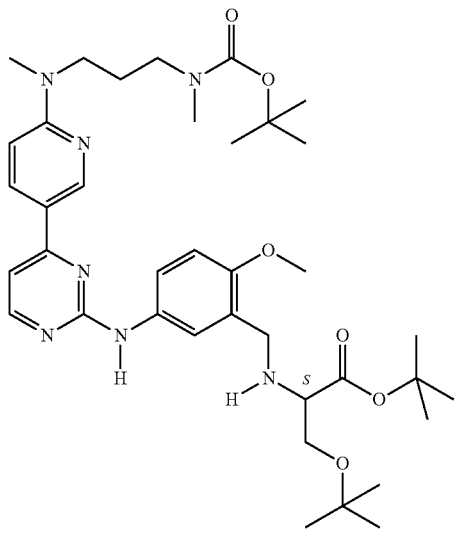

A mixture of tert-butyl-O-tert-butyl-L-serinate, hydrochloride (1:1) (0.0047 mol) in intermediate (57) (0.001 mol) was stirred for 20 hours at 60° C. The solvent was evaporated. The residue was diluted with H₂O. This mixture was extracted 2 times with CH₂Cl₂. The 2 separated organic layers were combined, washed with H₂O and then dried (MgSO₄), filtered and the solvent was evaporated. The residue was purified by column chromatography over silica gel (eluent: CH₂Cl₂/(CH₃OH/NH₃) 96/4). The product fractions were collected and the solvent was evaporated, yielding 0.5 g (71%) of intermediate (58) (S-enantiomer).

e) Preparation of Intermediate (59)

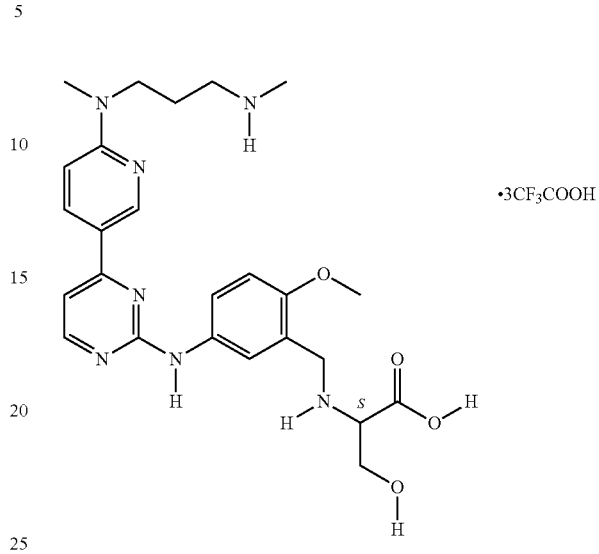

Intermediate (58) (0.0007 mol) in CF₃COOH (20 ml) and CH₂Cl₂ (p.a.; 20 ml) was stirred for 20 hours at room temperature. The solvent was evaporated, yielding 0.8 g of intermediate (59) (S-enantiomer; 0.3CF₃COOH).

Example A14 a) Preparation of Intermediate (60)

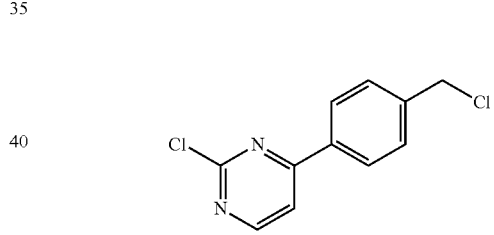

A solution of [4-(2-chloropyrimidin-4-yl)phenyl]methanol (0.032 mol) in CH₂Cl₂ (65 ml) was stirred vigorously for 10 minutes at 0° C. Then thionyl chloride (0.065 mol) was added and the mixture was stirred for 2 hours at room temperature. The solvent was evaporated and the residue was dried under vacuum (oil pump), yielding intermediate (60) used as such in the next reaction step.

b) Preparation of Intermediate (61)

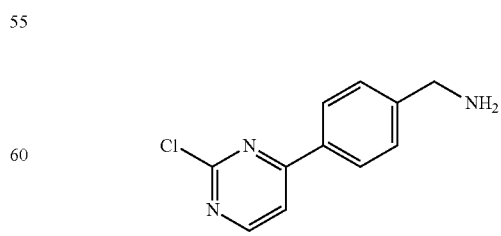

Intermediate (60) (0.032 mol) was dissolved in CH₃CN (100 ml). This solution was added dropwise to a mixture of 25% aqueous NH₃ solution (640 ml) and CH₃CN (860 ml).

The reaction mixture was stirred overnight at room temperature. Then half of the CH₃CN was evaporated and CH₂Cl₂ and H₂O were added to the concentrate. The layers were separated and the aqueous layer was extracted once more with CH₂Cl₂. The combined organic layers were washed with brine, dried (MgSO₄), filtered and the solvent was evaporated. The residue was dried under vacuum (oil pump), yielding intermediate (61) used as such in the next reaction step.

c) Preparation of Intermediate (62)

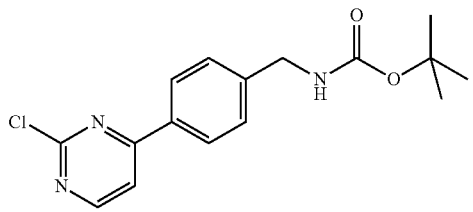 [SMILES: CC(C)(C)OC(=O)NCc1ccc(-c2ccnc(Cl)n2)cc1]

Di-tert-butyl dicarbonate (0.0384 mol) was added to a solution of intermediate (61) (0.032 mol; crude) in CH₂Cl₂ (130 ml). The mixture was stirred overnight vigorously at room temperature. The solvent was evaporated and the residue was purified by flash column chromatography (eluent: hexane/EtOAc 3/1). The desired fractions were collected and the solvent was evaporated, yielding 7.96 g (77.86%) of intermediate (62).

d) Preparation of Intermediate (63)

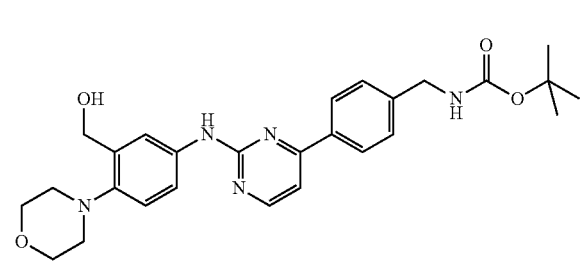 [SMILES: CC(C)(C)OC(=O)NCc1ccc(-c2ccnc(Nc3ccc(N4CCOCC4)c(CO)c3)n2)cc1]

A solution of intermediate (62) (0.00927 mol), (5-amino-2-morpholin-4-ylphenyl)methanol (0.0139 mol) and 4-methyl-benzenesulfonic acid, hydrate (1:1) (0.00463 mol) in 1,4-dioxane/2-propanol (4/1; 40 ml) was stirred overnight vigorously at reflux temperature (80° C.). The mixture was cooled to room temperature and CH₂Cl₂ and Et₃N (1.29 ml) were added. Subsequently di-tert-butyl dicarbonate (1.5 g) was added. The flask was capped and bubbled and was stirred overnight. Na₂CO₃ (1M) was added and the mixture was extracted twice with CH₂Cl₂. The organic phase was dried (MgSO₄), filtered and the solvent was evaporated. The residue was purified by flash column chromatography (eluent: CH₂Cl₂/CH₃OH 40/1). The desired fractions were collected and the solvent was evaporated, yielding 3.44 g (75.6%) of intermediate (63).

e) Preparation of Intermediate (64)

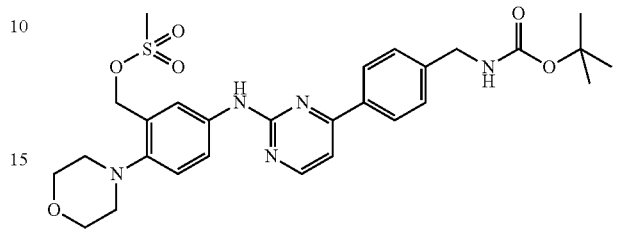

Intermediate (63) (0.00540 mol) and DIPEA (0.032 mol) were suspended in CH₃CN (120 ml) and the suspension was cooled at 0° C. Methanesulfonyl chloride (0.0081 mol) was added and the mixture was stirred for 1 hour. DMF (120 ml) was added and the mixture was again stirred for 1 hour, yielding intermediate (64) used as such in the next reaction step.

f) Preparation of Intermediate (65)

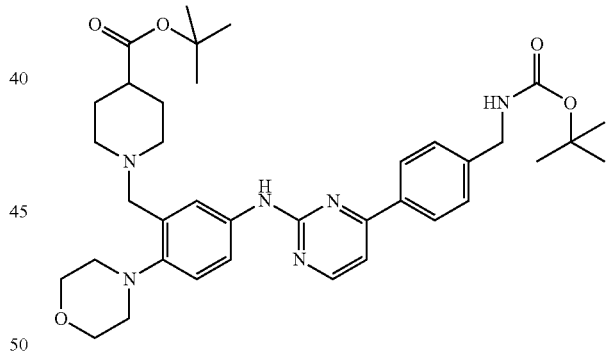

A solution (20 ml) of intermediate (64) (0.00045 mol) and DIPEA in CH₃CN and DMF was added to a tube containing tert-butyl piperidine-4-carboxylate, hydrochloride (1:1) (0.000675 mol; HCl-salt). The reaction mixture was shaken for 1 hour at room temperature. Then the mixtures were heated at 80° C. Finally scavenging was done overnight with ScavengePore® benzyl isocyanate. The resin was filtered off and was washed with CH₃OH and CH₂Cl₂/CH₃OH 4/1. The filtrate's solvent was evaporated and the residue was taken in CH₂Cl₂. This organic layer was washed with a saturated NaHCO₃ solution (5 ml) and subsequently the separated organic layer was dried (MgSO₄), filtered and the solvent was evaporated, yielding intermediate (65) used as such in the next reaction step.

g) Preparation of Intermediate (66)

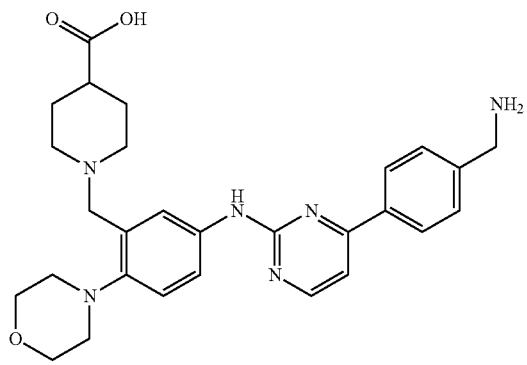 [SMILES: NCc1ccc(-c2ccnc(Nc3ccc(N4CCOCC4)c(CN4CCC(C(=O)O)CC4)c3)n2)cc1]

Intermediate (65) (0.00045 mol) was taken up in TFA/CH₂Cl₂/TIS (49/49/2; 10 ml; stock solution). The mixture was shaken overnight at room temperature. Then the solvent was evaporated and the residue was used as intermediate (66) in the next reaction step.

Example A15 a) Preparation of Intermediate (67)

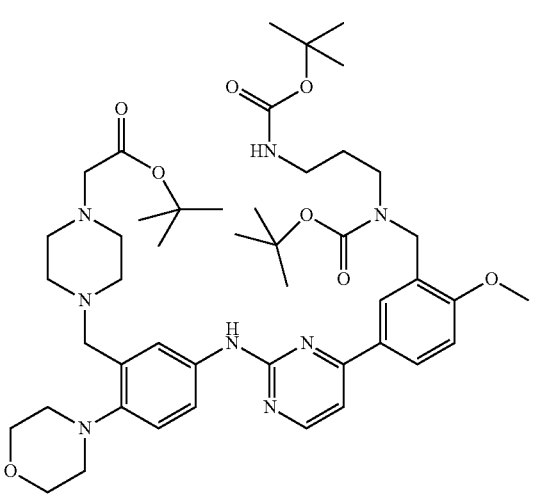 [SMILES: COc1ccc(-c2ccnc(Nc3ccc(N4CCOCC4)c(CN4CCN(CC(=O)OC(C)(C)C)CC4)c3)n2)cc1CN(CCCNC(=O)OC(C)(C)C)C(=O)OC(C)(C)C]

The reaction was done analogously to Example A4 f), using intermediate (17) prepared as described in Example A4 f) and tert-butyl piperazin-1-ylacetate, yielding intermediate (67).

b) Preparation of Intermediate (68)

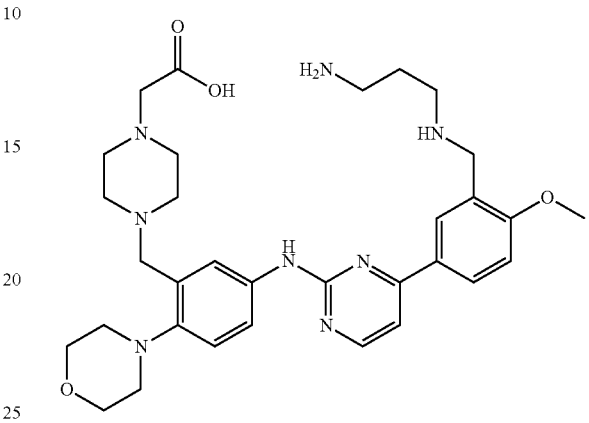

The reaction was done analogously to Example A4 g), using intermediate (67) prepared as described in Example A15a), yielding intermediate (68).

Example A16 a) Preparation of Intermediate (69)

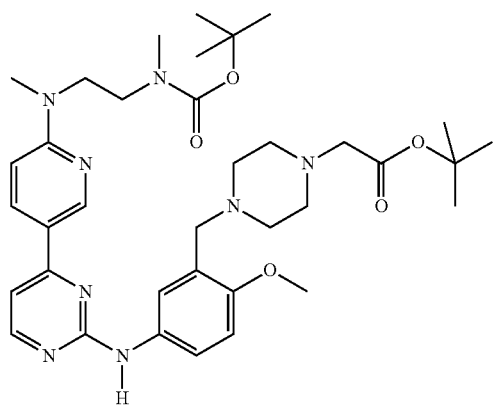 [SMILES: COc1ccc(Nc2nccc(-c3ccc(N(C)CCN(C)C(=O)OC(C)(C)C)nc3)n2)cc1CN1CCN(CC(=O)OC(C)(C)C)CC1]

Intermediate (22) (0.001 mol) and tert-butyl piperazin-1-ylacetate, dihydrochloride (0.0012 mol) was stirred at 60° C. for 20 hours. MP-NCO (0.500 g) was added and the reaction mixture was stirred another 20 hours at 60° C. The reaction mixture was filtered and the filtrate's solvent was evaporated, yielding intermediate (69).

b) Preparation of Intermediate (70)

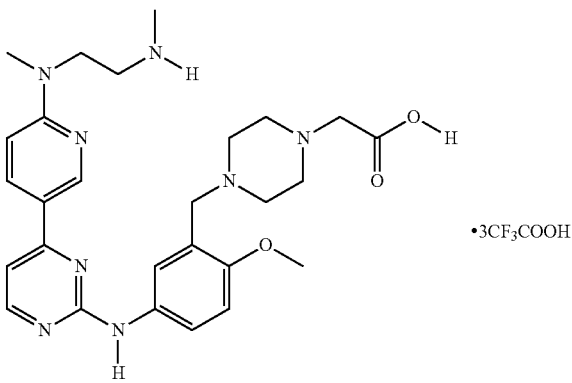 [SMILES: CNCCN(C)c1ccc(-c2ccnc(Nc3ccc(OC)c(CN4CCN(CC(=O)O)CC4)c3)n2)cn1]

•3CF₃COOH

Intermediate (69) (0.001 mol) in CF₃COOH (p.a.; 20 ml) and CH₂Cl₂ (20 ml) was stirred for 20 hours at room temperature. The solvent was evaporated, yielding (100%) intermediate (70) (0.3CF₃COOH) used in the next reaction steps without further purification.

Example A17 a) Preparation of Intermediate (71)

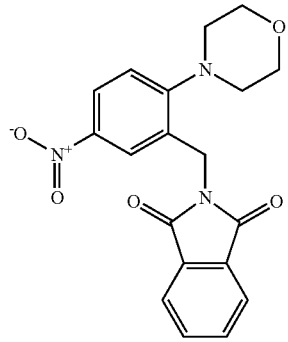

Thionyl chloride (0.011 mol) was added to a solution of intermediate (2) (0.00839 mol) in CH₂Cl₂ (24 ml). The reaction mixture was left stirring at room temperature for 1 hour. Then the CH₂Cl₂ was concentrated. DMF (24 ml), DIPEA (0.012 mol) and 1H-isoindole-1,3(2H)-dione, potassium salt (1:1) (0.012 mol) were added to the mixture. The mixture stirred overnight at 50° C. Then the mixture was worked up with water/ice. The product was filtered off, washed and dried with ether, yielding 3.31 g of intermediate (71).

b) Preparation of Intermediate (72)

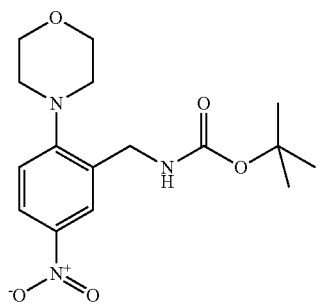

Hydrazine.H₂O (0.063 mol) was added to a solution of intermediate (71) (0.00901 mol) in EtOH (27 ml). The reaction mixture was left stirring at 50° C. for 2 hours. NaOH was added and the product was extracted 2 times with CH₂Cl₂. The combined organic layers were dried (MgSO₄), filtered and the solvent was evaporated. Then CH₂Cl₂ was added. The flask was taken in an ice bath and BOC (q.s.) was added, yielding 1.4 g of intermediate (72).

c) Preparation of Intermediate (73)

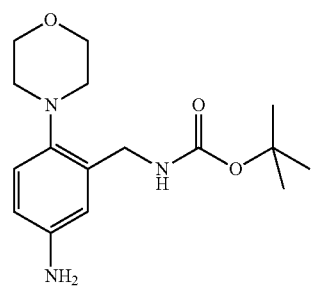 [SMILES: CC(C)(C)OC(=O)NCc1cc(N)ccc1N1CCOCC1]

A solution of NH₄Cl (0.027 mol) in H₂O (40 ml) and Fe (0.027 mol) were added to a solution of intermediate (72) (0.00545 mol) in toluene (20 ml). The reaction mixture was left stirring at 100° C. for 2 hours. Then Fe was removed by filtration over celite. Toluene was separated and the aqueous layer was washed with EtOAc. The combined organic layers were dried (MgSO$_4$), filtered and the solvent was evaporated, yielding 1.4 g of intermediate (73).

d) Preparation of Intermediate (74)

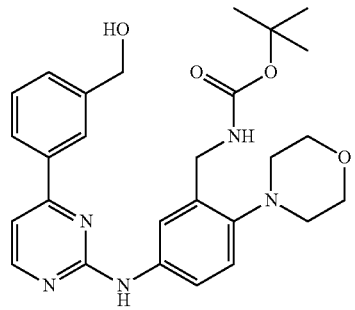 [SMILES: CC(C)(C)OC(=O)NCc1cc(Nc2nccc(-c3cccc(CO)c3)n2)ccc1N1CCOCC1]

Intermediate (73) (0.00468 mol) and 2-propanol (4 ml) were added to a solution of 3-(2-chloro-4-pyrimidinyl)-benzenemethanol (0.00390 mol) in dioxane (16 ml). 15 minutes after that, 4-methyl-benzenesulfonic acid, hydrate (1:1) (0.00409 mol) was added. The reaction mixture was left stirring at 80° C. for 4 hours. Then Et$_3$N (2.2 equiv.) and Di-tert-butyl dicarbonate (1.1 equiv.) were added. Saturated NaHCO$_3$ was added and the product was extracted 3 times with CH$_2$Cl$_2$. The combined organic layers were dried (MgSO$_4$), filtered and the solvent was evaporated. The residue was purified by flash chromatography (eluent: Hexane/EtOAc). The desired fractions were collected and the solvent was evaporated, yielding 1.48 g of intermediate (74).

e) Preparation of Intermediate (75)

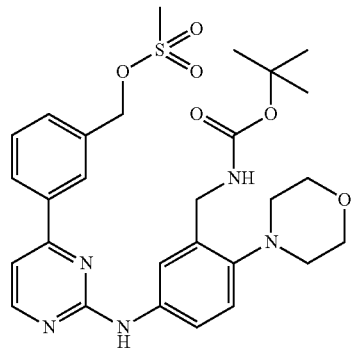 [SMILES: CC(C)(C)OC(=O)NCc1cc(Nc2nccc(-c3cccc(COS(C)(=O)=O)c3)n2)ccc1N1CCOCC1]

Methanesulfonyl chloride (0.00481 mol) was added to a solution of intermediate (74) (0.003 mol) and DIPEA (0.018 mol) in CH$_3$CN (48 ml) at 0-5° C. The reaction mixture was stirred for 4 hours at room temperature. The crude material was used as intermediate (75) in the next reaction step.

f) Preparation of Intermediate (76)

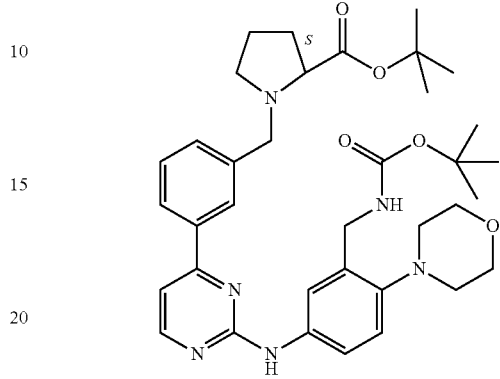

The amino ester tert-butyl L-prolinate (0.000851 mol) was added to a mixture of intermediate (75) (0.000501 mol) and DIPEA (0.003 mol) in CH$_3$CN (8 ml). The reaction mixture was heated overnight at 50° C. and then another 5 hours at 70° C. The solvent was evaporated and the residue was dissolved in CH$_2$Cl$_2$ and washed with saturated NaHCO$_3$. The separated organic layer was dried (MgSO$_4$), filtered and the solvent was evaporated under vacuum. The residue was used as intermediate (76) (S-enantiomer) in the next reaction step.

g) Preparation of Intermediate (77)

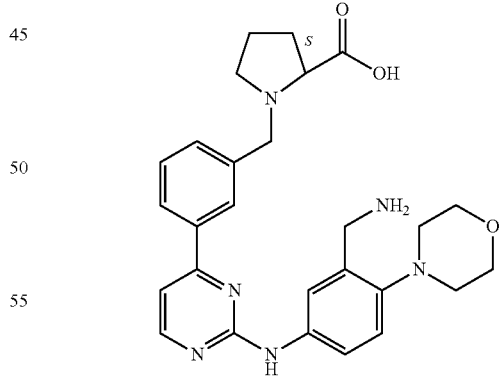

A mixture of the intermediate (76) (0.000501 mol) and TFA/CH$_2$Cl$_2$/TIS (6 ml) was stirred overnight at room temperature. The solvent and THF were evaporated under vacuum and the crude was used as intermediate (77) (S-enantiomer) in the next reaction step.

Example A18 a) Preparation of Intermediate (78)

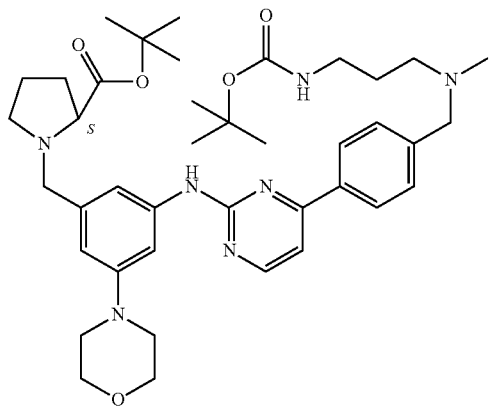

The amino ester tert-butyl L-prolinate, hydrochloride (1:1) (0.001 mol; HCl-salt) was weighed in a reaction tube. A solution (10 ml) of intermediate (52) (0.0005 mol), DIPEA and CH$_3$CN was added and the mixture was stirred at room temperature for 3 hours. Then the mixture was heated overnight at 70° C. Scavenging was done overnight with ScavengePore® benzyl isocyanate. The resin was filtered off and washed with CH$_3$OH and CH$_2$Cl$_2$/CH$_3$OH (4/1). The filtrate was evaporated. The residue was taken in CH$_2$Cl$_2$ and washed with saturated NaHCO$_3$ (3 ml). The separated organic layer was dried (MgSO$_4$), filtered and the solvent was removed, yielding intermediate (78) (S-enantiomer) used as such in the next reaction step.

b) Preparation of Intermediate (79)

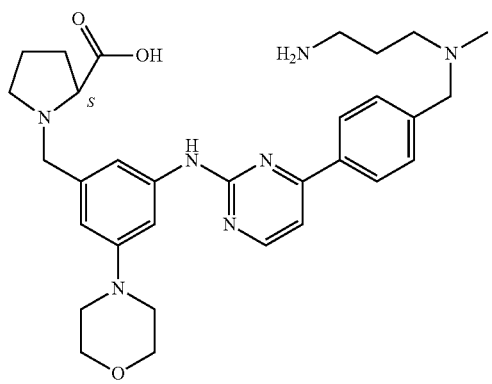

A mixture of the intermediate (78) (0.0005 mol) and TFA/CH$_2$Cl$_2$/TIS (49/49/2; 10 ml, stock solution) was stirred overnight at room temperature. The mixture was concentrated to dryness, yielding intermediate (79) (S-enantiomer) used as such in the next reaction step.

Example A19 a) Preparation of Intermediate (80)

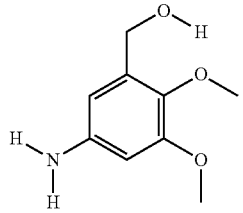

A mixture of 2,3-dimethoxy-5-nitro-benzenemethanol (0.0375 mol) in CH$_3$OH (150 ml) was hydrogenated at room temperature for 20 hours with Pt/C$_5$% (2 g) as a catalyst in the presence of a thiophene solution (1 ml; 4% in DIPE). After uptake of H$_2$ (3 equiv), the catalyst was filtered off and the filtrate was evaporated. The residue was suspended in DIPE. The precipitate was filtered off, washed with DIPE and dried (vacuo), yielding 5.5 g (80%) of intermediate (80).

Example A20 a) Preparation of Intermediate (81)

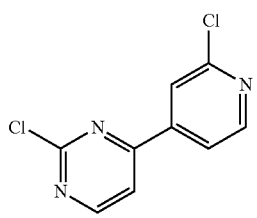 [SMILES: Clc1cc(-c2ccnc(Cl)n2)ccn1]

Buthyllithium (2.5M) (0.0100 mol) was added drop wise at −70° C./−60° C. to a mixture of 2-chloro-4-iodo-pyridine (0.0100 mol) in THF (35 ml) and then stirred for 15 minutes at −70° C./−60° C. 2-Chloro-pyrimidine (0.0100 mol) in THF (15 ml) was added rapidly to the reaction mixture keeping the temperature below −60° C. The reaction mixture was stirred for 15 minutes and then quenched with Et$_2$O/THF (1 ml/3 ml). 4,5-Dichloro-3,6-dioxo-1,4-cyclohexadiene-1,2-dicarbonitrile (0.0100 mol) was added and the reaction mixture was stirred for 15 minutes. Then NaOH (30 ml, 1M) and Et$_2$O (100 ml) were added and stirred overnight. H$_2$O (50 ml) was added to the mixture. The organic layer was separated. The aqueous layer was re-extracted 2 times with Et$_2$O. The organic layers were combined, dried (MgSO$_4$), filtered and the filtrate's solvent was evaporated. The residue was recrystallized with hexane and the precipitate was filtered off, yielding 0.85 g (38.6%) of intermediate (81).

b) Preparation of Intermediate (82)

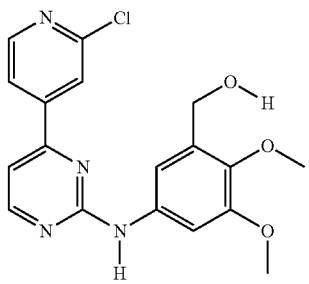 [SMILES: COc1cc(Nc2nccc(-c3ccnc(Cl)c3)n2)cc(CO)c1OC]

A mixture of intermediate (81) (0.02 mol), intermediate (80) (0.02 mol), p-toluene-sulfonic acid (250 ml) and 1,4-dioxane (0.675 g; p.a.) was stirred for 20 hours at 100° C. Then the solvent was evaporated. The residue was suspended in CH$_2$Cl$_2$. The precipitate was collected on a filter, washed with CH$_2$Cl$_2$ and dried (in vacuo), yielding 4.4 g (59.4%) of intermediate (82).

c) Preparation of Intermediate (83)

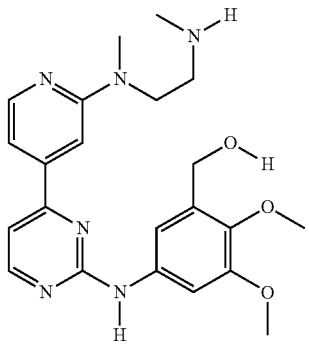 [SMILES: CNCCN(C)c1cc(-c2ccnc(Nc3cc(CO)c(OC)c(OC)c3)n2)ccn1]

A mixture of intermediate (82) (0.006 mol) and N,N'-dimethyl-1,2-ethanediamine (100 ml) was stirred at reflux temperature for 20 hours. Then the solvent was evaporated and the residue was diluted with H$_2$O (50 ml). The product was extracted with CH$_2$Cl$_2$ (2 x). The combined organic lay-ers were washed with H$_2$O, dried (MgSO$_4$), filtered and the solvent was evaporated, yielding 2.3 g (90%) of intermediate (83).

d) Preparation of Intermediate (84)

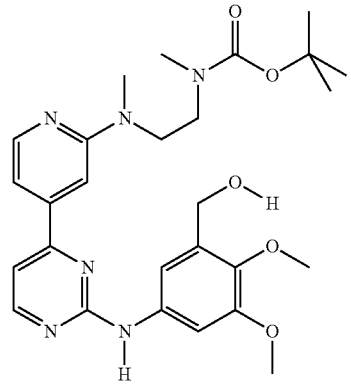 [SMILES: COc1cc(Nc2nccc(-c3ccnc(N(C)CCN(C)C(=O)OC(C)(C)C)c3)n2)cc(CO)c1OC]

A mixture of intermediate (83) (0.005 mol), 1,4-dioxane (90 ml) and Et$_3$N (0.012 mol) was stirred at room temperature. A solution of di-tert-butyl dicarbonate (0.006 mol) in 1,4-dioxane (10 ml) was added dropwise at room temperature. The reaction mixture was stirred at room temperature for 1 hour and was then evaporated. The residue was diluted with H$_2$O and the product was extracted with CH$_2$Cl$_2$. The separated organic layer was dried (MgSO$_4$), filtered and evaporated. The residue (2.8 g) was purified by column chromatography over silicagel (eluent: CH$_2$Cl$_2$/(CH$_3$OH/NH$_3$) 95/5). The desired fractions were collected and the solvent was evaporated, yielding 2 g (76.3%) of intermediate (84).

e) Preparation of Intermediate (85)

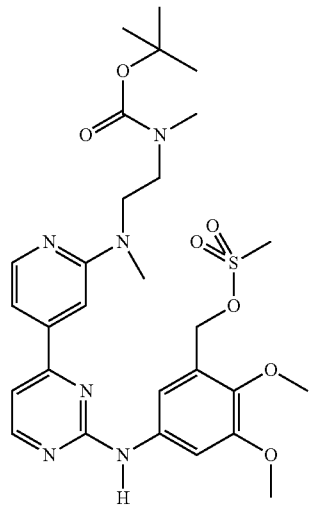 [SMILES: COc1cc(Nc2nccc(-c3ccnc(N(C)CCN(C)C(=O)OC(C)(C)C)c3)n2)cc(COS(C)(=O)=O)c1OC]

A mixture of intermediate (84) (0.0036 mol), CH$_3$CN (190 ml, p.a.) and DIPEA (0.036 mol) was stirred at room temperature. Methanesulfonyl chloride (1.12 ml) was added dropwise at room temperature. The reaction mixture was stirred for 3 hours at room temperature and this mixture was used as intermediate (85) in the next reaction step.

f) Preparation of Intermediate (86)

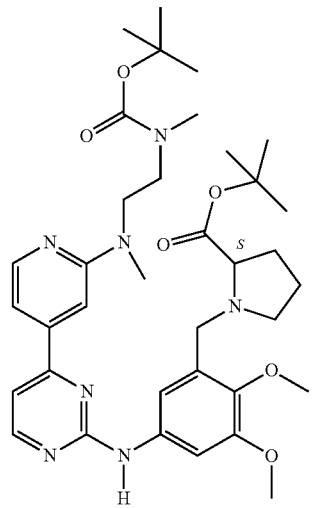

A mixture of intermediate (85) (0.0010 mol), tert-butyl L-prolinate (0.0012 mol) and DIPEA (1 ml) was stirred for 20 hours at 70° C. Then MP-NCO (0.5 g) was added and the reaction mixture was stirred for another 7 hours. The mixture was filtered and the filtrate was evaporated, yielding intermediate (86) (S-enantiomer).

g) Preparation of Intermediate (87)

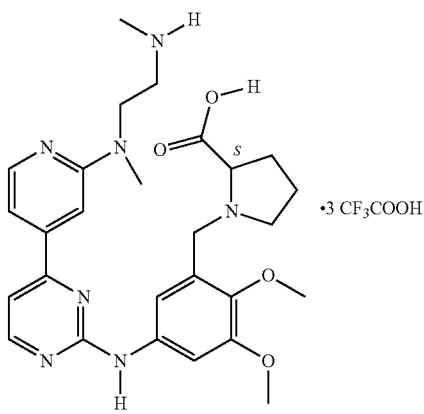

A mixture of intermediate (86) (0.001 mol), $CH_2Cl_2$ (20 ml) and $CF_3COOH$ (20 ml) was stirred at room temperature for 20 hours. Then the mixture was evaporated.

Toluene was added and evaporated again, yielding 1.5 g (crude residue) of intermediate (87) (S-enantiomer; $3CF_3COOH$).

Example A21 a) Preparation of Intermediate (88)

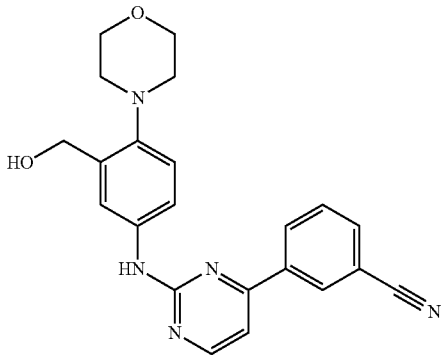 [SMILES: N#Cc1cccc(-c2ccnc(Nc3ccc(N4CCOCC4)c(CO)c3)n2)c1]

Intermediate (1) (0.0450 mol), (5-amino-2-morpholin-4-ylphenyl)methanol (0.0450 mol), 1,4-dioxane (500 ml) and 4-methyl-benzenesulfonic acid, hydrate (1:1) (0.0045 mol) were stirred at 100° C. for 20 hours. The reaction mixture was filtrated and the filtrate evaporated. The residue was dissolved in $CH_2Cl_2$ (150 ml) and washed with NaOH (0.1 N; 100 ml). The organic layer was washed, dried ($MgSO_4$), filtrated and evaporated. The residue was purified over column (silicagel: eluent: $CH_2Cl_2/CH_3OH$ 97/3). The pure fractions were collected and evaporated. The residue was crystallized from $CH_3CN$ (30 ml). The precipitate was collected on a filter and dried in vacuo, yielding 5.30 g (30.4%) of intermediate (88).

b) Preparation of Intermediate (89)

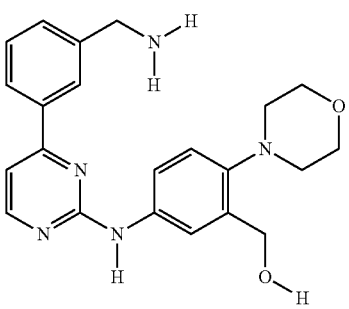 [SMILES: NCc1cccc(-c2ccnc(Nc3ccc(N4CCOCC4)c(CO)c3)n2)c1]

Intermediate (88) (0.0137 mol), Raney Nickel (cat. quant.), $H_2$ (0.0274 mol) and $NH_3/CH_3OH$ (250 ml) were stirred at 14° C. for 20 hours. The reaction mixture was filtrated over hyflo and the filtrate evaporated. The residue was crystallized from CH₃CN (100 ml), filtered off and dried, yielding 4.25 g (79.3%) of intermediate (89).

c) Preparation of Intermediate (90)

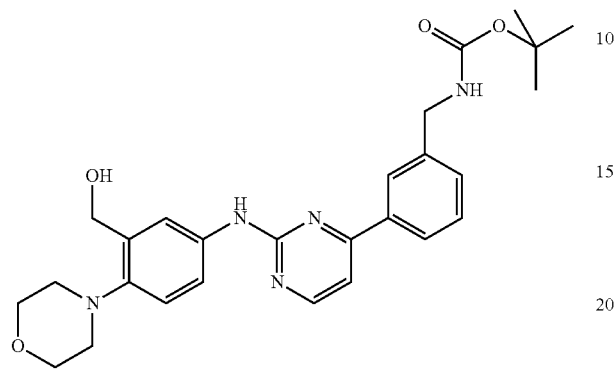

Intermediate (89) (0.0108 mol), 1,4-dioxane (30 ml) and Et₃N (0.0440 mol) was stirred at room temperature. Di-tert-butyl dicarbonate (0.0110 mol) dissolved in 1,4-dioxane (10 ml) was added dropwise at room temperature. The reaction mixture was stirred at room temperature for 30 minutes. The solvent was evaporated. The residue was diluted with H₂O and the product extracted with CH₂Cl₂ (2×100 ml). The organic layers were combined, washed with 100 ml H₂O, dried (MgSO₄), filtrated and evaporated, yielding: 5.3 g (100%) of intermediate (90).

d) Preparation of Intermediate (91)

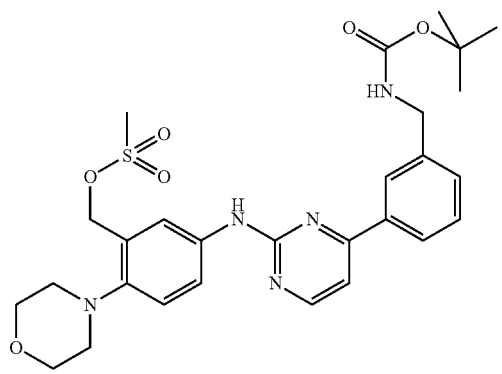 [SMILES: CC(C)(C)OC(=O)NCc1cccc(-c2ccnc(Nc3ccc(N4CCOCC4)c(COS(C)(=O)=O)c3)n2)c1]

Intermediate (90) (0.0040 mol), CH₃CN (125 ml) and DIPEA (0.0400 mol) was stirred at room temperature. Methanesulfonyl chloride was added dropwise at ambient temperature (slightly exotherm). The reaction mixture was stirred at room temperature for 30 minutes. The reaction mixture was used as intermediate (91) in the next reaction step.

e) Preparation of Intermediate (92)

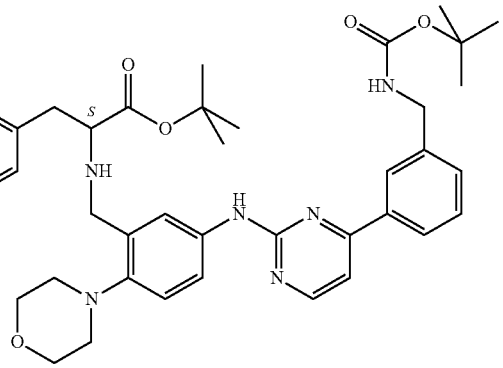

The amino ester tert-butyl L-phenylalaninate, hydrochloride (1:1) (0.00129 mol; HCl-salt) was weighed in a reaction tube. A solution (10 ml) of intermediate (91) (0.00043 mol) and DIPEA in CH₃CN, was added. The mixture was shaken at room temperature for 1 hour. Then the mixture was heated overnight at 45° C. Scavenging was done overnight with Wang aldehyde resin (q.s.). The resin was filtered off, washed with CH₃OH and a mixture of CH₂Cl₂/CH₃OH (4:1). The filtrate's solvent was removed. Then the residue was taken in CH₂Cl₂ and washed with saturated NaHCO₃ (5 ml). The separated organic layer was dried (MgSO₄), filtered and the solvent was evaporated. The crude was used as intermediate (92) in the next reaction step.

f) Preparation of Intermediate (93)

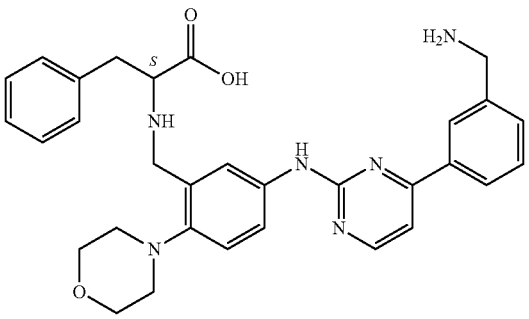

A mixture of intermediate (92) (0.00043 mol) and TFA/CH₂Cl₂/TIS (49/49/2; 10 ml, stock solution) was shaken overnight at room temperature. The solvent was evaporated and the crude was used as intermediate (93) (S-enantiomer) in the next reaction step.

Example A22 a) Preparation of Intermediate (94)

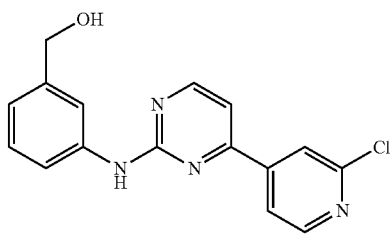 [SMILES: OCc1cccc(Nc2nccc(-c3ccnc(Cl)c3)n2)c1]

2-Chloro-4-(2-chloropyridin-4-yl)pyrimidine (0.0055 mol), 3-amino-benzenemethanol (0.008 mol) and 4-methyl-benzenesulfonic acid, hydrate (1:1) (0.0008 mol) was dissolved in 1,4-dioxane (40 ml) and stirred overnight at 100° C. The supernatant was decanted and the residue was discarded. The supernatant's solvent was evaporated. The residue was triturated under $CH_3CN$. The precipitate was filtered off, washed with $CH_3CN$ and dried (in vacuo, 60° C.), yielding 1.2788 g (100%) of intermediate (94) (m.p.: 130.6° C.-132.3° C.).

b) Preparation of Intermediate (95)

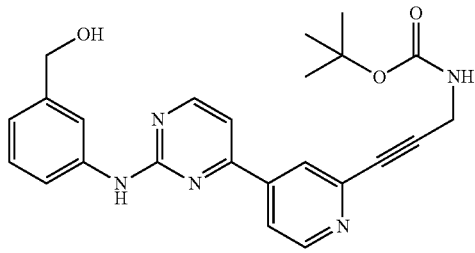 [SMILES: CC(C)(C)OC(=O)NCC#Cc1cc(-c2ccnc(Nc3cccc(CO)c3)n2)ccn1]

A mixture of intermediate (94) (0.00375 mol), tert-butyl prop-2-yn-1-ylcarbamate (0.005625 mol), $Pd(PPh_3)Cl_2$ (0.132 g), diethylamine (0.05625 mol), copper iodide (0.036 g) and $PPh_3$ (0.197 g) in DMF (150 ml) was degassed with $N_2$ for 5 minutes and then stirred for 16 hours at 60° C. Diethylamine (0.0505 mol) was added again and stirred for 24 hours at 80° C. $H_2O$ (20 ml) was added to the reaction mixture. The solvent was evaporated. The residue was dissolved in $CH_2Cl_2$ and $H_2O$. The separated organic layer was washed with brine, dried ($Na_2SO_4$ anhydrous), filtered and the solvent was evaporated. The residue was purified by flash column chromatography over silica gel (eluent: $CH_2Cl_2/CH_3OH/(7N\ NH_3$ in $CH_3OH$) from 100/0/0 to 90/5/5). The product fractions were collected and the solvent was evaporated. The residue was triturated under $CH_3CN$ (50 ml) for 48 hours. The precipitate was filtered off resulting in filter residue. This residue was washed with $CH_3CN$ and dried (vacuo, 75° C.), yielding 0.5759 g (36%) of intermediate (95) (m.p.: 154.6° C.-155.2° C.).

c) Preparation of Intermediate (96)

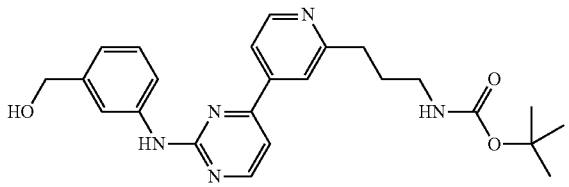 [SMILES: CC(C)(C)OC(=O)NCCCc1cc(-c2ccnc(Nc3cccc(CO)c3)n2)ccn1]

A mixture of intermediate (95) (0.0014 mol) in $CH_3OH$ (50 ml) was hydrogenated with Raney Nickel (catalytic quantities) as a catalyst. After uptake of $H_2$ (2 equiv), the catalyst was filtered off and the filtrate's solvent was evaporated. The residue was washed 2 times with hexane (100 ml) and dried (vacuo). This residue was dissolved in $CH_3CN$ and was stood overnight in the fridge. The precipitate was filtered off, washed with $CH_3CN$ and dried (vacuo, 75° C.), yielding 0.4469 g (73%; m.p.: 115.9° C.-116.9° C.) of intermediate (96).

d) Preparation of Intermediate (97)

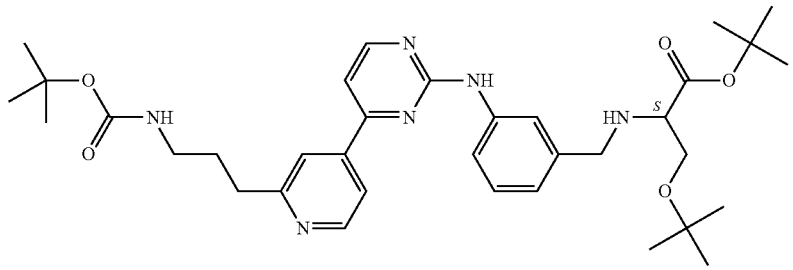

DIPEA (0.0018 mol) and then methanesulfonyl chloride (0.00045 mol) were added to a solution of intermediate (96) (0.0003 mol) in DMF (5 ml) and stirred for 5 minutes. tert-butyl-O-tert-butyl-L-serinate, hydrochloride (1:1) (0.0012 mol) was added and the reaction mixture was stirred overnight at 65° C. PS-CHO (1.5 g) was added to the reaction mixture and shaken over the weekend at room temperature. The reaction mixture was filtered, the filter residue was washed with DMF and the combined filtrate's solvent was evaporated to dryness, yielding intermediate (97) (S-enantiomer) used as such in next reaction step.

e) Preparation of Intermediate (98)

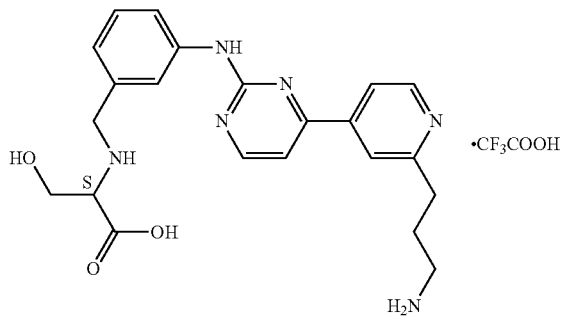

Intermediate (97) (0.0003 mol) was dissolved in CH$_2$Cl$_2$/CF$_3$COOH (10 ml; 1/1) and stirred for 1 hour at 40° C. The solvent was evaporated to dryness, yielding intermediate (98) (S-enantiomer; CF$_3$COOH) used as such in next reaction step.

Example A23 a) Preparation of Intermediate (99)

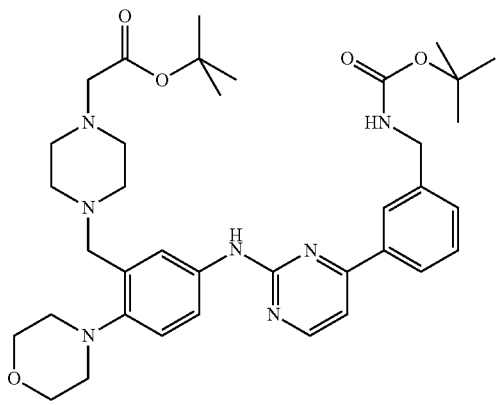 [SMILES: CC(C)(C)OC(=O)CN1CCN(Cc2cc(Nc3nccc(-c4cccc(CNC(=O)OC(C)(C)C)c4)n3)ccc2N2CCOCC2)CC1]

The amino ester 1-piperazineacetic acid, tert-butyl piperazin-1-ylacetate dihydrochloride (0.000645 mol) was weighed in a reaction tube. 10 ml of a solution of intermediate (91) (0.00043 mol) and DIPEA in CH$_3$CN was added. The mixture was shaken at room temperature for 1 hour. Then the mixture was heated overnight at 45° C. Scavenging was done overnight with ScavengePore® benzyl isocyanate (q.s.). The resin was filtered off, washed with CH$_3$OH and a mixture of CH$_2$Cl$_2$/CH$_3$OH (4:1). The filtrate's solvent was removed. Then the residue was taken in CH$_2$Cl$_2$ and washed with saturated NaHCO$_3$ (5 ml). The separated organic layer was dried (MgSO$_4$), filtered and the solvent was evaporated. The crude intermediate (99) was used as such in the next reaction step.

b) Preparation of Intermediate (100)

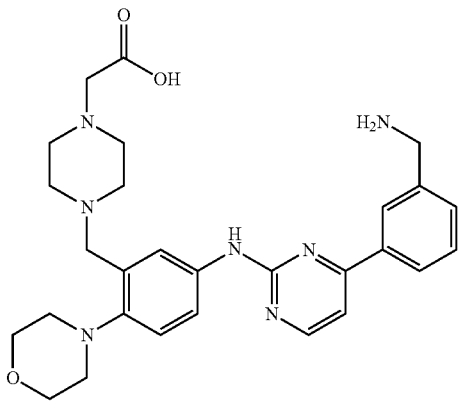 [SMILES: NCc1cccc(-c2ccnc(Nc3ccc(N4CCOCC4)c(CN4CCN(CC(=O)O)CC4)c3)n2)c1]

A mixture of the intermediate (99) (0.00043 mol) and TFA/CH$_2$Cl$_2$/TIS (49/49/2; 10 ml, stock solution) was shaken overnight at room temperature. The solvent was evaporated and the crude intermediate (100) was used as such in the next reaction step.

Example A24 a) Preparation of Intermediate (101)

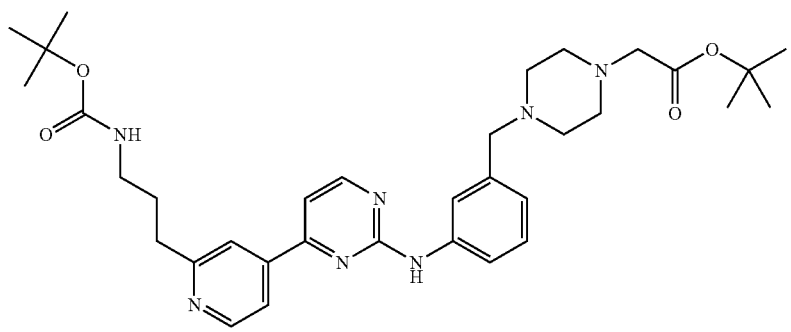 [SMILES: CC(C)(C)OC(=O)CN1CCN(Cc2cccc(Nc3nccc(-c4ccnc(CCCNC(=O)OC(C)(C)C)c4)n3)c2)CC1]

Methanesulfonyl chloride (0.0018 mol) and then DIPEA (0.00045 mol) were added to a solution of intermediate (96) (0.0003 mol) in DMF (5 ml) and stirred for 5 minutes. 1-tert-butyl piperazin-1-ylacetate, dihydrochloride (0.0006 mol) was added and the reaction mixture was stirred overnight at 65° C. PS-NCO resin (0.900 g) was added to the reaction mixture and shaken over the weekend at room temperature. The reaction mixture was filtered, the filter residue was washed with DMF and the combined filtrate's solvent was evaporated to dryness, yielding crude intermediate (101) used as such in next reaction step.

b) Preparation of Intermediate (102)

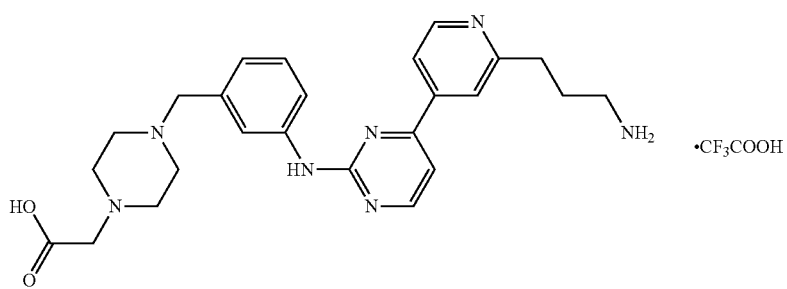 [SMILES: NCCCc1cc(-c2ccnc(Nc3cccc(CN4CCN(CC(=O)O)CC4)c3)n2)ccn1 ; "·CF3COOH"]

Intermediate (101) (0.0003 mol) was dissolved in $CH_2Cl_2$/$CF_3COOH$ (1/1; 10 ml) and stirred for 1 hour at 40° C. The solvent was evaporated to dryness, yielding crude intermediate (102) ($CF_3COOH$) used as such in next reaction step.

B. Preparation of the Compounds

Example B1 a) Preparation of Compound (1)

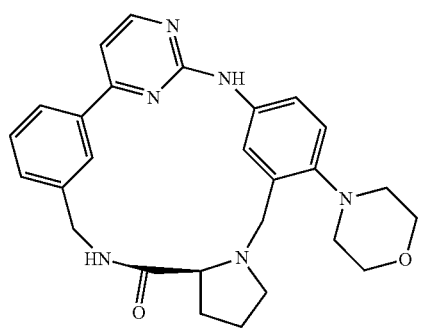 [SMILES: O=C1NCc2cccc(c2)-c2ccnc(n2)Nc2ccc(N3CCOCC3)c(c2)CN2CCC[C@@H]12]

Intermediate (6) (0.0270 mol) dissolved in DMF (500 ml) was added dropwise (Watson-Marlow pump, 2 rpm) to a solution of HBTU (0.0660 mol) in DMF (q.s.) and DIPEA (75 ml). The reaction was quenched with of $CH_3OH/NH_3$ (7N; 50 ml) and then concentrated. The residue was dissolved in $CH_2Cl_2$ (1000 ml) and washed with 1M NaOH and three times with water (300 ml). The organic layer was dried ($MgSO_4$), filtered and concentrated to give a brown oil. This oil was chromatographed (Reversed Phase). After work-up, the residue was triturated with $CH_3OH$ and stirred overnight. The solid was collected and chromatographed. After work-up, the obtained residue was suspended in DIPE and a small amount of $CH_3OH$, and was subsequently stirred for 6 hours. The solid was collected and dried for 20 hours at 85° C. (in vacuo). This fraction was suspended in $EtOH/CH_3CN$, boiled for 3 hours, cooled and concentrated and dried in at 65° C. (in vacuo), yielding 1.421 g (11.1%) of compound (1) (S-enantiomer).

b) Preparation of Compound (2)

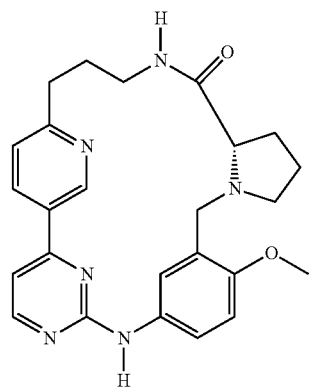 [SMILES: COc1ccc2cc1CN1CCC[C@H]1C(=O)NCCCc1ccc(cn1)-c1ccnc(n1)N2]

HBTU (1 g) in DIPEA (10 ml) and DMF (20 ml) was stirred at room temperature. Intermediate (12) (0.001 mol) in DMF (60 ml) was added drop wise at room temperature to the reaction mixture over a period of 90 minutes. The reaction mixture was stirred for 20 hours at room temperature. $Na_2CO_3$ 10% aqueous solution (10 ml) was added to the reaction mixture. The solvent was evaporated. The residue was diluted with $H_2O$. This mixture was extracted 2 times with $CH_2Cl_2$. The combined separated organic layers were washed with $H_2O$, dried ($MgSO_4$), filtered and the solvent was evaporated. The residue was purified by reversed-phase high-performance liquid chromatography (Shandon Hyperprep® C18 BDS (Base Deactivated Silica) 8 µm, 250 g, I.D. 5 cm). A gradient with two or three mobile phases was applied (phase A: a 0.25% $NH_4HCO_3$ solution in water; phase B (optional): $CH_3OH$; phase C: $CH_3CN$). The product fractions were collected and after work-up, the residue was recrystallized from $CH_3CN$ and the precipitate was filtered, yielding 0.025 g (5.6%) of compound (2) (S-enantiomer).

Example B2 a) Preparation of Compound (3)

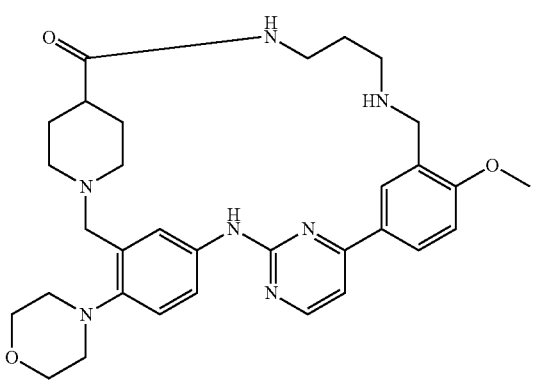 [SMILES: COc1ccc2cc1CNCCCNC(=O)C1CCN(CC1)Cc1cc(ccc1N1CCOCC1)Nc1nccc-2n1]

A mixture of intermediate (19) (0.000250 mol) in DMF (10 ml) was added dropwise over 90 minutes to a solution of HBTU (0.000750 mol) and DIPEA (0.01176 mol) in DMF (10 ml). The reaction mixture was stirred for 30 minutes and was then concentrated to dryness. The residue was taken up in THF (10 ml) and treated overnight with 10 g AMBERLYST™ A260H. The mixture was filtered and the solvent was evaporated. The residue was purified by column chromatography (eluent: $CH_2Cl_2/CH_3OH$ from 50/1 to 10/1 (v/v)). The desired fractions were collected and the solvent was evaporated, yielding compound (3).

b) Preparation of Compound (4)

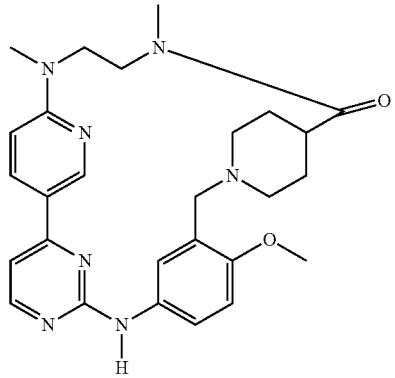 [SMILES: COc1ccc2cc1CN1CCC(CC1)C(=O)N(C)CCN(C)c1ccc(cn1)-c1ccnc(n1)N2]

Intermediate (25) (0.001 mol) dissolved in DMF (20 ml) was added dropwise over a period of 90 minutes to a mixture at room temperature of HBTU (1 g) and DIPEA (10 ml) in DMF (60 ml). The reaction mixture was stirred for 90 minutes at room temperature. The solvent was evaporated. The residue was dissolved in $CH_2Cl_2$ and this mixture was washed with $H_2O$. The separated organic layer was dried ($MgSO_4$), filtered and the solvent was evaporated. The residue was purified by reversed-phase high-performance liquid chromatography (Shandon Hyperprep® C18 BDS (Base Deactivated Silica) 8 μm, 250 g, I.D. 5 cm). A gradient with two or three mobile phases was applied (phase A (=buffer): (0.25% $NH_4HCO_3$ in $H_2O$); phase B: $CH_3OH$ (optional); phase C: $CH_3CN$). The product fractions were collected and after work-up the residue was re-crystallized from $CH_3CN$, the precipitate was filtered off and dried (in vacuo), yielding 0.075 g (15.4%) of compound (4).

Example B3

Preparation of Compound (5)

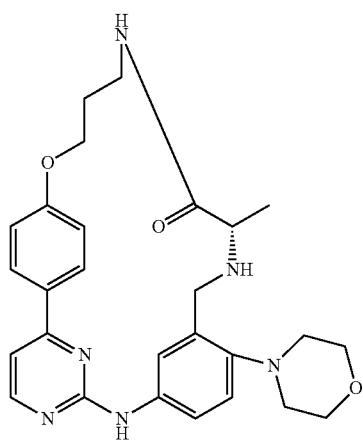 [SMILES: C[C@@H]1NCc2cc(ccc2N2CCOCC2)Nc2nccc(n2)-c2ccc(cc2)OCCCNC1=O]

A mixture of intermediate (31) (0.00050 mol) in DMF (10 ml) was added dropwise to a solution of HBTU (0.00125 mol) and DIPEA (0.015 mol) in DMF (10 ml), using a Watson-Marlow peristaltic pump (1 rpm). After addition, the reaction mixture was stirred at room temperature for 30 minutes. The solvent was evaporated. Then THF (10 ml) and Amberlyst A26(OH) (15 g) were added and the mixture was shaken overnight. The resin was filtered off and washed with a mixture of $CH_2Cl_2/CH_3OH$ (10:1) and the filtrate's solvent was evaporated. When desired the resulting crude can be further purified by flash chromatography, resulting in 0.007 g of compound (5) (S-enantiomer).

Example B4

Preparation of Compound (6)

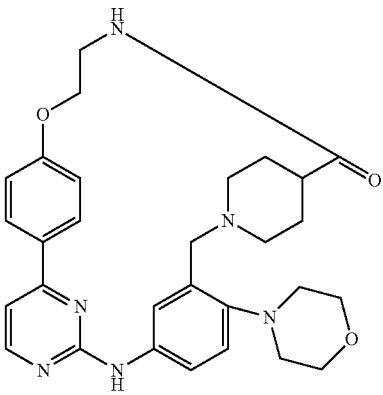 [SMILES: O=C1NCCOc2ccc(cc2)-c2ccnc(n2)Nc2ccc(N3CCOCC3)c(c2)CN2CCC1CC2]

A mixture of intermediate (36) (0.00025 mol) and DMF (10 ml) was added dropwise to a solution of HBTU (0.00075 mol) and DMF (0.00075 mol) in DMF (10 ml), using a Watson-Marlow peristaltic pump (1 rpm). After addition the mixture was stirred at room temperature one additional hour. The solvent was evaporated. Then THF (10 ml) and Amberlyst A26(OH) (10 g) were added and the mixture was shaken overnight. The resin was filtered off and washed with a mixture of $CH_2Cl_2/CH_3OH$ (10:1) and the filtrate's solvent was evaporated. The resulting crude was purified by flash chromatography over silica gel (eluent: $CH_2Cl_2/CH_3OH$). The desired fractions were collected and the solvent was evaporated. The product was dried in a DD4 vacuum centrifuge (Genevac), yielding 0.008 g of compound (6).

Example B5

Preparation of Compound (7)

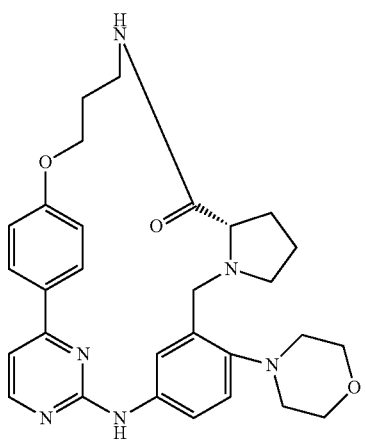 [SMILES: O=C1NCCCOc2ccc(cc2)-c2ccnc(n2)Nc2ccc(N3CCOCC3)c(c2)CN2CCC[C@@H]12]

A solution of crude intermediate (38) (0.0003 mol) in DMF (10 ml) was added dropwise to a mixture of HBTU (0.0009 mol) and DIPEA (0.009 mol) in DMF (10 ml). The mixture was stirred for 30 minutes at room temperature. The solvent was evaporated. The crudes were dissolved in THF and treated with Amberlyst A26 OH. Then the product was purified by flash chromatography. The desired fractions were collected and the solvent was evaporated, yielding 0.010 g of compound (7) (S-enantiomer).

Example B6

Preparation of Compound (8)

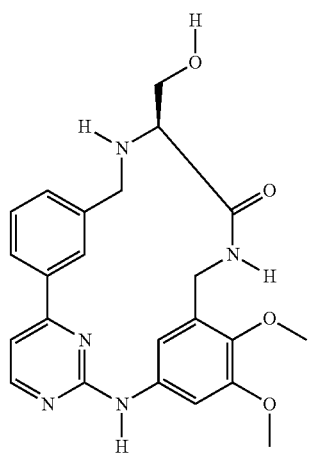 [SMILES: COc1cc2cc(c1OC)CNC(=O)[C@H](CO)NCc1cccc(c1)-c1ccnc(n1)N2]

HBTU (0.0013 mol) DMF (20 ml) and DIPEA (10 ml) were stirred at room temperature. Intermediate (46) (0.0010 mol) dissolved in DMF (60 ml) was added dropwise at room temperature over a 90 minutes period. The reaction mixture was evaporated. The residue was diluted with $H_2O$ (50 ml) and NaOH 1N (5 ml). The product was extracted with $CH_2Cl_2$ (2×80 ml). The combined organic layers were washed with $H_2O$, dried ($MgSO_4$), filtrated and evaporated. The residue was purified over column chromatography (silicagel: $CH_2Cl_2/(CH_3OH/NH_3)$ 96/4). The pure fractions were collected and evaporated. The residue was crystallized from $CH_3CN$ (10 ml). The precipitate was collected on a filter, washed with a little $CH_3CN$ and dried in vacuo, yielding 0.047 g (10.08%) of compound (8) (S-enantiomer).

Example B7

Preparation of Compound (9)

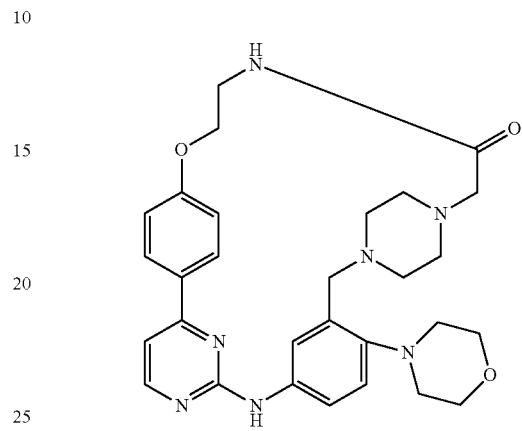

The reaction was done analogously to Example B4, using intermediate (48) prepared as described in Example A11 b), yielding compound (9).

Example B8 a) Preparation of Compound (10)

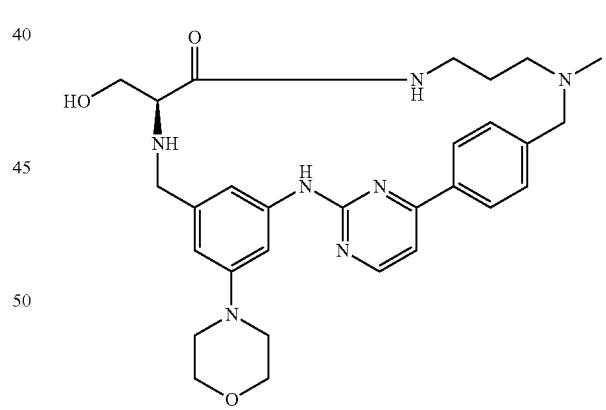

The crude intermediate (54) (0.0005 mol) was dissolved in DMF (15 ml). The resulting solution was added slowly over 2 hours to a solution of HBTU (0.0015 mol) and DIPEA (0.025 mol) in DMF (100 ml). Then the reaction mixture was stirred for 30 minutes. $NH_3$ (aqueous; 1 ml) was added and the reaction mixture was stirred for another 15 minutes. The residue was taken in $CH_2Cl_2$ and washed with $Na_2CO_3$ (1M). The phases were separated and the organic layer was washed once more with $H_2O$. The separated organic phase was dried ($MgSO_4$), filtered and the solvent was evaporated. The crude residue was purified by column chromatography over silica gel. The desired fractions were collected and the solvent was evaporated, yielding compound (10) (S-enantiomer).

b) Preparation of Compound (11)

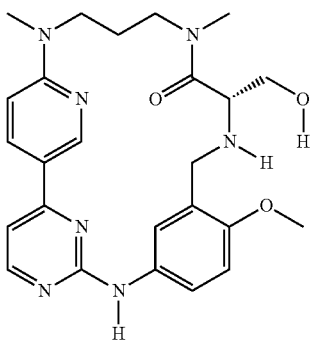

Intermediate (59) (0.0007 mol) dissolved in DMF (50 ml) was added drop wise over a period of 90 minutes to a stirring mixture at room temperature of HBTU (7 g) in DIPEA (10 ml) and DMF (10 ml). The reaction mixture was stirred for 2 hours at room temperature. The solvent was evaporated. The residue was diluted with $H_2O/Na_2CO_3$ 0.4M aqueous solution (5 ml) and then extracted 2 times with $CH_2Cl_2$. The 2 separated organic layers were combined and was washed with $H_2O$, dried ($MgSO_4$), filtered and the solvent was evaporated. The residue was purified by reversed-phase high-performance liquid chromatography (Shandon Hyperprep® C18 BDS (Base Deactivated Silica) 8 μm, 250 g, I.D. 5 cm). A gradient with two or three mobile phases was applied (phase A: a 0.25% $NH_4HCO_3$ solution in water (buffer); phase B (optional): $CH_3OH$; phase C: $CH_3CN$). The product fractions were collected and after work-up, the residue was re-crystallized from $CH_3CN$ and the precipitate was filtered off, yielding 0.026 g (8%) of compound (11) (S-enantiomer).

Example B9

Preparation of Compound (12)

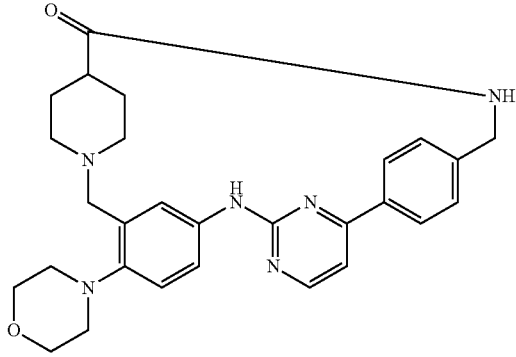 [SMILES: O=C1NCc2ccc(cc2)-c2ccnc(n2)Nc2ccc(N3CCOCC3)c(c2)CN2CCC1CC2]

Intermediate (66) (0.00045 mol) was taken up in DMF (40 ml). This solution was added slowly (over 6 hours) to a solution of HBTU (0000135 mol) and DIPEA (0.025 mol) in DMF (100 ml). The reaction mixture was stirred for 30 minutes and then $NH_3$ (aqueous, 25%, 1 ml) was added and the mixture was stirred for 30 minutes. The solvent was evaporated and the residue was taken up in $CH_2Cl_2$. The organic layer was washed with $Na_2CO_3$ (1 M) and once more with $H_2O$. The separated organic layer was dried ($MgSO_4$), filtered and the solvent was evaporated. The crude residue was purified by column chromatography over silica gel. The desired fractions were collected and the solvent was evaporated, yielding 0.010 g of compound (12).

Example B10 a) Preparation of Compound (13)

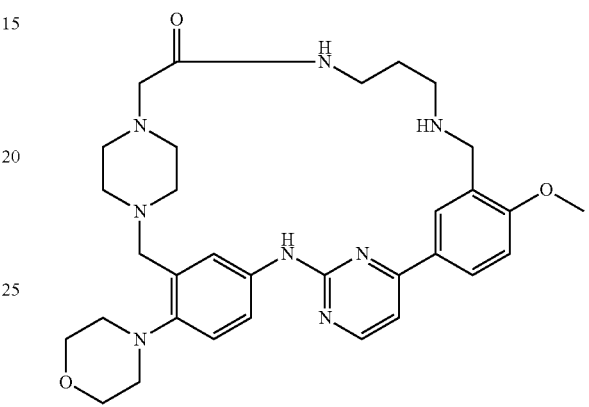

The reaction was done analogously to Example B2a), using intermediate (68) prepared as described in Example A15 b), yielding compound (13).

b) Preparation of Compound (14)

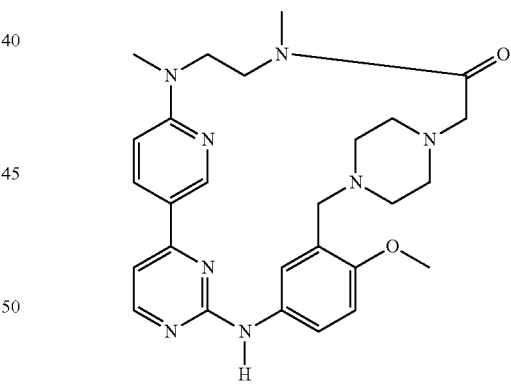

Intermediate (70) (0.001 mol) dissolved in DMF (20 ml; p.a.) was added drop wise over a period of 90 minutes to a mixture at room temperature of HBTU (1 g) and DIPEA (10 ml) in DMF (60 ml). The reaction mixture was stirred for 6 hours at room temperature. The solvent was evaporated. The residue was diluted with $H_2O$ and then extracted 2 times with $CH_2Cl_2$. The separated organic layer was washed with $H_2O$, dried ($MgSO_4$), filtered and the solvent was evaporated. The residue was purified by reversed-phase high-performance liquid chromatography (Shandon Hyperprep® C18 BDS (Base Deactivated Silica) 8 μm, 250 g, I.D. 5 cm). A gradient with two or three mobile phases was applied (phase A: a 0.25% $NH_4HCO_3$ solution in water (buffer); phase B (optional):

CH₃OH; phase C: CH₃CN). The product fractions were collected and after work-up, the residue was re-crystallized from CH₃CN, the precipitate was filtered off and dried, yielding 0.136 g (26.1%) of compound (14).

Example B11

Preparation of Compound (15)

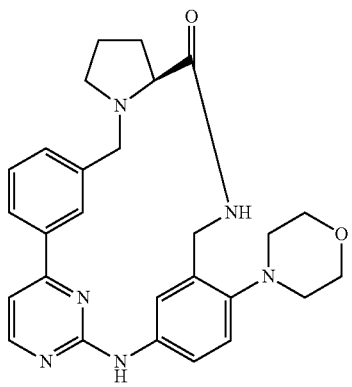 [SMILES: O=C1NCc2cc(ccc2N2CCOCC2)Nc2nccc(n2)-c2cccc(c2)CN2CCC[C@@H]12]

A solution of intermediate (77) (0.000501 mol) in DMF (15 ml) was added slowly to a mixture of HBTU (0.001503 mol) and DIPEA (0.015 mol) in DMF (20 ml) at room temperature. The reaction mixture was additionally stirred for 30 minutes. Then ammonia in CH₃OH was added. The solvent was evaporated and the residue was dissolved in CH₂Cl₂ and washed with Na₂CO₃ (1M). The separated organic phase was concentrated to dryness. The residue was purified by flash chromatography over silica gel (eluent: CH₂Cl₂/CH₃OH 60/1 to 10/1). The desired fractions were collected and the solvent was evaporated, yielding 0.077 g of compound (15) (S-enantiomer).

Example B12 a) Preparation of Compound (16)

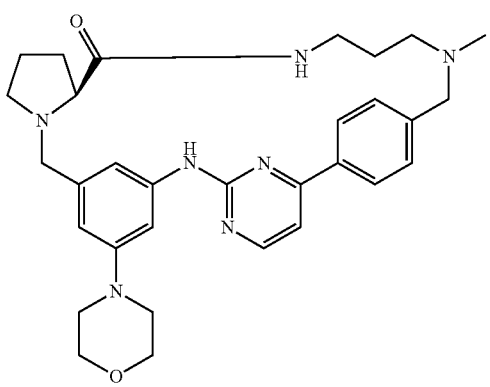 [SMILES: CN1CCCNC(=O)[C@@H]2CCCN2Cc2cc(cc(N3CCOCC3)c2)Nc2nccc(n2)-c2ccc(cc2)C1]

The crude intermediate (79) (0.0005 mol) was dissolved in DMF (15 ml). The resulting solution was added slowly over 2 hours to a solution of HBTU (0.0015 mol) and DIPEA (0.025 mol) in DMF (20 ml). Then the reaction mixture was stirred for 30 minutes. NH₃ (aqueous; 1 ml) was added and the reaction mixture was stirred for another 15 minutes. The residue was taken in CH₂Cl₂ and washed with Na₂CO₃ (1M). The phases were separated and the organic layer was washed once more with H₂O. The separated organic phase was dried (MgSO₄), filtered and the solvent was evaporated. The crude residue was purified by column chromatography over silica gel. The desired fractions were collected and the solvent was evaporated, yielding compound (16) (S-enantiomer).

b) Preparation of Compound (17)

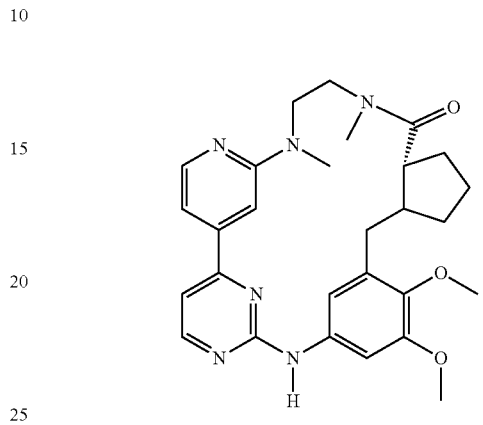

A mixture of HBTU (1 g), DMF (20 ml) and DIPEA (10 ml) was stirred at room temperature. A solution of intermediate (87) (0.001 mol) in DMF (60 ml) added dropwise to this mixture in 90 minutes. The reaction mixture was stirred for 20 hours at room temperature and was then evaporated. The residue was diluted with H₂O and an aqueous NaOH solution (5 ml; 1N). The product was extracted with CH₂Cl₂ (2×). The combined organic layers were washed with H₂O, dried (MgSO₄), filtered and the solvent was evaporated. The residue was purified by reversed phase high-performance liquid chromatography (Shandon Hyperprep® C18 BDS (Base Deactivated Silica) 8 μm, 250 g, I.D. 5 cm). A gradient with two or three mobile phases was applied (phase A (buffer): 90% of a 0.5% NH₄OAc solution in water+10% CH₃CN; phase B (optional): CH₃OH; phase C: CH₃CN). The desired fractions were collected and after work-up, the product yielded 0.017 g of compound (17) (S-enantiomer).

Example B13 a) Preparation of Compound (18)

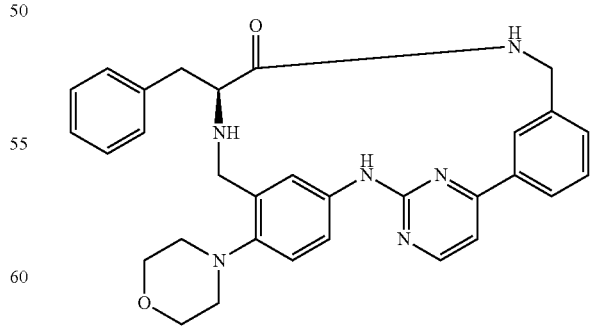

A mixture of intermediate (93) (0.00043 mol) and DMF (15 ml) was added slowly to a solution of HBTU (0.00172 mol) and DIPEA (0.025 mol) in DMF (100 ml). The reaction mixture stirred for 30 minutes and then aqueous NH₃ (1 ml;

25%) was added. The mixture stirred for another 30 minutes. The solvent was evaporated and the residue was taken in CH₂Cl₂ and washed with Na₂CO₃ (1M). The separated organic layer was washed again with H₂O. The combined organic layers were dried (MgSO₄), filtered and the solvent was evaporated. The residue was purified by flash chromatography over silica gel. The desired fractions were collected and the solvent was evaporated, yielding 0.074 g of compound (18) (S-enantiomer).

b) Preparation of Compound (19)

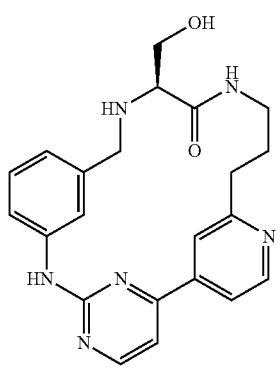 [SMILES: O=C1NCCCc2cc(ccn2)-c2ccnc(n2)Nc2cccc(c2)CN[C@H]1CO]

Intermediate (98) (0.0003 mol) dissolved in DMF (20 ml) was added drop wise to a mixture of HBTU (0.0006 mol) and DIPEA (0.006 mol) in DMF (20 ml). The reaction mixture was added drop wise to DIPEA (1 ml). After addition, NH₃ in CH₃OH 7N (10 ml) was added to the reaction mixture. The solvent was evaporated. The residue was dissolved in CH₂Cl₂ (50 ml) and Na₂CO₃ 10% aqueous solution (50 ml). The layers were separated into an organic layer and an aqueous layer. The aqueous layer was re-extracted 3 times with CH₂Cl₂/CH₃OH (95/5, 50 ml) to obtain 3 organic layers. All organic layers were combined, dried (Na₂SO₄), filtered and the solvent was evaporated. The residue was purified by reversed-phase high-performance liquid chromatography (Shandon Hyperprep® C18 BDS (Base Deactivated Silica) 8 µm, 250 g, I.D. 5 cm). A gradient with two or three mobile phases was applied (phase A: a 0.25% NH₄HCO₃ solution in water (buffer); phase B (optional): CH₃OH; phase C: CH₃CN). The product fractions were collected and after work-up, the residue was re-crystallized from CH₃CN and the precipitate was filtered off, yielding 0.0193 g of compound (19) (S-enantiomer).

Example B14 a) Preparation of Compound (20)

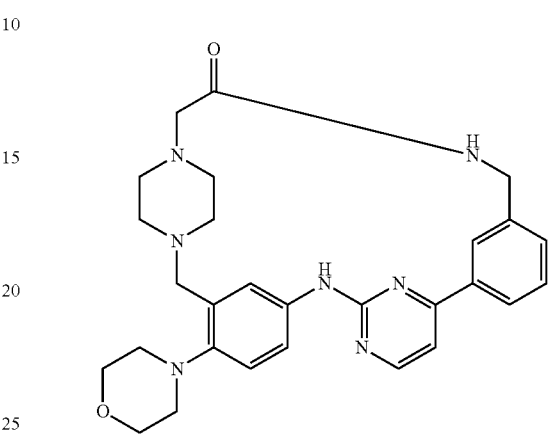

A solution of intermediate (100) (0.00043 mol) and DMF (15 ml) was added slowly over 2 hours to a mixture of HBTU (0.00129 mol) and DIPEA (0.025 mol) in DMF (20 ml). The reaction mixture stirred for 30 minutes and then aqueous NH₃ (1 ml; 25%) was added. The mixture stirred for another 30 minutes. The solvent was evaporated and the residue was taken in CH₂Cl₂ and washed with Na₂CO₃ (1M). The separated organic layer was washed again with H₂O. The combined organic layers were dried (MgSO₄), filtered and the solvent was evaporated. The residue was purified by column chromatography over silica gel. The desired fractions were collected and the solvent was evaporated, yielding 0.082 g of compound (20).

b) Preparation of Compound (21)

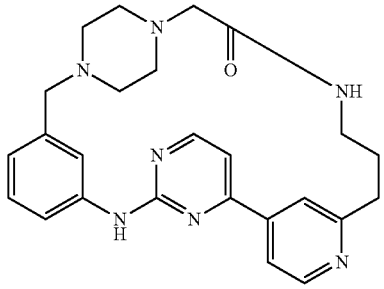 [SMILES: O=C1CN2CCN(CC2)Cc2cccc(c2)Nc2nccc(n2)-c2ccnc(c2)CCCN1]

Intermediate (102) (0.0003 mol) dissolved in DMF (20 ml) was added drop wise to a mixture of HBTU (0.0006 mol) and DIPEA (0.006 mol) in DMF (20 ml). The reaction mixture was added drop wise to DIPEA (1 ml). After addition, NH₃ in CH₃OH 7N (10 ml) was added to the reaction mixture. The solvent was evaporated. The residue was dissolved in CH₂Cl₂ (50 ml) and Na₂CO₃ 10% aqueous solution (50 ml). The layers were separated into an organic layer and an aqueous layer. The aqueous layer was re-extracted 3 times with CH₂Cl₂/CH₃OH (95/5, 50 ml) to obtain 3 organic layers. All organic layers were combined, dried (Na$_2$SO$_4$ anhydrous), filtered and the solvent was evaporated. The residue was purified by reversed-phase high-performance liquid chromatography (Shandon Hyperprep® C18 BDS (Base Deactivated Silica) 8 μm, 250 g, I.D. 5 cm). A gradient with two or three mobile phases was applied (phase A: a 0.25% NH$_4$HCO$_3$ solution in water (buffer); phase B (optional): CH$_3$OH; phase C: CH$_3$CN). The product fractions were collected and after work-up, the residue was re-crystallized from CH$_3$CN and the precipitate was filtered of, yielding 0.0333 g of compound (21).

TABLE 1 compounds according to the invention

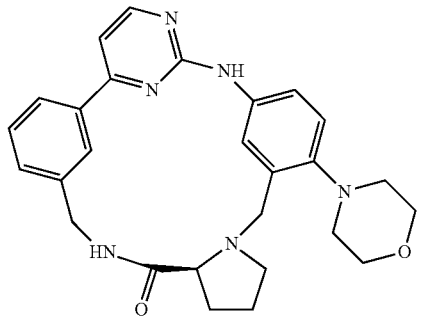 [SMILES: O=C1NCc2cccc(c2)-c2ccnc(n2)Nc2ccc(N3CCOCC3)c(c2)CN2CCC[C@@H]12]

Co. No. (1)

EX. B1

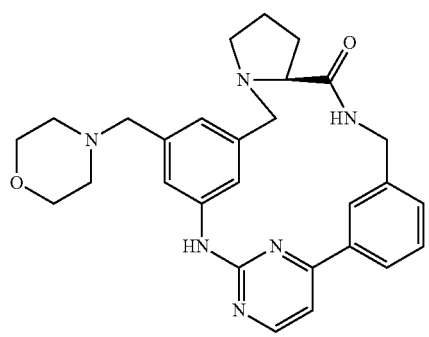 [SMILES: O=C1NCc2cccc(c2)-c2ccnc(n2)Nc2cc(CN3CCOCC3)cc(c2)CN2CCC[C@@H]12]

Co. No. (22)

EX. B1

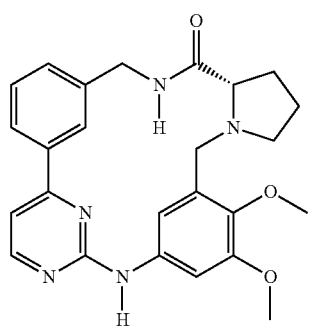 [SMILES: COc1cc2cc(c1OC)CN1CCC[C@H]1C(=O)NCc1cccc(c1)-c1ccnc(n1)N2]

Co. No. (23)

EX. B1

TABLE 1-continued
compounds according to the invention
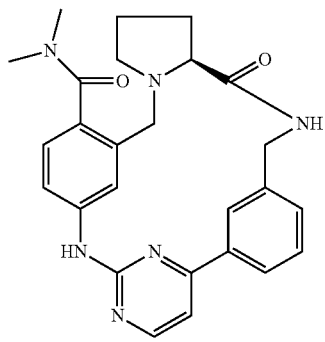 [SMILES: CN(C)C(=O)c1ccc2cc1CN1CCC[C@H]1C(=O)NCc1cccc(c1)-c1ccnc(n1)N2]
EX. B1
Co. No. (24)
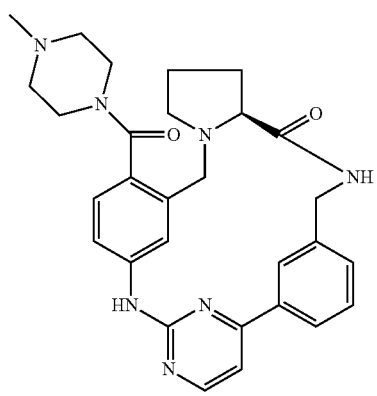 [SMILES: CN1CCN(C(=O)c2ccc3cc2CN2CCC[C@H]2C(=O)NCc2cccc(c2)-c2ccnc(n2)N3)CC1]
EX. B1
Co. No. (25)
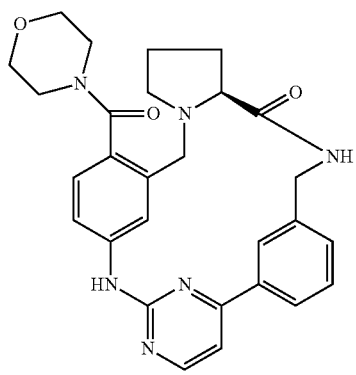 [SMILES: O=C1NCc2cccc(c2)-c2ccnc(n2)Nc2ccc(C(=O)N3CCOCC3)c(c2)CN2CCC[C@@H]12]
EX. B1
Co. No. (26)
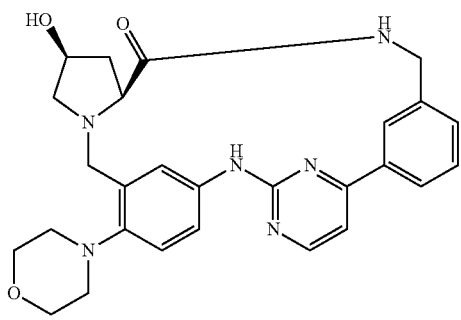 [SMILES: O=C1NCc2cccc(c2)-c2ccnc(n2)Nc2ccc(N3CCOCC3)c(c2)CN2C[C@@H](O)C[C@@H]12]
EX. B1
Co. No. (27)

TABLE 1-continued
compounds according to the invention
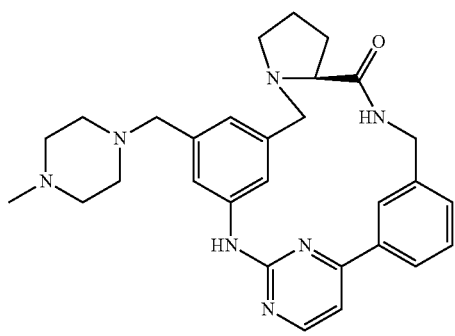 [SMILES: CN1CCN(Cc2cc3cc(c2)Nc2nccc(n2)-c2cccc(c2)CNC(=O)[C@@H]2CCCN2C3)CC1]
Co. No. (28)
EX. B1
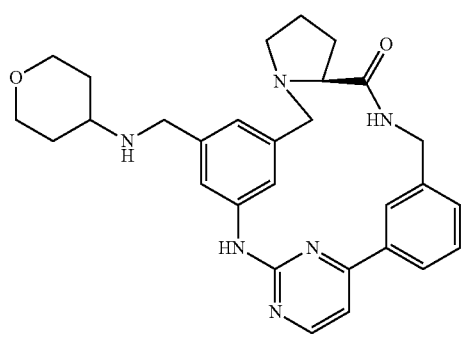 [SMILES: O=C1NCc2cccc(c2)-c2ccnc(n2)Nc2cc(CNC3CCOCC3)cc(c2)CN2CCC[C@@H]12]
Co. No. (29)
EX. B1
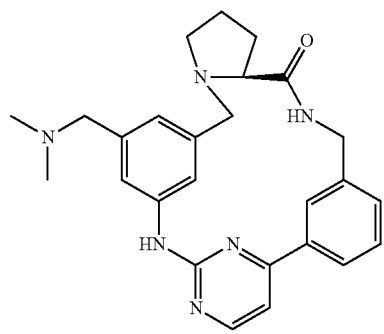 [SMILES: CN(C)Cc1cc2cc(c1)Nc1nccc(n1)-c1cccc(c1)CNC(=O)[C@@H]1CCCN1C2]
Co. No. (30)
EX. B1
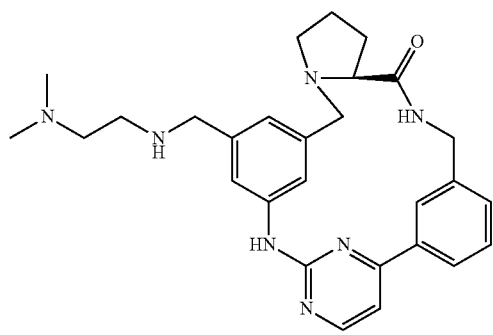 [SMILES: CN(C)CCNCc1cc2cc(c1)Nc1nccc(n1)-c1cccc(c1)CNC(=O)[C@@H]1CCCN1C2]
Co. No. (31)
EX. B1

TABLE 1-continued
compounds according to the invention
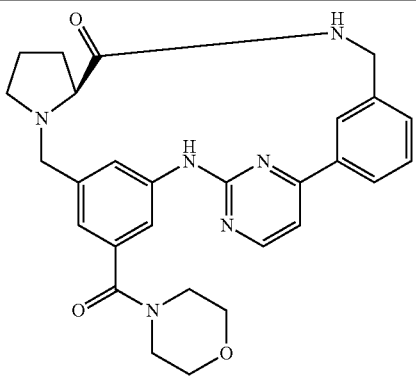
Co. No. (32)
EX. B1
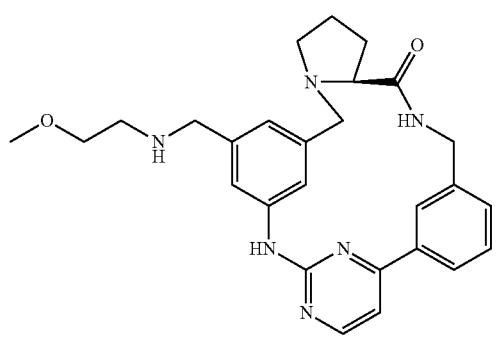 [SMILES: COCCNCc1cc2cc(c1)Nc1nccc(n1)-c1cccc(c1)CNC(=O)[C@@H]1CCCN1C2]
Co. No. (33)
EX. B1
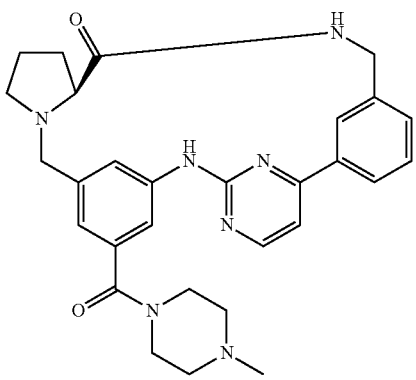 [SMILES: CN1CCN(C(=O)c2cc3cc(c2)Nc2nccc(n2)-c2cccc(c2)CNC(=O)[C@@H]2CCCN2C3)CC1]
Co. No. (34)
EX. B1
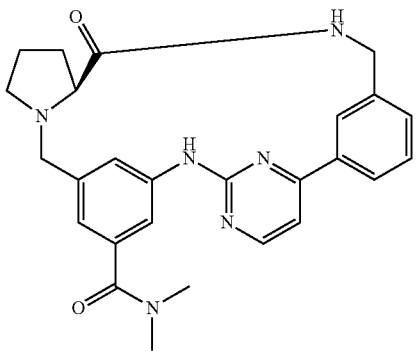 [SMILES: CN(C)C(=O)c1cc2cc(c1)Nc1nccc(n1)-c1cccc(c1)CNC(=O)[C@@H]1CCCN1C2]
Co. No. (35)
EX. B1

TABLE 1-continued
compounds according to the invention
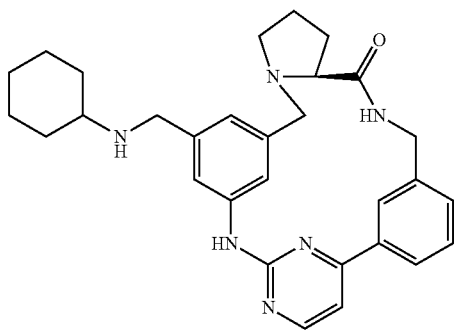 [SMILES: O=C1NCc2cccc(c2)-c2ccnc(n2)Nc2cc(CNC3CCCCC3)cc(c2)CN2CCC[C@@H]12]
Co. No. (36)
EX. B1
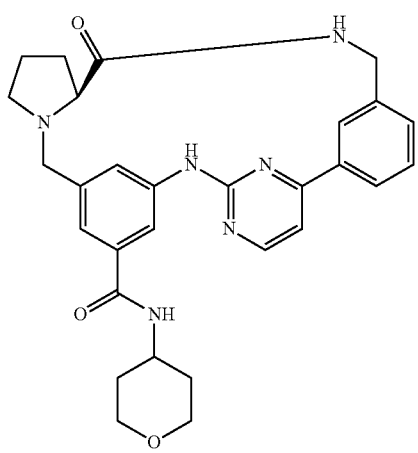 [SMILES: O=C(NC1CCOCC1)c1cc2cc(c1)Nc1nccc(n1)-c1cccc(c1)CNC(=O)[C@@H]1CCCN1C2]
Co. No. (37)
EX. B1
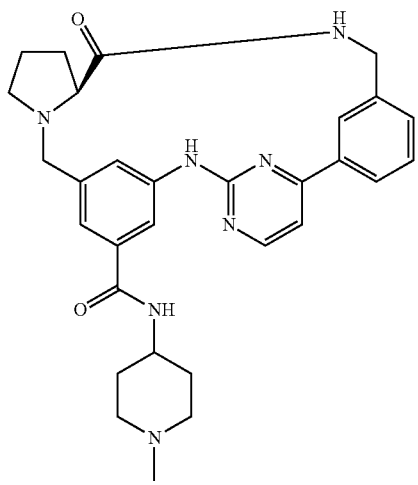 [SMILES: CN1CCC(NC(=O)c2cc3cc(c2)Nc2nccc(n2)-c2cccc(c2)CNC(=O)[C@@H]2CCCN2C3)CC1]
Co. No. (38)
EX. B1

TABLE 1-continued
compounds according to the invention
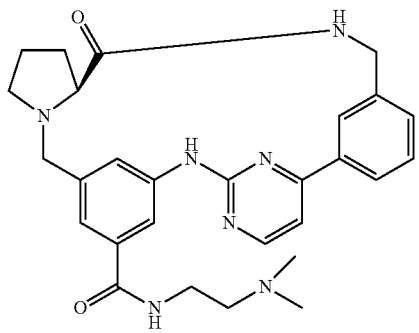 [SMILES: CN(C)CCNC(=O)c1cc2cc(c1)Nc1nccc(n1)-c1cccc(c1)CNC(=O)[C@@H]1CCCN1C2]
Co. No. (39)
EX. B1
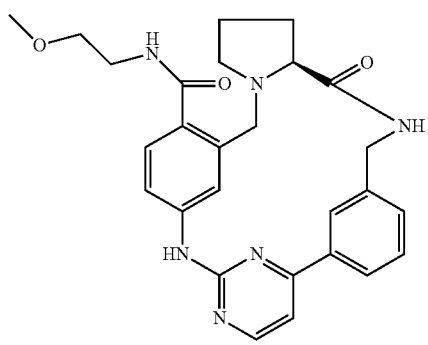 [SMILES: COCCNC(=O)c1ccc2cc1CN1CCC[C@H]1C(=O)NCc1cccc(c1)-c1ccnc(n1)N2]
Co. No. (40)
EX. B1
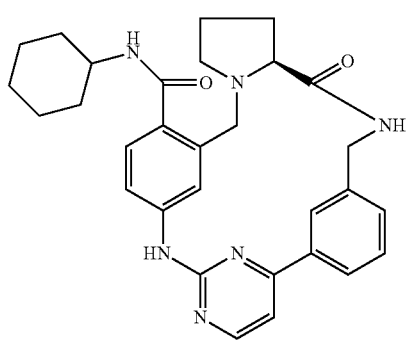 [SMILES: O=C(NC1CCCCC1)c1ccc2cc1CN1CCC[C@H]1C(=O)NCc1cccc(c1)-c1ccnc(n1)N2]
Co. No. (41)
EX. B1
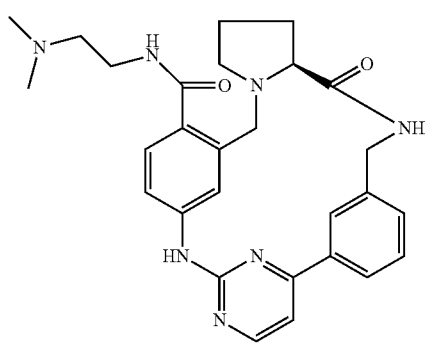 [SMILES: CN(C)CCNC(=O)c1ccc2cc1CN1CCC[C@H]1C(=O)NCc1cccc(c1)-c1ccnc(n1)N2]
Co. No. (42)
EX. B1

TABLE 1-continued
compounds according to the invention
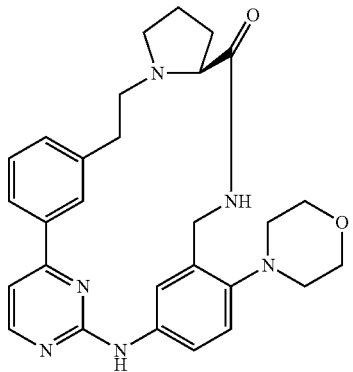 [SMILES: O=C1NCc2cc(ccc2N2CCOCC2)Nc2nccc(n2)-c2cccc(c2)CCN2CCC[C@@H]12]
EX. B1
Co. No. (43)
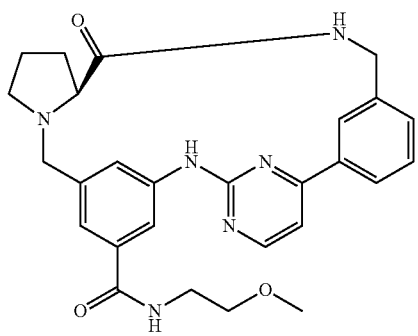 [SMILES: COCCNC(=O)c1cc2cc(c1)Nc1nccc(n1)-c1cccc(c1)CNC(=O)[C@@H]1CCCN1C2]
EX. B1
Co. No. (44)
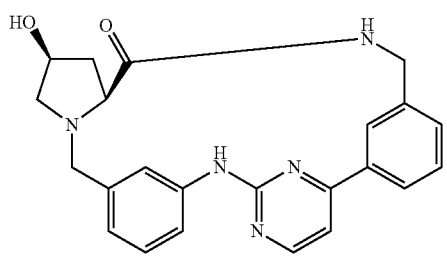 [SMILES: O=C1NCc2cccc(c2)-c2ccnc(n2)Nc2cccc(c2)CN2C[C@@H](O)C[C@@H]12]
EX. B1
Co. No. (45)
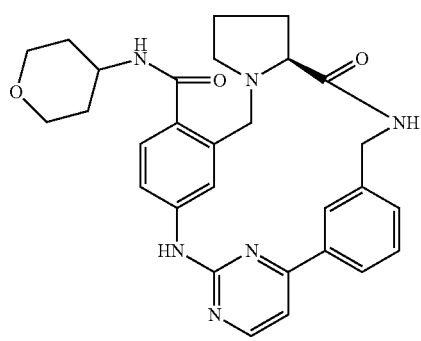 [SMILES: O=C(NC1CCOCC1)c1ccc2cc1CN1CCC[C@H]1C(=O)NCc1cccc(c1)-c1ccnc(n1)N2]
EX. B1
Co. No. (46)

TABLE 1-continued
compounds according to the invention
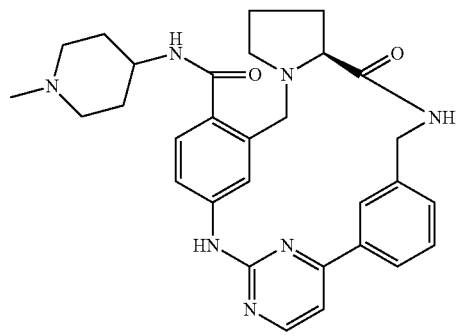 [SMILES: CN1CCC(NC(=O)c2ccc3cc2CN2CCC[C@H]2C(=O)NCc2cccc(c2)-c2ccnc(n2)N3)CC1]
Co. No. (47)
EX. B1
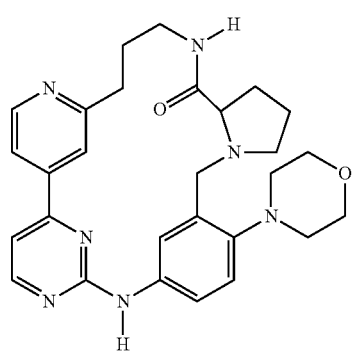 [SMILES: O=C1NCCCc2cc(ccn2)-c2ccnc(n2)Nc2ccc(N3CCOCC3)c(c2)CN2CCCC12]
Co. No. (48)
EX. B1
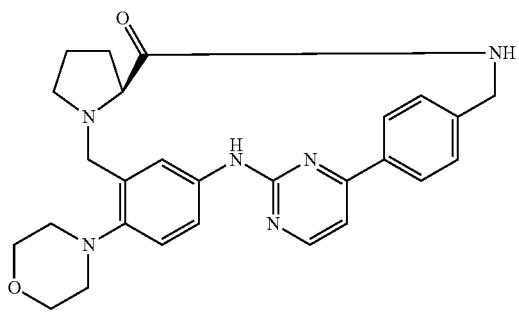 [SMILES: O=C1NCc2ccc(cc2)-c2ccnc(n2)Nc2ccc(N3CCOCC3)c(c2)CN2CCC[C@@H]12]
Co. No. (49)
EX. B1
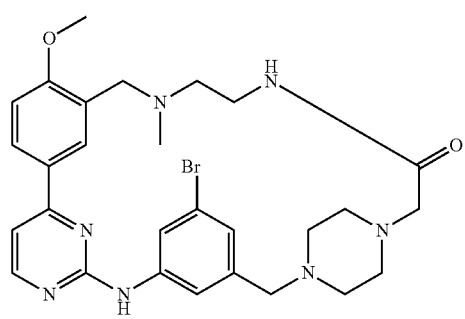 [SMILES: COc1ccc2cc1CN(C)CCNC(=O)CN1CCN(CC1)Cc1cc(Br)cc(c1)Nc1nccc-2n1]
Co. No. (50)
EX. B1

TABLE 1-continued
compounds according to the invention
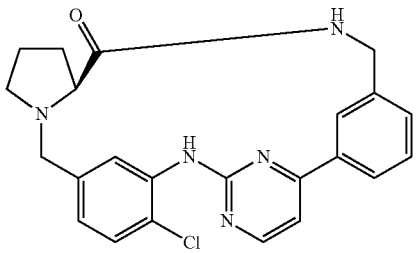 [SMILES: O=C1NCc2cccc(c2)-c2ccnc(n2)Nc2cc(ccc2Cl)CN2CCC[C@@H]12]
Co. No. (51)
EX. B1
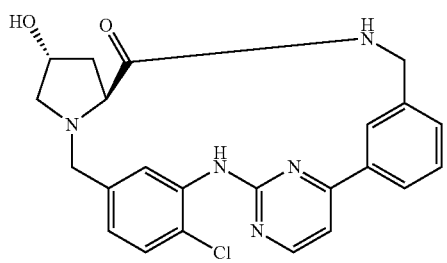 [SMILES: O=C1NCc2cccc(c2)-c2ccnc(n2)Nc2cc(ccc2Cl)CN2C[C@H](O)C[C@@H]12]
Co. No. (52)
EX. B1
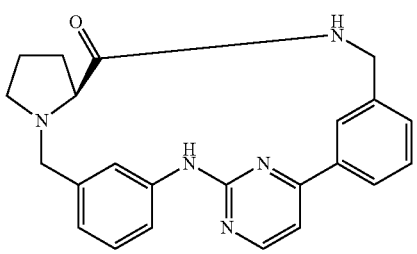 [SMILES: O=C1NCc2cccc(c2)-c2ccnc(n2)Nc2cccc(c2)CN2CCC[C@@H]12]
Co. No. (53)
EX. B1
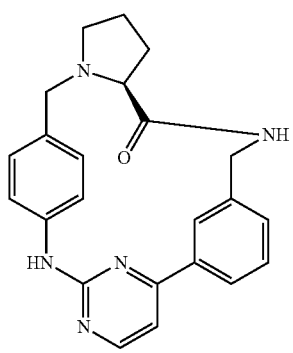 [SMILES: O=C1NCc2cccc(c2)-c2ccnc(n2)Nc2ccc(cc2)CN2CCC[C@@H]12]
Co. No. (54)
EX. B1

TABLE 1-continued
compounds according to the invention
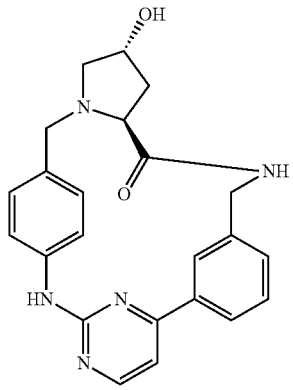 [SMILES: O=C1NCc2cccc(c2)-c2ccnc(n2)Nc2ccc(cc2)CN2C[C@H](O)C[C@@H]12]
Co. No. (55)
EX. B1
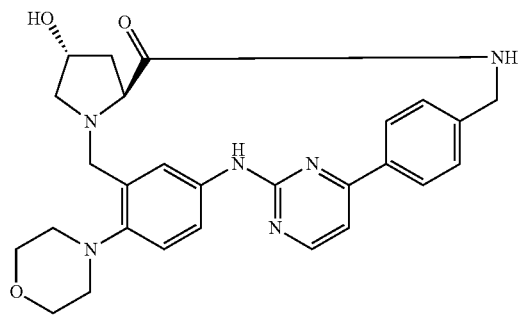 [SMILES: O=C1NCc2ccc(cc2)-c2ccnc(n2)Nc2ccc(N3CCOCC3)c(c2)CN2C[C@H](O)C[C@@H]12]
Co. No. (56)
EX. B1
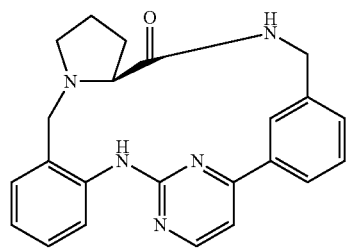 [SMILES: O=C1NCc2cccc(c2)-c2ccnc(n2)Nc2ccccc2CN2CCC[C@@H]12]
Co. No. (57)
EX. B1
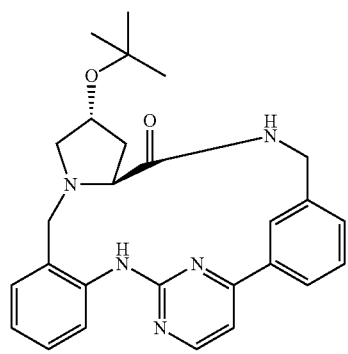 [SMILES: CC(C)(C)O[C@@H]1C[C@H]2C(=O)NCc3cccc(c3)-c3ccnc(n3)Nc3ccccc3CN2C1]
Co. No. (58)
EX. B1

TABLE 1-continued
compounds according to the invention
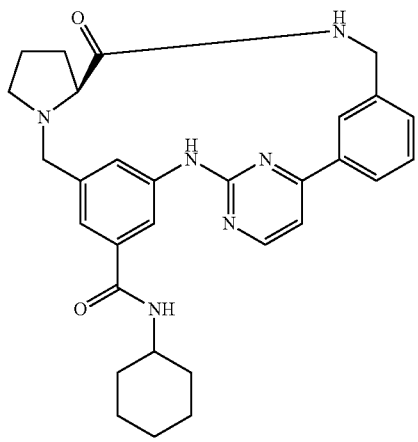 [SMILES: O=C(NC1CCCCC1)c1cc2cc(c1)Nc1nccc(n1)-c1cccc(c1)CNC(=O)[C@@H]1CCCN1C2]
Co. No. (59)
EX. B1
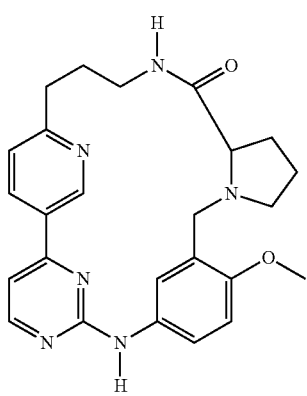 [SMILES: COc1ccc2cc1CN1CCCC1C(=O)NCCCc1ccc(cn1)-c1ccnc(n1)N2]
Co. No. (2)
EX. B1b
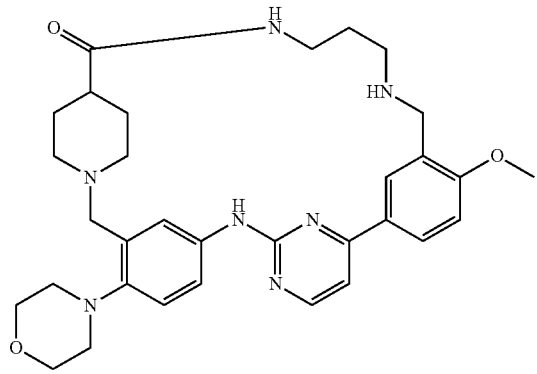 [SMILES: COc1ccc2cc1CNCCCNC(=O)C1CCN(CC1)Cc1cc(ccc1N1CCOCC1)Nc1nccc-2n1]
Co. No. (3)
EX. B2

TABLE 1-continued
compounds according to the invention
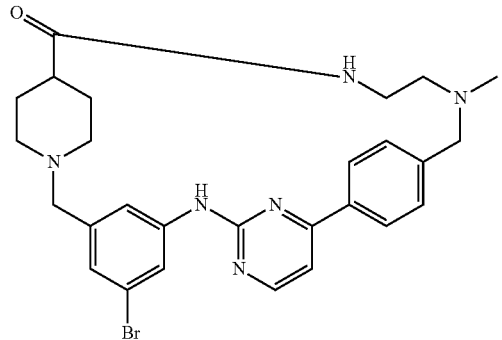 [SMILES: CN1CCNC(=O)C2CCN(CC2)Cc2cc(Br)cc(c2)Nc2nccc(n2)-c2ccc(cc2)C1]
Co. No. (60)
EX. B2
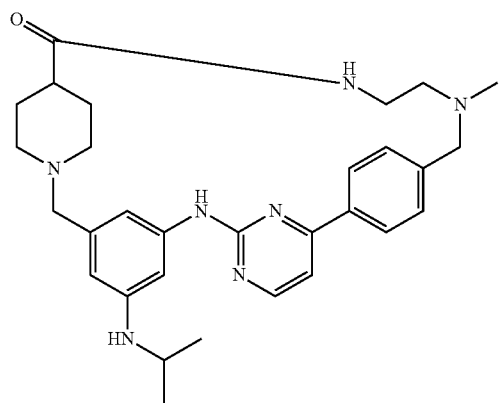 [SMILES: CC(C)Nc1cc2cc(c1)Nc1nccc(n1)-c1ccc(cc1)CN(C)CCNC(=O)C1CCN(CC1)C2]
Co. No. (61)
EX. B2
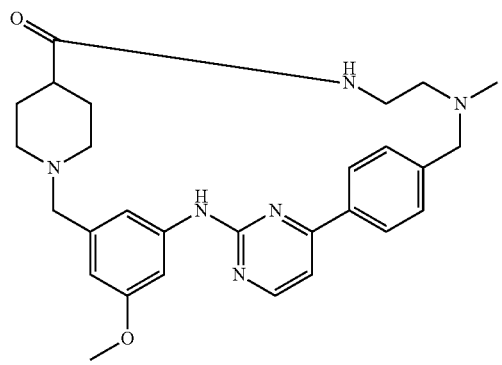 [SMILES: COc1cc2cc(c1)Nc1nccc(n1)-c1ccc(cc1)CN(C)CCNC(=O)C1CCN(CC1)C2]
Co. No. (62)
EX. B2

TABLE 1-continued
compounds according to the invention
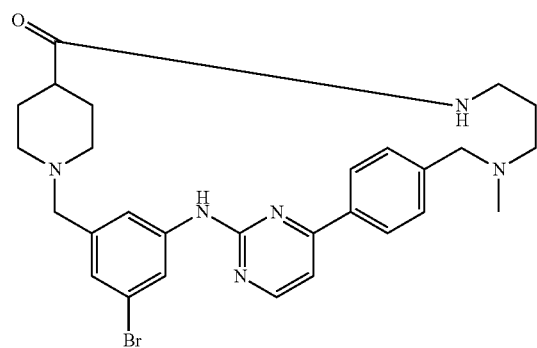 [SMILES: CN1CCCNC(=O)C2CCN(CC2)Cc2cc(Br)cc(c2)Nc2nccc(n2)-c2ccc(cc2)C1]
Co. No. (63)
EX. B2
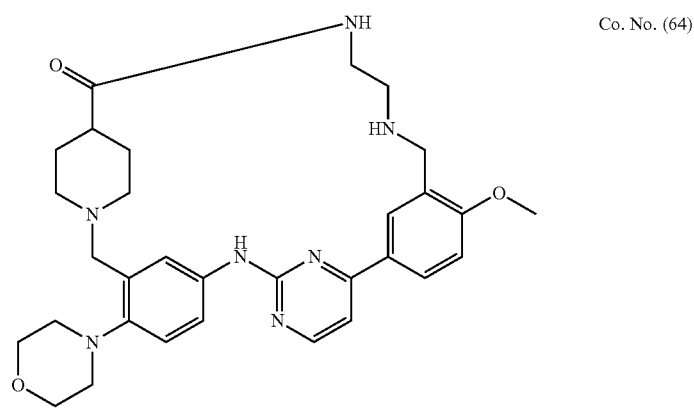
Co. No. (64)
EX. B2
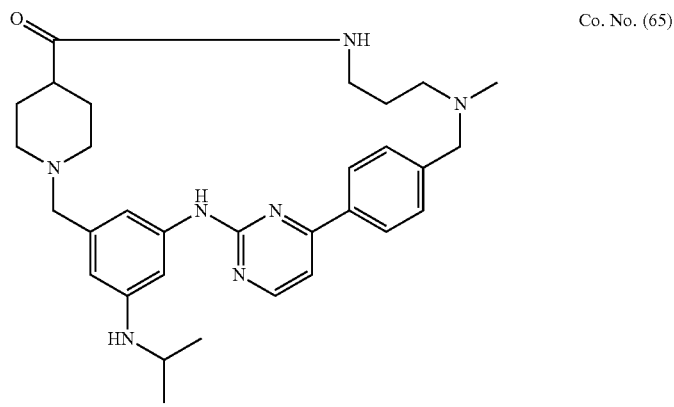
Co. No. (65)
EX. B2

TABLE 1-continued
compounds according to the invention
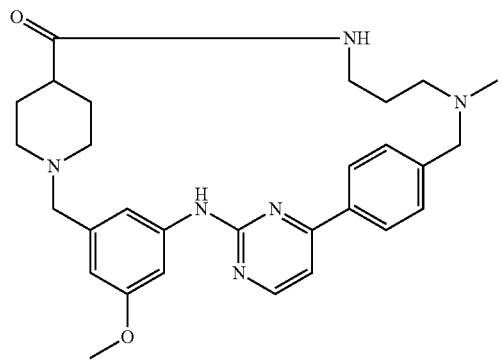 [SMILES: COc1cc2cc(c1)Nc1nccc(n1)-c1ccc(cc1)CN(C)CCCNC(=O)C1CCN(CC1)C2]
Co. No. (66)
EX. B2
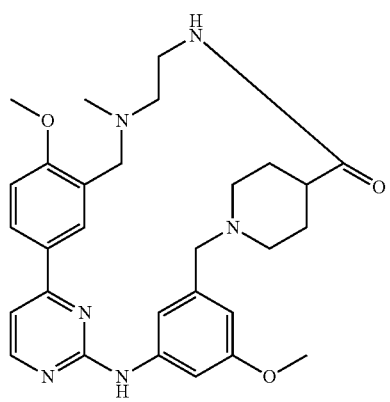 [SMILES: COc1cc2cc(c1)Nc1nccc(n1)-c1ccc(OC)c(c1)CN(C)CCNC(=O)C1CCN(CC1)C2]
Co. No. (67)
EX. B2
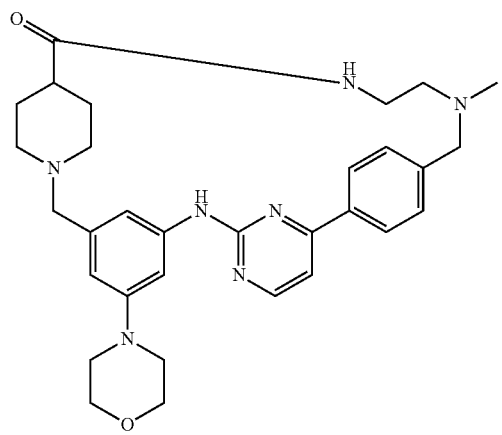 [SMILES: CN1CCNC(=O)C2CCN(CC2)Cc2cc(cc(N3CCOCC3)c2)Nc2nccc(n2)-c2ccc(cc2)C1]
Co. No. (68)
EX. B2

TABLE 1-continued
compounds according to the invention
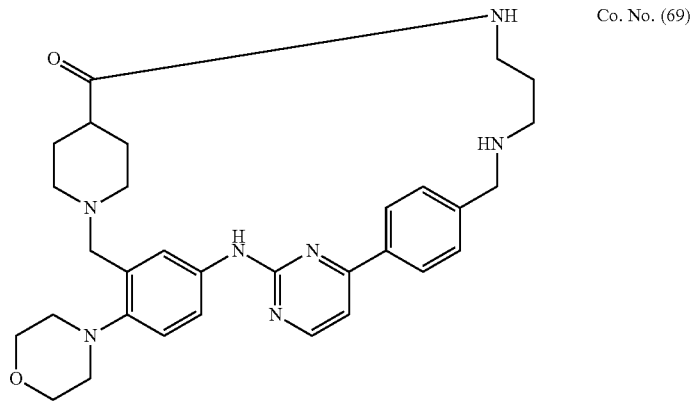
Co. No. (69)
EX. B2
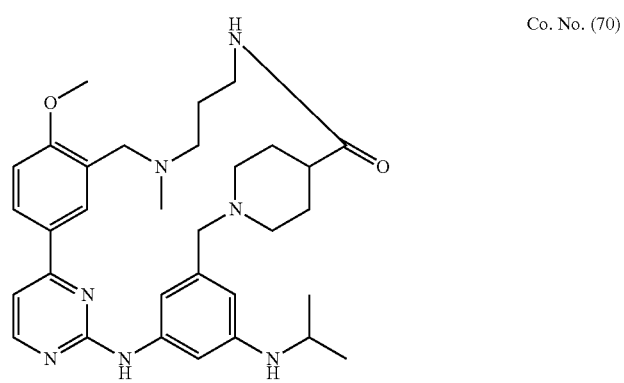
Co. No. (70)
EX. B2
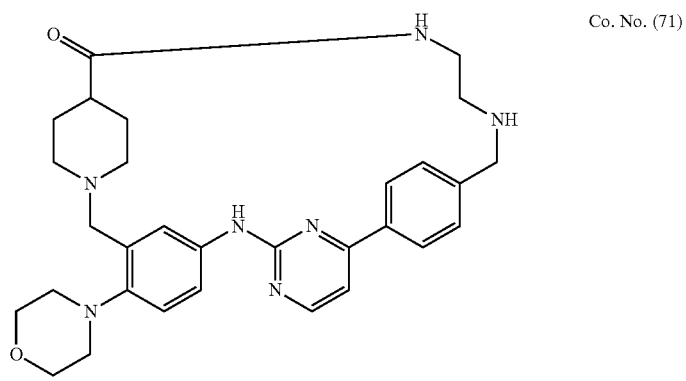
Co. No. (71)
EX. B2

TABLE 1-continued
compounds according to the invention
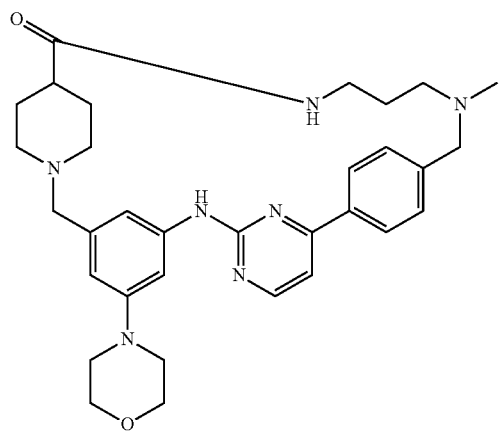 [SMILES: CN1CCCNC(=O)C2CCN(CC2)Cc2cc(cc(N3CCOCC3)c2)Nc2nccc(n2)-c2ccc(cc2)C1]
Co. No. (72)
EX. B2
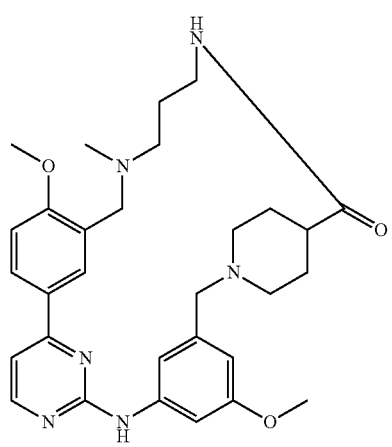 [SMILES: COc1cc2cc(c1)Nc1nccc(n1)-c1ccc(OC)c(c1)CN(C)CCCNC(=O)C1CCN(CC1)C2]
Co. No. (73)
EX. B2
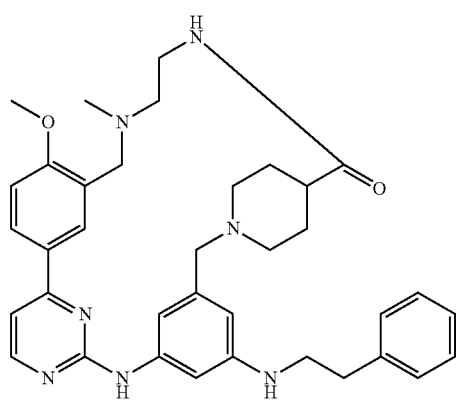 [SMILES: COc1ccc2cc1CN(C)CCNC(=O)C1CCN(CC1)Cc1cc(NCCc3ccccc3)cc(c1)Nc1nccc-2n1]
Co. No. (74)
EX. B2

TABLE 1-continued
compounds according to the invention
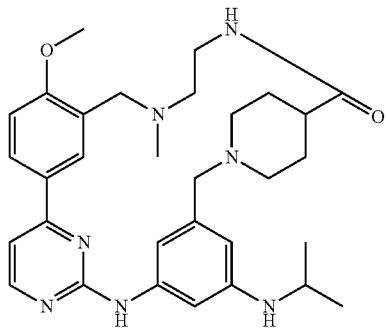 [SMILES: COc1ccc2cc1CN(C)CCNC(=O)C1CCN(CC1)Cc1cc(cc(NC(C)C)c1)Nc1nccc-2n1]
Co. No. (75)
EX. B2
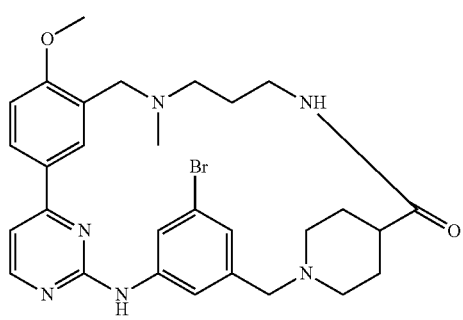 [SMILES: COc1ccc2cc1CN(C)CCCNC(=O)C1CCN(CC1)Cc1cc(Br)cc(c1)Nc1nccc-2n1]
Co. No. (76)
EX. B2
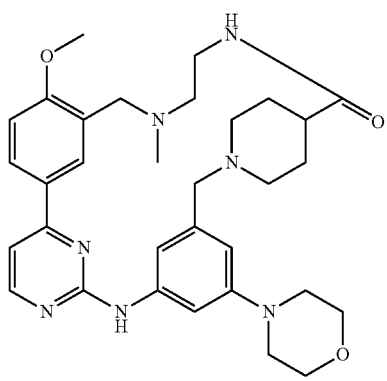 [SMILES: COc1ccc2cc1CN(C)CCNC(=O)C1CCN(CC1)Cc1cc(cc(N3CCOCC3)c1)Nc1nccc-2n1]
Co. No. (77)
EX. B2
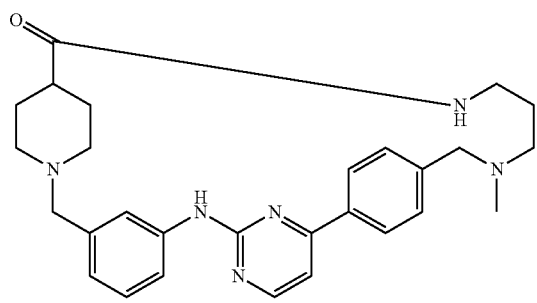 [SMILES: CN1CCCNC(=O)C2CCN(CC2)Cc2cccc(c2)Nc2nccc(n2)-c2ccc(cc2)C1]
Co. No. (78)
EX. B2

147
TABLE 1-continued
compounds according to the invention
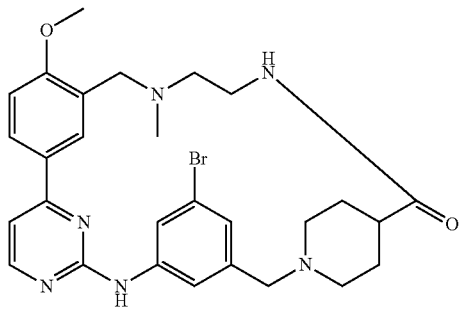 [SMILES: COc1ccc2cc1CN(C)CCNC(=O)C1CCN(CC1)Cc1cc(Br)cc(c1)Nc1nccc-2n1]
Co. No. (79)
EX. B2
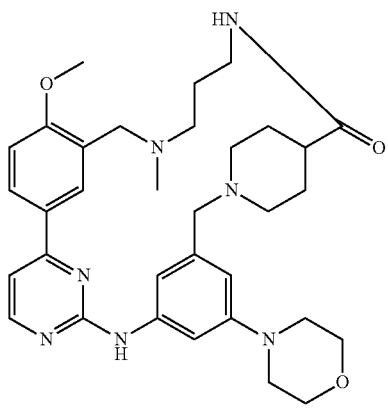 [SMILES: COc1ccc2cc1CN(C)CCCNC(=O)C1CCN(CC1)Cc1cc(cc(N3CCOCC3)c1)Nc1nccc-2n1]
Co. No. (80)
EX. B2
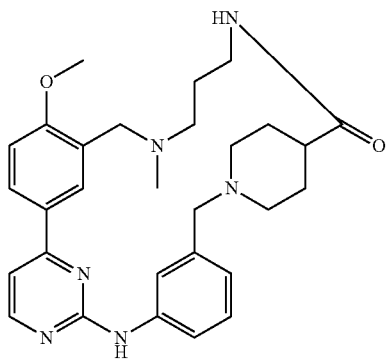 [SMILES: COc1ccc2cc1CN(C)CCCNC(=O)C1CCN(CC1)Cc1cccc(c1)Nc1nccc-2n1]
Co. No. (81)
EX. B2
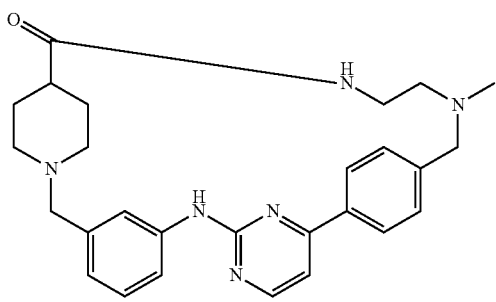 [SMILES: CN1CCNC(=O)C2CCN(CC2)Cc2cccc(c2)Nc2nccc(n2)-c2ccc(cc2)C1]
Co. No. (82)
EX. B2

TABLE 1-continued
compounds according to the invention
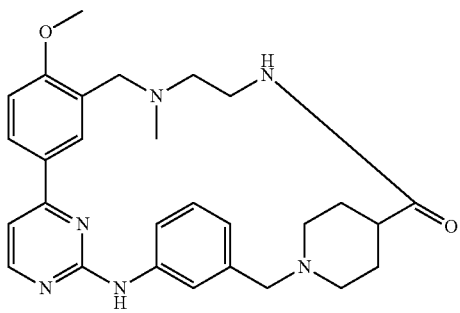 [SMILES: COc1ccc2cc1CN(C)CCNC(=O)C1CCN(CC1)Cc1cccc(c1)Nc1nccc-2n1]
Co. No. (83)
EX. B2
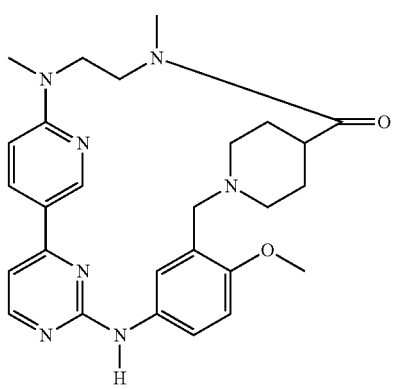 [SMILES: COc1ccc2cc1CN1CCC(CC1)C(=O)N(C)CCN(C)c1ccc(cn1)-c1ccnc(n1)N2]
Co. No. (4)
EX. B2b
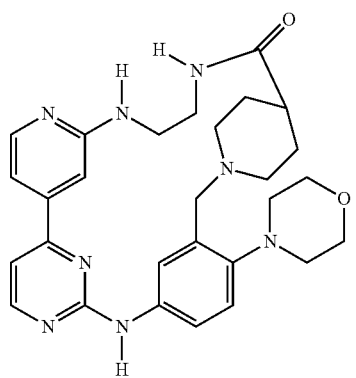 [SMILES: O=C1NCCNc2cc(ccn2)-c2ccnc(n2)Nc2ccc(N3CCOCC3)c(c2)CN2CCC1CC2]
Co. No. (84)
EX. B2b
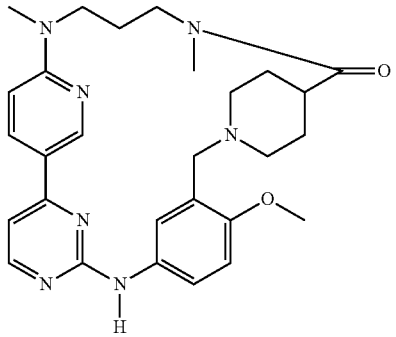 [SMILES: COc1ccc2cc1CN1CCC(CC1)C(=O)N(C)CCCN(C)c1ccc(cn1)-c1ccnc(n1)N2]
Co. No. (85)
EX. B2b TABLE 1-continued
compounds according to the invention
Co. No. (5)
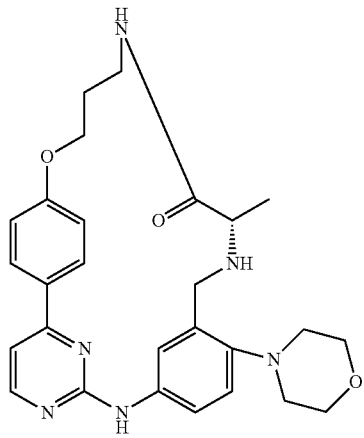 [SMILES: C[C@@H]1NCc2cc(ccc2N2CCOCC2)Nc2nccc(n2)-c2ccc(cc2)OCCCNC1=O]
EX. B3
Co. No. (86)
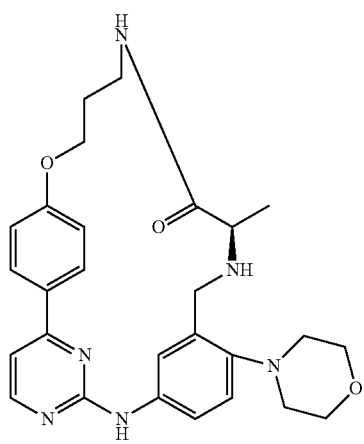
EX. B3
Co. No. (87)
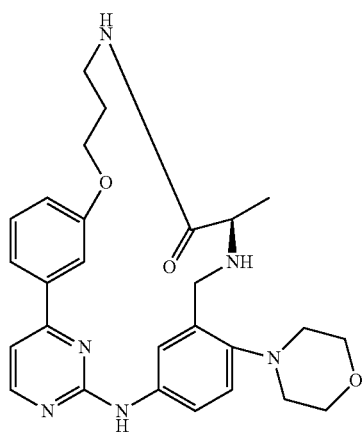 [SMILES: C[C@H]1NCc2cc(ccc2N2CCOCC2)Nc2nccc(n2)-c2cccc(c2)OCCCNC1=O]
EX. B3

TABLE 1-continued
compounds according to the invention
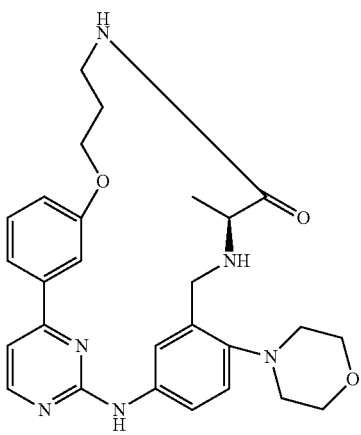 [SMILES: C[C@@H]1NCc2cc(ccc2N2CCOCC2)Nc2nccc(n2)-c2cccc(c2)OCCCNC1=O]
Co. No. (88)
EX. B3
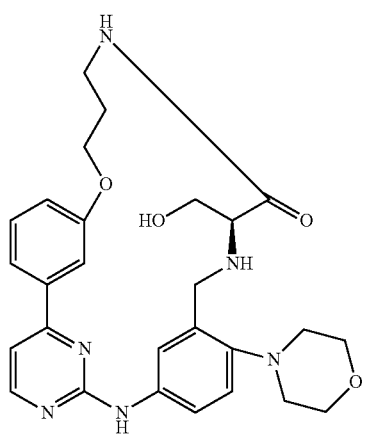 [SMILES: O=C1NCCCOc2cccc(c2)-c2ccnc(n2)Nc2ccc(N3CCOCC3)c(c2)CN[C@H]1CO]
Co. No. (89)
EX. B3
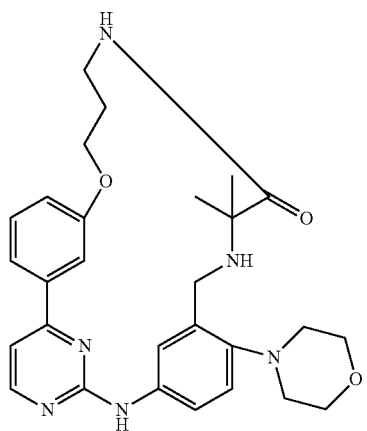 [SMILES: CC1(C)NCc2cc(ccc2N2CCOCC2)Nc2nccc(n2)-c2cccc(c2)OCCCNC1=O]
Co. No. (90)
EX. B3

TABLE 1-continued
compounds according to the invention
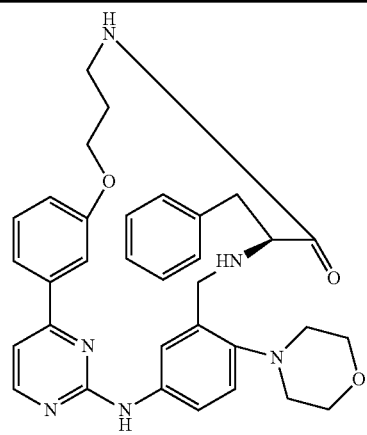
Co. No. (91)
EX. B3
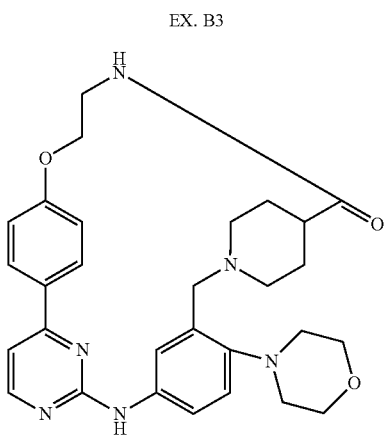
Co. No. (6)
EX. B4
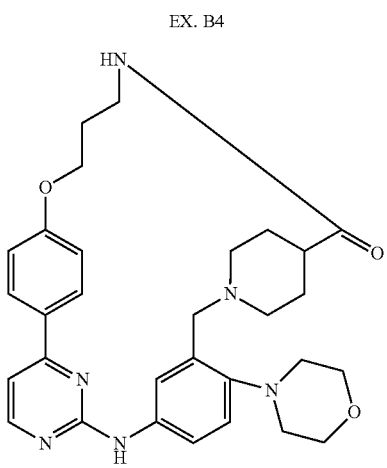
Co. No. (92)
EX. B4

TABLE 1-continued
compounds according to the invention
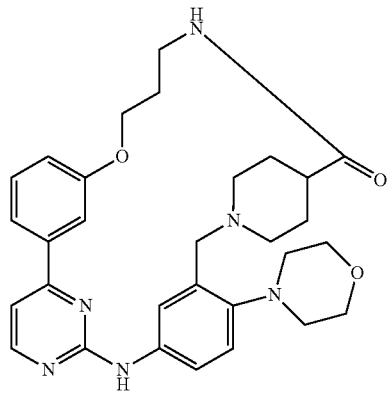 [SMILES: O=C1NCCCOc2cccc(c2)-c2ccnc(n2)Nc2ccc(N3CCOCC3)c(c2)CN2CCC1CC2]
Co. No. (93)
EX. B4
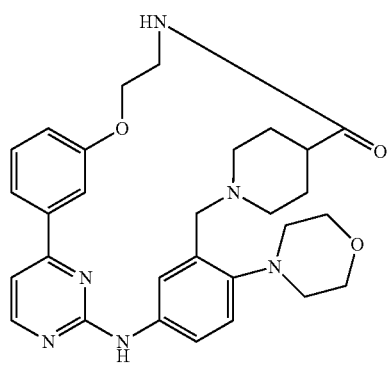 [SMILES: O=C1NCCOc2cccc(c2)-c2ccnc(n2)Nc2ccc(N3CCOCC3)c(c2)CN2CCC1CC2]
Co. No. (94)
EX. B4
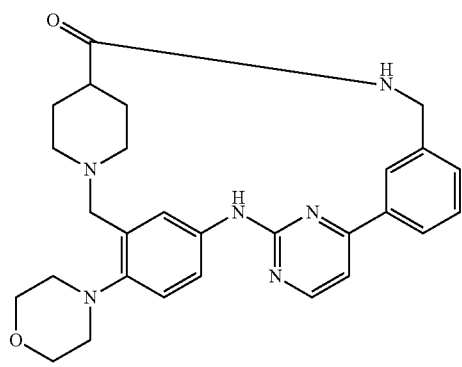 [SMILES: O=C1NCc2cccc(c2)-c2ccnc(n2)Nc2ccc(N3CCOCC3)c(c2)CN2CCC1CC2]
Co. No. (95)
EX. B4

TABLE 1-continued
compounds according to the invention
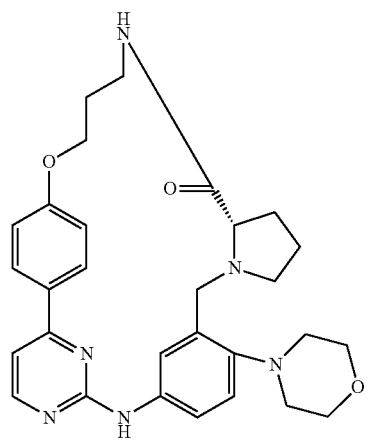 [SMILES: O=C1NCCCOc2ccc(cc2)-c2ccnc(n2)Nc2ccc(N3CCOCC3)c(c2)CN2CCC[C@@H]12]
Co. No. (7)
EX. B5
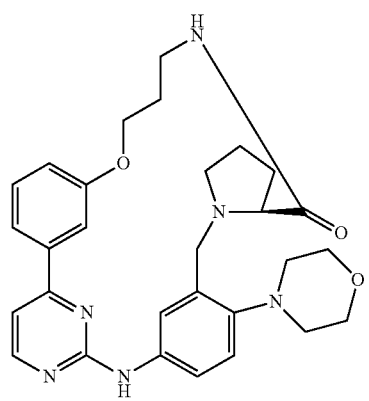 [SMILES: O=C1NCCCOc2cccc(c2)-c2ccnc(n2)Nc2ccc(N3CCOCC3)c(c2)CN2CCC[C@@H]12]
Co. No. (96)
EX. B5
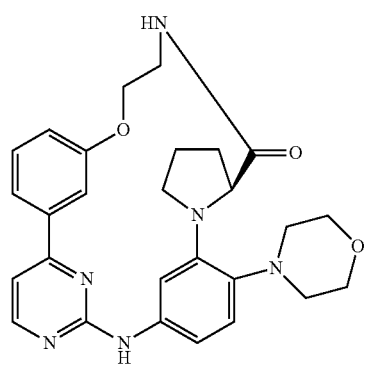 [SMILES: O=C1NCCOc2cccc(c2)-c2ccnc(n2)Nc2ccc(N3CCOCC3)c(c2)N2CCC[C@@H]12]
Co. No. (97)
EX. B5

TABLE 1-continued
compounds according to the invention
Co. No. (98)
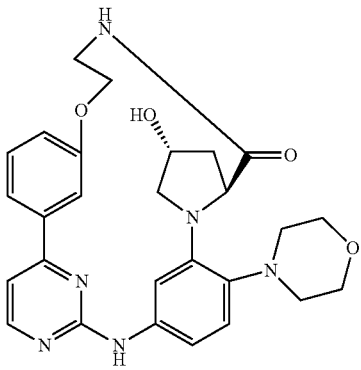 [SMILES: O=C1NCCOc2cccc(c2)-c2ccnc(n2)Nc2ccc(N3CCOCC3)c(c2)N2C[C@H](O)C[C@@H]12]
EX. B5
Co. No. (99)
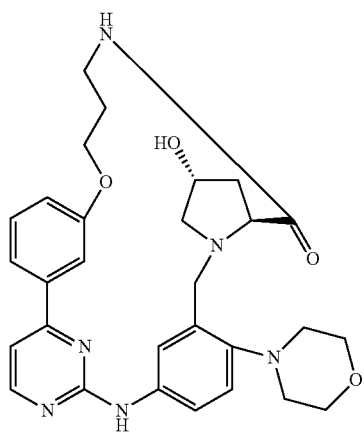 [SMILES: O=C1NCCCOc2cccc(c2)-c2ccnc(n2)Nc2ccc(N3CCOCC3)c(c2)CN2C[C@H](O)C[C@@H]12]
EX. B5
Co. No. (8)
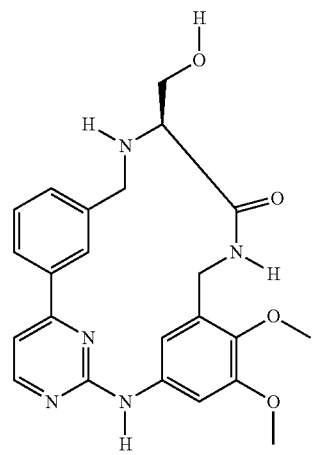 [SMILES: COc1cc2cc(c1OC)CNC(=O)[C@H](CO)NCc1cccc(c1)-c1ccnc(n1)N2]
EX. B6

TABLE 1-continued
compounds according to the invention
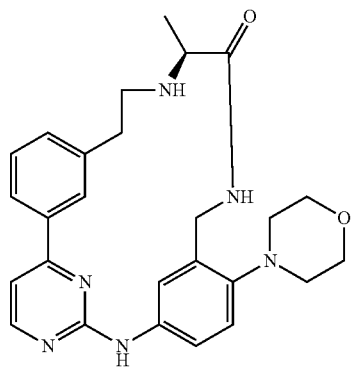 [SMILES: C[C@@H]1NCCc2cccc(c2)-c2ccnc(n2)Nc2ccc(N3CCOCC3)c(c2)CNC1=O]
Co. No. (100)
EX. B6
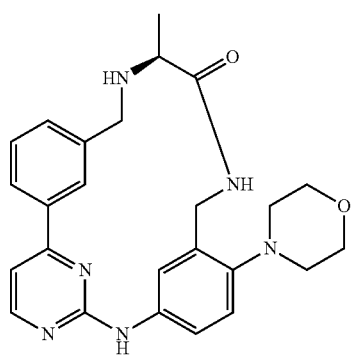 [SMILES: C[C@@H]1NCc2cccc(c2)-c2ccnc(n2)Nc2ccc(N3CCOCC3)c(c2)CNC1=O]
Co. No. (101)
EX. B6
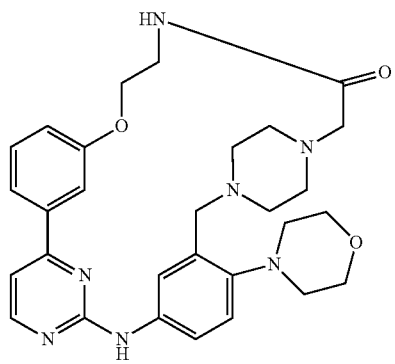 [SMILES: O=C1CN2CCN(CC2)Cc2cc(ccc2N2CCOCC2)Nc2nccc(n2)-c2cccc(c2)OCCN1]
Co. No. (102)
EX. B7

TABLE 1-continued
compounds according to the invention
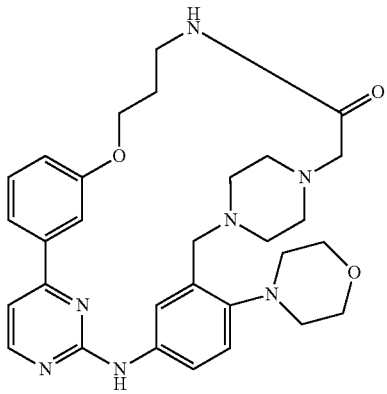 [SMILES: O=C1CN2CCN(CC2)Cc2cc(ccc2N2CCOCC2)Nc2nccc(n2)-c2cccc(c2)OCCCN1]
Co. No. (103)
EX. B7
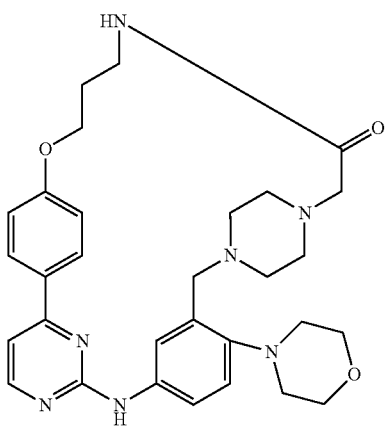 [SMILES: O=C1CN2CCN(CC2)Cc2cc(ccc2N2CCOCC2)Nc2nccc(n2)-c2ccc(cc2)OCCCN1]
Co. No. (104)
EX. B7
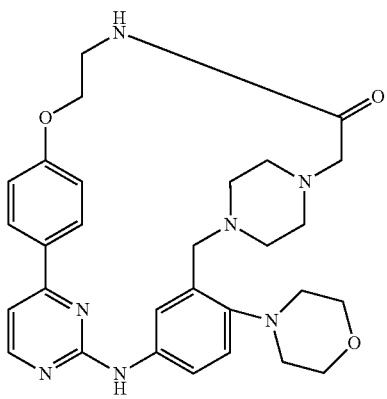 [SMILES: O=C1CN2CCN(CC2)Cc2cc(ccc2N2CCOCC2)Nc2nccc(n2)-c2ccc(cc2)OCCN1]
Co. No. (9)
EX. B7

TABLE 1-continued
compounds according to the invention
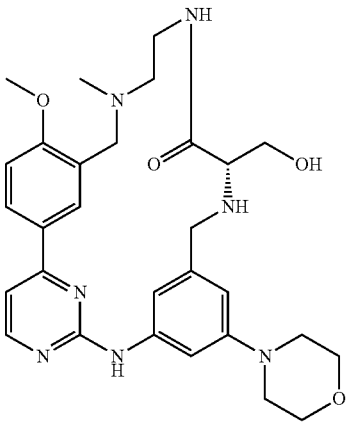 [SMILES: COc1ccc2cc1CN(C)CCNC(=O)[C@H](CO)NCc1cc(cc(N3CCOCC3)c1)Nc1nccc-2n1]
Co. No. (105)
EX. B8
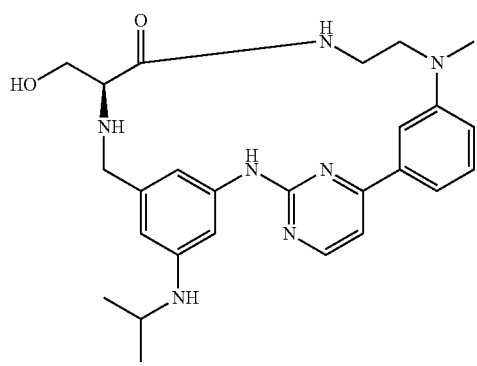 [SMILES: CC(C)Nc1cc2cc(c1)Nc1nccc(n1)-c1cccc(c1)N(C)CCNC(=O)[C@H](CO)NC2]
Co. No. (106)
EX. B8
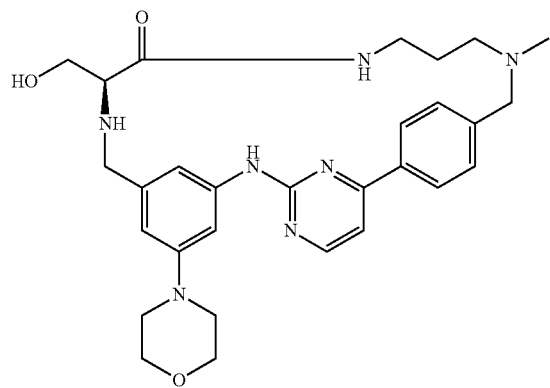 [SMILES: CN1CCCNC(=O)[C@H](CO)NCc2cc(cc(N3CCOCC3)c2)Nc2nccc(n2)-c2ccc(cc2)C1]
Co. No. (10)
EX. B8

TABLE 1-continued
compounds according to the invention
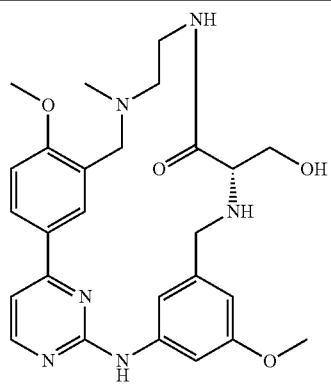
Co. No. (107)
EX. B8
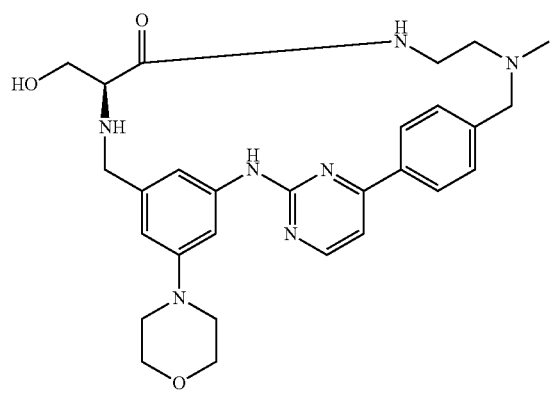 [SMILES: CN1CCNC(=O)[C@H](CO)NCc2cc(cc(N3CCOCC3)c2)Nc2nccc(n2)-c2ccc(cc2)C1]
Co. No. (108)
EX. B8
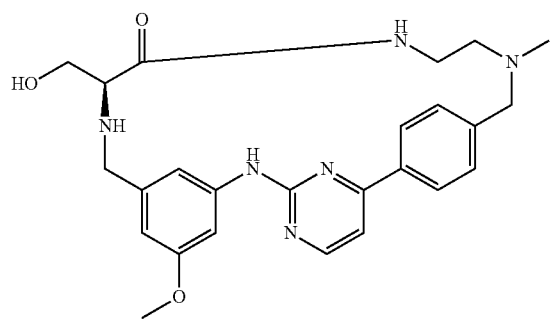 [SMILES: COc1cc2cc(c1)Nc1nccc(n1)-c1ccc(cc1)CN(C)CCNC(=O)[C@H](CO)NC2]
Co. No. (109)
EX. B8
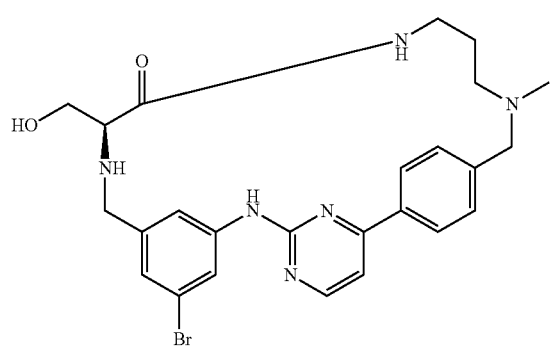 [SMILES: CN1CCCNC(=O)[C@H](CO)NCc2cc(Br)cc(c2)Nc2nccc(n2)-c2ccc(cc2)C1]
Co. No. (110)
EX. B8

TABLE 1-continued
compounds according to the invention
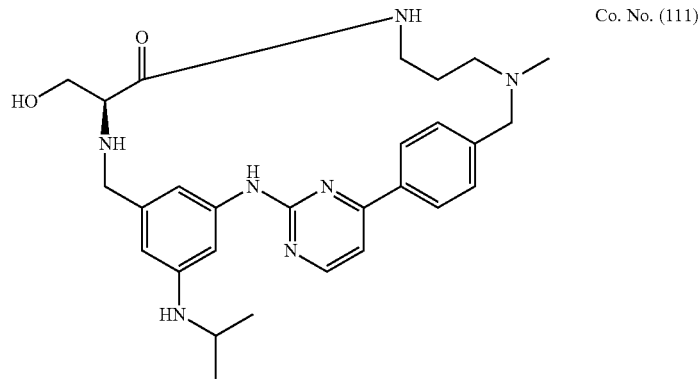
Co. No. (111)
EX. B8
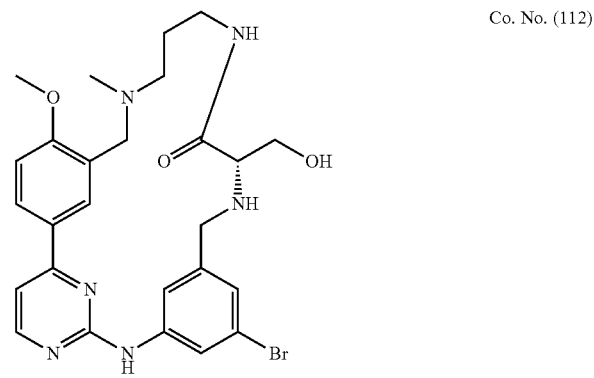
Co. No. (112)
EX. B8
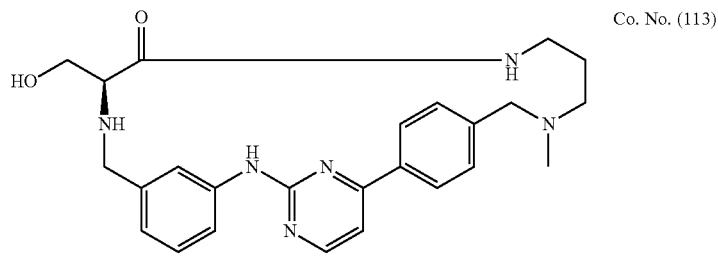
Co. No. (113)
EX. B8
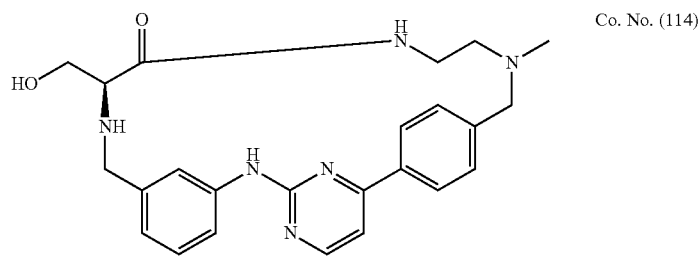
Co. No. (114)
EX. B8

TABLE 1-continued
compounds according to the invention
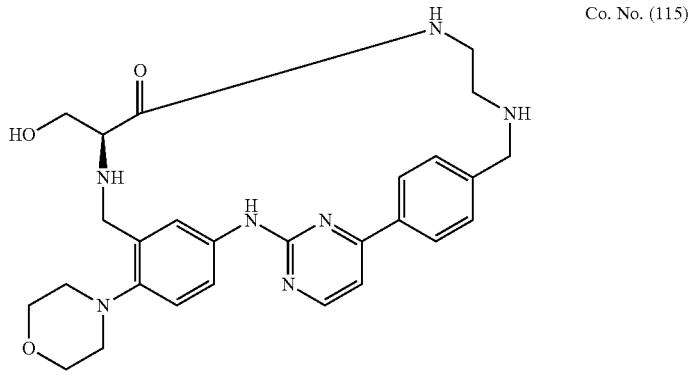
Co. No. (115)
EX. B8
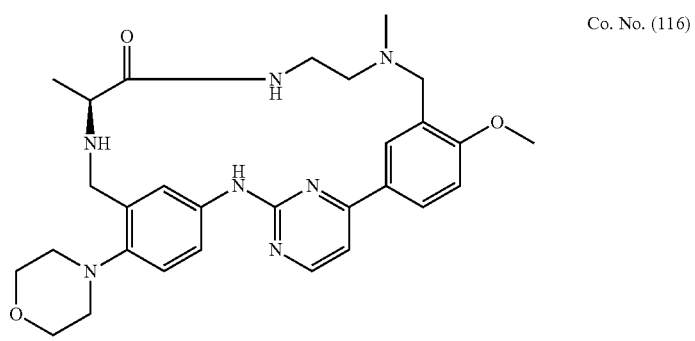
Co. No. (116)
EX. B8
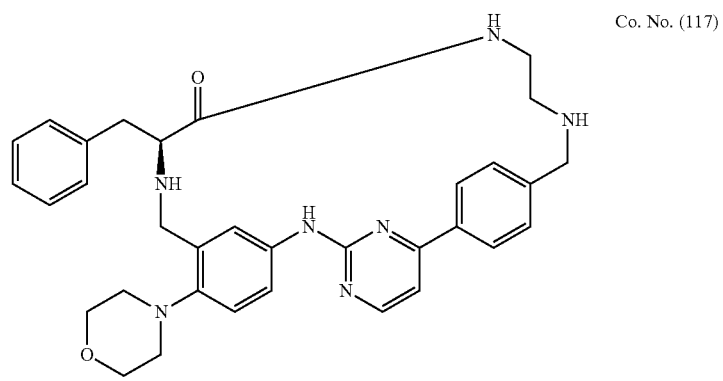
Co. No. (117)
EX. B8

TABLE 1-continued
compounds according to the invention
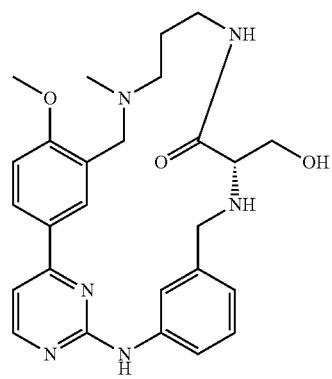 [SMILES: COc1ccc2cc1CN(C)CCCNC(=O)[C@H](CO)NCc1cccc(c1)Nc1nccc-2n1]
Co. No. (118)
EX. B8
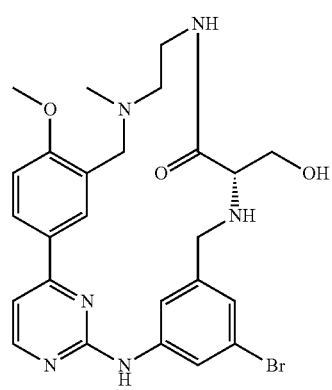 [SMILES: COc1ccc2cc1CN(C)CCNC(=O)[C@H](CO)NCc1cc(Br)cc(c1)Nc1nccc-2n1]
Co. No. (119)
EX. B8
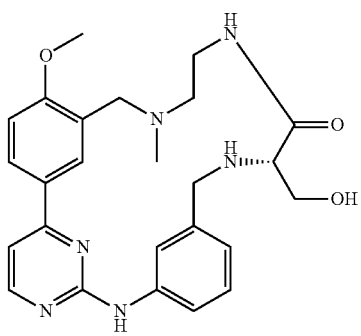 [SMILES: COc1ccc2cc1CN(C)CCNC(=O)[C@H](CO)NCc1cccc(c1)Nc1nccc-2n1]
Co. No. (120)
EX. B8
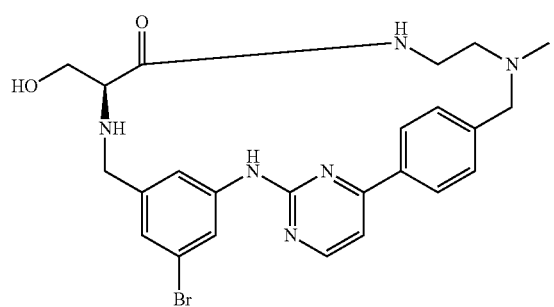 [SMILES: CN1CCNC(=O)[C@H](CO)NCc2cc(Br)cc(c2)Nc2nccc(n2)-c2ccc(cc2)C1]
Co. No. (121)
EX. B8

TABLE 1-continued
compounds according to the invention
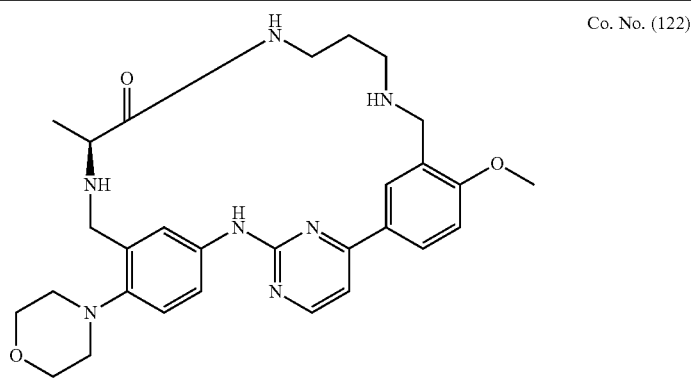
EX. B8
Co. No. (122)
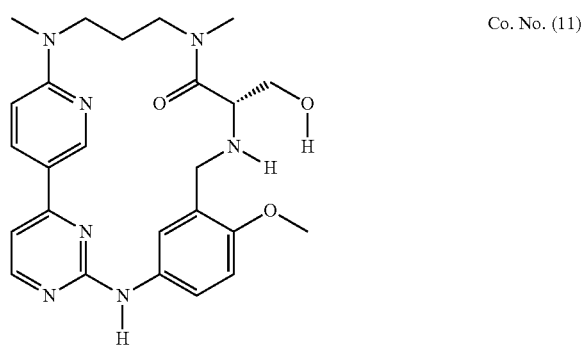
EX. B8b
Co. No. (11)
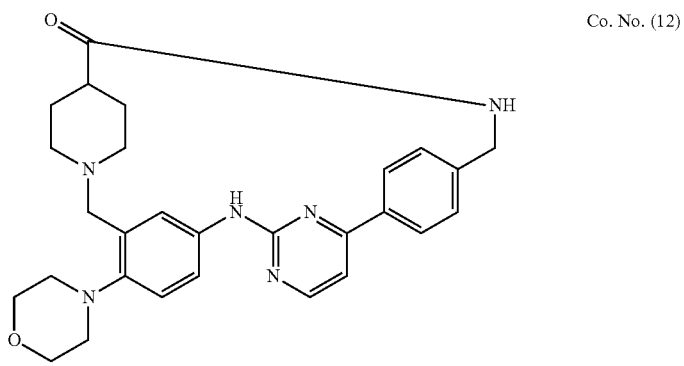
EX. B9
Co. No. (12)
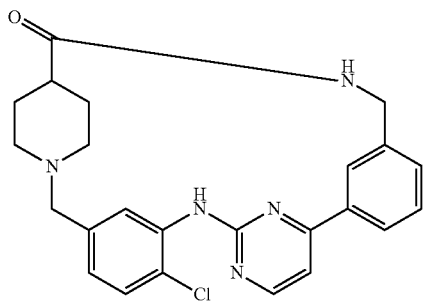 [SMILES: O=C1NCc2cccc(c2)-c2ccnc(n2)Nc2cc(ccc2Cl)CN2CCC1CC2]
EX. B9
Co. No. (123)

TABLE 1-continued
compounds according to the invention
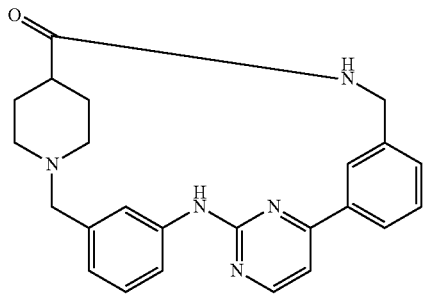 [SMILES: O=C1NCc2cccc(c2)-c2ccnc(n2)Nc2cccc(c2)CN2CCC1CC2]
Co. No. (124)
EX. B9
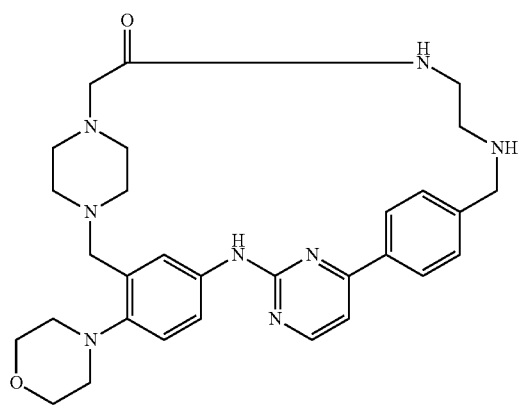 [SMILES: O=C1CN2CCN(CC2)Cc2cc(ccc2N2CCOCC2)Nc2nccc(n2)-c2ccc(cc2)CNCCN1]
Co. No. (125)
EX. B10
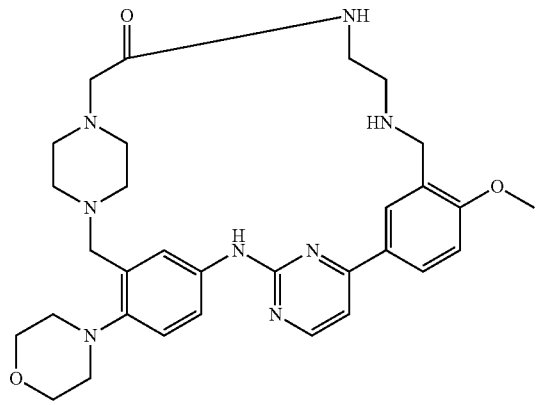 [SMILES: COc1ccc2cc1CNCCNC(=O)CN1CCN(CC1)Cc1cc(ccc1N1CCOCC1)Nc1nccc-2n1]
Co. No. (126)
EX. B10

TABLE 1-continued
compounds according to the invention
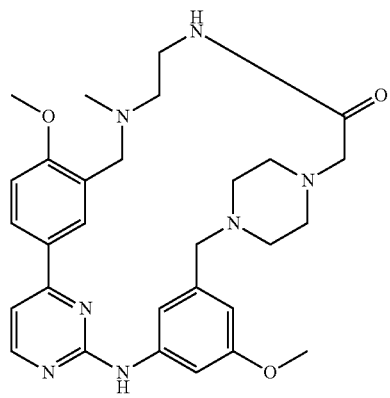 [SMILES: COc1cc2cc(c1)Nc1nccc(n1)-c1ccc(OC)c(c1)CN(C)CCNC(=O)CN1CCN(CC1)C2]
Co. No. (127)
EX. B10
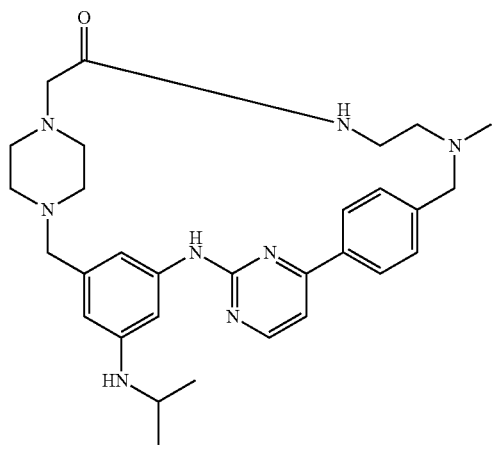 [SMILES: CC(C)Nc1cc2cc(c1)Nc1nccc(n1)-c1ccc(cc1)CN(C)CCNC(=O)CN1CCN(CC1)C2]
Co. No. (128)
EX. B10
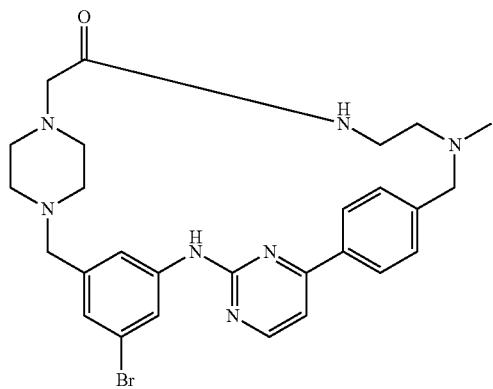 [SMILES: CN1CCNC(=O)CN2CCN(CC2)Cc2cc(Br)cc(c2)Nc2nccc(n2)-c2ccc(cc2)C1]
Co. No. (129)
EX. B10

TABLE 1-continued
compounds according to the invention
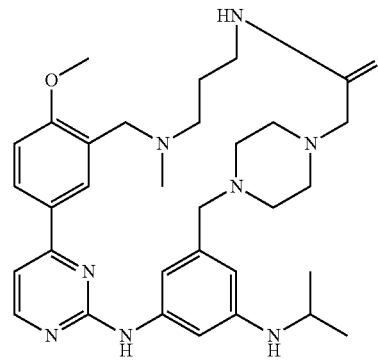
Co. No. (130)
EX. B10
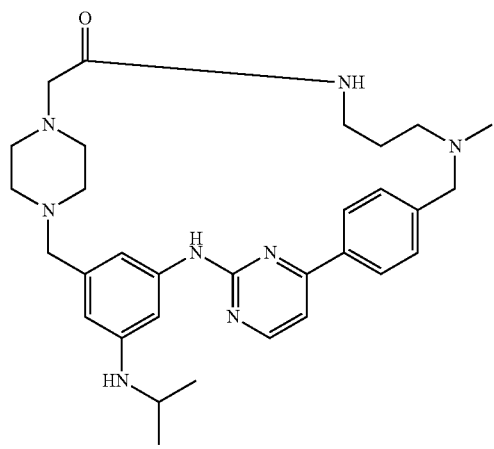 [SMILES: CC(C)Nc1cc2cc(c1)Nc1nccc(n1)-c1ccc(cc1)CN(C)CCCNC(=O)CN1CCN(CC1)C2]
Co. No. (131)
EX. B10
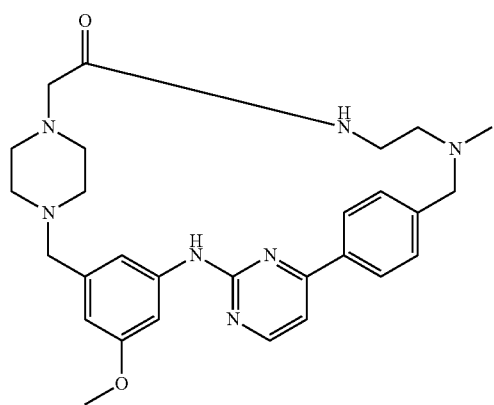 [SMILES: COc1cc2cc(c1)Nc1nccc(n1)-c1ccc(cc1)CN(C)CCNC(=O)CN1CCN(CC1)C2]
Co. No. (132)
EX. B10

TABLE 1-continued
compounds according to the invention
Co. No. (133)
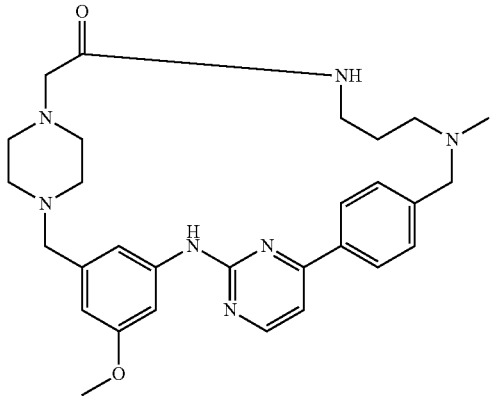 [SMILES: COc1cc2cc(c1)Nc1nccc(n1)-c1ccc(cc1)CN(C)CCCNC(=O)CN1CCN(CC1)C2]
EX. B10
Co. No. (134)
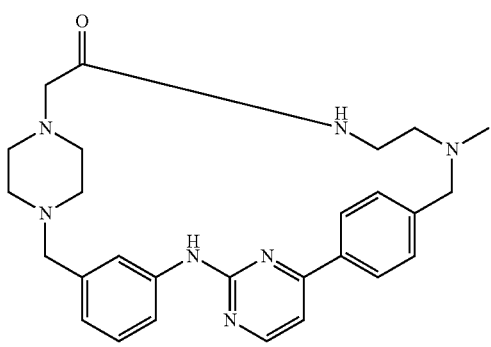 [SMILES: CN1CCNC(=O)CN2CCN(CC2)Cc2cccc(c2)Nc2nccc(n2)-c2ccc(cc2)C1]
EX. B10
Co. No. (135)
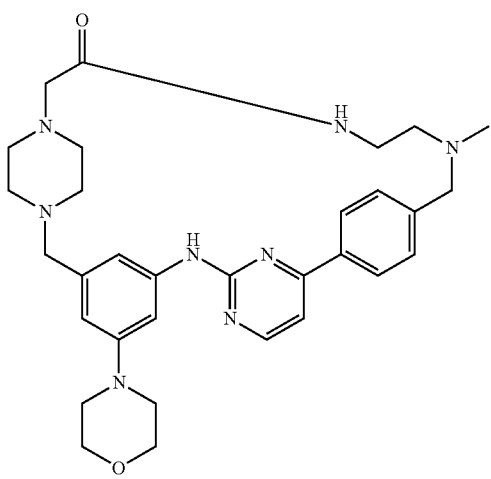 [SMILES: CN1CCNC(=O)CN2CCN(CC2)Cc2cc(cc(N3CCOCC3)c2)Nc2nccc(n2)-c2ccc(cc2)C1]
EX. B10

TABLE 1-continued
compounds according to the invention
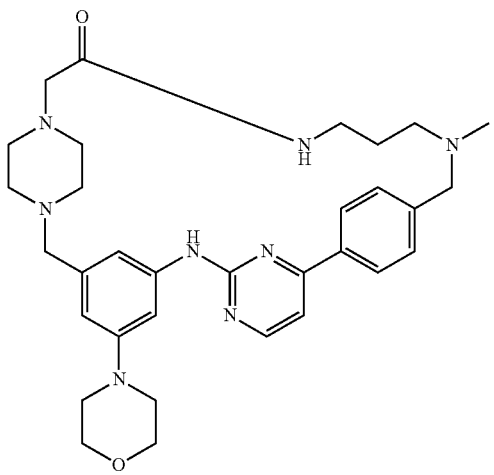 [SMILES: CN1CCCNC(=O)CN2CCN(CC2)Cc2cc(cc(N3CCOCC3)c2)Nc2nccc(n2)-c2ccc(cc2)C1]
Co. No. (136)4
EX. B10
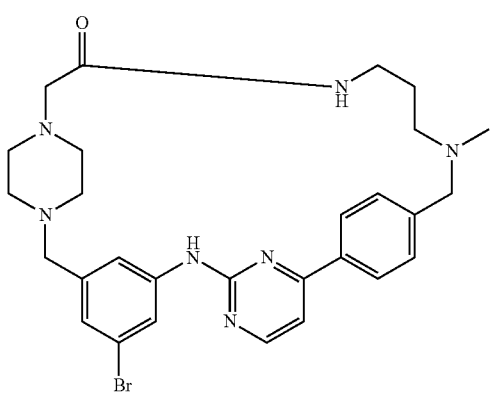 [SMILES: CN1CCCNC(=O)CN2CCN(CC2)Cc2cc(Br)cc(c2)Nc2nccc(n2)-c2ccc(cc2)C1]
Co. No. (137)
EX. B10
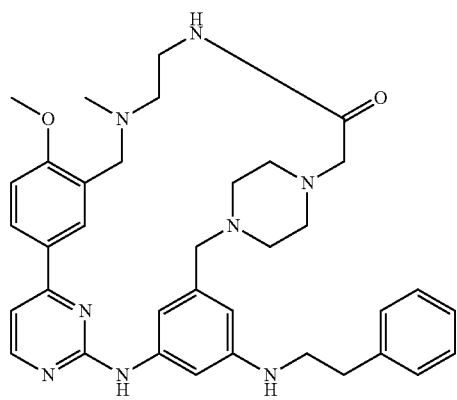 [SMILES: COc1ccc2cc1CN(C)CCNC(=O)CN1CCN(CC1)Cc1cc(NCCc3ccccc3)cc(c1)Nc1nccc-2n1]
Co. No. (138)
EX. B10

TABLE 1-continued
compounds according to the invention
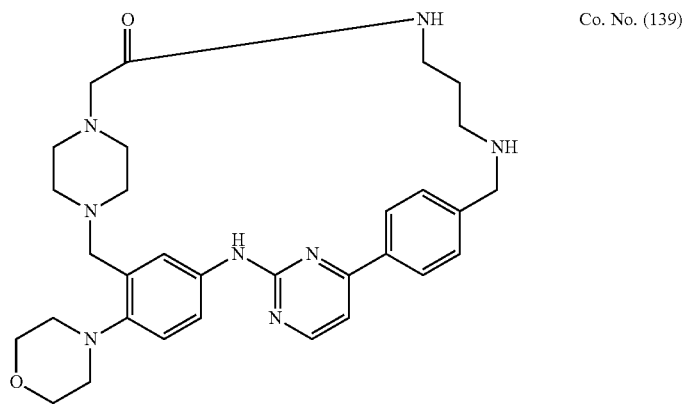
Co. No. (139)
EX. B10
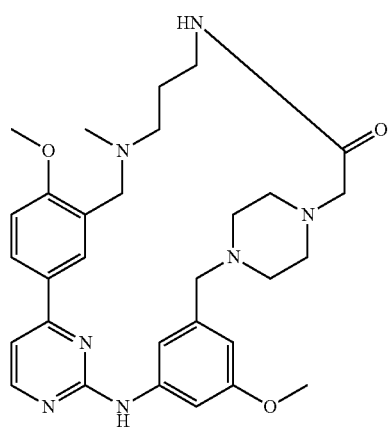 [SMILES: COc1cc2cc(c1)Nc1nccc(n1)-c1ccc(OC)c(c1)CN(C)CCCNC(=O)CN1CCN(CC1)C2]
Co. No. (140)
EX. B10
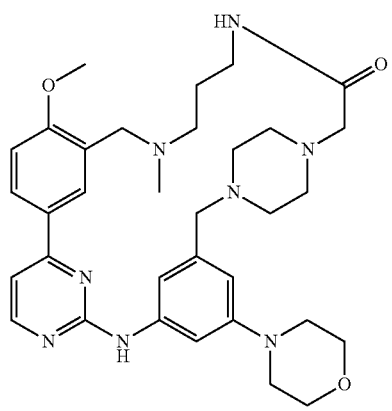 [SMILES: COc1ccc2cc1CN(C)CCCNC(=O)CN1CCN(CC1)Cc1cc(cc(N3CCOCC3)c1)Nc1nccc-2n1]
Co. No. (141)
EX. B10

TABLE 1-continued
compounds according to the invention
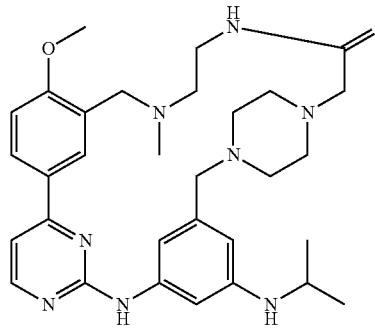
Co. No. (142)
EX. B10
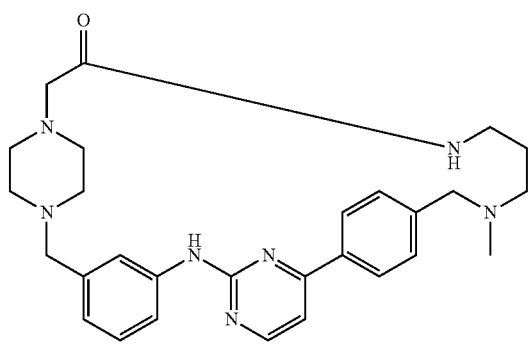 [SMILES: CN1CCCNC(=O)CN2CCN(CC2)Cc2cccc(c2)Nc2nccc(n2)-c2ccc(cc2)C1]
Co. No. (143)
EX. B10
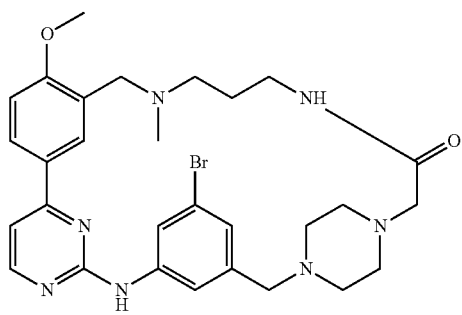 [SMILES: COc1ccc2cc1CN(C)CCCNC(=O)CN1CCN(CC1)Cc1cc(Br)cc(c1)Nc1nccc-2n1]
Co. No. (144)
EX. B10
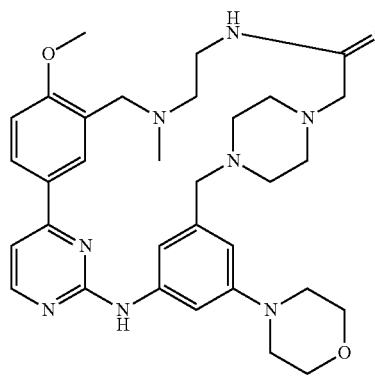
Co. No. (145)
EX. B10

TABLE 1-continued
compounds according to the invention
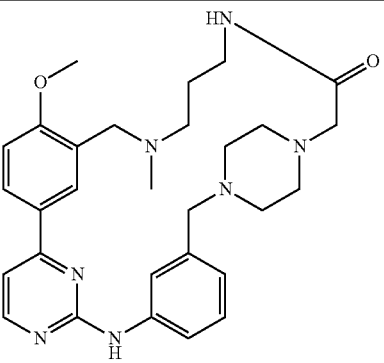
Co. No. (146)
EX. B10
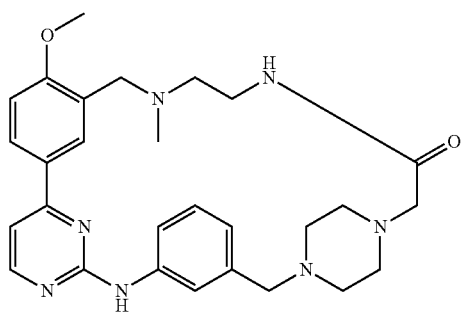 [SMILES: COc1ccc2cc1CN(C)CCNC(=O)CN1CCN(CC1)Cc1cccc(c1)Nc1nccc-2n1]
Co. No. (147)
EX. B10
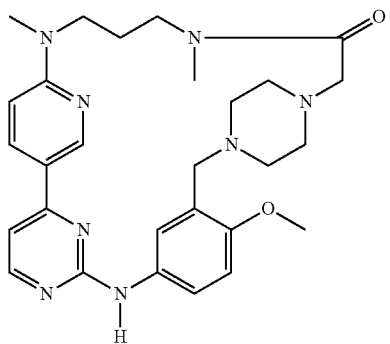 [SMILES: COc1ccc2cc1CN1CCN(CC1)CC(=O)N(C)CCCN(C)c1ccc(cn1)-c1ccnc(n1)N2]
Co. No. (148)
EX. B10
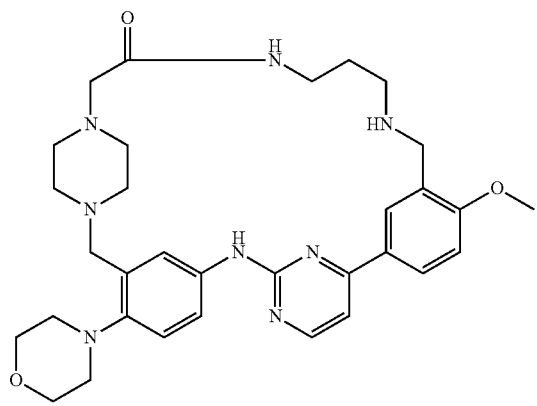 [SMILES: COc1ccc2cc1CNCCCNC(=O)CN1CCN(CC1)Cc1cc(ccc1N1CCOCC1)Nc1nccc-2n1]
Co. No. (13)
EX. B10

TABLE 1-continued
compounds according to the invention
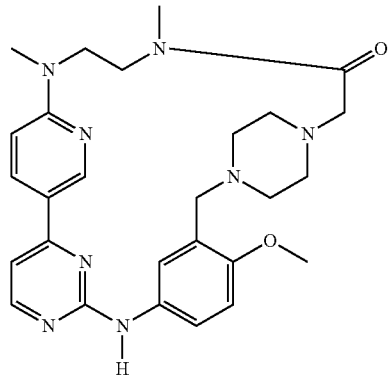 [SMILES: COc1ccc2cc1CN1CCN(CC1)CC(=O)N(C)CCN(C)c1ccc(cn1)-c1ccnc(n1)N2]
Co. No. (14)
EX. B10b
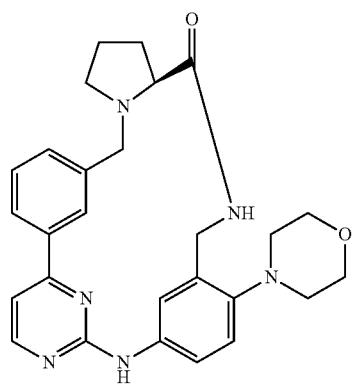 [SMILES: O=C1NCc2cc(ccc2N2CCOCC2)Nc2nccc(n2)-c2cccc(c2)CN2CCC[C@@H]12]
Co. No. (15)
EX. B11
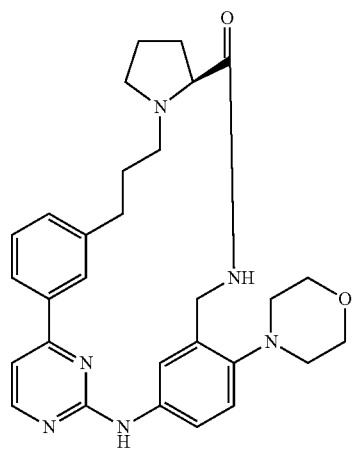 [SMILES: O=C1NCc2cc(ccc2N2CCOCC2)Nc2nccc(n2)-c2cccc(c2)CCCN2CCC[C@@H]12]
Co. No. (149)
EX. B11

TABLE 1-continued
compounds according to the invention
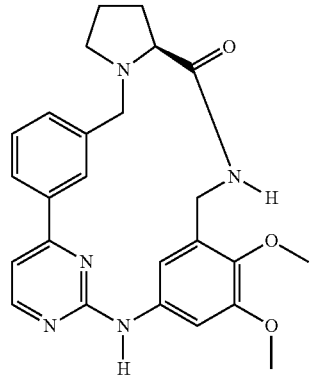 [SMILES: COc1cc2cc(c1OC)CNC(=O)[C@@H]1CCCN1Cc1cccc(c1)-c1ccnc(n1)N2]
Co. No. (150)
EX. B11
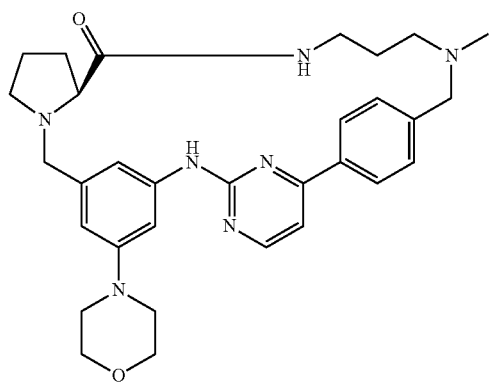 [SMILES: CN1CCCNC(=O)[C@@H]2CCCN2Cc2cc(cc(N3CCOCC3)c2)Nc2nccc(n2)-c2ccc(cc2)C1]
Co. No. (16)
EX. B12
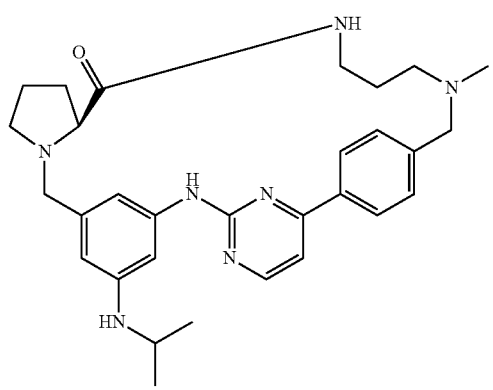 [SMILES: CC(C)Nc1cc2cc(c1)Nc1nccc(n1)-c1ccc(cc1)CN(C)CCCNC(=O)[C@@H]1CCCN1C2]
Co. No. (151)
EX. B12

TABLE 1-continued
compounds according to the invention
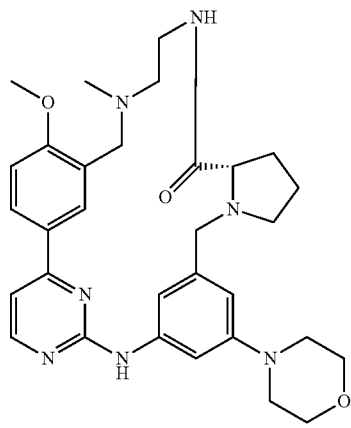 [SMILES: COc1ccc2cc1CN(C)CCNC(=O)[C@@H]1CCCN1Cc1cc(cc(N3CCOCC3)c1)Nc1nccc-2n1]
Co. No. (152)
EX. B12
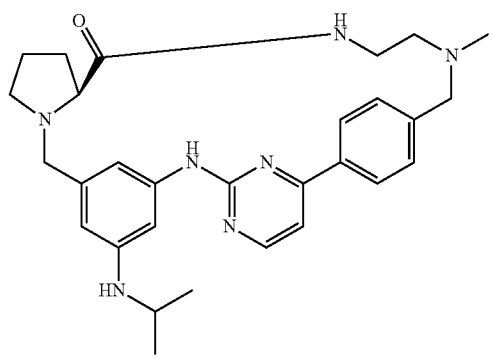 [SMILES: CC(C)Nc1cc2cc(c1)Nc1nccc(n1)-c1ccc(cc1)CN(C)CCNC(=O)[C@@H]1CCCN1C2]
Co. No. (153)
EX. B12
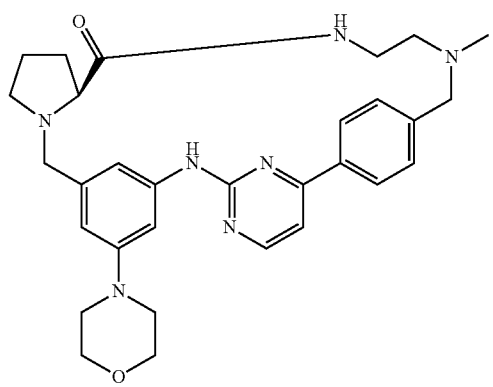 [SMILES: CN1CCNC(=O)[C@@H]2CCCN2Cc2cc(cc(N3CCOCC3)c2)Nc2nccc(n2)-c2ccc(cc2)C1]
Co. No. (154)
EX. B12

TABLE 1-continued
compounds according to the invention
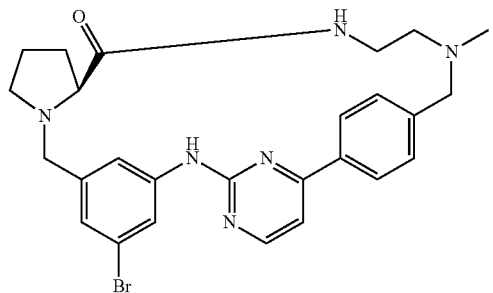 [SMILES: CN1CCNC(=O)[C@@H]2CCCN2Cc2cc(Br)cc(c2)Nc2nccc(n2)-c2ccc(cc2)C1]
Co. No. (155)
EX. B12
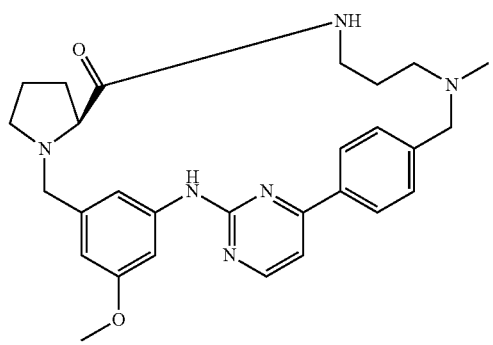 [SMILES: COc1cc2cc(c1)Nc1nccc(n1)-c1ccc(cc1)CN(C)CCCNC(=O)[C@@H]1CCCN1C2]
Co. No. (156)
EX. B12
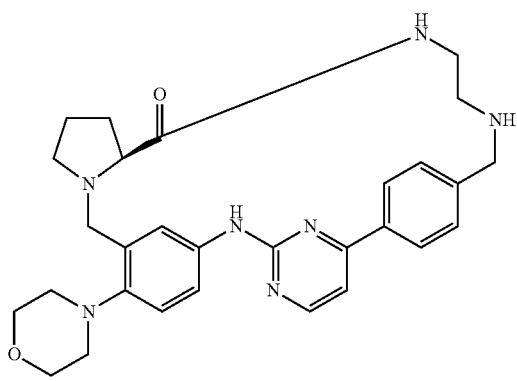 [SMILES: O=C1NCCNCc2ccc(cc2)-c2ccnc(n2)Nc2ccc(N3CCOCC3)c(c2)CN2CCC[C@@H]12]
Co. No. (157)
EX. B12
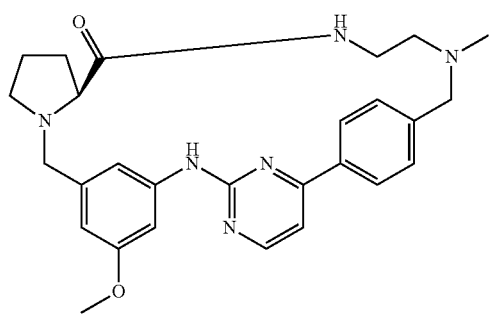 [SMILES: COc1cc2cc(c1)Nc1nccc(n1)-c1ccc(cc1)CN(C)CCNC(=O)[C@@H]1CCCN1C2]
Co. No. (158)
EX. B12

TABLE 1-continued
compounds according to the invention
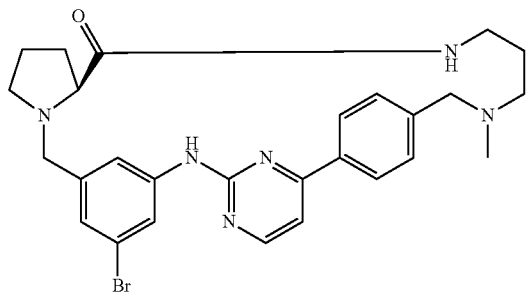 [SMILES: CN1CCCNC(=O)[C@@H]2CCCN2Cc2cc(Br)cc(c2)Nc2nccc(n2)-c2ccc(cc2)C1]
Co. No. (159)
EX. B12
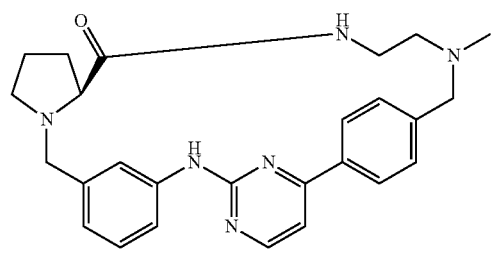 [SMILES: CN1CCNC(=O)[C@@H]2CCCN2Cc2cccc(c2)Nc2nccc(n2)-c2ccc(cc2)C1]
Co. No. (160)
EX. B12
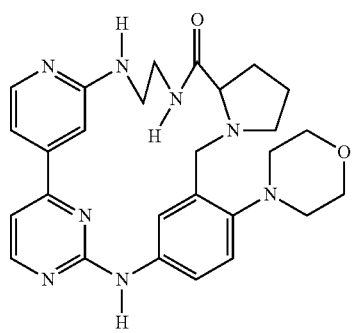 [SMILES: O=C1NCCNc2cc(ccn2)-c2ccnc(n2)Nc2ccc(N3CCOCC3)c(c2)CN2CCCC12]
Co. No. (161)
EX. B12
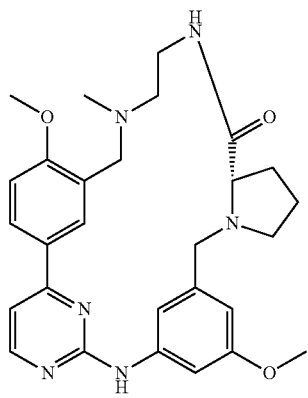 [SMILES: COc1cc2cc(c1)Nc1nccc(n1)-c1ccc(OC)c(c1)CN(C)CCNC(=O)[C@@H]1CCCN1C2]
Co. No. (162)
EX. B12

TABLE 1-continued
compounds according to the invention
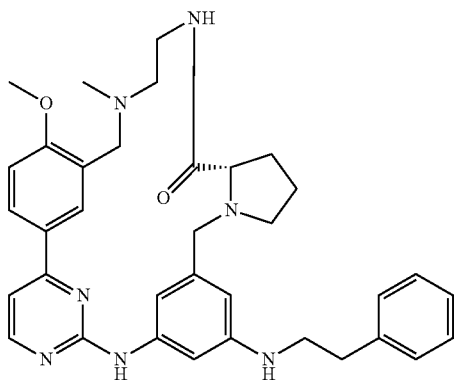 [SMILES: COc1ccc2cc1CN(C)CCNC(=O)[C@@H]1CCCN1Cc1cc(NCCc3ccccc3)cc(c1)Nc1nccc-2n1]
Co. No. (163)
EX. B12
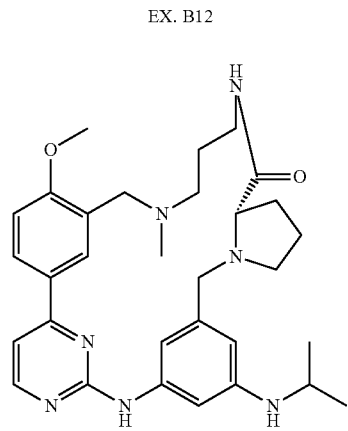
Co. No. (164)
EX. B12
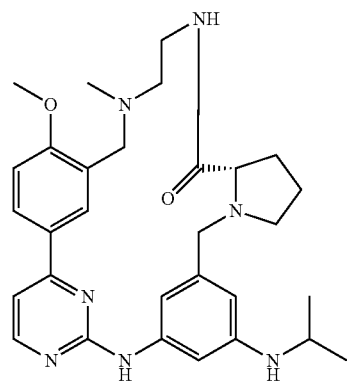 [SMILES: COc1ccc2cc1CN(C)CCNC(=O)[C@@H]1CCCN1Cc1cc(cc(NC(C)C)c1)Nc1nccc-2n1]
Co. No. (165)
EX. B12

TABLE 1-continued
compounds according to the invention
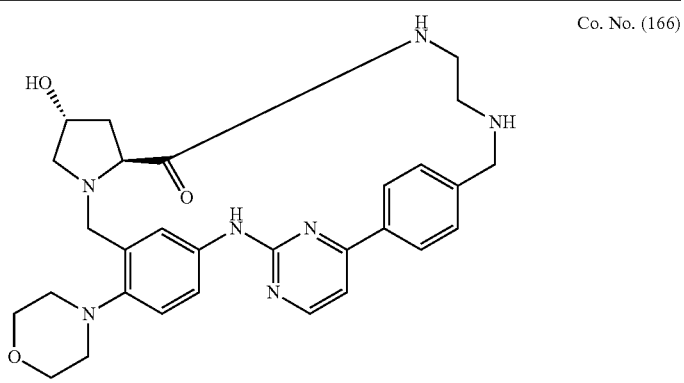
Co. No. (166)
EX. B12
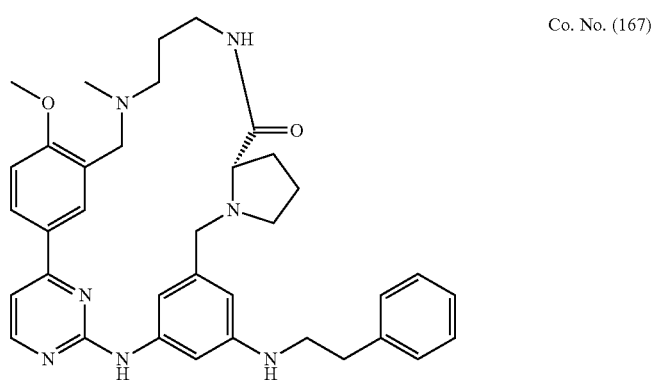
Co. No. (167)
EX. B12
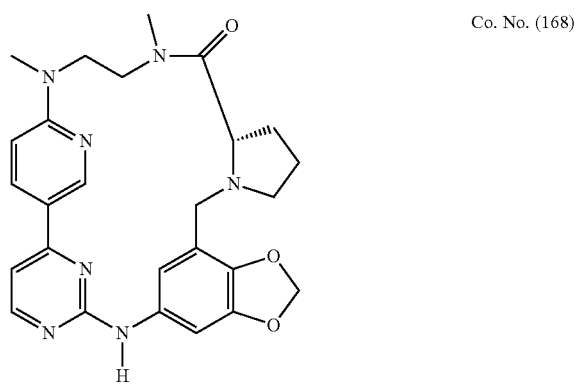
Co. No. (168)
EX. B12

TABLE 1-continued
compounds according to the invention
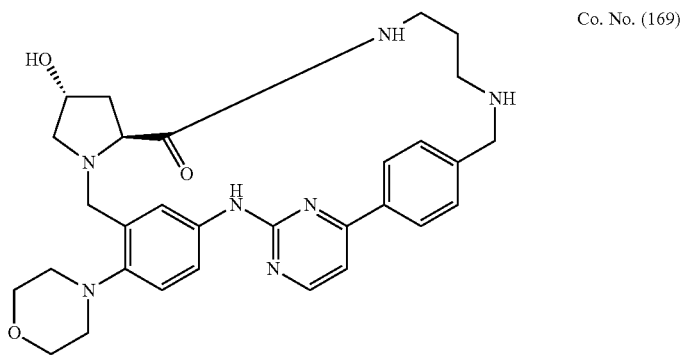
Co. No. (169)
EX. B12
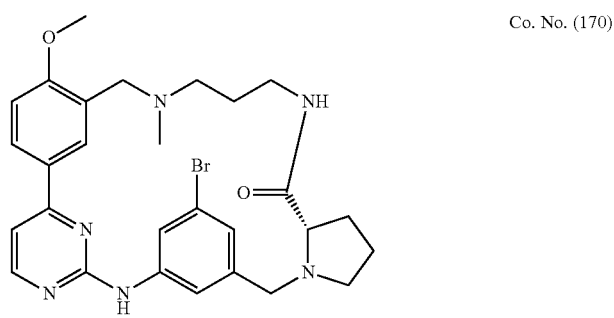
Co. No. (170)
EX. B12
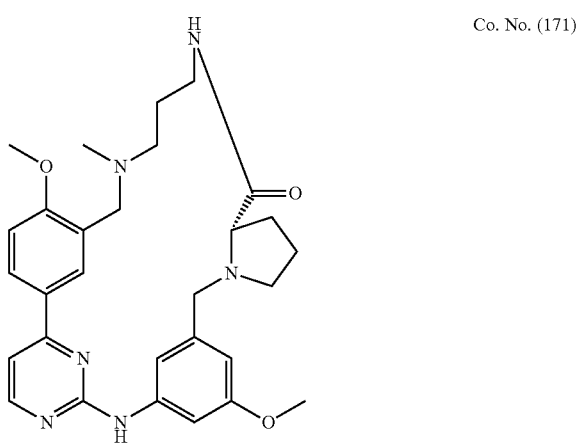
Co. No. (171)
EX. B12

TABLE 1-continued
compounds according to the invention
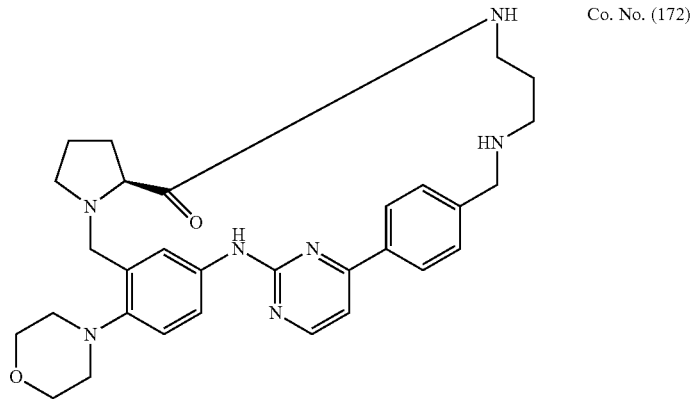
Co. No. (172)
EX. B12
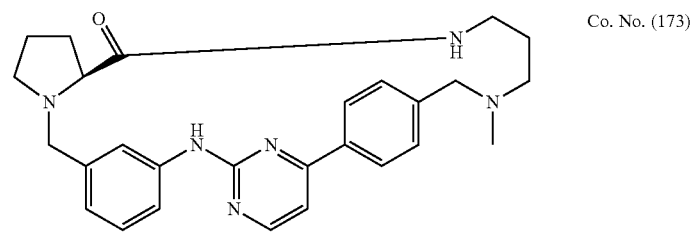
Co. No. (173)
EX. B12
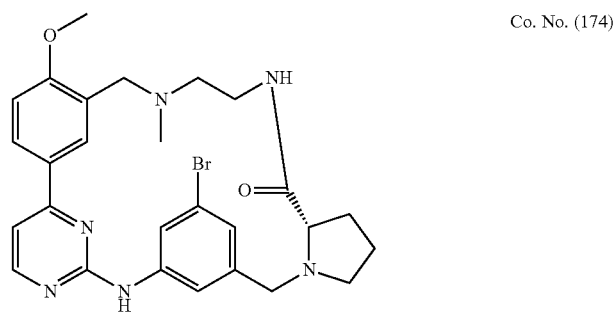
Co. No. (174)
EX. B12
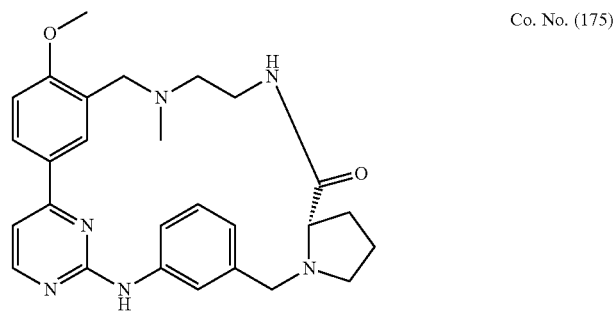
Co. No. (175)
EX. B12

TABLE 1-continued
compounds according to the invention
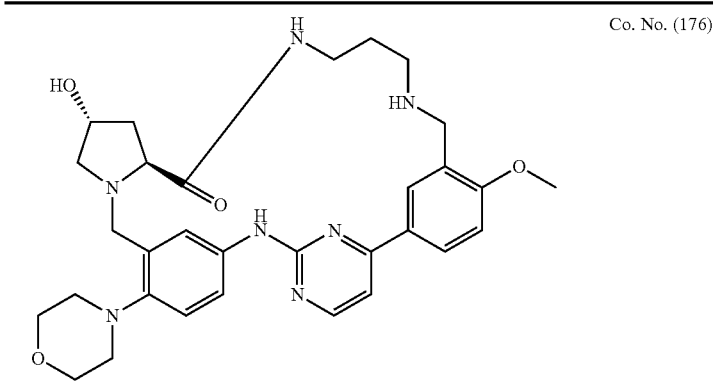
Co. No. (176)
EX. B12
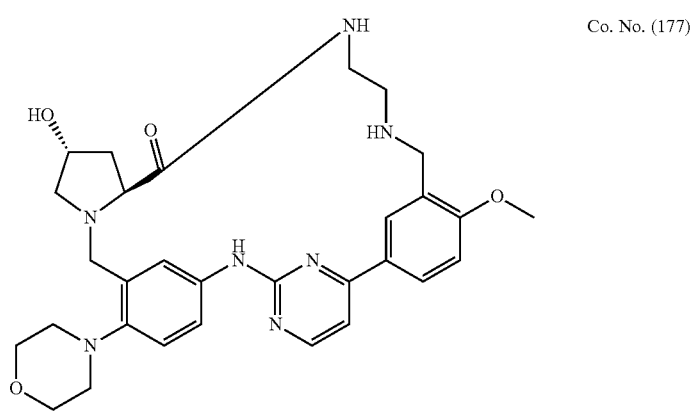
Co. No. (177)
EX. B12
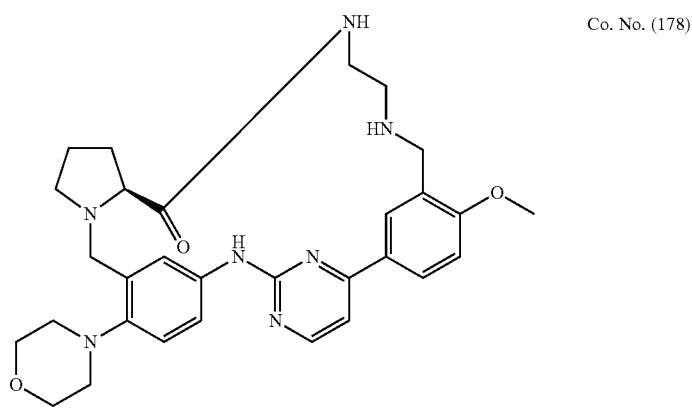
Co. No. (178)
EX. B12

TABLE 1-continued
compounds according to the invention
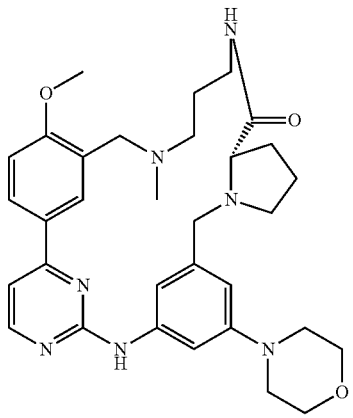 [SMILES: COc1ccc2cc1CN(C)CCCNC(=O)[C@@H]1CCCN1Cc1cc(cc(N3CCOCC3)c1)Nc1nccc-2n1]
Co. No. (179)
EX. B12
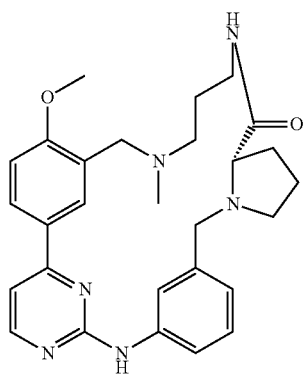 [SMILES: COc1ccc2cc1CN(C)CCCNC(=O)[C@@H]1CCCN1Cc1cccc(c1)Nc1nccc-2n1]
Co. No. (180)
EX. B12
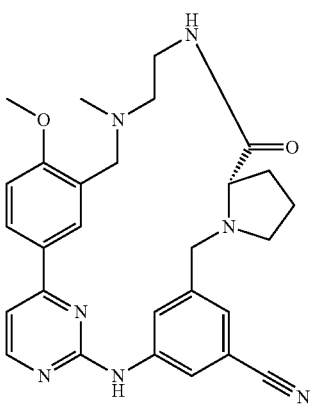 [SMILES: COc1ccc2cc1CN(C)CCNC(=O)[C@@H]1CCCN1Cc1cc(C#N)cc(c1)Nc1nccc-2n1]
Co. No. (181)
EX. B12

TABLE 1-continued
compounds according to the invention
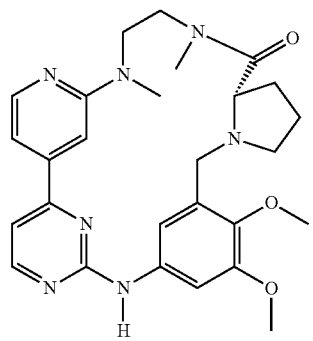 [SMILES: COc1cc2cc(c1OC)CN1CCC[C@H]1C(=O)N(C)CCN(C)c1cc(ccn1)-c1ccnc(n1)N2]
EX. B12b
Co. No. (17)
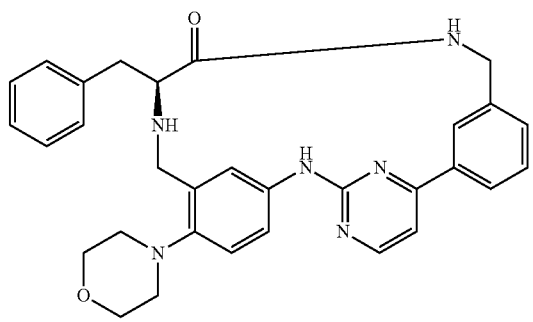 [SMILES: O=C1NCc2cccc(c2)-c2ccnc(n2)Nc2ccc(N3CCOCC3)c(c2)CN[C@H]1Cc1ccccc1]
EX. B13
Co. No. (18)
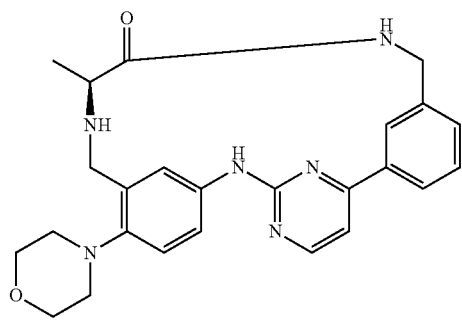 [SMILES: C[C@@H]1NCc2cc(ccc2N2CCOCC2)Nc2nccc(n2)-c2cccc(c2)CNC1=O]
EX. B13
Co. No. (182)
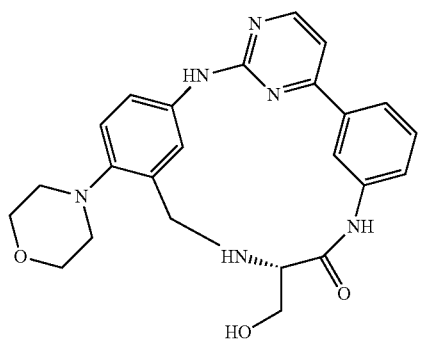 [SMILES: O=C1Nc2cccc(c2)-c2ccnc(n2)Nc2ccc(N3CCOCC3)c(c2)CN[C@H]1CO]
EX. B13
Co. No. (183)

TABLE 1-continued
compounds according to the invention
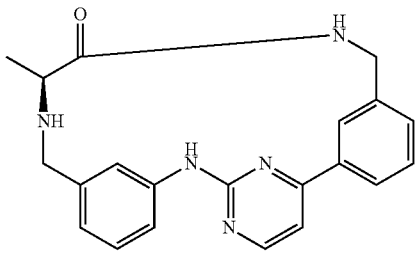 [SMILES: C[C@@H]1NCc2cccc(c2)Nc2nccc(n2)-c2cccc(c2)CNC1=O]
EX. B13
Co. No. (184)
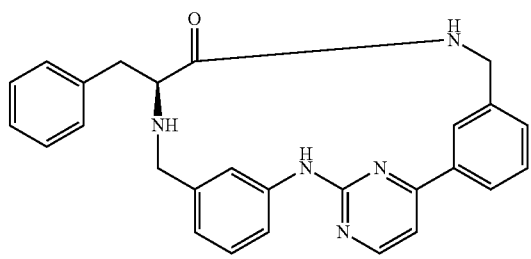 [SMILES: O=C1NCc2cccc(c2)-c2ccnc(n2)Nc2cccc(c2)CN[C@H]1Cc1ccccc1]
EX. B13
Co. No. (185)
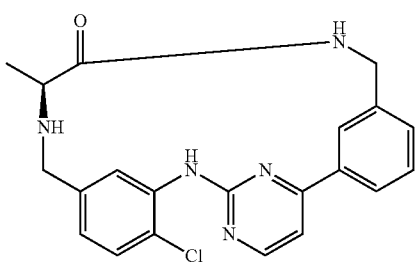 [SMILES: C[C@@H]1NCc2ccc(Cl)c(c2)Nc2nccc(n2)-c2cccc(c2)CNC1=O]
EX. B13
Co. No. (186)
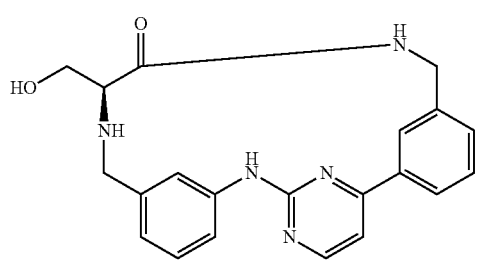 [SMILES: O=C1NCc2cccc(c2)-c2ccnc(n2)Nc2cccc(c2)CN[C@H]1CO]
EX. B13
Co. No. (187)
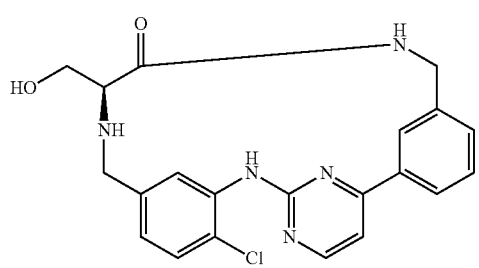 [SMILES: O=C1NCc2cccc(c2)-c2ccnc(n2)Nc2cc(ccc2Cl)CN[C@H]1CO]
EX. B13
Co. No. (188)

TABLE 1-continued
compounds according to the invention
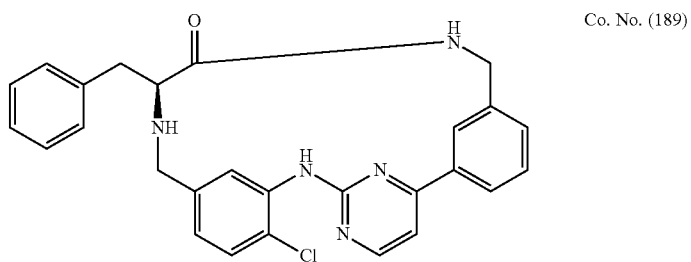
EX. B13
Co. No. (189)
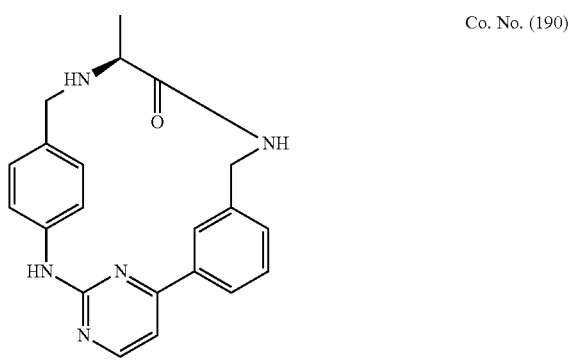
EX. B13
Co. No. (190)
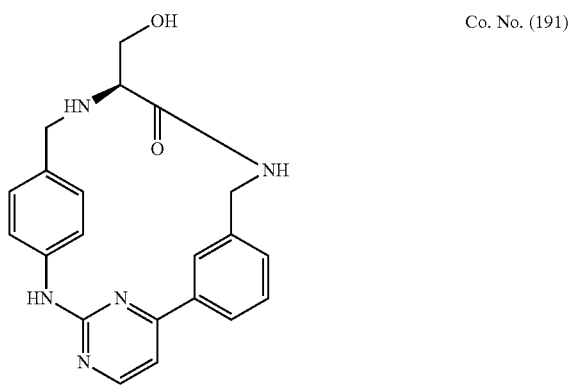
EX. B13
Co. No. (191)
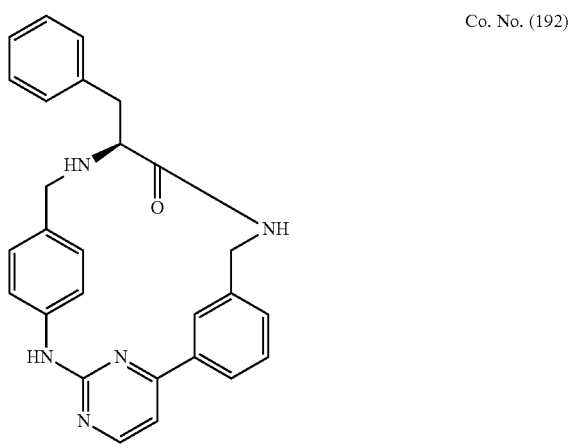
EX. B13
Co. No. (192)

TABLE 1-continued
compounds according to the invention
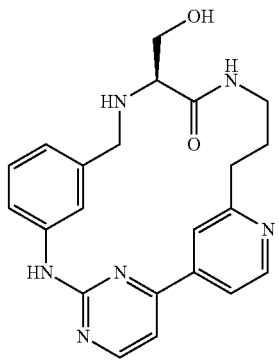 [SMILES: O=C1NCCCc2cc(ccn2)-c2ccnc(n2)Nc2cccc(c2)CN[C@H]1CO]
Co. No. (19)
EX. B13b
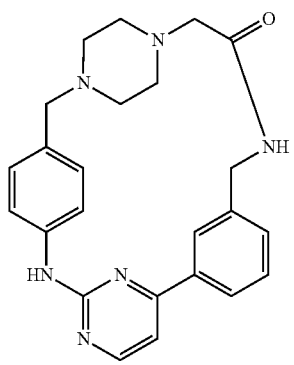 [SMILES: O=C1CN2CCN(CC2)Cc2ccc(cc2)Nc2nccc(n2)-c2cccc(c2)CN1]
Co. No. (193)
EX. B14
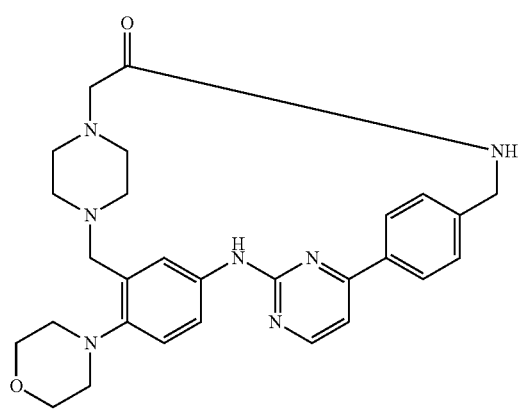 [SMILES: O=C1CN2CCN(CC2)Cc2cc(ccc2N2CCOCC2)Nc2nccc(n2)-c2ccc(cc2)CN1]
Co. No. (194)
EX. B14a TABLE 1-continued
compounds according to the invention
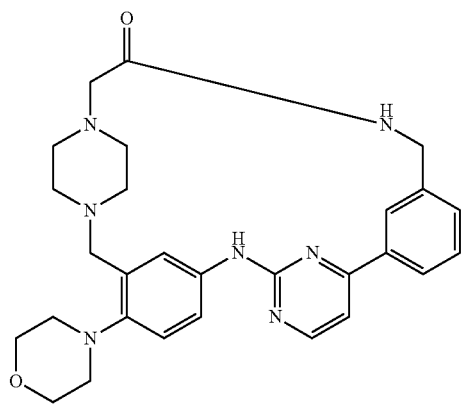 [SMILES: O=C1CN2CCN(CC2)Cc2cc(ccc2N2CCOCC2)Nc2nccc(n2)-c2cccc(c2)CN1]
EX. B14a
Co. No. (20)
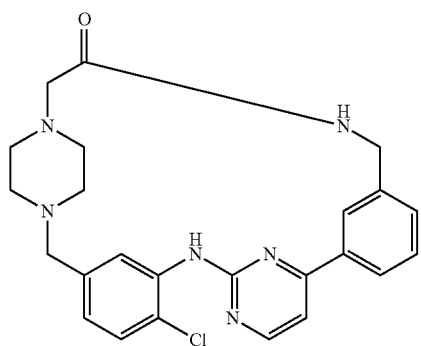 [SMILES: O=C1CN2CCN(CC2)Cc2ccc(Cl)c(c2)Nc2nccc(n2)-c2cccc(c2)CN1]
EX. B14a
Co. No. (195)
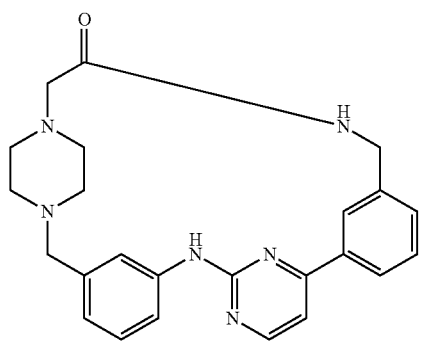 [SMILES: O=C1CN2CCN(CC2)Cc2cccc(c2)Nc2nccc(n2)-c2cccc(c2)CN1]
EX. B14a
Co. No. (196)
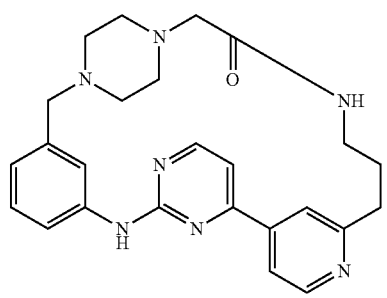 [SMILES: O=C1CN2CCN(CC2)Cc2cccc(c2)Nc2nccc(n2)-c2ccnc(c2)CCCN1]
EX. B14B
Co. No. (21)

Analytical Part

LCMS General Procedure A

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

LCMS General Procedure B

The HPLC measurement was performed using an Agilent 1100 series liquid chromatography system comprising a binary pump with degasser, an autosampler, a column oven, a UV detector and a column as specified in the respective methods below. Flow from the column was split to a MS spectrometer. The MS detector was configured with an electrospray ionization source. The capillary voltage was 3 kV, the quadrupole temperature was maintained at 100° C. and the desolvation temperature was 300° C. Nitrogen was used as the nebulizer gas. Data acquisition was performed with an Agilent Chemstation data system.

LCMS—Procedure 1

In addition to general procedure A: Reversed phase HPLC was carried out on an Xterra MS C18 column (3.5 nm, 4.6×100 mm) with a flow rate of 1.6 ml/min. Three mobile phases (mobile phase A: 95% 25 mM ammonium acetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS—Procedure 2

In addition to general procedure A: Column heater was set at 60° C. Reversed phase HPLC was carried out on an Xterra MS C18 column (3.5 nm, 4.6×100 mm) with a flow rate of 1.6 ml/min. Three mobile phases (mobile phase A: 95% 25 mM ammonium acetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS—Procedure 3

In addition to general procedure B: Reversed phase HPLC was carried out on a YMC-Pack ODS-AQ C18 column (4.6×50 mm) with a flow rate of 2.6 ml/min. A gradient run was used from 95% water and 5% acetonitrile to 95% acetonitrile in 4.80 minutes and was hold for 1.20 minutes. Mass spectra were acquired by scanning from 100 to 1400. Injection volume was 10 μl. Column temperature was 35° C.

LCMS—Procedure 4

In addition to general procedure B: Reversed phase HPLC was carried out on a YMC-Pack ODS-AQ C18 column (4.6×50 mm) with a flow rate of 2.6 ml/min. A gradient run was used from 88% water and 12% acetonitrile to 88% acetonitrile in 3.40 minutes and was hold for 1.20 minutes. Mass spectra were acquired by scanning from 110 to 1000. Injection volume was 10 μl. Column temperature was 35° C.

LCMS—Procedure 5

In addition to general procedure B: Reversed phase HPLC was carried out on a SB-C18 1pk column (2.1×30 mm, 1.8 nm) with a flow rate of 1.5 ml/min. A gradient run was used from 88% water and 12% acetonitrile to 88% acetonitrile in 1.30 minutes and was hold for 0.50 minutes. Mass spectra were acquired by scanning from 100 to 1000. Injection volume was 1 μA Column temperature was 65° C.

LCMS—Procedure 6

In addition to general procedure B: Reversed phase HPLC was carried out on a YMC-Pack ODS-AQ C18 column (4.6×50 mm) with a flow rate of 2.6 ml/min. A gradient run was used from 95% water and 5% acetonitrile to 95% acetonitrile in 7.30 minutes and was hold for 1.20 minutes. Mass spectra were acquired by scanning from 100 to 1000. Injection volume was 104 Column temperature was 35° C.

Melting Points

For a number of compounds, melting points were determined with a DSC823e from Mettler-Toledo (indicated by m.p.$^a$). Melting points were measured with a temperature gradient of 30° C./minute. Values are peak values.

For a number of compounds, melting points were obtained with a Büchi melting point apparatus B-540 or B-545 in open capillary tubes (indicated by m.p.$^b$). The heating medium was a metal block. The melting of the sample was visually observed by a magnifying lense and a big light contrast. Melting points were measured with a temperature gradient of either 3 or 10° C./minute. Maximum temperature was 300° C.

For a number of compounds, melting points (indicated by m.p.$^c$) were obtained with a Kofler hot bench, consisting of a heated plate with linear temperature gradient, a sliding pointer and a temperature scale in degrees Celsius.

Values were obtained with experimental uncertainties that are commonly associated with this analytical method.

TABLE 2

Analytical data - Retention time ($R_t$ in minutes of the major component), (MH$^+$) peak (of the free base), LCMS procedure, melting points (m.p. is defined as melting point) and salt forms.

| Co. Nr. | $R_t$ | (MH)$^+$ | LCMS Procedure | m.p. (° C.) and salt forms |
|---|---|---|---|---|
| 3 | 1.40 | 572 | 3 | |
| 13 | 1.42 | 587 | 3 | |
| 176 | 1.48 | 574 | 3 | |
| 122 | 0.46 | 532 | 5 | |
| 97 | 2.04 | 501 | 3 | |
| 94 | 1.85 | 515 | 3 | |
| 102 | 1.90 | 530 | 3 | |
| 98 | 1.99 | 517 | 3 | |
| 157 | 1.05 | 514 | 4 | |
| 71 | 0.95 | 528 | 4 | |
| 125 | 0.85 | 543 | 4 | |
| 166 | 1.04 | 530 | 4 | |
| 172 | 1.04 | 528 | 4 | |
| 69 | 0.95 | 542 | 4 | |
| 64 | 1.46 | 558 | 3 | |
| 126 | 1.33 | 573 | 3 | |
| 177 | 1.44 | 560 | 3 | |
| 139 | 1.30 | 557 | 3 | |
| 115 | 1.30 | 504 | 3 | |
| 178 | 1.49 | 544 | 3 | |
| 96 | 2.17 | 515 | 3 | |
| 117 | 1.54 | 564 | 3 | |
| 169 | 1.46 | 544 | 3 | |
| 93 | 1.97 | 529 | 3 | |
| 103 | 1.89 | 544 | 3 | |
| 91 | 2.29 | 565 | 3 | |
| 87 | 1.98 | 489 | 3 | |

TABLE 2-continued

Analytical data - Retention time ($R_t$ in minutes of the major component), $(MH^+)$ peak (of the free base), LCMS procedure, melting points (m.p. is defined as melting point) and salt forms.

| Co. Nr. | $R_t$ | $(MH)^+$ | LCMS Procedure | m.p. (° C.) and salt forms |
|---|---|---|---|---|
| 89 | 1.92 | 505 | 3 | |
| 99 | 2.01 | 531 | 3 | |
| 90 | 2.03 | 503 | 3 | |
| 88 | 1.99 | 489 | 3 | |
| 6 | 1.78 | 515 | 3 | |
| 9 | 1.71 | 530 | 3 | |
| 5 | 1.87 | 489 | 3 | |
| 104 | 1.72 | 544 | 3 | |
| 92 | 1.80 | 529 | 3 | |
| 48 | | | | >260° C. (m.p.$^c$) |
| 116 | 1.35 | 532 | 3 | |
| 19 | | | | 253.6-254.9 (m.p.$^b$) |
| 21 | | | | 243.2-244.3 (m.p.$^b$) |
| 84 | 3.99 | 515 | 1 | 190 (m.p.$^c$) |
| 161 | — | 501 | | |
| 7 | 1.93 | 515 | 3 | |
| 86 | 1.80 | 489 | 3 | |
| 175 | 1.23 | 473 | 3 | |
| 147 | 1.13 | 502 | 3 | |
| 83 | 1.28 | 487 | 3 | |
| 173 | 1.27 | 457 | 3 | |
| 78 | 1.15 | 471 | 3 | |
| 143 | 1.11 | 486 | 3 | |
| 113 | 1.08 | 447 | 3 | |
| 170 | 1.49 | 565 | 3 | |
| 76 | 1.44 | 579 | 3 | |
| 144 | 1.43 | 594 | 3 | |
| 2 | 4.59 | 445 | 2 | 202.8 (m.p.$^a$) |
| 159 | 1.50 | 535 | 3 | |
| 63 | 1.31 | 549 | 3 | |
| 137 | 1.39 | 564 | 3 | |
| 110 | 1.31 | 525 | 3 | |
| 174 | 1.43 | 551 | 3 | |
| 79 | 1.50 | 565 | 3 | |
| 50 | 1.34 | 580 | 3 | |
| 1 | 5.78 | 471 | 1 | 286.3 (m.p.$^a$) |
| 183 | 1.69 | 461 | 3 | |
| 14 | 4.74 | 503 | 1 | 245.7 (m.p.$^a$) |
| 4 | 4.55 | 488 | 1 | 305.2 (m.p.$^a$) |
| 77 | 1.39 | 572 | 3 | |
| 82 | 1.22 | 457 | 3 | |
| 68 | 1.36 | 542 | 3 | |
| 135 | 1.23 | 557 | 3 | |
| 145 | 1.25 | 587 | 3 | |
| 153 | 1.16 | 500 | 3 | |
| 61 | 1.27 | 514 | 3 | |
| 128 | 1.13 | 529 | 3 | |
| 179 | 1.40 | 572 | 3 | |
| 141 | 1.30 | 601 | 3 | |
| 16 | 1.40 | 542 | 3 | |
| 72 | 1.30 | 556 | 3 | |
| 136 | 1.30 | 571 | 3 | |
| 10 | 1.30 | 532 | 3 | |
| 180 | 1.29 | 487 | 3 | |
| 81 | 1.22 | 501 | 3 | |
| 146 | 1.21 | 516 | 3 | |
| 80 | 1.33 | 586 | 3 | |
| 164 | 1.40 | 544 | 3 | |
| 70 | 1.26 | 558 | 3 | |
| 130 | 1.24 | 573 | 3 | |
| 155 | 1.50 | 521 | 3 | |
| 60 | 1.42 | 535 | 3 | |
| 129 | 1.31 | 550 | 3 | |
| 121 | 1.46 | 511 | 3 | |
| 142 | 1.21 | 559 | 3 | |
| 75 | 1.32 | 544 | 3 | |
| 120 | 1.29 | 463 | 3 | |
| 85 | 4.75 | 502 | 1 | 289.3 (m.p.$^a$) |
| 148 | 5.60 | 517 | 1 | 281.6 (m.p.$^a$) |
| 11 | 4.82 | 478 | 1 | 187.3 (m.p.$^a$) |
| 160 | 1.30 | 443 | 3 | |
| 134 | 1.12 | 472 | 3 | |
| 114 | 1.24 | 433 | 3 | |
| 154 | 1.42 | 528 | 3 | |
| 108 | 1.37 | 518 | 3 | |
| 151 | 1.26 | 514 | 3 | |
| 65 | 1.22 | 528 | 3 | |
| 131 | 1.21 | 543 | 3 | |
| 111 | 1.17 | 504 | 3 | |
| 112 | 1.55 | 555 | 3 | |
| 152 | 1.41 | 558 | 3 | |
| 163 | 1.81 | 592 | 3 | |
| 74 | 1.81 | 606 | 3 | |
| 165 | 1.36 | 530 | 3 | |
| 118 | 1.28 | 477 | 3 | |
| 156 | 1.35 | 487 | 3 | |
| 66 | 1.23 | 501 | 3 | |
| 133 | 1.23 | 516 | 3 | |
| 158 | 1.67 | 473 | 6 | |
| 62 | 1.37 | 487 | 3 | |
| 132 | 1.22 | 502 | 3 | |
| 109 | 1.33 | 463 | 3 | |
| 106 | 1.17 | 490 | 3 | |
| 162 | 1.41 | 503 | 3 | |
| 67 | 1.42 | 517 | 3 | |
| 127 | 1.27 | 532 | 3 | |
| 107 | 1.39 | 493 | 3 | |
| 138 | 1.76 | 621 | 3 | |
| 105 | 1.42 | 548 | 3 | |
| 171 | 1.42 | 517 | 3 | |
| 140 | 1.30 | 546 | 3 | |
| 167 | 1.82 | 606 | 3 | |
| 73 | 1.32 | 531 | 3 | |
| 181 | 1.40 | 498 | 3 | |
| 119 | 1.53 | 541 | 3 | |
| 15 | 1.87 | 471 | 3 | |
| 101 | 1.80 | 445 | 3 | |
| 95 | 1.75 | 485 | 3 | |
| 20 | 1.78 | 500 | 3 | |
| 27 | 1.78 | 487 | 3 | |
| 182 | 1.69 | 445 | 3 | |
| 18 | 2.10 | 521 | 3 | |
| 51 | 2.20 | 420 | 3 | |
| 123 | 1.84 | 434 | 3 | |
| 195 | 1.83 | 449 | 3 | |
| 52 | 2.14 | 436 | 3 | |
| 188 | 1.82 | 410 | 3 | |
| 189 | 2.38 | 470 | 3 | |
| 43 | 1.93 | 485 | 3 | |
| 100 | 1.84 | 459 | 3 | |
| 53 | 1.78 | 386 | 3 | |
| 124 | 1.65 | 400 | 3 | |
| 196 | 1.66 | 415 | 3 | |
| 45 | 1.75 | 402 | 3 | |
| 187 | 1.58 | 376 | 3 | |
| 185 | 2.10 | 436 | 3 | |
| 149 | 2.03 | 499 | 3 | |
| 54 | 1.46 | 386 | 3 | |
| 193 | 1.62 | 415 | 3 | |
| 55 | 1.40 | 402 | 3 | |
| 190 | 1.49 | 360 | 3 | |
| 186 | 7.51 | 394 | 2 | |
| 184 | 6.29 | 360 | 2 | |
| 23 | 5.93 | 446 | 1 | 282.8 (m.p.$^a$) |
| 49 | 1.95 | 471 | 3 | |
| 12 | 1.87 | 485 | 3 | |
| 194 | 1.73 | 500 | 3 | |
| 56 | 1.82 | 487 | 3 | |
| 191 | 1.43 | 376 | 3 | |
| 192 | 1.95 | 436 | 3 | |
| 17 | 4.44 | 504 | 1 | |
| 57 | 1.81 | 386 | 3 | |
| 58 | 1.91 | 458 | 3 | |
| 168 | 4.87 | 488 | 1 | |
| 32 | 1.75 | 499 | 3 | |
| 34 | 1.31 | 512 | 3 | |

TABLE 2-continued

Analytical data - Retention time ($R_t$ in minutes of the major component), (MH+) peak (of the free base), LCMS procedure, melting points (m.p. is defined as melting point) and salt forms.

| Co. Nr. | $R_t$ | (MH)+ | LCMS Procedure | m.p. (° C.) and salt forms |
|---|---|---|---|---|
| 44 | 1.78 | 487 | 3 | |
| 8 | 4.48 | 436 | 1 | |
| 150 | 5.69 | 446 | 1 | •HCl |
| 59 | 2.22 | 511 | 3 | |
| 39 | 1.36 | 500 | 3 | |
| 38 | 1.39 | 526 | 3 | |
| 37 | 1.81 | 513 | 3 | |
| 35 | 1.72 | 457 | 3 | |
| 26 | 1.86 | 499 | 3 | |
| 25 | 1.40 | 512 | 3 | |
| 47 | 1.35 | 526 | 3 | |
| 41 | 2.27 | 511 | 3 | |
| 46 | 1.84 | 513 | 3 | |
| 42 | 1.30 | 500 | 3 | |
| 40 | 1.76 | 487 | 3 | |
| 24 | 1.81 | 457 | 3 | |
| 22 | 1.34 | 485 | 3 | |
| 28 | 1.37 | 498 | 3 | |
| 36 | 1.57 | 497 | 3 | |
| 29 | 1.38 | 499 | 3 | |
| 33 | 1.37 | 473 | 3 | |
| 30 | 1.32 | 443 | 3 | |
| 31 | 1.11 | 486 | 3 | |

C. Pharmacological Example

C1. Kinase Profiling

The in vitro inhibition of a panel of kinases was assessed using either the scintillation proximity assay (SPA) as described by Cook, N. D. et al., Advances in Experimental Medicine and Biology (1991), 36; p. 525-528. The results are given in Table 3.

In the SPA technology the activity of the kinase of interest is measured using an appropriate biotinylated substrate that is incubated with the aforementioned kinase protein in the presence of ($^{33}$P) radiolabeled ATP. ($^{33}$P) Phosphorylation of the substrate is subsequently measured through binding of the phosphorylated substrate to streptavidine coated beads that are based on the scintillant poly(vinyl toluene) (PVT-Beads). The scintillation intensity is detected by imaging on Leadseeker.

Detailed Description

All kinases are pre-diluted to a 10x working concentration prior to addition into the assay. The composition of the dilution buffer for each kinase is detailed below.

C1.1 PLK-4 Human

In a final reaction volume of 30 µl, PLK4 (h) (19 µg/ml) is incubated with 50 mM Hepes pH 8.0, 10 mM MgCl$_2$, 50 mM NaCl, 1 mM NaF, 1 mM DTT, 10 µM of peptide Biotin-RPRGQRDSSYYWE-OH, 1 µM ATP and 2 nM [γ-$^{33}$P-ATP] (6.0 µCi/ml). After incubation of 60 minutes at room temperature, the reaction is stopped by addition of 40 µL of stop solution containing 8.7 mM EDTA, BSA 0.17%, 0.17% Triton X-100, 1.7 mg/ml SPA beads (GE-healthcare). The plate is centrifuged and read for Scintillation imaging on Leadseeker.

C1.2 Aurora-B Human

In a final reaction volume of 30 µl, AuroraB (h) (0.5 µg/ml) is incubated with 60 mM Hepes pH 7.5, 3 mM MgCl$_2$, 3 mM MnCl$_2$, 3 µM Na$_3$VO$_4$, 0.05 mg/ml PEG, 2 mM DTT, 3 µM Biotin-LRRWSLGLRRWSLGLRRWSLGLRRWSLG-OH, 0.5 µM ATP and 2.2 nM [γ-$^{33}$P-ATP] (6.8 µCi/ml). After incubation of 60 minutes at room temperature, the reaction is stopped by addition of 40 µL of stop solution containing 8.7 mM EDTA, BSA 0.17%, 0.17% Triton X-100, 5 mg/ml SPA beads (GE-healthcare). The plate is centrifuged and read for Scintillation imaging on Leadseeker.

C1.3 GSK-3β Human

In a final reaction volume of 30 µl, GSK3β (h) (1 µg/ml) is incubated with 25 mM Tris pH 7.4, 10 mM MgCl$_2$, 1 mM DTT, 1 µM peptide Biotin-KRREILSRRPSYR-OH, 1 µM ATP and 2 nM [γ-$^{33}$P-ATP] (6.0 µCi/ml). After incubation of 60 minutes at room temperature, the reaction is stopped by addition of 40 µL of stop solution containing 8.7 mM EDTA, BSA 0.17%, 0.17% Triton X-100, 6.25 mg/ml SPA beads (GE-healthcare). The plate is centrifuged and read for Scintillation imaging on Leadseeker.

C1.4 CDK1/CyclinB Human

In a final reaction volume of 10 µl, CDK1/CyclinB (h) (0.2 µg/ml) is incubated with 50 mM Hepes pH 7.5, 10 mM MgCl$_2$, 1 mM EGTA, 0.01% Brij-35, 2 µM Z'lyte Ser/Thr peptide 12 and 10 µM ATP (Invitrogen's FRET assay). After incubation of 60 minutes at room temperature, the reaction is stopped by addition of 5 µL development reagent containing protease mix. After 60 minutes room temperature the development reaction is stopped by adding 5 µl stop solution. The plate is then read in fluorescence plate reader with excitation: 390 nm and dual emission: 460 and 538 nm. Emission ratio is determined to the formula=Emission signal intensity at 460 nm/Emission signal intensity at 538 nm.

C1.5 CDK4/CyclinD1 Human

In a final reaction volume of 30 µl, CDK4/CyclinD1 (h) (2.5 µg/ml) is incubated with 50 mM Hepes pH 7.5, 8 mM NaF, 20 mM MgCl$_2$, 1 mM DTT, 40 µg/ml of substrate GST-pRb, 2 nM [γ-$^{33}$P-ATP] (6.0 µCi/ml). After incubation of 60 minutes at room temperature, the reaction is stopped by addition of 40 µL of stop solution containing 8.7 mM EDTA, 0.17% Triton X-100, 25 mg/ml Glutathion SPA Beads (GE-healthcare). The plate is centrifuged and read for Scintillation topcount analyzer.

C1.6 PLK1 Human

In a final reaction volume of 30 µl, PLK1 T210D (h) (0.125 ng/ml) is incubated with 50 mM Hepes pH 8.0, 2 mM MnCl$_2$, 1 mM DTT, 2 µM of peptide Biotin-Tds linker-TRTD-SLEESSEDESYEEVSQEEDSSEE, 0.1 µM ATP and 2 nM [γ-$^{33}$P-ATP] (6.0 µCi/ml). After incubation of 40 minutes at room temperature, the reaction is stopped by addition of 40 µL of stop solution containing 8.7 mM EDTA, BSA 0.17%, 0.17% Triton X-100, 25 mg/ml SPA beads (GE-healthcare). The plate is centrifuged and read for Scintillation imaging on Leadseeker.

C1.7 PLK2 Human

In a final reaction volume of 30 µl, PLK2 (h) (30 µg/ml) is incubated with 50 mM Hepes pH 8.0, 2 mM MnCl$_2$, 1 mM DTT, 2 µM of peptide Biotin-Tds linker-TRTDSLEESSED-ESYEEVSQEEDSSEE, 0.1 µM ATP and 2 nM [γ-$^{33}$P-ATP] (6.0 µCi/ml). After incubation of 20 minutes at room temperature, the reaction is stopped by addition of 40 µL of stop solution containing 8.7 mM EDTA, BSA 0.17%, 0.17% Triton X-100, 25 mg/ml SPA beads (GE-healthcare). The plate is centrifuged and read for Scintillation imaging on Leadseeker.

C1.8 PLK3 Human

In a final reaction volume of 30 µl, PLK3 (h) (30 µg/ml) is incubated with 50 mM Hepes pH 8.0, 2 mM MnCl$_2$, 1 mM DTT, 2 µM of peptide Biotin-Tds linker-TRTDSLEESSED-ESYEEVSQEEDSSEE, 0.1 µM ATP and 2 nM [γ-$^{33}$P-ATP] (6.0 µCi/ml). After incubation of 20 minutes at room temperature, the reaction is stopped by addition of 40 µL of stop solution containing 8.7 mM EDTA, BSA 0.17%, 0.17% Triton X-100, 25 mg/ml SPA beads (GE-healthcare). The plate is centrifuged and read for Scintillation imaging on Leadseeker.

TABLE 3

Effect of the compound on kinase activity

| Co. No. | AuroraB pIC50 | PLK4 pIC50 | PLK1 pIC50 | PLK2 pIC50 | PLK3 pIC50 | CDK1 pIC50 | CDK4 pIC50 | GSK3b pIC50 |
|---|---|---|---|---|---|---|---|---|
| 3 | 5.81 | 7.06 | <5 | <5 | <5 | <5 | <5 | <5 |
| 13 | 5.38 | 6.31 | <5 | <5 | <5 | <5 | <5 | <5 |
| 176 | n.d. | <5 | <5 | n.d. | n.d. | n.d. | n.d. | n.d. |
| 122 | n.d. | n.d. | n.d. | n.d. | n.d. | n.d. | n.d. | n.d. |
| 97 | n.d. | 5.86 | <5 | n.d. | n.d. | n.d. | n.d. | n.d. |
| 94 | <5 | 5.58 | <5 | <5 | <5 | <5 | 5.44 | 5.53 |
| 102 | <5 | 6.1 | <5 | <5 | <5 | 5.59 | 5.09 | 6.62 |
| 98 | n.d. | 5.74 | <5 | n.d. | n.d. | n.d. | n.d. | n.d. |
| 157 | 5.02 | 5.97 | <5 | <5 | 5.02 | <5 | <5 | 5.18 |
| 71 | <5 | 5.77 | <5 | <5 | <5 | 5.01 | <5 | <5 |
| 125 | <5 | 6.16 | <5 | <5 | <5 | <5 | <5 | <5 |
| 166 | n.d. | 5.45 | <5 | n.d. | n.d. | n.d. | n.d. | n.d. |
| 172 | n.d. | 5.27 | <5 | n.d. | n.d. | n.d. | n.d. | n.d. |
| 69 | n.d. | 5.8 | <5 | n.d. | n.d. | n.d. | n.d. | n.d. |
| 64 | 5.13 | 5.92 | <5 | <5 | <5 | <5 | <5 | <5 |
| 126 | 5.06 | 6.09 | <5 | <5 | <5 | <5 | <5 | <5 |
| 177 | <5 | <5 | <5 | <5 | <5 | <5 | <5 | <5 |
| 139 | <5 | 5.66 | <5 | <5 | <5 | <5 | <5 | <5 |
| 115 | <5 | 5.87 | <5 | <5 | <5 | <5 | <5 | <5 |
| 178 | <5 | <5 | <5 | <5 | <5 | <5 | <5 | <5 |
| 96 | <5 | 6.4 | <5 | <5 | <5 | <5 | <5 | 5.55 |
| 117 | <5 | 5.65 | <5 | <5 | <5 | <5 | <5 | 6 |
| 169 | <5 | 5.41 | <5 | <5 | <5 | <5 | <5 | <5 |
| 93 | <5 | 5.95 | <5 | <5 | <5 | <5 | 5.13 | 5.33 |
| 103 | <5 | 5.96 | <5 | <5 | <5 | <5 | <5 | 5.81 |
| 91 | <5 | 5.85 | <5 | <5 | <5 | <5 | <5 | 5.57 |
| 87 | <5 | 6.39 | <5 | <5 | <5 | 5.15 | 5.9 | 6.67 |
| 89 | <5 | 6.28 | <5 | <5 | <5 | <5 | 5.44 | 6.23 |
| 99 | <5 | 5.44 | <5 | <5 | <5 | <5 | <5 | 6.38 |
| 90 | <5 | 6.19 | <5 | <5 | <5 | 5.33 | 5.78 | 6.38 |
| 88 | 5.19 | 6.35 | <5 | <5 | <5 | 5.32 | 5.85 | 6.71 |
| 6 | 5.78 | 6.5 | <5 | <5 | <5 | 6.71 | 6.25 | 6.13 |
| 9 | <5 | 6.38 | <5 | <5 | <5 | <5 | 5.1 | 5.84 |
| 5 | <5 | 6.79 | <5 | <5 | <5 | <5 | 5.89 | 6.87 |
| 104 | n.d. | n.d. | n.d. | n.d. | n.d. | n.d. | n.d. | n.d. |
| 92 | <5 | 6.4 | <5 | <5 | <5 | 5.99 | 6.05 | 5.88 |
| 48 | <5 | 6.18 | <5 | <5 | <5 | <5 | <5 | 5.04 |
| 116 | <5 | 5.83 | <5 | <5 | <5 | <5 | <5 | <5 |
| 19 | <5 | 5.92 | <5 | <5 | <5 | 7.25 | 5.9 | 7.43 |
| 21 | <5 | 5.37 | <5 | <5 | <5 | 6.98 | 5.89 | 7.78 |
| 84 | 5.15 | 5.27 | <5 | <5 | <5 | <5 | 5.14 | 5.81 |
| 161 | 5.21 | 5.8 | <5 | <5 | <5 | 5.29 | <5 | 6.74 |
| 7 | 5.2 | 6.5 | <5 | <5 | <5 | 5.46 | 5.19 | 6.43 |
| 86 | 4.98 | 6.68 | <5 | <5 | <5 | <5 | 6.31 | 7.16 |
| 175 | <5 | 5.07 | <5 | <5 | <5 | <5 | <5 | <5 |
| 147 | <5 | <5 | <5 | <5 | <5 | <5 | <5 | <5 |
| 83 | <5 | <5 | <5 | <5 | <5 | <5 | <5 | <5 |
| 173 | <5 | 5.21 | <5 | <5 | <5 | <5 | <5 | <5 |
| 78 | <5 | 5.31 | <5 | <5 | <5 | <5 | <5 | <5 |
| 143 | <5 | 5.45 | <5 | <5 | <5 | <5 | <5 | <5.52 |
| 113 | <5 | 5.93 | <5 | <5 | <5 | <5 | <5 | <5 |
| 170 | 5.28 | 5.41 | <5 | <5 | <5 | <5 | <5 | <5 |
| 76 | 5.26 | 5.49 | <5 | <5 | <5 | <5 | <5 | <5 |
| 144 | 5.1 | 5.38 | <5 | <5 | <5 | <5 | <5 | <5 |
| 2 | <5 | <5 | <5 | <5 | <5 | <5 | <5 | <5 |
| 159 | 5.24 | 5.83 | <5 | <5 | <5 | <5 | <5 | 5.2 |
| 63 | <5 | 5.95 | <5 | <5 | <5 | <5 | <5 | 5.72 |
| 137 | <5 | 5.68 | <5 | <5 | <5 | <5 | <5 | 5.53 |
| 110 | 5.59 | 6.12 | <5 | <5 | <5 | <5 | <5 | 5.19 |
| 174 | 5.06 | ~5.16 | <5 | <5 | <5 | <5 | <5 | 5.32 |
| 79 | <5 | 5.28 | <5 | <5 | <5 | <5 | <5 | 6.08 |
| 50 | <5 | 5.03 | <5 | <5 | <5 | <5 | <5 | 5.29 |
| 1 | 5.36 | 7.32 | <5 | <5 | <5 | 5.38 | 5.67 | 6.14 |
| 183 | 5.24 | 6.11 | <5 | <5 | <5 | <5 | 5.48 | 6.51 |
| 14 | <5 | 5.87 | <5 | <5 | <5 | <5.52 | <5 | 5.31 |
| 4 | <5 | 5.62 | <5 | <5 | <5 | <5 | 5.72 | 5.44 |
| 77 | <5 | 5.32 | <5 | <5 | <5 | <5 | <5 | 5.42 |
| 82 | <5 | 5.2 | <5 | <5 | <5 | <5 | <5 | <5 |
| 68 | <5 | 5.81 | <5 | <5 | <5 | <5 | <5 | 5.23 |
| 135 | <5 | 5.76 | <5 | <5 | <5 | <5 | <5 | 5.36 |
| 145 | <5 | 5.36 | <5 | <5 | <5 | <5 | <5 | <5 |
| 153 | <5 | 6.11 | <5 | <5 | <5 | 5.55 | <5 | 5.49 |
| 61 | 5.08 | 6.14 | <5 | <5 | <5 | <5 | 5.13 | 5.12 |
| 128 | <5 | 5.99 | <5 | <5 | <5 | 5.86 | <5 | 5.71 |
| 179 | <5 | <5 | <5 | <5 | <5 | <5 | <5 | <5 |

TABLE 3-continued

Effect of the compound on kinase activity

| Co. No. | AuroraB pIC50 | PLK4 pIC50 | PLK1 pIC50 | PLK2 pIC50 | PLK3 pIC50 | CDK1 pIC50 | CDK4 pIC50 | GSK3b pIC50 |
|---|---|---|---|---|---|---|---|---|
| 141 | <5 | 5.52 | <5 | <5 | <5 | <5 | <5 | <5 |
| 16 | <5 | 6.21 | <5 | <5 | <5 | <5 | <5 | <5 |
| 72 | <5 | 5.63 | <5 | <5 | <5 | <5 | <5 | <5 |
| 136 | <5 | 5.74 | <5 | <5 | <5 | <5 | <5 | 5.17 |
| 10 | 5.03 | 6.29 | <5 | <5 | <5 | <5 | <5 | ~5 |
| 180 | <5 | <5 | <5 | <5 | <5 | <5 | <5 | <5 |
| 81 | <5 | 5.26 | <5 | <5 | <5 | <5 | <5 | <5 |
| 146 | <5 | 5.17 | <5 | <5 | <5 | <5 | <5 | <5 |
| 80 | <5 | 5.27 | <5 | <5 | <5 | <5 | <5 | <5 |
| 164 | <5 | 5.58 | <5 | <5 | <5 | <5 | <5 | <5 |
| 70 | 5.22 | 5.8 | <5 | <5 | <5 | <5 | <5 | <5 |
| 130 | 5.2 | 5.91 | <5 | <5 | <5 | 5.11 | <5 | 5.27 |
| 155 | <5 | 6.08 | <5 | <5 | <5 | <5 | <5 | 5.63 |
| 60 | 5.2 | 6.27 | <5 | <5 | <5 | <5 | <5 | 5.56 |
| 129 | <5 | 5.95 | <5 | <5 | <5.52 | 5.38 | <5 | 6.31 |
| 121 | n.d. | n.d. | n.d. | n.d. | n.d. | n.d. | n.d. | n.d. |
| 142 | <5 | 5.48 | <5 | <5 | <5 | 5.07 | <5 | <5 |
| 75 | <5 | 5.51 | <5 | <5 | <5 | <5 | <5 | <5 |
| 120 | <5 | 5.15 | <5 | <5 | <5 | <5 | <5 | <5 |
| 85 | <5 | 5.23 | <5 | <5 | <5 | <5 | 5 | 5.53 |
| 148 | n.d. | n.d. | n.d. | n.d. | n.d. | n.d. | n.d. | n.d. |
| 11 | <5 | 6.03 | <5 | <5 | <5 | <5 | <5 | 5.68 |
| 160 | <5 | 5.81 | <5 | <5.52 | 5.03 | <5 | <5 | 5.26 |
| 134 | <5 | 5.79 | <5 | 5.54 | <5 | 5.32 | <5 | 5.88 |
| 114 | 5.15 | 5.92 | <5 | ~5.52 | <5 | <5 | <5 | 5.55 |
| 154 | <5 | 6.09 | <5 | <5.52 | <5 | <5 | <5 | <5 |
| 108 | 5.22 | 6.22 | <5 | <5.52 | <5 | <5 | <5 | 5.18 |
| 151 | <5 | 6.19 | <5 | <5.52 | <5 | <5 | <5 | <5 |
| 65 | <5 | 5.91 | <5 | <5 | <5 | <5 | <5 | 5.49 |
| 131 | <5 | 5.9 | <5 | <5 | <5 | <5 | <5 | 5.36 |
| 111 | <5 | 6.09 | <5 | <5.52 | <5 | <5 | <5 | <5 |
| 112 | 5.48 | 6.04 | <5 | <5 | <5 | <5 | <5 | 5.41 |
| 152 | 5.1 | 6.16 | <5 | <5 | <5 | <5 | <5 | 5.29 |
| 163 | <5 | 5.61 | <5 | <5 | <5 | <5 | <5 | <5 |
| 74 | <5 | 5.53 | <5 | <5 | <5 | <5 | <5 | <5 |
| 165 | <5 | 5.55 | <5 | <5 | <5 | <5 | <5 | <5 |
| 118 | 5.18 | 5.49 | <5 | <5.52 | <5 | <5 | <5 | <5 |
| 156 | <5 | 6.04 | <5 | <5.52 | 5.07 | <5 | <5 | <5 |
| 66 | <5 | 5.87 | <5 | <5.52 | <5 | <5 | <5 | 5.97 |
| 133 | <5 | 5.82 | <5 | <5.52 | <5 | <5 | <5 | 5.52 |
| 158 | <5 | 5.94 | <5 | <5.52 | 5.15 | 5.06 | <5 | <5 |
| 62 | <5 | 6.06 | <5 | <5 | 5.01 | <5 | <5 | 5.72 |
| 132 | <5 | 5.85 | <5 | <5.52 | <5 | <5 | <5 | 5.7 |
| 109 | 5.13 | 6.13 | <5 | <5 | <5 | <5 | <5 | 5.32 |
| 106 | 5.12 | 6.3 | <5 | <5 | <5 | 5.19 | <5 | 5.25 |
| 162 | 5.18 | 5.69 | <5 | <5.52 | <5 | <5 | <5 | 5.08 |
| 67 | 5.29 | 5.82 | <5 | <5.52 | <5 | <5 | <5 | 5.51 |
| 127 | 5.7 | 6.09 | <5 | <5 | <5 | <5 | <5 | 5.3 |
| 107 | 5.69 | 6.23 | <5 | <5 | <5 | <5 | <5 | 5.2 |
| 138 | <5 | 5.67 | <5 | <5.52 | <5 | <5 | <5 | <5 |
| 105 | 5.32 | 6.35 | <5 | <5.52 | <5 | <5 | <5 | <5 |
| 171 | <5 | 5.3 | <5 | <5 | <5 | <5 | <5 | <5 |
| 140 | <5 | 5.57 | <5 | <5 | <5 | <5 | <5 | 5.13 |
| 167 | <5 | 5.45 | <5 | <5 | <5 | <5 | <5 | <5 |
| 73 | <5 | 5.59 | <5 | <5 | <5 | <5 | <5 | <5 |
| 181 | <5 | <5 | <5 | <5 | <5 | <5 | <5 | <5 |
| 119 | <5 | 5.41 | <5 | <5 | <5 | <5 | <5 | 5.22 |
| 15 | 5.53 | 6.24 | <5 | <5 | <5 | <5 | 5.35 | 6.43 |
| 101 | <5 | 5.74 | <5 | <5 | <5 | <5 | 5.59 | 6.74 |
| 95 | <5 | 5.18 | <5 | <5 | <5 | 5.14 | 5.89 | 5.43 |
| 20 | <5 | 5.28 | <5 | <5 | <5 | <5 | <5 | 5.22 |
| 27 | <5 | 6.96 | <5 | <5 | <5 | 5.72 | 5.75 | 6.85 |
| 182 | <5 | 6.16 | <5 | <5 | <5 | 5.12 | 5.22 | 6.18 |
| 18 | <5 | 6.19 | <5 | <5 | <5 | <5 | <5 | 6.41 |
| 51 | <5 | <5 | <5 | <5 | <5 | <5 | <5 | <5 |
| 123 | <5 | 5.09 | <5 | <5 | <5 | 5.72 | 5.87 | 5.56 |
| 195 | <5 | <5 | <5 | <5 | <5 | <5 | <5 | <5 |
| 52 | <5 | <5 | <5 | <5 | <5 | <5 | <5 | <5 |
| 188 | <5 | 5.68 | <5 | <5 | <5 | 5.04 | <5 | 5.18 |
| 189 | <5 | <5 | <5 | <5 | <5 | 5.25 | 5.24 | 5.16 |
| 43 | <5 | 6.44 | <5 | <5 | <5 | 6.37 | 6.37 | 6.73 |
| 100 | <5 | 5.94 | <5 | <5 | <5 | 6.82 | 6.7 | 7.12 |
| 53 | <5 | <5 | <5 | <5 | <5 | n.d. | <5 | 6.9 |
| 124 | <5 | 5.06 | <5 | <5 | <5 | 6.43 | 5.77 | 6.34 |
| 196 | <5 | <5 | <5 | <5 | <5 | <5 | 5.21 | 5.97 |

TABLE 3-continued

Effect of the compound on kinase activity

| Co. No. | AuroraB pIC50 | PLK4 pIC50 | PLK1 pIC50 | PLK2 pIC50 | PLK3 pIC50 | CDK1 pIC50 | CDK4 pIC50 | GSK3b pIC50 |
|---|---|---|---|---|---|---|---|---|
| 45 | <5 | 6.38 | <5 | <5 | <5 | 7.15 | 6.03 | 7.14 |
| 187 | <5 | 5.97 | <5 | <5 | <5 | 6.19 | 5.92 | 7.27 |
| 185 | <5 | 6.1 | <5 | <5 | <5 | 5.32 | <5 | 7.56 |
| 149 | 4.96 | 6.09 | <5 | <5 | <5 | 8.44 | 7.14 | 6.93 |
| 54 | <5 | <5 | <5 | <5 | <5 | <5 | 5.13 | <5 |
| 193 | <5 | <5 | <5 | <5 | <5 | <5 | 5.36 | 5.49 |
| 55 | <5 | <5 | <5 | <5 | <5 | <5 | <5 | <5 |
| 190 | <5 | <5 | <5 | <5 | <5 | 5.19 | <5 | 5.89 |
| 186 | <5 | 5.99 | <5 | <5 | <5 | <5 | <5 | <5 |
| 184 | <5 | 6.11 | <5 | <5 | <5 | 6.4 | 5.93 | 6.99 |
| 23 | <5 | 7.13 | <5 | <5 | <5 | <5 | <5 | 6.71 |
| 49 | <5 | 5.23 | <5 | <5 | <5 | <5 | <5 | <5 |
| 12 | 5.64 | 6.31 | <5 | <5 | <5 | <5 | 5.8 | ~4.98 |
| 194 | <5 | 5.95 | <5 | <5 | <5 | <5 | 5.77 | 5.22 |
| 56 | <5 | ~5 | <5 | <5 | <5 | <5 | <5 | <5 |
| 191 | <5 | <5 | <5 | <5 | <5 | <5 | 5.13 | 5.1 |
| 192 | <5 | <5 | <5 | <5 | <5 | <5 | <5 | <5 |
| 17 | <5 | 5.57 | <5 | <5 | <5 | 5.09 | <5 | 6.07 |
| 57 | <5 | <5 | <5 | <5 | <6 | <5 | <5 | <5 |
| 58 | <5 | <5 | <5 | <5 | <5 | <5 | <5 | <5 |
| 168 | 5.59 | 5.45 | <5 | <5 | <5 | 5.09 | 5.67 | 5.84 |
| 32 | <5 | 6.75 | <5 | <5 | <5 | 6.26 | 5.48 | 6.73 |
| 34 | <5 | 6.73 | <5 | <5 | <5 | 5.91 | 5.06 | 6.28 |
| 44 | <5 | 6.39 | <5 | <5 | <5 | 6.37 | 5.44 | 6.78 |
| 8 | 5.33 | 6.44 | <5 | 5.44 | 5.33 | <5 | n.d. | 6.51 |
| 150 | <5 | 6.08 | <5 | <5 | <5 | 5.23 | n.d. | 7 |
| 59 | n.d. | n.d. | n.d. | n.d. | n.d. | n.d. | n.d. | n.d. |
| 39 | <5 | 6.55 | <5 | <5 | <5 | 5.84 | 5.95 | 6.44 |
| 38 | <5 | 6.58 | <5 | <5 | <5.52 | 5.78 | 5.46 | 6.73 |
| 37 | 5.31 | 6.61 | <5 | <5 | <5 | 5.27 | <5 | 6.17 |
| 35 | <5 | 6.69 | <5 | <5 | <5 | 6.54 | 5.87 | 6.69 |
| 26 | <5 | 7.01 | <5 | <5 | <5 | <5 | <5 | 7.17 |
| 25 | <5 | 7.03 | <5 | <5 | <5 | <5 | <5 | 7.09 |
| 47 | <5 | 6.19 | <5 | <5 | <6 | 5.7 | 5.92 | 6.4 |
| 41 | <5 | 6.46 | <5 | <5 | <5 | <5 | 5.25 | 6.58 |
| 46 | <5 | 6.37 | <5 | <5 | <5 | <5 | 5.24 | 6.69 |
| 42 | <5 | 6.45 | <5 | <5 | <5.52 | ~5.87 | 6.34 | 6.48 |
| 40 | <5 | 6.54 | <5 | <5 | <5 | 5.51 | 5.79 | 6.79 |
| 24 | <5 | 7.11 | <5 | <5 | <5 | <5 | 5.37 | 7.06 |
| 22 | 4.99 | 7.16 | <5 | <5 | <5 | 6.6 | 5.56 | 7.51 |
| 28 | <5 | 6.91 | <5 | <5 | <5 | 6.22 | 5.78 | 6.95 |
| 36 | 5.09 | 6.66 | <5 | <5 | <5 | 6.34 | 5.92 | 6.89 |
| 29 | <5 | 6.79 | <5 | <5 | <5 | 6.17 | 5.91 | 6.95 |
| 33 | 5.08 | 6.75 | <5 | <5 | <5 | 6.27 | 5.9 | 6.84 |
| 30 | <5 | 6.79 | <5 | <5 | <5 | 6.57 | 6.05 | 7.62 |
| 31 | <5 | 6.78 | <5 | <5 | <5 | 6.03 | 6 | 6.96 | n.d.: not determined

C.2. Cellular Proliferation Assay

In vivo functional properties of these compounds were tested in cellular proliferation assays on a panel of different cell lines in the presence of 10% FCS serum (37° C. and 5% (v/v) $CO_2$). In a first step these cells were seeded and incubated for 24 hours in the absence of compound. In the second step the cells were incubated for 72 hours with the compounds to be tested for 72 hours. The viable cell number was finally assessed in a standard Alamar blue cell viability assay. The results are shown in Table 4.

Detailed Description

The viable cell number was assessed by incubation for either 4 h (HCT-116, H1299) 6 h (U87-MG) or 24 h (A2780, MDA-MB-231) with Alamar blue (Resazurin 9 µg/ml, K-Ferrocyanide 90 µM, K-Ferricyanide 90 µM) and the converted fluorescent product was quantified on a fluorescent plate reader (544 nm/590 nm). Effect of the compounds is calculated as of on control cells.

TABLE 4

| Co. No. | A2780 | HCT-116 | H1299 | MDA/ MB231 | U87-MG |
|---|---|---|---|---|---|
| 3 | n.d. | <5 | <5 | <5 | n.d. |
| 13 | n.d. | <5 | <5 | <5 | n.d. |
| 176 | <5 | <5 | <5 | <5 | <5 |
| 122 | n.d. | n.d. | n.d. | n.d. | n.d. |
| 97 | n.d. | <5 | n.d. | n.d. | <5 |
| 94 | <5 | 5.04 | 5.09 | <5 | <5 |
| 102 | 5.19 | 5.89 | 5.94 | 5.18 | 5.51 |
| 98 | 5.26 | <5 | n.d. | <5 | <5 |
| 157 | 5.19 | 5.19 | 5.29 | <5 | <5 |
| 71 | n.d. | 5.29 | <5 | 5.17 | n.d. |
| 125 | n.d. | <5 | <5 | <5 | n.d. |
| 166 | <5 | <5 | n.d. | <5 | <5.52 |
| 172 | <5 | <5 | n.d. | <5 | 5.32 |
| 69 | <5 | <5 | 5.58 | <5 | 5.25 |
| 64 | n.d. | n.d. | n.d. | n.d. | n.d. |
| 126 | 5.27 | 5.06 | <5 | <5 | <5 |
| 177 | <5 | <5 | <5 | <5 | <5 |
| 139 | 5.13 | 5.13 | <5 | <5 | 5.68 |
| 115 | <5 | <5 | <5 | <5 | <5 |

TABLE 4-continued

| Co. No. | A2780 | HCT-116 | H1299 | MDA/MB231 | U87-MG |
|---|---|---|---|---|---|
| 178 | <5 | <5 | <5 | <5 | 5.05 |
| 96 | 5.19 | 5.27 | <5 | <5 | 5.38 |
| 117 | 5.22 | 5.37 | 5.12 | <5 | 5.41 |
| 169 | <5 | <5 | <5 | <5 | <5 |
| 93 | 5.14 | 5.44 | <5 | 5 | <5 |
| 103 | <5 | <5 | <5 | <5 | <5 |
| 91 | <5 | 5.21 | <5 | <5 | <5 |
| 87 | 5.06 | 5.42 | <5 | 5.09 | 5.21 |
| 89 | 5.17 | 5.36 | <5 | <5 | <5 |
| 99 | 5.11 | 5.16 | <5 | <5 | 5.16 |
| 90 | 5.22 | 5.77 | 5.06 | 5.27 | 5.34 |
| 88 | 5.47 | 5.79 | 5.09 | 5.17 | 5.45 |
| 6 | 6.71 | 6.98 | 6.42 | 6.44 | 6.24 |
| 9 | <5 | 5.11 | <5 | <5 | 5.81 |
| 5 | <5 | 5.76 | <5 | <5 | <5 |
| 104 | n.d. | n.d. | n.d. | n.d. | n.d. |
| 92 | 6.28 | 6.51 | 6.08 | 5.6 | 6.75 |
| 48 | <5 | <5 | <5 | <5 | <5 |
| 116 | <5 | 5.39 | <5 | <5 | 5.24 |
| 19 | 5.84 | 6.14 | n.d. | 5.21 | 5.97 |
| 21 | 5.12 | 5.64 | n.d. | <5 | 5.55 |
| 84 | <5 | <5 | <5 | <5 | 5.03 |
| 161 | 5.01 | 5.33 | 5 | <5 | <5 |
| 7 | <5 | 5.22 | <5 | <5 | 5.36 |
| 86 | <5 | <5 | <5 | <5 | <5 |
| 175 | <5 | <5 | <5 | <5 | <5 |
| 147 | <5 | <5 | <5 | <5 | <5 |
| 83 | <5 | <5 | <5 | <5 | <5 |
| 173 | <5 | <5 | <5 | <5 | <5 |
| 78 | <5 | <5 | <5 | 5.12 | 5.15 |
| 143 | <5 | <5 | n.d. | n.d. | <5 |
| 113 | <5 | <5 | <5 | <5 | <5 |
| 170 | 5.38 | <5 | n.d. | n.d. | 5.28 |
| 76 | <5 | <5 | <5 | 5.17 | 5.14 |
| 144 | <5 | <5 | <5 | <5 | 5.03 |
| 2 | n.d. | <5 | n.d. | n.d. | <5 |
| 159 | 5.57 | <5 | n.d. | n.d. | 5.16 |
| 63 | 5.57 | <5 | n.d. | n.d. | 5.23 |
| 137 | 5.41 | <5 | n.d. | n.d. | 5.1 |
| 110 | 5.26 | <5 | n.d. | n.d. | 5.07 |
| 174 | 5.78 | <5 | n.d. | n.d. | <5 |
| 79 | 5.32 | <5 | n.d. | n.d. | 5.12 |
| 50 | <5 | <5 | n.d. | n.d. | <5 |
| 1 | 5.63 | 5.42 | 5.16 | <5 | 5.17 |
| 183 | 5.04 | 5.29 | n.d. | <5 | 5.04 |
| 14 | <5 | 5.23 | <5 | <5 | <5 |
| 4 | <5 | 5.28 | <5 | <5 | <5 |
| 77 | <5 | <5 | <5 | <5 | <5 |
| 82 | <5 | <5 | <5 | <5 | <5 |
| 68 | <5 | 5.09 | <5 | <5 | 5.12 |
| 135 | <5 | <5 | <5 | <5 | 5.01 |
| 145 | <5 | <5 | <5 | <5 | <5 |
| 153 | <5 | 5.26 | <5 | <5 | 5.24 |
| 61 | 5.2 | 5.1 | <5 | <5 | 5.25 |
| 128 | <5 | <5 | <5 | <5 | 5.1 |
| 179 | <5 | <5 | <5 | <5 | <5 |
| 141 | 5.05 | 5.64 | <5 | <5 | 5.23 |
| 16 | 5.02 | <5 | <5 | <5 | 5.09 |
| 72 | <5 | 5.47 | <5 | <5 | 5.21 |
| 136 | 5.63 | 6.45 | 5.52 | <5 | 5.77 |
| 10 | <5 | <5 | <5 | <5 | <5 |
| 180 | <5 | <5 | <5 | <5 | <5 |
| 81 | <5 | <5 | <5 | <5 | <5 |
| 146 | <5 | <5 | <5 | <5 | <5 |
| 80 | <5 | <5 | <5 | <5 | <5 |
| 164 | <5 | <5 | <5 | <5 | 5.68 |
| 70 | <5 | <5 | <5 | <5 | 5.04 |
| 130 | <5 | <5 | <5 | <5 | <5 |
| 155 | <5 | <5 | <5 | <5 | <5 |
| 60 | 5.12 | 5.8 | <5 | <5 | 5.59 |
| 129 | <5 | 5.07 | <5 | <5 | 5.31 |
| 121 | 5 | 5.72 | 5.22 | 5.11 | 5.14 |
| 142 | <5 | <5 | <5 | <5 | 5.25 |
| 75 | <5 | 5.14 | <5 | <5 | 5.29 |
| 120 | <5 | <5 | <5 | <5 | <5 |
| 85 | <5 | 5.32 | 5.23 | <5 | <5 |
| 148 | <5 | 6.5 | <5 | <5 | 5.33 |
| 11 | <5 | <5 | <5 | <5 | <5 |
| 160 | <5 | <5 | <5 | <5 | <5 |
| 134 | <5 | 5.28 | <5 | <5 | <5 |
| 114 | <5 | <5 | <5 | <5 | <5 |
| 154 | <5 | <5 | <5 | <5 | <5 |
| 108 | <5 | 5.08 | <5 | <5 | 5.05 |
| 151 | <5 | 5.45 | <5 | <5 | 5.12 |
| 65 | <5 | <5 | <5 | <5 | 5.14 |
| 131 | <5 | 5.28 | <5 | <5 | <5 |
| 111 | <5 | <5 | <5 | <5 | <5 |
| 112 | <5 | <5 | <5 | <5 | <5 |
| 152 | <5 | <5 | <5 | <5 | <5 |
| 163 | 5.18 | 5.38 | <5 | <5 | 5.16 |
| 74 | 5.52 | 5.33 | <5 | 5.23 | 5.4 |
| 165 | <5 | 5.25 | <5 | <5 | 5.21 |
| 118 | <5 | <5 | <5 | <5 | <5 |
| 156 | <5 | <5 | <5 | <5 | <5 |
| 66 | 5.2 | 5.99 | <5 | 5.08 | 5.54 |
| 133 | <5 | 5.71 | <5 | <5 | 5.05 |
| 158 | <5 | <5 | <5 | <5 | <5 |
| 62 | 5.23 | 5.56 | <5 | 5.04 | 5.16 |
| 132 | <5 | 5.23 | <5 | <5 | 5.06 |
| 109 | <5 | 5.57 | <5 | <5 | 5.25 |
| 106 | n.d. | n.d. | n.d. | n.d. | n.d. |
| 162 | <5 | <5 | <5 | <5 | <5 |
| 67 | <5 | <5 | <5 | <5 | <5 |
| 127 | <5 | 5.19 | <5 | <5 | <5 |
| 107 | <5 | 5.36 | <5 | <5 | 5.05 |
| 138 | 5.26 | 5.51 | 5 | 5.23 | 5.49 |
| 105 | <5 | <5 | <5 | <5 | <5 |
| 171 | <5 | 5.18 | <5 | <5 | 5.21 |
| 140 | <5 | 5.81 | <5 | <5 | 5.39 |
| 167 | 5.56 | 5.65 | <5 | 5.19 | 5.43 |
| 73 | <5 | 5.51 | <5 | <5 | 5.29 |
| 181 | <5 | 5.31 | <5 | <5 | 5.04 |
| 119 | <5 | 5.64 | <5 | <5 | 5.06 |
| 15 | 5.15 | 5.08 | <5 | <5 | 5.1 |
| 101 | 5.33 | 5.57 | 5.18 | 5.09 | 5.3 |
| 95 | <5 | <5 | <5 | <5 | <5 |
| 20 | <5 | <5 | <5 | <5.52 | <5 |
| 27 | 6.18 | 6.05 | 5.53 | 5.42 | 5.27 |
| 182 | <5 | <5 | <5 | <5 | <5 |
| 18 | 5.03 | 5.17 | <5 | <5 | 5.17 |
| 51 | <5 | <5 | <5 | <5 | <5 |
| 123 | <5 | <5 | <5 | <5 | <5 |
| 195 | <5 | <5 | <5 | <5 | <5 |
| 52 | <5 | <5 | <5 | <5 | <5 |
| 188 | <5 | <5 | <5 | <5 | <5 |
| 189 | <5 | <5 | <5 | <5 | <5 |
| 43 | 5.6 | 5.75 | <5 | 5.25 | <5 |
| 100 | 5.52 | 6.14 | 5.53 | 5.46 | 6.22 |
| 53 | <5 | 5.06 | <5 | <5 | 5.18 |
| 124 | <5 | 5.54 | <5 | <5 | 5.22 |
| 196 | <5 | <5 | <5 | <5 | <5 |
| 45 | 5.78 | 6.53 | 5.93 | 5.17 | 6.04 |
| 187 | 5.26 | 5.87 | 5.21 | 5.1 | <5 |
| 185 | <5 | 5.16 | 5.58 | <5 | 5.17 |
| 149 | 6.61 | 6.93 | 6.08 | 6.3 | 6.6 |
| 54 | <5 | <5 | <5 | <5 | <5 |
| 193 | <5 | <5 | <5 | <5 | <5 |
| 55 | <5 | <5 | <5 | <5 | <5 |
| 190 | <5 | <5 | <5 | <5 | <5 |
| 186 | <5 | <5 | <5 | <5 | <5 |
| 184 | 5.3 | 5.27 | 5.01 | <5 | <5 |
| 23 | <5 | <5 | <5 | <5 | <5 |
| 49 | 5.39 | <5 | <5 | <5 | 5.76 |
| 12 | 5.76 | 5.42 | 5.8 | 5.03 | 6.02 |
| 194 | <5 | <5 | <5 | <5 | <5 |
| 56 | <5 | <5 | <5 | <5 | <5 |
| 191 | n.d. | n.d. | n.d. | n.d. | n.d. |
| 192 | <5 | <5 | <5 | <5 | <5 |
| 17 | <5 | <5 | <5 | <5 | <5 |
| 57 | <5 | <5 | <5 | <5 | <5 |
| 58 | <5 | <5 | <5 | <5 | <5 |
| 168 | <5 | <5 | <5 | <5 | 5.17 |
| 32 | <5 | 5.29 | <5 | <5 | <5 |
| 34 | <5 | 5.23 | 5.21 | <5 | 5.06 |

TABLE 4-continued

| Co. No. | A2780 | HCT-116 | H1299 | MDA/MB231 | U87-MG |
|---|---|---|---|---|---|
| 44 | 5.22 | 5.74 | <5 | <5 | 5.72 |
| 8 | <5 | 5.1 | <5 | <5 | <5 |
| 150 | <5 | 5.37 | <5 | <5 | <5 |
| 59 | n.d. | n.d. | n.d. | n.d. | n.d. |
| 39 | 5.68 | 5.91 | <5 | 5.17 | 5.97 |
| 38 | 5.57 | 5.91 | <5 | 5.2 | 6 |
| 37 | <5 | <5 | <5 | <5 | <5 |
| 35 | 5.47 | 5.88 | <5 | <5 | 5.84 |
| 26 | 5.38 | 5.66 | 5.61 | 5.09 | <5 |
| 25 | 5.35 | 5.43 | 5.48 | <5 | <5 |
| 47 | 5.43 | 5.61 | 5.02 | 5.29 | 5.15 |
| 41 | <5 | 5.41 | <5 | <5 | 5.64 |
| 46 | 5.26 | 5.65 | <5 | <5 | <5 |
| 42 | 5.84 | 6.02 | 5.47 | 5.72 | 5.74 |
| 40 | 5.33 | 5.66 | <5 | <5 | 5.64 |
| 24 | 5.23 | 5.42 | <5 | <5 | 5.37 |
| 22 | 6.36 | 6.76 | 5.56 | 5.77 | 6.63 |
| 28 | 6.26 | 6.44 | 5.65 | 5.79 | 6.8 |
| 36 | 6.26 | 6.43 | 5.47 | 5.74 | 6.55 |
| 29 | 6.15 | 6.19 | 5.42 | 5.68 | 6.34 |
| 33 | 6.65 | 6.9 | 5.96 | 6.08 | 7.29 |
| 30 | 6.76 | 6.97 | 6.72 | 6.59 | 6.84 |
| 31 | 5.3 | 5.99 | 5.75 | 5.81 | 5.65 | n.d.: not determined

The invention claimed is:

1. A method of treating cancer in a warm-blooded animal in need of such treatment, comprising administrating an effective amount of a compound of Formula (Ia) or (Ib),

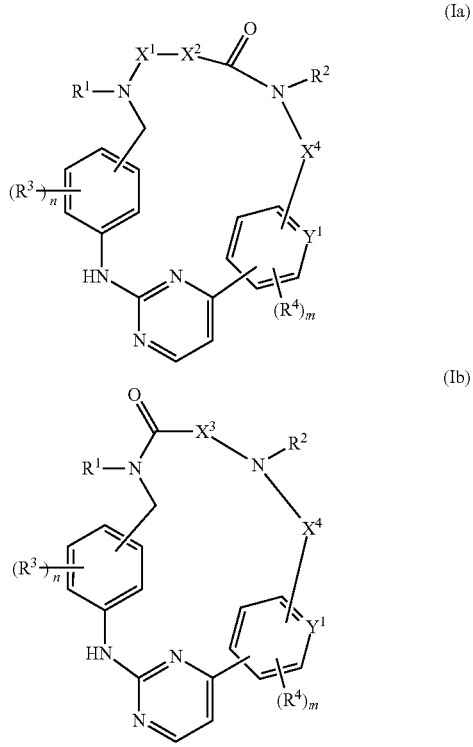

N-oxide form, pharmaceutically acceptable addition salt, quaternary amine, stereoisomer, tautomer, racemic, prodrug, hydrate, or solvate thereof, wherein
n is an integer selected from 1, 2, 3 or 4;
m is an integer selected from 1, 2, or 3;
$Y^1$ represents CH or N,
$R^1$ is hydrogen or $C_{1-6}$alkyl;
$X^1$ represents —$CR^5R^6$—; wherein $R^5$ and $R^6$ are each independently selected from the group comprising hydrogen, $C_{1-6}$alkyl, hydroxy$C_{1-6}$alkyl, $C_{6-10}$aryl$C_{1-6}$alkyl, and $C_{1-6}$alkoxy;
or $X^1$ and $R^1$ together with the nitrogen atom to which they are bound form a $Het^1$,
$X^2$ represents a single bond or —$CR^7R^8$—; wherein $R^7$ and $R^8$ are each independently selected from the group comprising hydrogen, $C_{1-6}$alkyl, hydroxy$C_{1-6}$alkyl, $C_{1-6}$alkoxy, and $C_{6-10}$aryl$C_{1-6}$alkyl;
$R^2$ is hydrogen or $C_{1-6}$alkyl;
$X^3$ represents a single bond or —$CR^9R^{10}$—; wherein $R^9$ and $R^{10}$ are each independently selected from the group comprising hydrogen, $C_{1-6}$alkyl, hydroxy$C_{1-6}$alkyl, $C_{6-10}$aryl$C_{1-6}$alkyl, and $C_{1-6}$alkoxy;
or $R^2$ and $X^3$ together with the nitrogen atom to which they are bound form a $Het^2$,
$X^4$ represents a single bond; —$C_{1-6}$alkylene-; —$C_{1-6}$alkylene-$NR^{14}$—; —$C_{1-6}$alkylene-$NR^{14}$—$C_{1-6}$alkylene-; or —$C_{1-6}$alkylene-O—; wherein each —$C_{1-6}$alkylene- in any of —$C_{1-6}$alkylene-; —$C_{1-6}$alkylene-$NR^{14}$—; —$C_{1-6}$alkylene-$NR^{14}$—$C_{1-6}$alkylene-; or —$C_{1-6}$alkylene-O—, is optionally substituted with one, two or three substituents each independently selected from the group comprising hydroxy, $C_{1-6}$alkyl, and $C_{6-10}$aryl; wherein $R^{14}$ is hydrogen or $C_{1-6}$alkyl; and wherein the left side of the —$C_{1-6}$alkylene-; —$C_{1-6}$alkylene-$NR^{14}$—; —$C_{1-6}$alkylene-$NR^{14}$—$C_{1-6}$alkylene-; or —$C_{1-6}$alkylene-O— is attached to the $NR^2$, and the right side thereof is attached to the

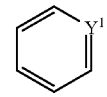

ring;
$R^3$ is hydrogen, halogen, cyano or is selected from the group comprising $C_{1-6}$alkyl, amino, aminocarbonyl, amino$C_{1-6}$alkyl, $Het^3$, $Het^3$-$C_{1-6}$alkyl, $C_{1-6}$alkoxy, $C_{1-6}$alkylaminocarbonyl, $C_{1-6}$alkyl-$Het^3$carbonyl, $Het^3$carbonyl, $C_{1-6}$alkyl-$Het^3$-$C_{1-6}$alkyl, $Het^3$amino$C_{1-6}$alkyl, $C_{1-6}$alkylamino$C_{1-6}$alkyl, $C_{1-6}$alkylamino-$C_{1-6}$alkylamino$C_{1-6}$alkyl, $C_{1-6}$alkoxy$C_{1-6}$alkylamino$C_{1-6}$alkyl, $C_{3-6}$cycloalkylamino-$C_{1-16}$alkyl, $Het^3$aminocarbonyl, $C_{3-6}$cycloalkylaminocarbonyl, $C_{1-6}$alkyl$Het^3$aminocarbonyl, $C_{1-6}$alkylamino, $C_{1-6}$alkylamino$C_{1-6}$alkylaminocarbonyl, $C_{1-6}$alkoxy$C_{1-6}$alkylaminocarbonyl, and $C_{6-10}$aryl$C_{1-6}$alkylamino; each group being optionally substituted with one or two substituents each independently selected from the group comprising $C_{1-6}$alkyl, $C_{6-10}$aryl$C_{1-6}$alkyl, $Het^3$, $C_{3-6}$cycloalkyl, $C_{1-6}$alkylamino$C_{1-6}$alkyl, $C_{1-6}$alkoxy$C_{1-6}$alkyl, $C_{6-10}$aryl, $C_{1-6}$alkylamino, and $C_{1-6}$alkoxy;
or two $R^3$ form together with the carbon atom to which they are bound a dioxolino ring;
$R^4$ is hydrogen; halo; cyano; or is selected from the group comprising $C_{1-6}$alkyl optionally substituted with one, two or three substituents each independently selected from halo or hydroxy; $C_{3-6}$cycloalkyl; $C_{1-6}$alkyloxy; $C_{3-6}$cycloalkyloxy; and $Het^4$;

Het¹ and Het² are each independently selected from the group comprising piperidinyl, piperazinyl, pyrrolidinyl and azetidinyl, wherein said Het¹ is optionally substituted with one, two or three substituents each independently selected from hydroxyl, $C_{1-4}$alkoxy, halo, cyano, amino, $C_{1-4}$alkyl, halo-$C_{1-4}$alkyl, polyhalo-$C_{1-4}$alkyl, $C_{3-6}$cycloalkyl, hydroxy-$C_{1-4}$alkyl, $C_{1-4}$alkyloxy$C_{1-4}$alkyl or polyhydroxy-$C_{1-4}$alkyl; and Het³ and Het⁴ are each independently selected from the group comprising morpholinyl, piperazinyl, piperidinyl, and tetrahydro-pyranyl.

2. The method of claim 1, wherein n is an integer selected from 1, or 2; and m is an integer selected from 1, or 2;

and $Y^1$, $R^1$; $X^1$; $X^2$; $R^2$; $X^3$; $X^4$; $R^3$; and $R^4$ have the same meaning as that defined in claim 1.

3. The method of claim 1, wherein $Y^1$ represents CH and n, m, $R^1$; $X^1$; $X^2$; $R^2$; $X^3$; $X^4$; $R^3$; and $R^4$ have the same meaning as that defined in claim 1.

4. The method of claim 1, wherein $Y^1$ represents N and n, m, $R^1$; $X^1$; $X^2$; $R^2$; $X^3$; $X^4$; $R^3$; and $R^4$ have the same meaning as that defined in claim 1.

5. The method of claim 1, wherein Het¹ and Het² are each independently selected from the group comprising piperidinyl, piperazinyl, and pyrrolidinyl, wherein said Het¹ is optionally substituted with one or where possible two or more substituents selected from hydroxyl, $C_{1-4}$alkoxy, halo, $C_{1-4}$alkyl, halo-$C_{1-4}$alkyl, polyhalo-$C_{1-4}$alkyl, $C_{3-6}$cycloalkyl, or hydroxy-$C_{1-4}$alkyl; and $Y^1$, n, m, $R^1$; $X^1$; $X^2$; $R^2$; $X^3$; $X^4$; $R^3$; and $R^4$ have the same meaning as that defined in any one of claim 1.

6. The method of claim 1, having one of the structural Formula (II), (III), (IV), or (V),

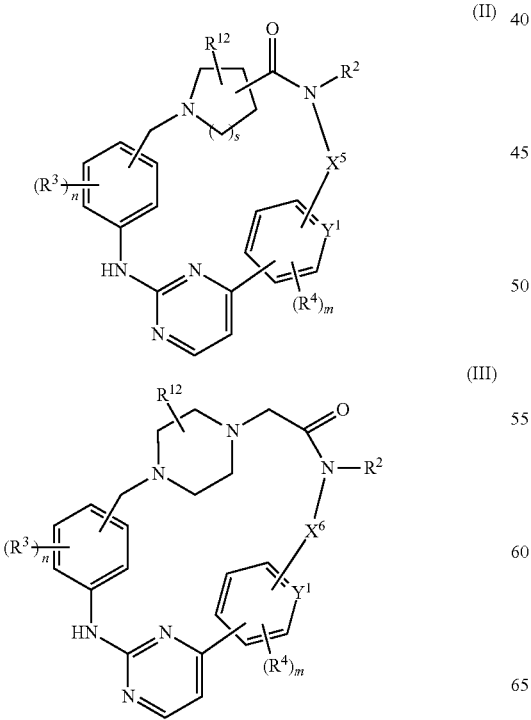

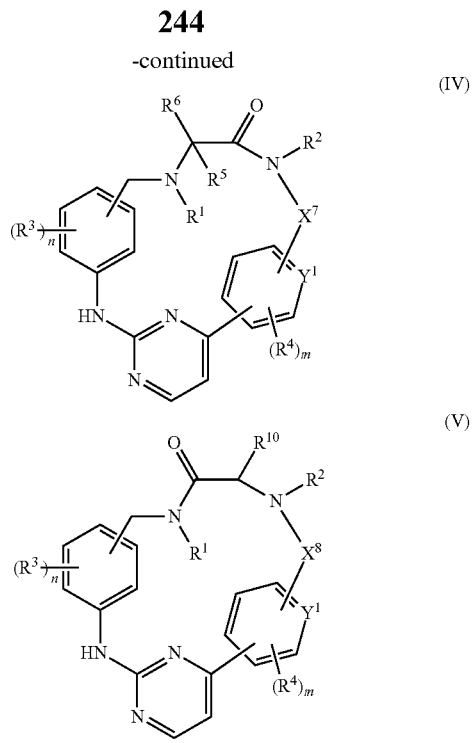

wherein:

s is an integer selected from 1 or 2;

$R^{12}$ is selected from hydrogen, hydroxyl, $C_{1-4}$alkoxy, halo, cyano, amino, $C_{1-4}$alkyl, halo-$C_{1-4}$alkyl, polyhalo-$C_{1-4}$alkyl, $C_{3-6}$cycloalkyl, hydroxy-$C_{1-4}$alkyl, $C_{1-4}$alkyloxy$C_{1-4}$alkyl or polyhydroxy-$C_{1-4}$alkyl;

$X^5$, $X^6$, $X^7$, and $X^8$ are each independently selected from a single bond or —$C_{1-6}$alkylene-;

—$C_{1-6}$alkylene-$NR^{14}$—;   —$C_{1-6}$alkylene-$NR^{14}$—$C_{1-6}$alkylene-; or —$C_{1-6}$alkylene-O—; wherein each —$C_{1-6}$alkylene- in any of —$C_{1-6}$alkylene-; —$C_{1-6}$alkylene-$NR^{14}$—;   —$C_{1-6}$alkylene-$NR^{14}$—$C_{1-6}$alkylene-; or —$C_{1-6}$alkylene-O— is optionally substituted with one, two or three substituents each independently selected from the group comprising hydroxy, $C_{1-6}$alkyl, $C_{6-10}$aryl; wherein $R^{14}$ is selected from the group comprising hydrogen or $C_{1-6}$alkyl; and wherein the left side of the —$C_{1-6}$alkylene-; —$C_{1-6}$alkylene-$NR^{14}$—; —$C_{1-6}$alkylene-$NR^{14}$—$C_{1-6}$alkylene-; or —$C_{1-6}$alkylene-O— is attached to the $NR^2$, and the right side of thereof is attached to the

ring;

or N—$R^2$ and $CHR^{10}$ form together a Het², wherein Het² is selected from piperidinyl, or, pyrrolidinyl, and $R^1$, $R^2$, $R^3$, $R^4$, $R^5$, $R^6$, $R^{10}$, $Y^1$, n and m have the same meaning as that defined in any one of claim 1.

7. The method of claim 1, having one of the structural Formula (VI), (VII), (VIII), (IX), (X), (XI), (XII), (XIII), (XIV), (XV), (XVI), (XVII),

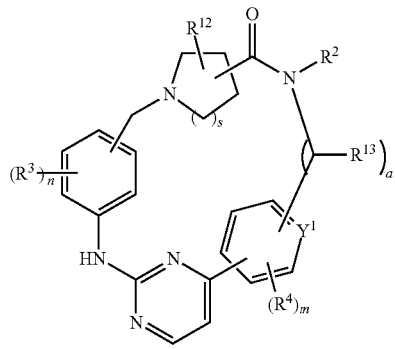 (VI)
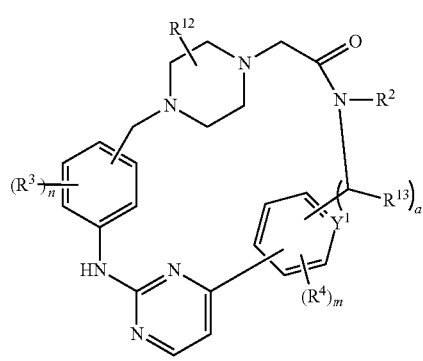 (VII)
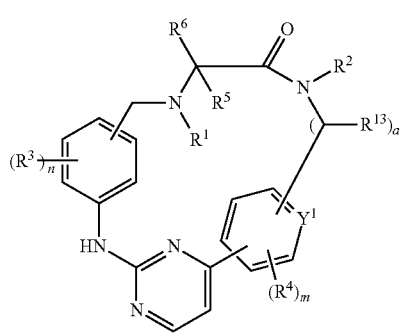 (VIII)
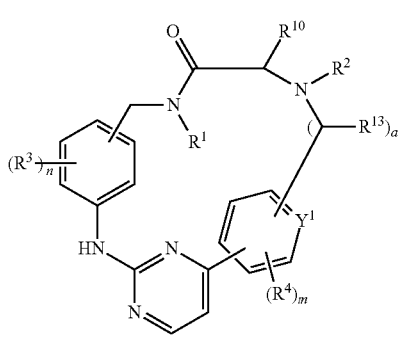 (IX)
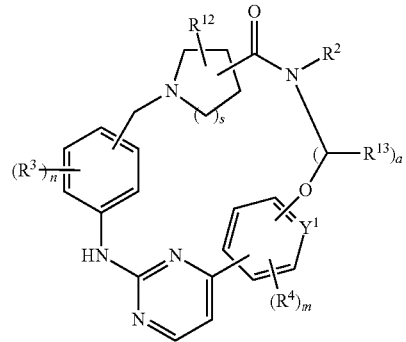 (X)
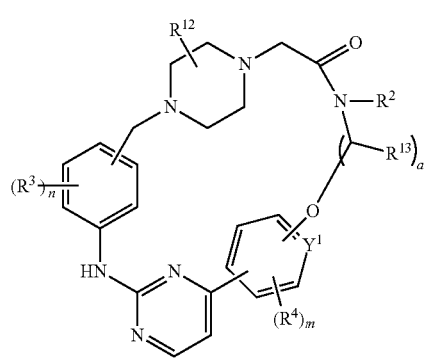 (XI)
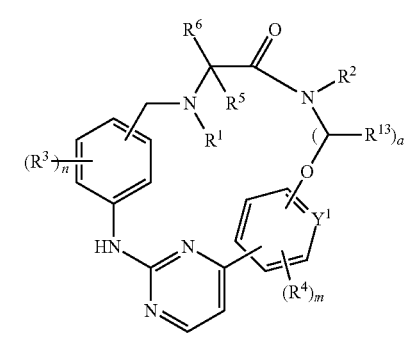 (XII)
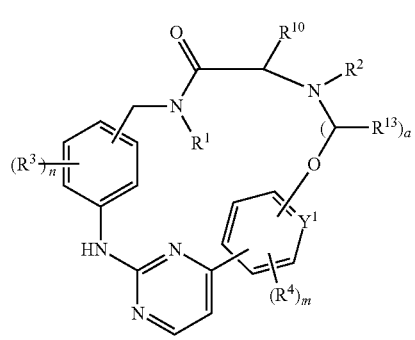 (XIII)

-continued

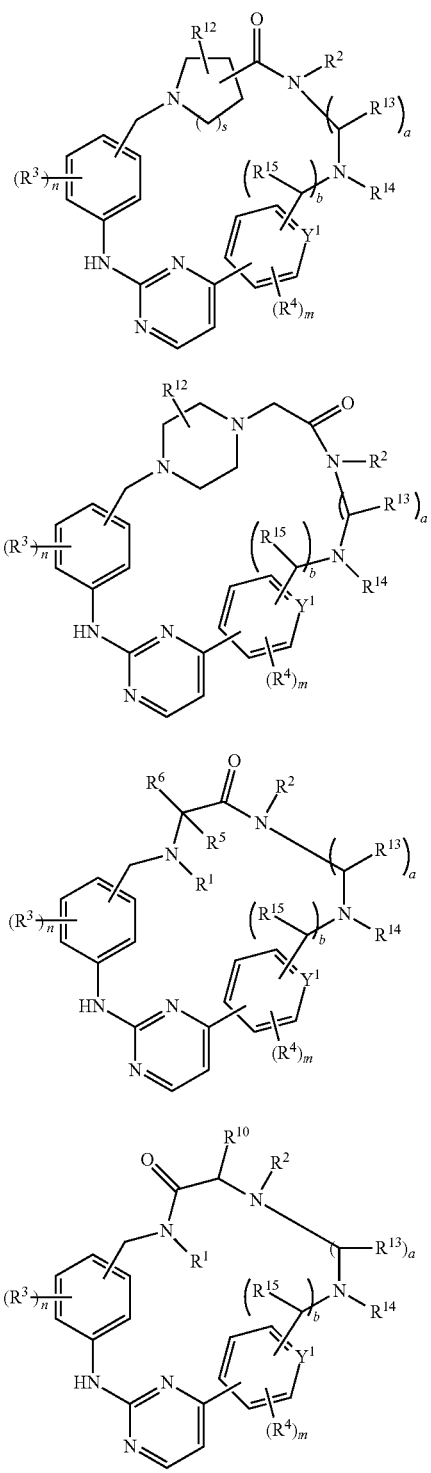

a is an integer selected from 1, 2 or 3;
b is an integer selected from 0 or 1;
$R^{13}$ and $R^{15}$ are each independently selected from the group comprising hydrogen, hydroxy, $C_{1-6}$alkyl, or $C_{6-10}$aryl; and
wherein $R^1$, $R^2$, $R^3$, $R^4$, $R^5$, $R^6$, $R^{10}$, $R^{12}$, $R^{14}$, $Y^1$, s, n and m have the same meaning as that defined in claim 1.

8. The method of claim 1, having one of the structural Formula (XVIII), (XIX), (XX), (XXI), (XXII), (XXIII), (XXIV), (XXV), (XXVI), (XXVII), (XXVIII), (XXIX), (XXX), (XXXI),

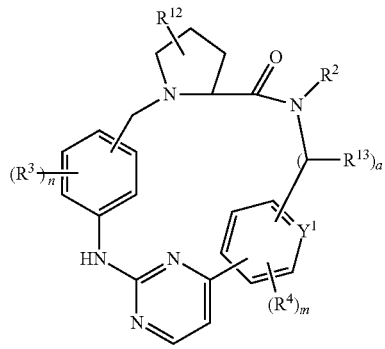

(XVIII)

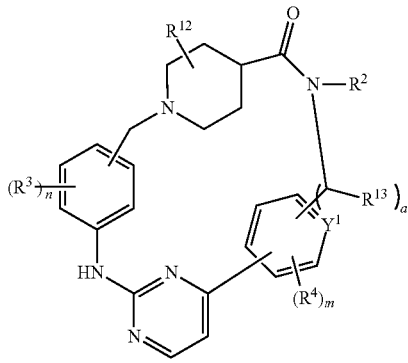

(XIX)

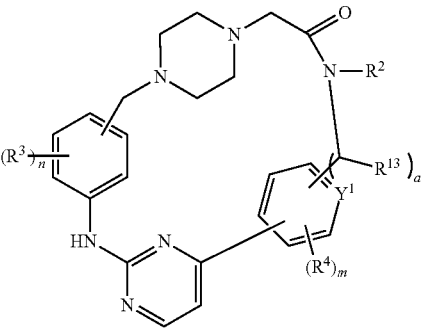

(XX)

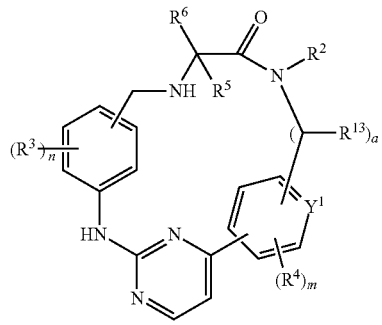

(XXI)

-continued
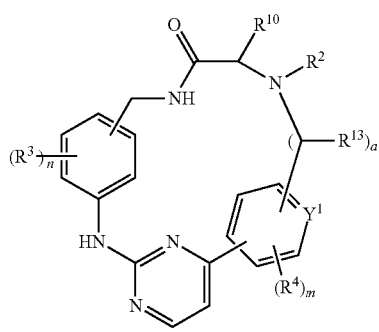
(XXII)
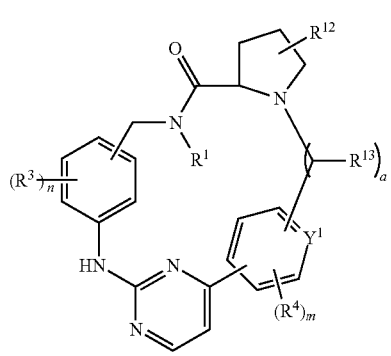
(XXIII)
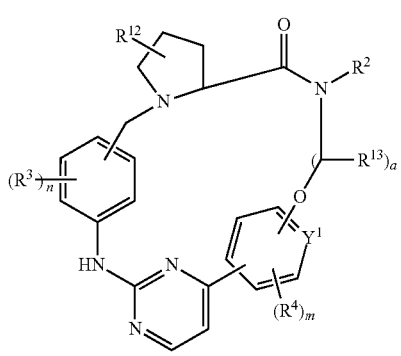
(XXIV)
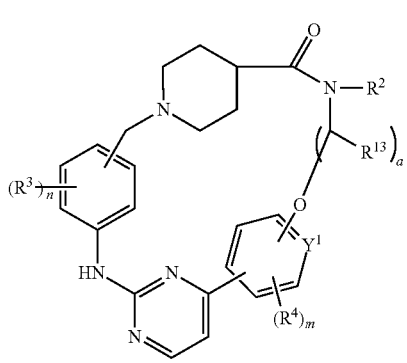
(XXV)
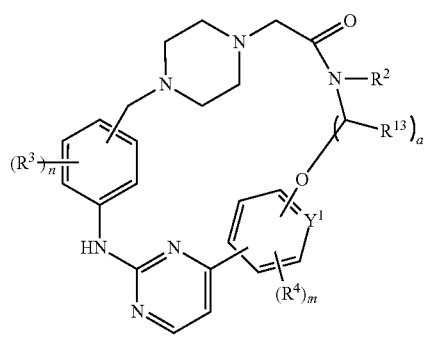
(XXVI)
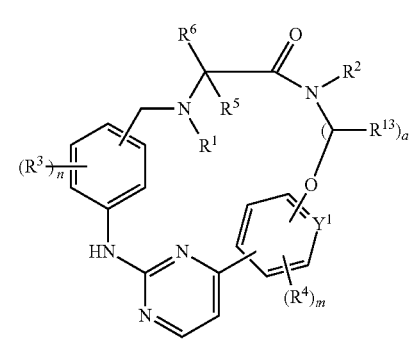
(XXVII)
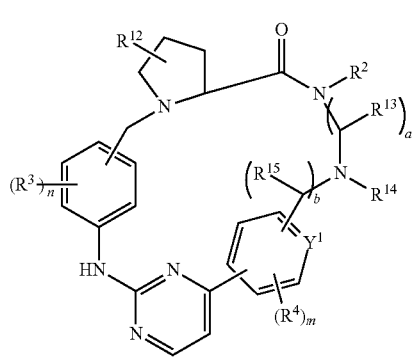
(XXVIII)
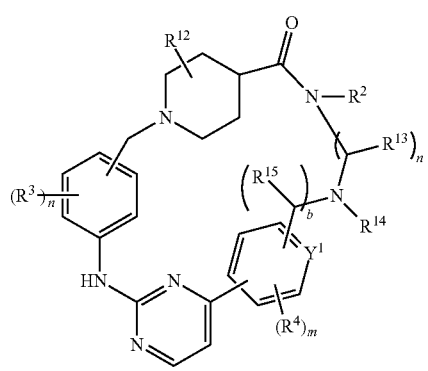
(XXIX)

-continued

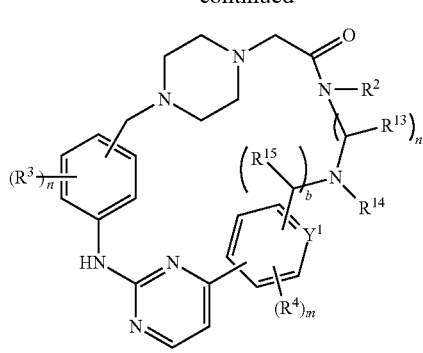

(XXX)

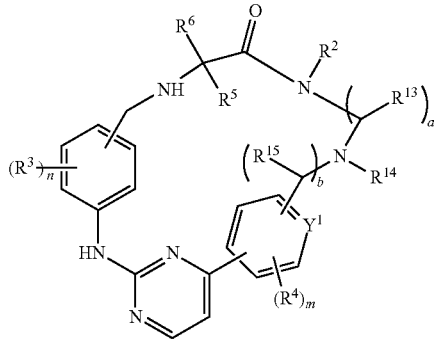

(XXXI)

wherein $R^1, R^2, R^3, R^4, R^5, R^6, R^{10}, R^{12}, R^{13}, R^{14}, R^{15}, Y^1$, a, b, s, n and m have the same meaning as that defined in claim 1.

9. The method of claim 1, wherein
$R^1$ is hydrogen, or $C_{1-4}$alkyl;
$R^2$ is hydrogen or $C_{1-4}$alkyl;
$R^3$ is hydrogen, halogen, cyano or is selected from the group comprising $C_{1-6}$alkyl, amino, aminocarbonyl, amino$C_{1-6}$alkyl, Het$^3$, Het$^3$-$C_{1-6}$alkyl, $C_{1-6}$alkoxy, $C_{1-6}$alkylaminocarbonyl, $C_{1-6}$alkyl-Het$^3$carbonyl, Het$^3$carbonyl, $C_{1-6}$alkyl-Het$^3$-$C_{1-6}$alkyl, Het$^3$amino$C_{1-6}$ alkyl, $C_{1-6}$alkylamino$C_{1-6}$alkyl, $C_{1-6}$alkylamino-$C_{1-6}$alkylamino$C_{1-6}$alkyl, $C_{1-6}$alkoxy$C_{1-6}$alkylamino$C_{1-6}$alkyl, $C_{3-6}$cycloalkylamino$C_{1-16}$alkyl, Het$^3$aminocarbonyl, $C_{3-6}$cycloalkylaminocarbonyl, $C_{1-6}$alkylHet$^3$aminocarbonyl, $C_{1-6}$alkylamino, $C_{1-6}$alkylamino-$C_{1-6}$alkylaminocarbonyl, $C_{1-6}$alkoxy$C_{1-6}$alkylaminocarbonyl, and $C_{6-10}$aryl-$C_{1-6}$alkylamino; each group being optionally substituted with one or two substituents each independently selected from the group comprising $C_{1-6}$alkyl, $C_{6-10}$aryl$C_{1-6}$alkyl, Het$^3$, $C_{3-6}$cycloalkyl, $C_{1-6}$alkylamino$C_{1-6}$alkyl, $C_{1-6}$alkoxy$C_{1-6}$alkyl, $C_{6-10}$aryl, $C_{1-6}$alkylamino, and $C_{1-6}$alkoxy;
or two $R^3$ form together with the carbon atom to which they are bound a dioxolino ring;
$R^4$ is hydrogen; halo; or is selected from the group comprising $C_{1-6}$alkyl optionally substituted with one, two or three substituents each independently selected from halo or hydroxy; and $C_{1-6}$alkyloxy; and
Het$^3$ is selected from the group comprising morpholinyl, piperazinyl, piperidinyl, and tetrahydro-pyranyl.

10. The method of claim 1, wherein
$R^1$ is hydrogen, or $C_{1-4}$alkyl;
$R^2$ is hydrogen or $C_{1-4}$alkyl;
$R^3$ is hydrogen, halogen, cyano or is selected from the group comprising Het$^3$, Het$^3$-$C_{1-6}$alkyl, $C_{1-6}$alkoxy, $C_{1-6}$alkylaminocarbonyl, $C_{1-6}$alkyl-Het$^3$carbonyl, Het$^3$carbonyl, $C_{1-6}$alkyl-Het$^3$-$C_{1-6}$alkyl, Het$^3$amino$C_{1-6}$ alkyl, $C_{1-6}$alkylamino-$C_{1-6}$alkyl, $C_{1-6}$alkylamino$C_{1-6}$alkylamino$C_{1-6}$alkyl, $C_{1-6}$alkoxy$C_{1-6}$alkylamino-$C_{1-6}$ alkyl, $C_{3-6}$cycloalkylamino$C_{1-6}$alkyl, Het$^3$aminocarbonyl, $C_{3-6}$cycloalkylaminocarbonyl, $C_{1-6}$alkylHet$^3$aminocarbonyl, $C_{1-6}$alkylamino, $C_{1-6}$alkylamino-$C_{1-6}$alkylaminocarbonyl, $C_{1-6}$alkoxy$C_{1-6}$alkylaminocarbonyl, and $C_{6-10}$aryl-$C_{1-6}$ alkylamino; each group being optionally substituted with one or two $C_{1-6}$alkyl substituents;
or two $R^3$ form together with the carbon atom to which they are bound a dioxolino ring;
$R^4$ is hydrogen, halo, $C_{1-6}$alkyl, or $C_{1-6}$alkyloxy; and
Het$^3$ is selected from the group comprising morpholinyl, piperazinyl, piperidinyl, and tetrahydro-pyranyl.

11. A method of treating lung cancer, breast cancer, liver cancer, ovarian cancer, prostate cancer, pancreatic cancer, colorectal cancer, gastrointestinal cancer; papillary carcinomas, squamous cell cancers of the head and neck, oesophageal cancers, and fast-dividing leukaemias, in a warm-blooded animal in need of such treatment, comprising administrating an effective amount of a compound of Formula (Ia) or (Ib), (Ia)

(Ib)

N-oxide form, pharmaceutically acceptable addition salt, quaternary amine, stereoisomer, tautomer, racemic, prodrug, hydrate, or solvate thereof, wherein
n is an integer selected from 1, 2, 3 or 4;
m is an integer selected from 1, 2, or 3;
$Y^1$ represents CH or N,
$R^1$ is hydrogen or $C_{1-6}$alkyl;
$X^1$ represents —CR$^5$R$^6$—; wherein $R^5$ and $R^6$ are each independently selected from the group comprising hydrogen, $C_{1-6}$alkyl, hydroxy$C_{1-6}$alkyl, $C_{6-10}$aryl$C_{1-6}$alkyl, and $C_{1-6}$alkoxy;

or X¹ and R¹ together with the nitrogen atom to which they are bound form a Het¹, X² represents a single bond or —CR⁷R⁸—; wherein R⁷ and R⁸ are each independently selected from the group comprising hydrogen, $C_{1-6}$alkyl, hydroxy$C_{1-6}$alkyl, $C_{1-6}$alkoxy, and $C_{6-10}$aryl$C_{1-6}$alkyl;

R² is hydrogen or $C_{1-6}$alkyl;

X³ represents a single bond or —CR⁹R¹⁰—; wherein R⁹ and R¹⁰ are each independently selected from the group comprising hydrogen, $C_{1-6}$alkyl, hydroxy$C_{1-6}$alkyl, $C_{6-10}$aryl$C_{1-6}$alkyl, and $C_{1-6}$alkoxy;

or R² and X³ together with the nitrogen atom to which they are bound form a Het², X⁴ represents a single bond; —$C_{1-6}$alkylene-; —$C_{1-6}$alkylene-NR¹⁴—;

—$C_{1-6}$alkylene-NR¹⁴—$C_{1-6}$alkylene-; or —$C_{1-6}$alkylene-O—; wherein each —$C_{1-6}$alkylene- in any of —$C_{1-6}$alkylene-; —$C_{1-6}$alkylene-NR¹⁴—; —$C_{1-6}$alkylene-NR¹⁴—$C_{1-6}$alkylene-; or —$C_{1-6}$alkylene-O—, is optionally substituted with one, two or three substituents each independently selected from the group comprising hydroxy, $C_{1-6}$alkyl, and $C_{6-10}$aryl; wherein R¹⁴ is hydrogen or $C_{1-6}$alkyl; and wherein the left side of the —$C_{1-6}$alkylene-; —$C_{1-6}$alkylene-NR¹⁴—;

—$C_{1-6}$alkylene-NR¹⁴—$C_{1-6}$alkylene-; or —$C_{1-6}$alkylene-O— is attached to the NR², and the right side thereof is attached to the

ring;

R³ is hydrogen, halogen, cyano or is selected from the group comprising $C_{1-6}$alkyl, amino, aminocarbonyl, amino$C_{1-6}$alkyl, Het³, Het³-$C_{1-6}$alkyl, $C_{1-6}$alkoxy, $C_{1-6}$alkylaminocarbonyl, $C_{1-6}$alkyl-Het³carbonyl, Het³carbonyl, $C_{1-6}$alkyl-Het³-$C_{1-6}$alkyl, Het³amino$C_{1-6}$ alkyl, $C_{1-6}$alkylamino$C_{1-6}$alkyl, $C_{1-6}$alkylamino-$C_{1-6}$ alkylamino$C_{1-6}$alkyl, $C_{1-6}$alkoxy$C_{1-6}$alkylamino$C_{1-6}$ alkyl, $C_{3-6}$cycloalkylamino-$C_{1-6}$alkyl, Het³aminocarbonyl, $C_{3-6}$cycloalkylaminocarbonyl, $C_{1-6}$alkylHet³aminocarbonyl, $C_{1-6}$alkylamino, $C_{1-6}$alkylamino$C_{1-6}$alkylaminocarbonyl, $C_{1-6}$alkoxy$C_{1-6}$ alkylaminocarbonyl, and $C_{6-10}$aryl$C_{1-6}$ alkylamino; each group being optionally substituted with one or two substituents each independently selected from the group comprising $C_{1-6}$alkyl, $C_{6-10}$aryl$C_{1-6}$alkyl, Het³, $C_{3-6}$cycloalkyl, $C_{1-6}$alkylamino$C_{1-6}$alkyl, $C_{1-6}$alkoxy$C_{1-6}$ alkyl, $C_{6-10}$aryl, $C_{1-6}$alkylamino, and $C_{1-6}$alkoxy;

or two R³ form together with the carbon atom to which they are bound a dioxolino ring;

R⁴ is hydrogen; halo; cyano; or is selected from the group comprising $C_{1-6}$alkyl optionally substituted with one, two or three substituents each independently selected from halo or hydroxy; $C_{3-6}$cycloalkyl; $C_{1-6}$alkyloxy; $C_{3-6}$cycloalkyloxy; and Het⁴;

Het¹ and Het² are each independently selected from the group comprising piperidinyl, piperazinyl, pyrrolidinyl and azetidinyl, wherein said Het¹ is optionally substituted with one, two or three substituents each independently selected from hydroxyl, $C_{1-4}$alkoxy, halo, cyano, amino, $C_{1-4}$alkyl, halo-$C_{1-4}$alkyl, polyhalo-$C_{1-4}$alkyl, $C_{3-6}$cycloalkyl, hydroxy-$C_{1-4}$alkyl, $C_{1-4}$alkyloxy$C_{1-4}$ alkyl or polyhydroxy-$C_{1-4}$alkyl; and Het³ and Het⁴ are each independently selected from the group comprising morpholinyl, piperazinyl, piperidinyl, and tetrahydro-pyranyl.

12. The method of claim 11, wherein n is an integer selected from 1, or 2; and m is an integer selected from 1, or 2;

and Y¹, R¹; X¹; X²; R²; X³; X⁴; R³; and R⁴ have the same meaning as that defined in claim 1.

13. The method of claim 11, wherein Y¹ represents CH and n, m, R¹; X¹; X²; R²; X³; X⁴; R³; and R⁴ have the same meaning as that defined in claim 1.

14. The method of claim 11, wherein Y¹ represents N and n, m, R¹; X¹; X²; R²; X³; X⁴; R³; and R⁴ have the same meaning as that defined in claim 1.

15. The method of claim 11, wherein Het¹ and Het² are each independently selected from the group comprising piperidinyl, piperazinyl, and pyrrolidinyl, wherein said Het¹ is optionally substituted with one or where possible two or more substituents selected from hydroxyl, $C_{1-4}$alkoxy, halo, $C_{1-4}$alkyl, halo-$C_{1-4}$alkyl, polyhalo-$C_{1-4}$alkyl, $C_{3-6}$cycloalkyl, or hydroxy-$C_{1-4}$alkyl; and Y¹, n, m, R¹; X¹; X²; R²; X³; X⁴; R³; and R⁴ have the same meaning as that defined in any one of claim 1.

16. The method of claim 11, having one of the structural Formula (II), (III), (IV), or (V),

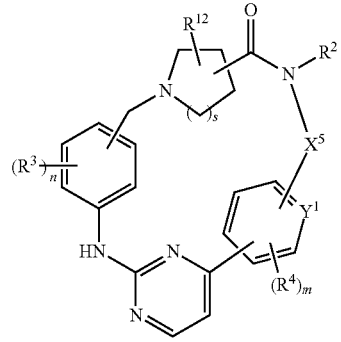

(II)

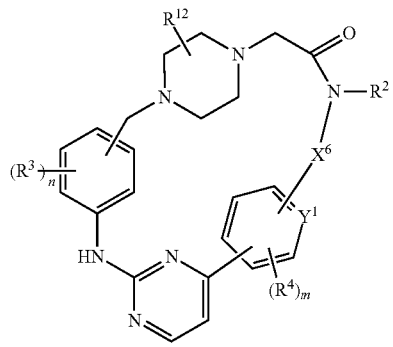

(III)

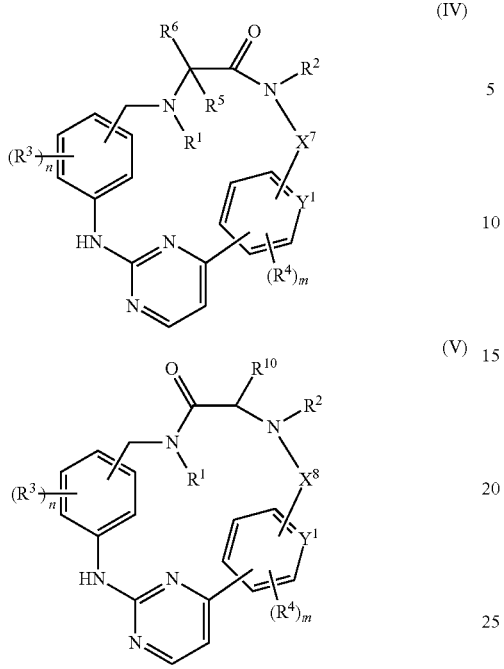

(IV)

(V)

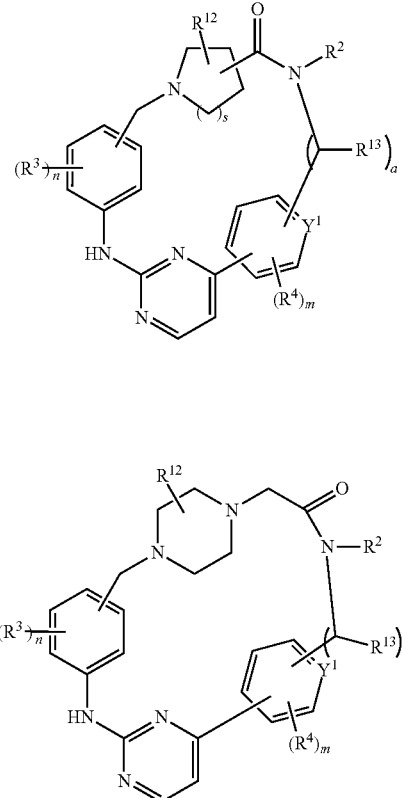

(VI)

(VII)

wherein:

s is an integer selected from 1 or 2;

R$^{12}$ is selected from hydrogen, hydroxyl, C$_{1-4}$alkoxy, halo, cyano, amino, C$_{1-4}$alkyl, halo-C$_{1-4}$alkyl, polyhalo-C$_{1-4}$alkyl, C$_{3-6}$cycloalkyl, hydroxy-C$_{1-4}$alkyl, C$_{1-4}$alkyloxyC$_{1-4}$alkyl or polyhydroxy-C$_{1-4}$alkyl;

X$^5$, X$^6$, X$^7$, and X$^8$ are each independently selected from a single bond or —C$_{1-6}$alkylene-;

—C$_{1-6}$alkylene-NR$^{14}$—; —C$_{1-6}$alkylene-NR$^{14}$—C$_{1-6}$alkylene-; or —C$_{1-6}$alkylene-O—; wherein each —C$_{1-6}$alkylene- in any of —C$_{1-6}$alkylene-; —C$_{1-6}$alkylene-NR$^{14}$—; —C$_{1-6}$alkylene-NR$^{14}$—C$_{1-6}$alkylene-; or —C$_{1-6}$alkylene-O— is optionally substituted with one, two or three substituents each independently selected from the group comprising hydroxy, C$_{1-6}$alkyl, C$_{6-10}$aryl; wherein R$^{14}$ is selected from the group comprising hydrogen or C$_{1-6}$alkyl; and wherein the left side of the —C$_{1-6}$alkylene-; —C$_{1-6}$alkylene-NR$^{14}$—; —C$_{1-6}$alkylene-NR$^{14}$—C$_{1-6}$alkylene-; or —C$_{1-6}$alkylene-O— is attached to the NR$^2$, and the right side of thereof is attached to the

ring;

or N—R$^2$ and CHR$^{10}$ form together a Het$^2$, wherein Het$^2$ is selected from piperidinyl, or, pyrrolidinyl, and R$^1$, R$^2$, R$^3$, R$^4$, R$^5$, R$^6$, R$^{10}$, Y$^1$, n and m have the same meaning as that defined in any one of claim 1.

17. The method of claim 11, having one of the structural Formula (VI), (VII), (VIII), (IX), (X), (XI), (XII), (XIII), (XIV), (XV), (XVI), (XVII),

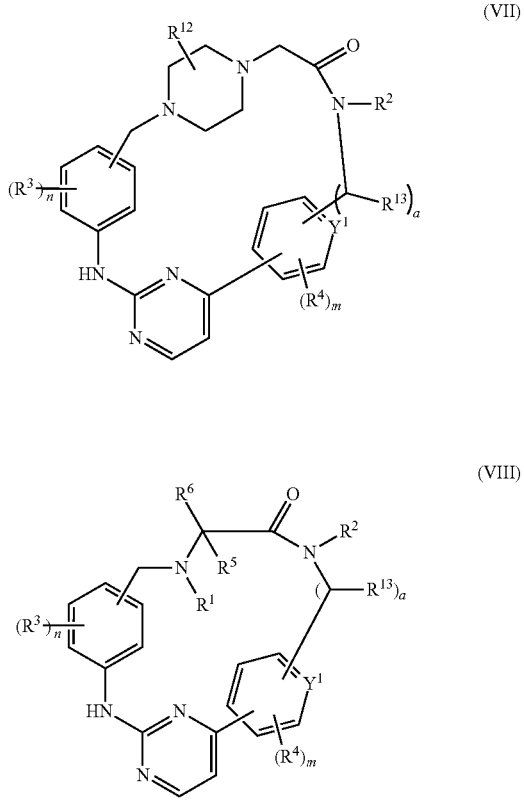

(VIII)

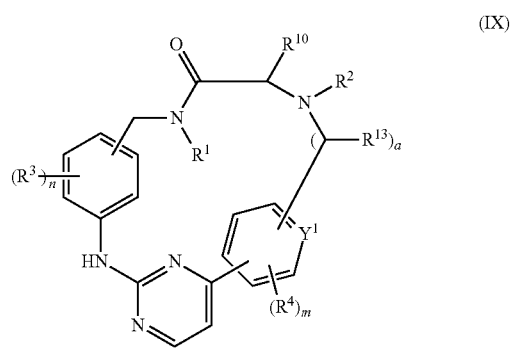

(IX)

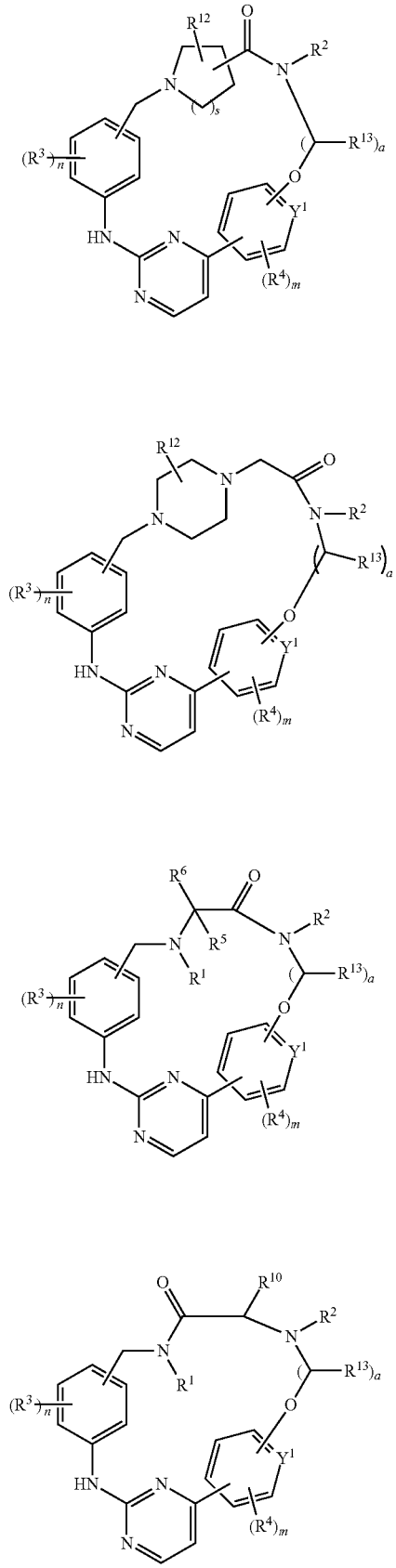
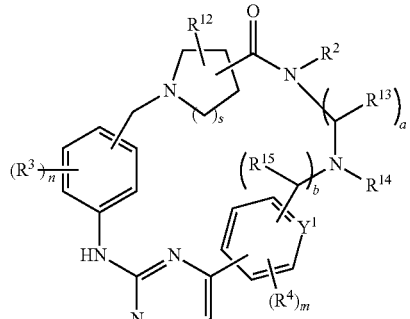
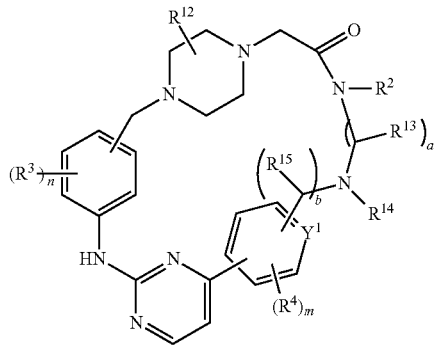
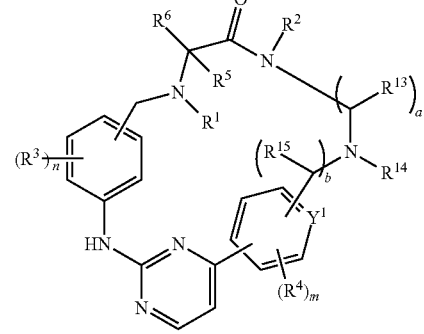
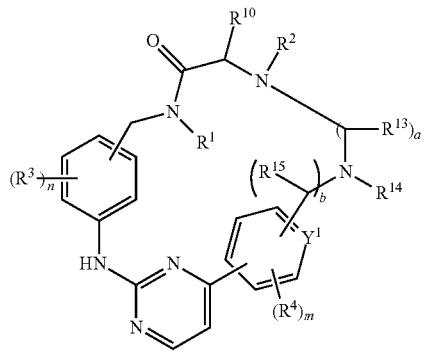
a is an integer selected from 1, 2 or 3;
b is an integer selected from 0 or 1;
$R^{13}$ and $R^{15}$ are each independently selected from the group comprising hydrogen, hydroxy, $C_{1-6}$alkyl, or $C_{6-10}$aryl; and
wherein $R^1$, $R^2$, $R^3$, $R^4$, $R^5$, $R^6$, $R^{10}$, $R^{12}$, $R^{14}$, $Y^1$, s, n and m have the same meaning as that defined in claim 1.

18. The method of claim 11, having one of the structural Formula (XVIII), (XIX), (XX), (XXI), (XXII), (XXIII), (XXIV), (XXV), (XXVI), (XXVII), (XXVIII), (XXIX), (XXX), (XXXI),
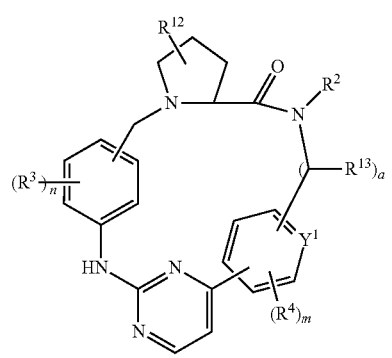
(XVIII)
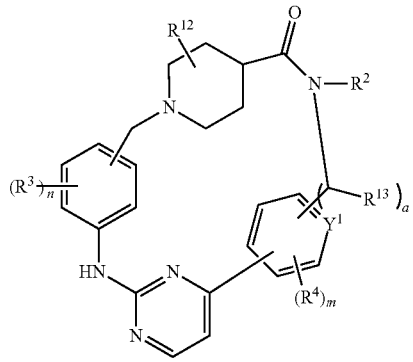
(XIX)
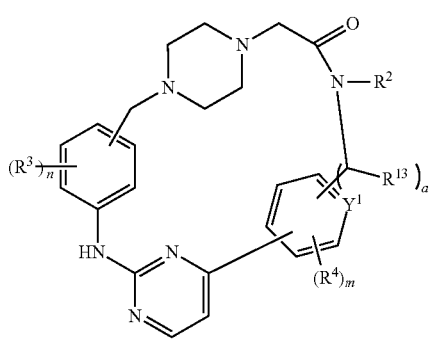
(XX)
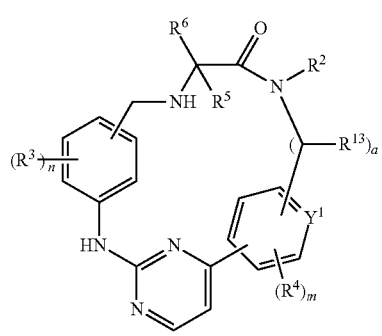
(XXI)
-continued
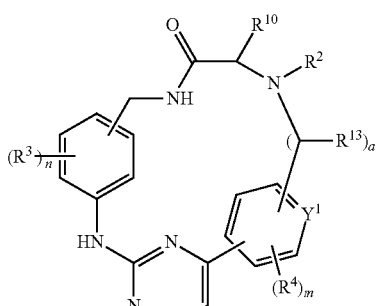
(XXII)
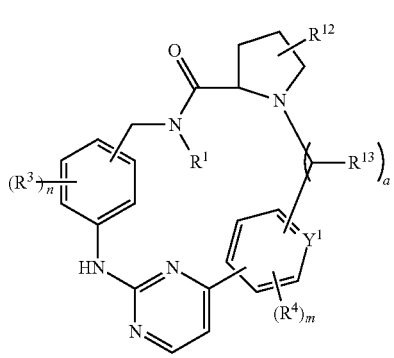
(XXIII)
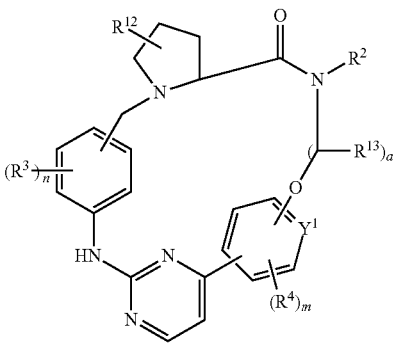
(XXIV)
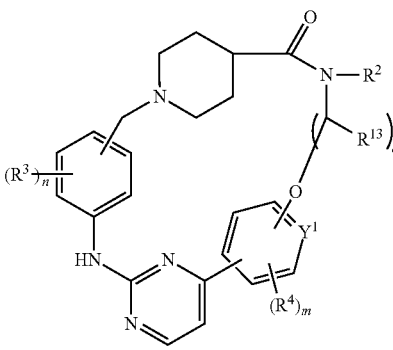
(XXV)

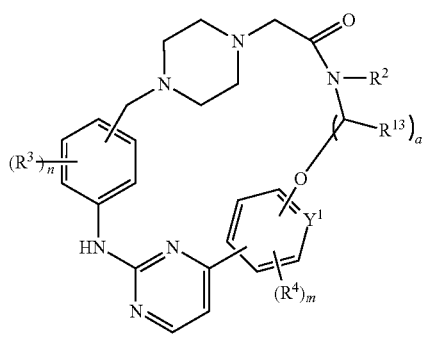 (XXVI)

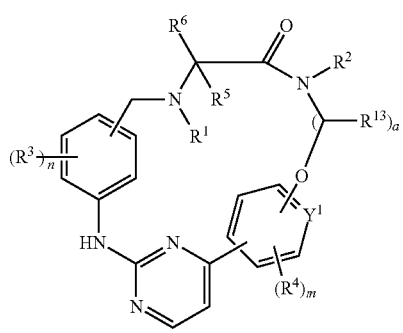 (XXVII)

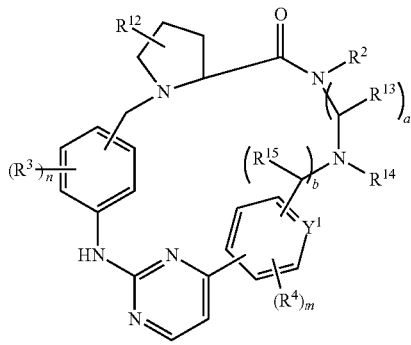 (XXVIII)

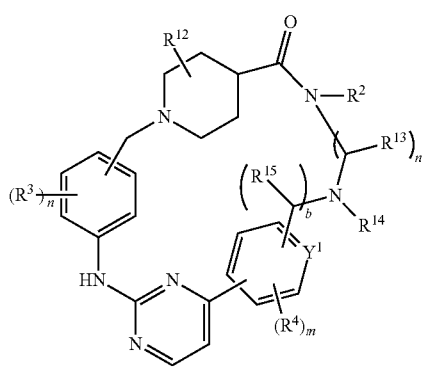 (XXIX)

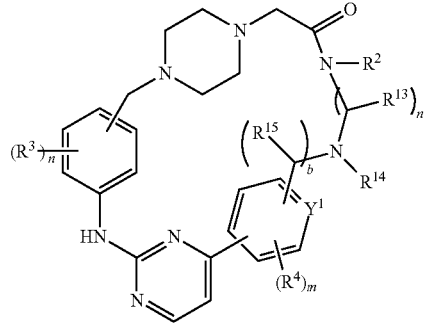 (XXX)

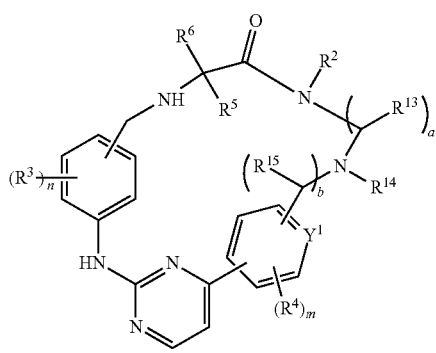 (XXXI)

wherein $R^1$, $R^2$, $R^3$, $R^4$, $R^5$, $R^6$, $R^{10}$, $R^{12}$, $R^{13}$, $R^{14}$, $R^{15}$, $Y^1$, a, b, s, n and m have the same meaning as that defined in claim 1.

19. The method of claim 11, wherein $R^1$ is hydrogen, or $C_{1-4}$alkyl;

$R^2$ is hydrogen or $C_{1-4}$alkyl;

$R^3$ is hydrogen, halogen, cyano or is selected from the group comprising $C_{1-6}$alkyl, amino, aminocarbonyl, amino$C_{1-6}$alkyl, Het$^3$, Het$^3$-$C_{1-6}$alkyl, $C_{1-6}$alkoxy, $C_{1-6}$alkylaminocarbonyl, $C_{1-6}$alkyl-Het$^3$carbonyl, Het$^3$carbonyl, $C_{1-6}$alkyl-Het$^3$-$C_{1-6}$alkyl, Het$^3$amino$C_{1-6}$ alkyl, $C_{1-6}$alkylamino$C_{1-6}$alkyl, $C_{1-6}$alkylamino-$C_{1-6}$ alkylamino$C_{1-6}$alkyl, $C_{1-6}$alkoxy$C_{1-6}$alkylamino$C_{1-6}$ alkyl, $C_{3-6}$cycloalkylamino$C_{1-6}$alkyl, Het$^3$aminocarbonyl, $C_{3-6}$cycloalkylaminocarbonyl, $C_{1-6}$alkylHet$^3$aminocarbonyl, $C_{1-6}$alkylamino, $C_{1-6}$alkylamino-$C_{1-6}$alkylaminocarbonyl, $C_{1-6}$alkoxy$C_{1-6}$alkylaminocarbonyl, and $C_{6-10}$aryl-$C_{1-6}$alkylamino; each group being optionally substituted with one or two substituents each independently selected from the group comprising $C_{1-6}$alkyl, $C_{6-10}$aryl$C_{1-6}$alkyl, Het$^3$, $C_{3-6}$cycloalkyl, $C_{1-6}$alkylamino$C_{1-6}$alkyl, $C_{1-6}$alkoxy$C_{1-6}$alkyl, $C_{6-10}$aryl, $C_{1-6}$alkylamino, and $C_{1-6}$alkoxy;

or two $R^3$ form together with the carbon atom to which they are bound a dioxolino ring;

$R^4$ is hydrogen; halo; or is selected from the group comprising $C_{1-6}$alkyl optionally substituted with one, two or three substituents each independently selected from halo or hydroxy; and $C_{1-6}$alkyloxy; and Het$^3$ is selected from the group comprising morpholinyl, piperazinyl, piperidinyl, and tetrahydro-pyranyl.

20. The method of claim 11, wherein $R^1$ is hydrogen, or $C_{1-4}$alkyl;

$R^2$ is hydrogen or $C_{1-4}$alkyl;

$R^3$ is hydrogen, halogen, cyano or is selected from the group comprising Het$^3$, Het$^3$-$C_{1-6}$alkyl, $C_{1-6}$alkoxy, $C_{1-6}$alkylaminocarbonyl, $C_{1-6}$alkyl-Het$^3$carbonyl, Het$^3$carbonyl, $C_{1-6}$alkyl-Het$^3$-$C_{1-6}$alkyl, Het$^3$amino$C_{1-6}$alkyl, $C_{1-6}$alkylamino-$C_{1-6}$alkyl, $C_{1-6}$alkylamino$C_{1-6}$alkylamino$C_{1-6}$alkyl, $C_{1-6}$alkoxy$C_{1-6}$alkylamino-$C_{1-6}$alkyl, $C_{3-6}$cycloalkylamino$C_{1-6}$alkyl, Het$^3$aminocarbonyl, $C_{3-6}$cycloalkylaminocarbonyl, $C_{1-6}$alkylHet$^3$aminocarbonyl, $C_{1-6}$alkylamino, $C_{1-6}$alkylamino-$C_{1-6}$alkylaminocarbonyl, $C_{1-6}$alkoxy$C_{1-6}$alkylaminocarbonyl, and $C_{6-10}$aryl-$C_{1-6}$alkylamino; each group being optionally substituted with one or two $C_{1-6}$alkyl substituents;

or two R$^3$ form together with the carbon atom to which they are bound a dioxolino ring;

R$^4$ is hydrogen, halo, $C_{1-6}$alkyl, or $C_{1-6}$alkyloxy; and

Het$^3$ is selected from the group comprising morpholinyl, piperazinyl, piperidinyl, and tetrahydro-pyranyl.

* * * * *